US012612456B2

(12) United States Patent
Cheung et al.

(10) Patent No.: US 12,612,456 B2
(45) Date of Patent: Apr. 28, 2026

(54) CD19 ANTIBODIES AND METHODS OF USING THE SAME

(71) Applicant: MEMORIAL SLOAN KETTERING CANCER CENTER, New York, NY (US)

(72) Inventors: Nai-Kong V. Cheung, New York, NY (US); Sayed Shahabuddin Hoseini, New York, NY (US); Mahiuddin Ahmed, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 1154 days.

(21) Appl. No.: 17/602,176

(22) PCT Filed: Apr. 7, 2020

(86) PCT No.: PCT/US2020/027071
§ 371 (c)(1),
(2) Date: Oct. 7, 2021

(87) PCT Pub. No.: WO2020/210232
PCT Pub. Date: Oct. 15, 2020

(65) Prior Publication Data
US 2022/0177579 A1      Jun. 9, 2022

Related U.S. Application Data

(60) Provisional application No. 62/831,123, filed on Apr. 8, 2019.

(51) Int. Cl.
| | |
|---|---|
| *C07K 16/28* | (2006.01) |
| *A61K 39/00* | (2006.01) |
| *A61K 51/04* | (2006.01) |
| *A61K 51/08* | (2006.01) |
| *A61P 35/00* | (2006.01) |
| *A61P 35/02* | (2006.01) |
| *A61P 37/02* | (2006.01) |
| *C07K 16/00* | (2006.01) |

(52) U.S. Cl.
CPC ...... *C07K 16/2803* (2013.01); *A61K 51/0497* (2013.01); *A61P 35/02* (2018.01); *A61P 37/02* (2018.01); *A61K 2039/505* (2013.01)

(58) Field of Classification Search
CPC ........... C07K 16/2896; C07K 2317/56; C07K 16/00; A61P 35/00; A61P 35/02; A61K 2039/505
See application file for complete search history.

(56) References Cited

U.S. PATENT DOCUMENTS

| | | | | |
|---|---|---|---|---|
| 8,679,492 B2 * | 3/2014 | Blein | ...................... | A61P 43/00 |
| | | | | 435/328 |
| 10,519,248 B2 * | 12/2019 | Cheung | .............. | A61K 39/4611 |
| 11,046,768 B2 * | 6/2021 | Cheung | ................. | C07K 16/32 |
| 11,529,371 B2 * | 12/2022 | Hoseini | .................. | A61P 35/02 |
| 11,555,072 B2 * | 1/2023 | Wu | ........................ | A61P 35/00 |
| 11,597,764 B2 * | 3/2023 | Cheung | .............. | C07K 16/2809 |
| 11,820,832 B2 * | 11/2023 | Cheung | ................. | A61P 35/00 |
| 2010/0215651 A1 | 8/2010 | Blein et al. | | |
| 2014/0271635 A1 | 9/2014 | Brogdon et al. | | |
| 2018/0312588 A1 | 11/2018 | Wiltzius et al. | | |

FOREIGN PATENT DOCUMENTS

| | | | | |
|---|---|---|---|---|
| WO | WO-2012136824 A1 * | 10/2012 | ........ | A61K 39/0005 |
| WO | WO-2015/109131 A2 | 7/2015 | | |
| WO | WO-2016014942 A1 * | 1/2016 | ....... | A61K 39/39558 |
| WO | WO-2016/048938 A1 | 3/2016 | | |
| WO | WO-2017/134140 A1 | 8/2017 | | |
| WO | WO-2018075807 A1 * | 4/2018 | ........ | A61K 39/4611 |
| WO | WO-2018/200496 A1 | 11/2018 | | |
| WO | WO-2019/057124 A1 | 3/2019 | | |
| WO | WO-2019/060750 A2 | 3/2019 | | |

OTHER PUBLICATIONS

Dijkers et al. Biodistribution of 89Zr-trastuzumab and PET Imaging of HER2-Positive Lesions in Patients With Metastatic Breast Cancer. Nature. 87(5): 586-592; Published: Mar. 31, 2010 (Year: 2010).*
International Search Report and Written Opinion on PCT/US2020/027071 dated Sep. 4, 2020.
Wu, et al., "T cell engaging bispecific antibody (T-BsAb): From technology to therapeutics", Pharmacy and Therapeutics, 182, Aug. 20, 2017, pp. 161-175.
Robinson Hannah R et al: "A CD19/CD3 bispecific antibody for effective immunotherapy of chronic lymphocytic leukemia in the ibrutinib era", BLOOD, vol. 132, No. 5, Aug. 2, 2018 (Aug. 2, 2018), pp. 521-532, XP55809571.
Wu et al., "T cell engaging bispecific antibody (T-BsAb): from technology to therapeutics," Pharmacol. Ther., Feb. 2018, 182:161-175.

* cited by examiner

*Primary Examiner* — Juliet C Switzer
*Assistant Examiner* — Katherine Ann Holtzman
(74) *Attorney, Agent, or Firm* — Foley & Lardner LLP

(57) ABSTRACT

The present disclosure relates generally to immunoglobulin-related compositions (e.g., antibodies or antigen binding fragments thereof) that can bind to the CD 19 protein. The antibodies of the present technology are useful in methods for detecting and treating a CD 19-associated autoimmune disease or a CD19-associated cancer in a subject in need thereof.

18 Claims, 74 Drawing Sheets

Specification includes a Sequence Listing.

Modular
IgG-scFv

| Peak# | Ret. Time | Area | Height | Mark | Area% |
|-------|-----------|---------|--------|------|---------|
| 1 | 12.805 | 102147 | 2996 | | 2.651 |
| 2 | 13.507 | 481537 | 9093 | V | 12.495 |
| 3 | 15.656 | 3270088 | 77149 | V | 84.854 |
| Total | | 3853771 | 89238 | | 100.000 |

NALM6

| AFFINITY | LOWEST (BC254) VL3 + VH8B | LOWER (BC253) VL3 + VH7B | MIDDLE (BC255) VL1 + VH1B | HIGHEST (BC250) VL2 + VH1B |
|---|---|---|---|---|
| EC50 (µg/ml) | 0.0003045 | 0.0001991 | 0.0001071 | 2.963E-005 |

FIG. 5C

NALM6 cells

Daudi cells

ATC/Blinatumomab vs. ATC/ BC250 at day 11 (p< 0.0001)

ATC/Blinatumomab vs. ATC/ BC250 at day 17 (p < 0.0061)

ATC/Blinatumomab vs. ATC/ BC250 at day 17 (p=ns)

NALM6

Bioluminescence signal

FIG. 12

*FMC63_V<sub>H</sub> (murine, humanness 63.6%) (SEQ ID NO: 1)*

EVKLQESGPGLVAPSQSLSVTCTVSGVSLPDYGVSWIRQPPRKGLEWLGV**IWGSET
TYYNSALKSRLTIIKDNSKSQVFLKMNSLQTDDTAIYYCAKHYYYGGSYAMDY**WG
QGTSVTVSS

*VH-1b (humanness 84.5%) (SEQ ID NO: 5)*
QVQLQESGPGLVKPSETLSVTCTVSGVSLPDYGVSWIRQPPGKGLEWIGVIWGSETT
YYNPSLKSRVTISVDTSKNQVSLKLSSVTAADTAVYYCAKHYYYGGSYAMDYWG
QGTSVTVSS

*VH-2b (humanness 84.5%) (SEQ ID NO: 6)*
QVQLQESGPGLVKPSETLSLTCTVSGVSLPDYGVSWIRQPPGKGLEWLGV**IWGSET
TNYNPSLKSRVTISKDTSKNQFSLKLSSLTAADTAVYYCAKHYYYGGSYAMDY**WG
QGTSVTVSS

*VH-3 (humanness 85.6%) (SEQ ID NO: 7)*
QVQLQESGPGLVKPSETLSLTCTVSGVSLPDYGVSWIRQPPGKGLEWIGVIWGSETT
NYNPSLKSRLTISVDTSKNQFSLKMSSVTAADTAVYYCAKHYYYGGSYAMDYWG
QGTSVTVSS

*VH-4 (humanness 85.6%) (SEQ ID NO: 8)*
QVQLQESGPGLVKPSETLSLTCTVSGVSLPDYGVSWIRQPPGKGLEWIGVIWGSETT
NYNPSLKSRVTISVDNSKNQFSLKLSSLTAADTAVYYCAKHYYYGGSYAMDYWGQ
GTSVTVSS

*VH-5b (humanness 84.5%) (SEQ ID NO: 9)*
QVQLQESGPGLVKPSETLSLTCTVSGVSLPDYGVSWIRQPPGKGLEWIGVIWGSETT
NYNPSLKSRVTISKDTSKSQVSLKLSSVTAADTAVYYCAKHYYYGGSYAMDYWGQ
GTSVTVSS

*VH-6b (humanness 84.5%) (SEQ ID NO: 10)*
QVQLQESGPGLVKPSETLSLTCTVSGVSLPDYGVSWIRQPPGKGLEWLGV**IWGSET
TYYNPSLKSRVTISVDNSKNQFSLKLSSVTAADTAVYYCAKHYYYGGSYAMDY**WG
QGTSVTVSS

*VH-7b (humanness 83.5%) (SEQ ID NO: 11)*
QVQLQESGPGLVKPSETLSLTCTVSGVSLPDYGVSWIRQPPGKGLEWIGVIWGSETT
YYNPSLKSRVTISKDTSKSQFSLKMSSVTAADTAVYYCAKHYYYGGSYAMDYWGQ
GTSVTVSS

*VH-8b (humanness 83.5%) (SEQ ID NO: 12)*
QVQLQESGPGLVKPSETLSVTCTVSGVSLPDYGVSWIRQPPGKGLEWIGVIWGSETT
YYNPSLKSRLTISKDTSKNQFSLKLSSVTAADTAVYYCAKHYYYGGSYAMDYWGQ
GTSVTVSS

FIG. 13

*FMC63_V$_L$ (murine, humanness 73.7%) (SEQ ID NO: 13)*

DIQMTQTTSSLSASLGDRVTISCRASQDISKYLNWYQQKPDGTVKLLIYHTSRLHSG
VPSRFSGSGSGTDYSLTISNLEQEDIATYFCQQGNTLPYTFGGGTKLEIT

*VL-1 (humanness 86.3%) (SEQ ID NO: 17)*
DIQMTQSPSSLSASVGDRVTITCRASQDISKYLNWYQQKPGKAVKLLIYHTSRLHTG
VPSRFSGSGSGTDYTLTISSLQPEDIATYFCQQGNTLPYTFGGGTKLEIT

*VL-2 (humanness 86.3%) (SEQ ID NO: 18)*
DIQMTQSPSSLSASVGDRVTITCQASQDISKYLNWYQQKPGKAVKLLIYHTSRLHSG
VPSRFSGSGSGTDYTLTISSLQPEDIATYFCQQGNTLPYTFGGGTKLEIT

*VL-3 (humanness 86.3%) (SEQ ID NO: 19)*
DIQMTQSTSSLSASVGDRVTITCRASQDISKYLNWYQQKPGKAVKLLIYHTSRLHSG
VPSRFSGSGSGTDYTFTISSLQPEDIATYYCQQGNTLPYTFGGGTKLEIT

FIG. 14A

*Chimeric BsAb (chFMC63) Light chain full amino acid sequence (N to C terminal) [signal peptide-FMC63 murine V_L-CL-linker-hOKT3 V_H-linker-hOKT3 V_L] (SEQ ID NO: 20)*

MGWSCIILFLVATATG*DIQMTQTTSSLSASLGDRVTISCRASQDISKYLNWYQQKPDGTV*

*KLLIYHTSRLHSGVPSRFSGSGSGTDYSLTISNLEQEDIATYFCQQGNTLPYTFGGGTKLEIT*

*R*TVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGECTSGGGGS

GGGGSGGGGS*QVQLVQSGGGVVQPGRSLRLSCKASGYTFTRYTMHWVRQAPGKCLEW*

*IGYINPSRGYTNYNQKFKDRFTISRDNSKNTAFLQMDSLRPEDTGVYFCARYYDDHYSLDY*

*WGQGTPVTVSS**GGGGSGGGGSGGGGSGGGGSGGGGSGGGGS**DIQMTQSPSSLSAS*

*VGDRVTITCSASSSVSYMNWYQQTPGKAPKRWIYDTSKLASGVPSRFSGSGSGTDYTFTISS*

*LQPEDIATYYCQQWSSNPFTFGCGTKLQITR*

FIG. 14B

*Chimeric BsAb (chFMC63) Light chain full nucleotide sequence. (SEQ ID NO: 21)*

ATGGGCTGGTCCTGCATCATCCTGTTCCTGGTGGCCACCGCCACCGGCGACATTC
AGATGACTCAGACTACTTCTTCACTGTCCGCCTCACTGGGGGATCGGGTCACTAT
TTCCTGCCGCGCAAGCCAGGATATTTCTAAGTACCTGAACTGGTATCAGCAGAAG
CCCGACGGCACCGTGAAGCTGCTGATCTACCACACAAGCAGGCTGCACTCCGGC
GTGCCTAGCCGGTTCAGCGGCTCCGGATCTGGCACCGACTACAGCCTGACAATCT
CCAATCTGGAGCAGGAGGATATCGCCACCTATTTTTGTCAGCAGGGGAATACTCT
GCCATACACCTTTGGAGGGGGAACTAAACTGGAAATCACCCGGACCGTGGCCGC
CCCCTCCGTGTTCATCTTCCCCCCCTCCGACGAGCAGCTGAAGTCCGGCACCGCC
TCCGTGGTGTGCCTGCTGAACAACTTCTACCCCGGGAGGCCAAGGTGCAGTGG
AAGGTGGACAACGCCCTGCAGTCCGGCAACTCCCAGGAGTCCGTGACCGAGCAG
GACTCCAAGGACTCCACCTACTCCCTGTCCTCCACCCTGACCCTGTCCAAGGCCG
ACTACGAGAAGCACAAGGTGTACGCCTGCGAGGTGACCCACCAGGGCCTGTCCT
CCCCCGTGACCAAGTCCTTCAACCGGGGCGAGTGCACTAGTGGCGGCGGAGGAT
CTGGCGGAGGTGGAAGTGGGGGAGGCGGATCTCAGGTGCAGCTGGTGCAGAGTG
GTGGCGGAGTGGTGCAGCCTGGCAGATCCCTGAGACTGTCTTGCAAGGCCAGCG
GCTACACCTTCACCCGGTACACCATGCACTGGGTGCGACAGGCCCCTGGCAAGT
GCCTGGAATGGATCGGCTACATCAACCCCTCCCGGGGCTACACCAACTACAACC
AGAAGTTCAAGGACCGGTTCACCATCAGCCGGGACAACTCCAAGAACACCGCCT
TTCTGCAGATGGACTCCCTGCGGCCTGAGGATACCGGCGTGTACTTTTGCGCCCG
GTACTACGACGACCACTACAGCCTGGACTACTGGGGCCAGGGAACCCCTGTGAC
AGTGTCTAGCGGAGGGGGAGGTTCAGGTGGCGGTGGATCAGGGGGCGGAGGAA
GTGGCGGGGGAGGTAGTGGTGGTGGTGGAAGCGGAGGTGGCGGCTCCGATATCC
AGATGACCCAGTCCCCCTCCAGCCTGTCTGCCTCTGTGGGAGACAGAGTGACAAT
TACATGCTCCGCCAGCTCCAGCGTGTCCTACATGAATTGGTATCAGCAGACCCCT
GGCAAGGCTCCCAAGCGGTGGATCTACGACACCTCCAAGCTGGCCTCCGGCGTG
CCCTCCAGATTTTCTGGCAGCGGCTCCGGCACAGACTATACCTTTACAATCAGCT
CCCTGCAGCCCGAAGATATCGCCACCTACTACTGCCAGCAGTGGTCCTCCAACCC
CTTCACCTTCGGCTGCGGCACAAAGCTGCAGATCACCAGATAG

FIG. 14C

*Chimeric BsAb (chFMC63) Heavy chain full amino acid sequence (N to C terminal)*

*[signal peptide-FMC63 murine V$_H$-CH$_{1-3}$] (SEQ ID NO: 22)*

MGWSCIILFLVATATG*EVKLQESGPGLVAPSQSLSVTCTVSGVSLPDYGVSWIRQP*

*PRKGLEWLGVIWGSETTYYNSALKSRLTIIKDNSKSQVFLKMNSLQTDDTAIYYCAKHYYYG*

*GSYAMDYWGQGTSVTVSS*ASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKR

VEPKSCDKTHTCPPCPAPELLGGPSVFLFPPKPKDTLMISRTPEVTCVVVDVSHEDPE

VKFNWYVDGVEVHNAKTKPREEQYASTYRVVSVLTVLHQDWLNGKEYKCKVSNK

ALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKS

LSLSPGK

FIG. 14D

*Chimeric BsAb (chFMC63) Heavy chain full nucleotide sequence (SEQ ID NO: 23)*

ATGGGCTGGTCCTGCATCATCCTGTTCCTGGTGGCCACCGCCACCGGCGAGGTGA
AACTGCAGGAATCCGGGCCTGGACTGGTCGCTCCAAGTCAGTCACTGAGCGTGA
CTTGTACCGTCAGTGGCGTGTCACTGCCCGATTACGGGGTCAGCTGGATCAGGCA
GCCACCTCGAAAGGGCCTGGAGTGGCTGGGCGTGATCTGGGGAAGCGAAACCAC
ATACTATAATAGCGCACTGAAATCCAGGCTGACCATCATTAAGGACAACTCCAA
ATCTCAGGTGTTTCTGAAGATGAACAGCCTGCAGACAGACGATACTGCCATCTAC
TATTGCGCTAAACACTACTATTACGGCGGGTCCTATGCAATGGATTACTGGGGCC
AGGGGACCTCTGTCACAGTGTCTAGTGCCTCCACCAAGGGCCCATCGGTCTTCCC
CCTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTG
ACCAGCGGCGTGCACACCTTCCCGGCCGTCCTACAGTCCTCAGGACTCTACTCCC
TCAGCAGCGTGGTGACCGTGCCCTCCAGCAGCTTGGGCACCCAGACCTACATCTG
CAACGTGAATCACAAGCCCAGCAACACCAAGGTGGACAAGAGAGTTGAGCCCA
AATCTTGTGACAAAACTCACACATGCCCACCGTGCCCAGCACCTGAACTCCTGGG
GGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAG
CCGCGGGAGGAGCAGTACGCCAGCACGTACCGTGTGGTCAGCGTCCTCACCGTC
CTGCACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCCCCGA
GAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACAACCAC
TACACGCAGAAGAGCCTCTCCCTGTCTCCGGGTAAATGA

FIG. 15A

*BC250 (hFMC63 VL-2 /VH-1b) light chain full amino acid sequence (N to C terminal)*

*[signal peptide-hFMC63 VL-2-CL-linker-hOKT3 V$_H$-linker-hOKT3 V$_L$] (SEQ ID NO: 24)*

MGWSCIILFLVATATG*DIQMTQSPSSLSASVGDRVTITCQASQDISKYLNWYQQKPGKAV*

*KLLIYHTSRLHSGVPSRFSGSGSGTDYTLTISSLQPEDIATYFCQQGNTLPYTFGGGTKLEIT*

*R*TVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGECTSGGGGS

GGGGSGGGGS*QVQLVQSGGGVVQPGRSLRLSCKASGYTFTRYTMHWVRQAPGKCLEW*

*IGYINPSRGYTNYNQKFKDRFTISRDNSKNTAFLQMDSLRPEDTGVYFCARYYDDHYSLDY*

*WGQGTPVTVSS*GGGGSGGGGSGGGGSGGGGSGGGGSGGGGS*DIQMTQSPSSLSAS*

*VGDRVTITCSASSSVSYMNWYQQTPGKAPKRWIYDTSKLASGVPSRFSGSGSGTDYTFTISS*

*LQPEDIATYYCQQWSSNPFTFGCGTKLQITR*

FIG. 15B

*BC250 (hFMC63 VL-2/VH-1b) light chain full nucleotide sequence. (SEQ ID NO: 25)*

ATGGGCTGGTCCTGCATCATCCTGTTCCTGGTGGCCACCGCCACCGGCGACATCC
AGATGACCCAGTCTCCAAGCTCCCTGTCCGCCTCTGTGGGCGACAGGGTGACCAT
CACATGCCAGGCCAGCCAGGATATCTCCAAGTACCTGAACTGGTATCAGCAGAA
GCCAGGCAAGGCCGTGAAGCTGCTGATCTACCACACATCTCGGCTGCACAGCGG
AGTGCCATCCAGATTCAGCGGCTCCGGCTCTGGCACCGACTATACCCTGACAATC
TCTAGCCTGCAGCCCGAGGATATCGCCACATACTTCTGTCAGCAGGGCAATACCC
TGCCTTATACATTTGGCGGCGGCACCAAGCTGGAGATCACACGGACCGTGGCCG
CCCCCTCCGTGTTCATCTTCCCCCCCTCCGACGAGCAGCTGAAGTCCGGCACCGC
CTCCGTGGTGTGCCTGCTGAACAACTTCTACCCCCGGGAGGCCAAGGTGCAGTGG
AAGGTGGACAACGCCCTGCAGTCCGGCAACTCCCAGGAGTCCGTGACCGAGCAG
GACTCCAAGGACTCCACCTACTCCCTGTCCTCCACCCTGACCCTGTCCAAGGCCG
ACTACGAGAAGCACAAGGTGTACGCCTGCGAGGTGACCCACCAGGGCCTGTCCT
CCCCCGTGACCAAGTCCTTCAACCGGGGCGAGTGCACTAGTGGCGGCGGAGGAT
CTGGCGGAGGTGGAAGTGGGGGAGGCGGATCTCAGGTGCAGCTGGTGCAGAGTG
GTGGCGGAGTGGTGCAGCCTGGCAGATCCCTGAGACTGTCTTGCAAGGCCAGCG
GCTACACCTTCACCCGGTACACCATGCACTGGGTGCGACAGGCCCCTGGCAAGT
GCCTGGAATGGATCGGCTACATCAACCCCTCCCGGGGCTACACCAACTACAACC
AGAAGTTCAAGGACCGGTTCACCATCAGCCGGGACAACTCCAAGAACACCGCCT
TTCTGCAGATGGACTCCCTGCGGCCTGAGGATACCGGCGTGTACTTTTGCGCCCG
GTACTACGACGACCACTACAGCCTGGACTACTGGGGCCAGGGAACCCCTGTGAC
AGTGTCTAGCGGAGGGGGAGGTTCAGGTGGCGGTGGATCAGGGGGCGGAGGAA
GTGGCGGGGGAGGTAGTGGTGGTGGTGGAAGCGGAGGTGGCGGCTCCGATATCC
AGATGACCCAGTCCCCCTCCAGCCTGTCTGCCTCTGTGGGAGACAGAGTGACAAT
TACATGCTCCGCCAGCTCCAGCGTGTCCTACATGAATTGGTATCAGCAGACCCCT
GGCAAGGCTCCCAAGCGGTGGATCTACGACACCTCCAAGCTGGCCTCCGGCGTG
CCCTCCAGATTTTCTGGCAGCGGCTCCGGCACAGACTATACCTTTACAATCAGCT
CCCTGCAGCCCGAAGATATCGCCACCTACTACTGCCAGCAGTGGTCCTCCAACCC
CTTCACCTTCGGCTGCGGCACAAAGCTGCAGATCACCAGATAG

FIG. 15C

*BC250 (hFMC63 VL-2VH-1b) heavy chain full amino acid sequence (N to C terminal)*

*[signal peptide-hFMC63 VH-1b -CH₁₋₃] (SEQ ID NO: 26)*

MGWSCIILFLVATATG*QVQLQESGPGLVKPSETLSVTCTVSGVSLPDYGVSWIRQPPGKG*

*LEWIGVIWGSETTYYNPSLKSRVTISVDTSKNQVSLKLSSVTAADTAVYYCAKHYYYGGSYA*

*MDYWGQGTSVTVSS*ASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKRVEPKS

CDKTHTCPPCPAPELLGGPSVFLFPPKPKDTLMISRTPEVTCVVVDVSHEDPEVKFNW

YVDGVEVHNAKTKPREEQYASTYRVVSVLTVLHQDWLNGKEYKCKVSNKALPAPI

EKTISKAKGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQKSLSLSP

*BC250 (hFMC63 VL-2/VH1b) heavy chain full nucleotide sequence (SEQ ID NO: 27)*

ATGGGCTGGTCCTGCATCATCCTGTTCCTGGTGGCCACCGCCACCGGCCAGGTGC
AGCTGCAGGAGTCCGGCCCAGGCCTGGTGAAGCCATCTGAGACCCTGAGCGTGA
CCTGCACAGTGTCCGGCGTGTCTCTGCCTGACTATGGCGTGTCTTGGATCAGACA
GCCACCTGGCAAGGGCCTGGAGTGGATCGGCGTGATCTGGGGCAGCGAGACCAC
ATACTATAACCCCAGCCTGAAGTCCAGAGTGACCATCTCCGTGGACACATCTAAG
AATCAGGTGTCTCTGAAGCTGAGCTCCGTGACCGCCGCCGATACAGCCGTGTACT
ATTGTGCCAAGCACTACTATTACGGCGGCAGCTATGCTATGGACTACTGGGGCCA
GGGCACCTCCGTGACAGTGTCTAGCGCCTCCACCAAGGGCCCATCGGTCTTCCCC
CTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTG
ACCAGCGGCGTGCACACCTTCCCGGCCGTCCTACAGTCCTCAGGACTCTACTCCC
TCAGCAGCGTGGTGACCGTGCCCTCCAGCAGCTTGGGCACCCAGACCTACATCTG
CAACGTGAATCACAAGCCCAGCAACACCAAGGTGGACAAGAGAGTTGAGCCCA
AATCTTGTGACAAAACTCACACATGCCCACCGTGCCCAGCACCTGAACTCCTGGG
GGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAG
CCGCGGGAGGAGCAGTACGCCAGCACGTACCGTGTGGTCAGCGTCCTCACCGTC
CTGCACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCCCCGA
GAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACAACCAC
TACACGCAGAAGAGCCTCTCCCTGTCTCCGGGTAAATGA

FIG. 16A

*Dota-engaging Bispecific antibody for radioimmunotherapy (based on murine FMC63):* anti-CD19 x C825 *light chain full amino acid sequence (N to C terminal)*

(CD19-mouse V$_L$-CL-(G$_4$S)$_3$-mouse C825 V$_H$-(G$_4$S)$_6$-mouse C825 V$_L$) *(SEQ ID NO: 28)*

MGWSCIILFLVATATG*DIQMTQTTSSLSASLGDRVTISCRASQDISKYLNWYQQKPDGTV*

*KLLIYHTSRLHSGVPSRFSGSGSGTDYSLTISNLEQEDIATYFCQQGNTLPYTFGGGTKLEIT*

*R*TVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGECTSGGGGS

GGGGSGGGGS*HVKLQESGPGLVQPSQSLSLTCTVSGFSLTDYGVHWVRQSPGKGLEWL*

*GVIWSGGGTAYNTALISRLNIYRDNSKNQVFLEMNSLQAEDTAMYYCARRGSYPYNYFDAW*

*GCGTTVTVSS*GGGGSGGGGSGGGGSGGGGSGGGGSGGGGS*QAVVIQESALTTPPGE*

*TVTLTCGSSTGAVTASNYANWVQEKPDHCFTGLIGGHNNRPPGVPARFSGSLIGDKAALTI*

*AGTQTEDEAIYFCALWYSDHWVIGGGTRLTVLG*

FIG. 16B

*Dota-engaging Bispecific antibody for radioimmunotherapy (based on murine FMC63):*
anti-CD19 x C825 *heavy chain full amino acid sequence (N to C terminal) [signal peptide-*
*mouse FMC63 $V_L$-CH$_{1-3}$] (SEQ ID NO: 29)*

MGWSCIILFLVATATG*EVKLQESGPGLVAPSQSLSVTCTVSGVSLPDYGVSWIRQPPRKG*

*LEWLGVIWGSETTYYNSALKSRLTIIKDNSKSQVFLKMNSLQTDDTAIYYCAKHYYYGGSYA*

*MDYWGQGTSVTVSS*ASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKRVEPKS

CDKTHTCPPCPAPELLGGPSVFLFPPKPKDTLMISRTPEVTCVVVDVSHEDPEVKFNW

YVDGVEVHNAKTKPREEQYASTYRVVSVLTVLHQDWLNGKEYKCAVSNKALPAPI

EKTISKAKGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQKSLSLSP

*Dota-engaging Bispecific antibody for radioimmunotherapy (based on murine FMC63):* anti-CD19 x huC825 *light chain full amino acid sequence (N to C terminal) (CD19-mouse*

$V_L$-CL-$(G_4S)_3$-huC825 $V_H$-$(G_4S)_6$-huC825 $V_L$) *(SEQ ID NO: 30)*

MGWSCIILFLVATATG*DIQMTQTTSSLSASLGDRVTISCRASQDISKYLNWYQQKPDGTV*

*KLLIYHTSRLHSGVPSRFSGSGSGTDYSLTISNLEQEDIATYFCQQGNTLPYTFGGGTKLEIT*

*R*TVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGECTSGGGGS

GGGGSGGGGS*HVQLVESGGGLVQPGGSLRLSCAASGFSLTDYGVHWVRQAPGKGLEW*

*LGVIWSGGGTAYNTALISRFTISRDNSKNTLYLQMNSLRAEDTAVYYCARRGSYPYNYFDAW*

*GCGTLVTVSS*GGGGSGGGGSGGGGSGGGGSGGGGSGGGGS*QAVVTQEPSLTVSPG*

*GTVTLTCGSSTGAVTASNYANWVQQKPGQCPRGLIGGHNNRPPGVPARFSGSLLGGKAAL*

*TLLGAQPEDEAEYYCALWYSDHWVIGGGTKLTVLG*

FIG. 17B

*Dota-engaging Bispecific antibody for radioimmunotherapy (based on murine FMC63):*
anti-CD19 x huC825 *heavy chain full amino acid sequence (N to C terminal) [signal*
*peptide-mouse FMC63 V<sub>L</sub>-CH<sub>1-3</sub>] (SEQ ID NO: 31)*

MGWSCIILFLVATATG*EVKLQESGPGLVAPSQSLSVTCTVSGVSLPDYGVSWIRQPPRKG*

*LEWLGVIWGSETTYYNSALKSRLTIIKDNSKSQVFLKMNSLQTDDTAIYYCAKHYYYGGSYA*

*MDYWGQGTSVTVSS*ASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKRVEPKS

CDKTHTCPPCPAPELLGGPSVFLFPPKPKDTLMISRTPEVTCVVVDVSHEDPEVKFNW

YVDGVEVHNAKTKPREEQYASTYRVVSVLTVLHQDWLNGKEYKCAVSNKALPAPI

EKTISKAKGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQKSLSLSP

*mouse FMC63 $V_L$-$(G_4S)_6$-mouse FMC63 $V_H$-$(G_4S)_4$-hC825 $V_H$-$(G_4S)_6$-hC825 $V_L$-spacer-linker-p53 tetramerization domain-spacer-H6 (SEQ ID NO: 32)*

MGWSCIILFLVATATG*DIQMTQTTSSLSASLGDRVTISCRASQDISKYLNWYQQKPDGTV*

*KLLIYHTSRLHSGVPSRFSGSGSGTDYSLTISNLEQEDIATYFCQQGNTLPYTFGGGTKLEIT*

*R*GGGGSGGGGSGGGGSGGGGSGGGGSGGGGS*EVKLQESGPGLVAPSQSLSVTCTV*

*SGVSLPDYGVSWIRQPPRKGLEWLGVIWGSETTYYNSALKSRLTIIKDNSKSQVFLKMNSLQ*

*TDDTAIYYCAKHYYYGGSYAMDYWGQGTSVTVSS*GGGGSGGGGSGGGGSGGGGS*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*GGG

GSGGGGSGGGGSGGGGSGGGGSGGGGS*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*TPLGDTTHTSGKPLDGEYFTLQIRGRERFEMFRE

LNEALELKDAQAGKEP*GGSGGAP*HHHHHH

FIG. 18B

*mouse FMC63 V_L-(G_4S)_6-mouse FMC63 V_H-(G_4S)_4-hC825 V_H-(G_4S)_6-hC825 V_L-spacer-linker-p53 tetramerization domain-spacer (SEQ ID NO: 33)*

<u>MGWSCIILFLVATATG</u>*DIQMTQTTSSLSASLGDRVTISCRASQDISKYLNWYQQKPDGTV*

*KLLIYHTSRLHSGVPSRFSGSGSGTDYSLTISNLEQEDIATYFCQQGNTLPYTFGGGTKLEIT*

*R*<u>GGGGSGGGGSGGGGSGGGGSGGGGSGGGGS</u>*EVKLQESGPGLVAPSQSLSVTCTV*

*SGVSLPDYGVSWIRQPPRKGLEWLGVIWGSETTYYNSALKSRLTIIKDNSKSQVFLKMNSLQ*

*TDDTAIYYCAKHYYYGGSYAMDYWGQGTSVTVSS*<u>GGGGSGGGGSGGGGSGGGGS</u>*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*<u>GGG</u>

<u>GSGGGGSGGGGSGGGGSGGGGSGGGGS</u>*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*<u>TPLGDTTHTSGKPLDGEYFTLQIRGRERFEMFRE</u>

<u>LNEALELKDAQAGKEP</u><u>GGSGGA</u>

FIG. 19A

*mouse FMC63 V$_L$-(G$_4$S)$_6$-mouse FMC63 V$_H$-(G$_4$S)$_4$-hC825 V$_H$-(G$_4$S)$_6$-hC825 V$_L$-spacer-linker-p63 tetramerization domain-spacer-H6 (SEQ ID NO: 34)*

<u>MGWSCIILFLVATATG</u>*DIQMTQTTSSLSASLGDRVTISCRASQDISKYLNWYQQKPDGTV*

*KLLIYHTSRLHSGVPSRFSGSGSGTDYSLTISNLEQEDIATYFCQQGNTLPYTFGGGTKLEIT*

*R*<u>GGGGSGGGGSGGGGSGGGGSGGGGSGGGGS</u>*EVKLQESGPGLVAPSQSLSVTCTV*

*SGVSLPDYGVSWIRQPPRKGLEWLGVIWGSETTYYNSALKSRLTIIKDNSKSQVFLKMNSLQ*

*TDDTAIYYCAKHYYYGGSYAMDYWGQGTSVTVSS*<u>GGGGSGGGGSGGGGSGGGGS</u>*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*<u>GGG</u>

<u>GSGGGGSGGGGSGGGGSGGGGSGGGGS</u>*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*<u>TPLGDTTHTSG</u>RSPDDELLYLPVRGRETYEMLLK

IKESLELMQYLPQHTIETYRQQQQQQHQHLLQKQ<u>GGSGGAP</u>HHHHHH

FIG. 19B

*mouse FMC63 V<sub>L</sub>-(G<sub>4</sub>S)<sub>6</sub>-mouse FMC63 V<sub>H</sub>-(G<sub>4</sub>S)<sub>4</sub>-hC825 V<sub>H</sub>-(G<sub>4</sub>S)<sub>6</sub>-hC825 V<sub>L</sub>-spacer-linker-p63 tetramerization domain-spacer (SEQ ID NO: 35)*

<u>MGWSCIILFLVATATG</u>*DIQMTQTTSSLSASLGDRVTISCRASQDISKYLNWYQQKPDGTV*

*KLLIYHTSRLHSGVPSRFSGSGSGTDYSLTISNLEQEDIATYFCQQGNTLPYTFGGGTKLEIT*

*R*<u>GGGGSGGGGSGGGGSGGGGSGGGGSGGGGS</u>*EVKLQESGPGLVAPSQSLSVTCTV*

*SGVSLPDYGVSWIRQPPRKGLEWLGVIWGSETTYYNSALKSRLTIIKDNSKSQVFLKMNSLQ*

*TDDTAIYYCAKHYYYGGSYAMDYWGQGTSVTVSS*<u>GGGGSGGGGSGGGGSGGGGS</u>*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*<u>GGG</u>

<u>GSGGGGSGGGGSGGGGSGGGGSGGGGS</u>*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*<u>TPLGDTTHTSG</u>RSPDDELLYLPVRGRETYEMLLK

IKESLELMQYLPQHTIETYRQQQQQQHQHLLQKQ<u>GGSGGA</u>

FIG. 20A

*mouse FMC63 V$_L$-(G$_4$S)$_6$-mouse FMC63 V$_H$-(G$_4$S)$_4$-hC825 V$_H$-(G$_4$S)$_6$-hC825 V$_L$-spacer-linker-p73 tetramerization domain-spacer-H6 (SEQ ID NO: 36)*

<u>MGWSCIILFLVATATG</u>*DIQMTQTTSSLSASLGDRVTISCRASQDISKYLNWYQQKPDGTV*

*KLLIYHTSRLHSGVPSRFSGSGSGTDYSLTISNLEQEDIATYFCQQGNTLPYTFGGGTKLEIT*

*R*<u>GGGGSGGGGSGGGGSGGGGSGGGGSGGGGS</u>*EVKLQESGPGLVAPSQSLSVTCTV*

*SGVSLPDYGVSWIRQPPRKGLEWLGVIWGSETTYYNSALKSRLTIIKDNSKSQVFLKMNSLQ*

*TDDTAIYYCAKHYYYGGSYAMDYWGQGTSVTVSS*<u>GGGGSGGGGSGGGGSGGGGS</u>*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*<u>GGG</u>

<u>GSGGGGSGGGGSGGGGSGGGGSGGGGS</u>*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*<u>TPLGDTTHTS</u>GRHGDEDTYYLQVRGRENFEILM

KLKESLELMELVPQPLVDSYRQQQQLLQRP<u>GGSGGAP</u>HHHHHH

FIG. 20B

*mouse FMC63 V$_L$-(G$_4$S)$_6$-mouse FMC63 V$_H$-(G$_4$S)$_4$-hC825 V$_H$-(G$_4$S)$_6$-hC825 V$_L$-spacer-*

*linker-p73 tetramerization domain-spacer (SEQ ID NO: 37)*

<u>MGWSCIILFLVATATG</u>*DIQMTQTTSSLSASLGDRVTISCRASQDISKYLNWYQQKPDGTV*

*KLLIYHTSRLHSGVPSRFSGSGSGTDYSLTISNLEQEDIATYFCQQGNTLPYTFGGGTKLEIT*

*R*__GGGGSGGGGSGGGGSGGGGSGGGGSGGGGS__*EVKLQESGPGLVAPSQSLSVTCTV*

*SGVSLPDYGVSWIRQPPRKGLEWLGVIWGSETTYYNSALKSRLTIIKDNSKSQVFLKMNSLQ*

*TDDTAIYYCAKHYYYGGSYAMDYWGQGTSVTVSS*__GGGGSGGGGSGGGGSGGGGS__*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*__GGG__

__GSGGGGSGGGGSGGGGSGGGGSGGGGS__*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*__TPLGDTTHTSG__RHGDEDTYYLQVRGRENFEILM

KLKESLELMELVPQPLVDSYRQQQQLLQRP<u>GGSGGA</u>

FIG. 21A

*mouse FMC63 V$_H$-(G$_4$S)$_6$-mouse FMC63 V$_L$-(G$_4$S)$_4$-hC825 V$_H$-(G$_4$S)$_6$-hC825 V$_L$-spacer-*

*linker-p53 tetramerization domain-spacer-H6 (SEQ ID NO: 38)*

<u>MGWSCIILFLVATATG</u>*EVKLQESGPGLVAPSQSLSVTCTVSGVSLPDYGVSWIRQPPRKG*

*LEWLGVIWGSETTYYNSALKSRLTIIKDNSKSQVFLKMNSLQTDDTAIYYCAKHYYYGGSYA*

*MDYWGQGTSVTVSS*<u>GGGGSGGGGSGGGGSGGGGSGGGGSGGGGS</u>*DIQMTQTTSSL*

*SASLGDRVTISCRASQDISKYLNWYQQKPDGTVKLLIYHTSRLHSGVPSRFSGSGSGTDYSL*

*TISNLEQEDIATYFCQQGNTLPYTFGGGTKLEITR*<u>GGGGSGGGGSGGGGSGGGGS</u>*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*<u>GGG</u>

<u>GSGGGGSGGGGSGGGGSGGGGSGGGGS</u>*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*<u>TPLGDTTHTSG</u>KPLDGEYFTLQIRGRERFEMFRE

LNEALELKDAQAGKEP<u>GGSGGAP</u>HHHHHH

FIG. 21B

*mouse FMC63 V<sub>H</sub>-(G<sub>4</sub>S)<sub>6</sub>-mouse FMC63 V<sub>L</sub>-(G<sub>4</sub>S)<sub>4</sub>-hC825 V<sub>H</sub>-(G<sub>4</sub>S)<sub>6</sub>-hC825 V<sub>L</sub>-spacer-linker-p53 tetramerization domain-spacer (SEQ ID NO: 39)*

MGWSCIILFLVATATG*EVKLQESGPGLVAPSQSLSVTCTVSGVSLPDYGVSWIRQPPRKG*

*LEWLGVIWGSETTYYNSALKSRLTIIKDNSKSQVFLKMNSLQTDDTAIYYCAKHYYYGGSYA*

*MDYWGQGTSVTVSS*GGGGSGGGGSGGGGSGGGGSGGGGSGGGGS*DIQMTQTTSSL*

*SASLGDRVTISCRASQDISKYLNWYQQKPDGTVKLLIYHTSRLHSGVPSRFSGSGSGTDYSL*

*TISNLEQEDIATYFCQQGNTLPYTFGGGTKLEITR*GGGGSGGGGSGGGGSGGGGS*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*GGG

GSGGGGSGGGGSGGGGSGGGGSGGGGS*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*TPLGDTTHTSGKPLDGEYFTLQIRGRERFEMFRE

LNEALELKDAQAGKEPGGSGGA

FIG. 22A

*mouse FMC63 V$_H$-(G$_4$S)$_6$-mouse FMC63 V$_L$-(G$_4$S)$_4$-hC825 V$_H$-(G$_4$S)$_6$-hC825 V$_L$-spacer-linker-p63 tetramerization domain-spacer-H6 (SEQ ID NO: 40)*

<u>MGWSCIILFLVATATG</u>*EVKLQESGPGLVAPSQSLSVTCTVSGVSLPDYGVSWIRQPPRKG*

*LEWLGVIWGSETTYYNSALKSRLTIIKDNSKSQVFLKMNSLQTDDTAIYYCAKHYYYGGSYA*

*MDYWGQGTSVTVSS*<u>GGGGSGGGGSGGGGSGGGGSGGGGSGGGGS</u>*DIQMTQTTSSL*

*SASLGDRVTISCRASQDISKYLNWYQQKPDGTVKLLIYHTSRLHSGVPSRFSGSGSGTDYSL*

*TISNLEQEDIATYFCQQGNTLPYTFGGGTKLEITR*<u>GGGGSGGGGSGGGGSGGGGS</u>*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*<u>GGG</u>

<u>GSGGGGSGGGGSGGGGSGGGGSGGGGS</u>*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*<u>TPLGDTTHTSG</u>RSPDDELLYLPVRGRETYEMLLK

IKESLELMQYLPQHTIETYRQQQQQQHQHLLQKQ<u>GGSGGAP</u>HHHHHH

FIG. 22B

*mouse FMC63 V$_H$-(G$_4$S)$_6$-mouse FMC63 V$_L$-(G$_4$S)$_4$-hC825 V$_H$-(G$_4$S)$_6$-hC825 V$_L$-spacer-*

*linker-p63 tetramerization domain-spacer (SEQ ID NO: 41)*

<u>MGWSCIILFLVATATG</u>*EVKLQESGPGLVAPSQSLSVTCTVSGVSLPDYGVSWIRQPPRKG*

*LEWLGVIWGSETTYYNSALKSRLTIIKDNSKSQVFLKMNSLQTDDTAIYYCAKHYYYGGSYA*

*MDYWGQGTSVTVSS*<u>GGGGSGGGGSGGGGSGGGGSGGGGSGGGGS</u>*DIQMTQTTSSL*

*SASLGDRVTISCRASQDISKYLNWYQQKPDGTVKLLIYHTSRLHSGVPSRFSGSGSGTDYSL*

*TISNLEQEDIATYFCQQGNTLPYTFGGGTKLEITR*<u>GGGGSGGGGSGGGGSGGGGS</u>*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*<u>GGG</u>

<u>GSGGGGSGGGGSGGGGSGGGGSGGGGS</u>*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*<u>TPLGDTTHTSG</u>RSPDDELLYLPVRGRETYEMLLK

IKESLELMQYLPQHTIETYRQQQQQQHQHLLQKQ<u>GGSGGA</u>

FIG. 23A

*mouse FMC63 V$_H$-(G$_4$S)$_6$-mouse FMC63 V$_L$-(G$_4$S)$_4$-hC825 V$_H$-(G$_4$S)$_6$-hC825 V$_L$-spacer-*

*linker-p73 tetramerization domain-spacer-H6 (SEQ ID NO: 42)*

MGWSCIILFLVATATG*EVKLQESGPGLVAPSQSLSVTCTVSGVSLPDYGVSWIRQPPRKG*

*LEWLGVIWGSETTYYNSALKSRLTIIKDNSKSQVFLKMNSLQTDDTAIYYCAKHYYYGGSYA*

*MDYWGQGTSVTVSS*GGGGSGGGGSGGGGSGGGGSGGGGSGGGGS*DIQMTQTTSSL*

*SASLGDRVTISCRASQDISKYLNWYQQKPDGTVKLLIYHTSRLHSGVPSRFSGSGSGTDYSL*

*TISNLEQEDIATYFCQQGNTLPYTFGGGTKLEITR*GGGGSGGGGSGGGGSGGGGS*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*GGG

GSGGGGSGGGGSGGGGSGGGGSGGGGS*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*TPLGDTTHTSGRHGDEDTYYLQVRGRENFEILM

KLKESLELMELVPQPLVDSYRQQQQLLQRPGGSGGAP*HHHHHH

FIG. 23B

*mouse FMC63 V<sub>H</sub>-(G₄S)₆-mouse FMC63 V<sub>L</sub>-(G₄S)₄-hC825 V<sub>H</sub>-(G₄S)₆-hC825 V<sub>L</sub>-spacer-linker-p73 tetramerization domain-spacer (SEQ ID NO: 43)*

MGWSCIILFLVATATG*EVKLQESGPGLVAPSQSLSVTCTVSGVSLPDYGVSWIRQPPRKG*

*LEWLGVIWGSETTYYNSALKSRLTIIKDNSKSQVFLKMNSLQTDDTAIYYCAKHYYYGGSYA*

*MDYWGQGTSVTVSS*GGGGSGGGGSGGGGSGGGGSGGGGSGGGGS*DIQMTQTTSSL*

*SASLGDRVTISCRASQDISKYLNWYQQKPDGTVKLLIYHTSRLHSGVPSRFSGSGSGTDYSL*

*TISNLEQEDIATYFCQQGNTLPYTFGGGTKLEITR*GGGGSGGGGSGGGGSGGGGS*HV*

*QLVESGGGLVQPGGSLRLSCAASGFSLTDYGVHWVRQAPGKGLEWLGVIWSGGGTAYNT*

*ALISRFTISRDNSKNTLYLQMNSLRAEDTAVYYCARRGSYPYNYFDAWGCGTLVTVSS*GGG

GSGGGGSGGGGSGGGGSGGGGSGGGGS*QAVVTQEPSLTVSPGGTVTLTCGSSTGAV*

*TASNYANWVQQKPGQCPRGLIGGHNNRPPGVPARFSGSLLGGKAALTLLGAQPEDEAEY*

*YCALWYSDHWVIGGGTKLTVLG*TPLGDTTHTSGRHGDEDTYYLQVRGRENFEILM**

KLKESLELMELVPQPLVDSYRQQQQLLQRPGGSGGA

FIG. 24A

*Dota-engaging Bispecific antibody for radioimmunotherapy light chain full amino acid sequence (N to C terminal) (based on hFMC63 VL-2VH-1b): anti-CD19 x C825 (CD19-VL-CL-(G₄S)₃-mouse C825 V_H-(G₄S)₆-mouse C825 V_L) (SEQ ID NO: 44)*

MGWSCIILFLVATATG*DIQMTQSPSSLSASVGDRVTITCQASQDISKYLNWYQQKPGKAV*

*KLLIYHTSRLHSGVPSRFSGSGSGTDYTLTISSLQPEDIATYFCQQGNTLPYTFGGGTKLEIT*

*R*TVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGECTSGGGGS

GGGGSGGGGS*HVKLQESGPGLVQPSQSLSLTCTVSGFSLTDYGVHWVRQSPGKGLEWL*

*GVIWSGGGTAYNTALISRLNIYRDNSKNQVFLEMNSLQAEDTAMYYCARRGSYPYNYFDAW*

*GCGTTVTVSS*GGGGSGGGGSGGGGSGGGGSGGGGSGGGGS*QAVVIQESALTTPPGE*

*TVTLTCGSSTGAVTASNYANWVQEKPDHCFTGLIGGHNNRPPGVPARFSGSLIGDKAALTI*

*AGTQTEDEAIYFCALWYSDHWVIGGGTRLTVLG*

FIG. 24B

*Dota-engaging Bispecific antibody for radioimmunotherapy heavy chain full amino acid*

*sequence (N to C terminal) [signal peptide-hFMC63 VH-1b-CH$_{1-3}$] (SEQ ID NO: 45)*

MGWSCIILFLVATATG*QVQLQESGPGLVKPSETLSVTCTVSGVSLPDYGVSWIRQPPGKG*

*LEWIGVIWGSETTYYNPSLKSRVTISVDTSKNQVSLKLSSVTAADTAVYYCAKHYYYGGSYA*

*MDYWGQGTSVTVSS*ASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKRVEPKS

CDKTHTCPPCPAPELLGGPSVFLFPPKPKDTLMISRTPEVTCVVVDVSHEDPEVKFNW

YVDGVEVHNAKTKPREEQYASTYRVVSVLTVLHQDWLNGKEYKCAVSNKALPAPI

EKTISKAKGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQKSLSLSP

*Dota-engaging Bispecific antibody for radioimmunotherapy light chain full amino acid*

*sequence (N to C terminal) (based on hFMC63 VL-2VH-1b): anti-CD19 x huC825 (CD19-*

*VL-CL-(G₄S)₃-huC825 V_H-(G₄S)₆-huC825 V_L) (SEQ ID NO: 46)*

MGWSCIILFLVATATG*DIQMTQSPSSLSASVGDRVTITCQASQDISKYLNWYQQKPGKAV*

*KLLIYHTSRLHSGVPSRFSGSGSGTDYTLTISSLQPEDIATYFCQQGNTLPYTFGGGTKLEIT*

*R*TVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGECTSGGGGS

GGGGSGGGGS*HVQLVESGGGLVQPGGSLRLSCAASGFSLTDYGVHWVRQAPGKGLEW*

*LGVIWSGGGTAYNTALISRFTISRDNSKNTLYLQMNSLRAEDTAVYYCARRGSYPYNYFDAW*

*GCGTLVTVSS*GGGGSGGGGSGGGGSGGGGSGGGGSGGGGS*QAVVTQEPSLTVSPG*

*GTVTLTCGSSTGAVTASNYANWVQQKPGQCPRGLIGGHNNRPPGVPARFSGSLLGGKAAL*

*TLLGAQPEDEAEYYCALWYSDHWVIGGGTKLTVLG*

FIG. 25B

*Dota-engaging Bispecific antibody for radioimmunotherapy heavy chain full amino acid sequence (N to C terminal) (based on hFMC63 VL-2VH-1b): Heavy chain full amino acid sequence (N to C terminal) [signal peptide-hFMC63 VH-1b-CH$_{1-3}$] (SEQ ID NO: 47)*

<u>MGWSCIILFLVATATG</u>*QVQLQESGPGLVKPSETLSVTCTVSGVSLPDYGVSWIRQPPGKG*

*LEWIGVIWGSETTYYNPSLKSRVTISVDTSKNQVSLKLSSVTAADTAVYYCAKHYYYGGSYA*

*MDYWGQGTSVTVSS*ASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKRVEPKS

CDKTHTCPPCPAPELLGGPSVFLFPPKPKDTLMISRTPEVTCVVVDVSHEDPEVKFNW

YVDGVEVHNAKTKPREEQYASTYRVVSVLTVLHQDWLNGKEYKCAVSNKALPAPI

EKTISKAKGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQKSLSLSP

*hFMC63 VL-2-(G₄S)₆-VH-1b-(G₄S)₄-hC825 V$_H$-(G₄S)₆-hC825 V$_L$-spacer-linker-p53*

*tetramerization domain-spacer-H6 (SEQ ID NO: 48)*

MGWSCIILFLVATATG*DIQMTQSPSSLSASVGDRVTITCQASQDISKYLNWYQQKPGKAV*

*KLLIYHTSRLHSGVPSRFSGSGSGTDYTLTISSLQPEDIATYFCQQGNTLPYTFGGGTKLEIT*

*R*GGGGSGGGGSGGGGSGGGGSGGGGSGGGGS*QVQLQESGPGLVKPSETLSVTCTV*

*SGVSLPDYGVSWIRQPPGKGLEWIGVIWGSETTYYNPSLKSRVTISVDTSKNQVSLKLSSVTA*

*ADTAVYYCAKHYYYGGSYAMDYWGQGTSVTVSS*GGGGSGGGGSGGGGSGGGGS*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*GGGG

SGGGGSGGGGSGGGGSGGGGSGGGGS*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*TPLGDTTHTSGKPLDGEYFTLQIRGRERFEMFREL

NEALELKDAQAGKEPGGSGGAPHHHHHH

FIG. 26B

*hFMC63 VL-2-(G₄S)₆-VH-1b-(G₄S)₄-hC825 Vₕ-(G₄S)₆-hC825 Vₗ-spacer-linker-p53*

*tetramerization domain-spacer (SEQ ID NO: 49)*

MGWSCIILFLVATATG*DIQMTQSPSSLSASVGDRVTITCQASQDISKYLNWYQQKPGKAV*

*KLLIYHTSRLHSGVPSRFSGSGSGTDYTLTISSLQPEDIATYFCQQGNTLPYTFGGGTKLEIT*

*R*GGGGSGGGGSGGGGSGGGGSGGGGSGGGGS*QVQLQESGPGLVKPSETLSVTCTV*

*SGVSLPDYGVSWIRQPPGKGLEWIGVIWGSETTYYNPSLKSRVTISVDTSKNQVSLKLSSVTA*

*ADTAVYYCAKHYYYGGSYAMDYWGQGTSVTVSS*GGGGSGGGGSGGGGSGGGGS*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*GGGG

SGGGGSGGGGSGGGGSGGGGSGGGGS*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*TPLGDTTHTSGKPLDGEYFTLQIRGRERFEMFREL

NEALELKDAQAGKEPGGSGGA

FIG. 27A

*hFMC63 VL-2-(G₄S)₆-VH-1b-(G₄S)₄-hC825 V$_H$-(G₄S)₆-hC825 V$_L$-spacer-linker-p63*

*tetramerization domain-spacer-H6 (SEQ ID NO: 50)*

<u>MGWSCIILFLVATATG</u>*DIQMTQSPSSLSASVGDRVTITCQASQDISKYLNWYQQKPGKAV*

*KLLIYHTSRLHSGVPSRFSGSGSGTDYTLTISSLQPEDIATYFCQQGNTLPYTFGGGTKLEIT*

*R*<u>GGGGSGGGGSGGGGSGGGGSGGGGSGGGGS</u>*QVQLQESGPGLVKPSETLSVTCTV*

*SGVSLPDYGVSWIRQPPGKGLEWIGVIWGSETTYYNPSLKSRVTISVDTSKNQVSLKLSSVTA*

*ADTAVYYCAKHYYYGGSYAMDYWGQGTSVTVSS*<u>GGGGSGGGGSGGGGSGGGGS</u>*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*<u>GGGG</u>

<u>SGGGGSGGGGSGGGGSGGGGSGGGGS</u>*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*<u>TPLGDTTHTSG</u>RSPDDELLYLPVRGRETYEMLLKI

KESLELMQYLPQHTIETYRQQQQQQHQHLLQKQ<u>GGSGGAP</u>HHHHHH

FIG. 27B

*hFMC63 VL-2-(G₄S)₆-VH-1b-(G₄S)₄-hC825 V_H-(G₄S)₆-hC825 V_L-spacer-linker-p63*

*tetramerization domain-spacer (SEQ ID NO: 51)*

<u>MGWSCIILFLVATATG</u>*DIQMTQSPSSLSASVGDRVTITCQASQDISKYLNWYQQKPGKAV*

*KLLIYHTSRLHSGVPSRFSGSGSGTDYTLTISSLQPEDIATYFCQQGNTLPYTFGGGTKLEIT*

*R*<u>GGGGSGGGGSGGGGSGGGGSGGGGSGGGGS</u>*QVQLQESGPGLVKPSETLSVTCTV*

*SGVSLPDYGVSWIRQPPGKGLEWIGVIWGSETTYYNPSLKSRVTISVDTSKNQVSLKLSSVTA*

*ADTAVYYCAKHYYYGGSYAMDYWGQGTSVTVSS*<u>GGGGSGGGGSGGGGSGGGGS</u>*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*<u>GGGG</u>

<u>SGGGGSGGGGSGGGGSGGGGSGGGGS</u>*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*<u>TPLGDTTHTSG</u>RSPDDELLYLPVRGRETYEMLLKI

KESLELMQYLPQHTIETYRQQQQQQHQHLLQKQ<u>GGSGGA</u>

FIG. 28A hFMC63 VL-2-(G₄S)₆-VH-1b-(G₄S)₄-hC825 Vₕ-(G₄S)₆-hC825 Vₗ-spacer-linker-p73

*tetramerization domain-spacer-H6 (SEQ ID NO: 52)*

MGWSCIILFLVATATG*DIQMTQSPSSLSASVGDRVTITCQASQDISKYLNWYQQKPGKAV*

*KLLIYHTSRLHSGVPSRFSGSGSGTDYTLTISSLQPEDIATYFCQQGNTLPYTFGGGTKLEIT*

*R*GGGGSGGGGSGGGGSGGGGSGGGGSGGGGS*QVQLQESGPGLVKPSETLSVTCTV*

*SGVSLPDYGVSWIRQPPGKGLEWIGVIWGSETTYYNPSLKSRVTISVDTSKNQVSLKLSSVTA*

*ADTAVYYCAKHYYYGGSYAMDYWGQGTSVTVSS*GGGGSGGGGSGGGGSGGGGS*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*GGGG

SGGGGSGGGGSGGGGSGGGGSGGGGS*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*TPLGDTTHTSG*RHGDEDTYYLQVRGRENFEILMK**

LKESLELMELVPQPLVDSYRQQQQLLQRPGGSGGAP**HHHHHH

FIG. 28B

*hFMC63 VL-2-(G₄S)₆-VH-1b-(G₄S)₄-hC825 V$_H$-(G₄S)₆-hC825 V$_L$-spacer-linker-p73*

*tetramerization domain-spacer (SEQ ID NO: 53)*

<u>MGWSCIILFLVATATG</u>*DIQMTQSPSSLSASVGDRVTITCQASQDISKYLNWYQQKPGKAV*

*KLLIYHTSRLHSGVPSRFSGSGSGTDYTLTISSLQPEDIATYFCQQGNTLPYTFGGGTKLEIT*

*R*<u>GGGGSGGGGSGGGGSGGGGSGGGGSGGGGS</u>*QVQLQESGPGLVKPSETLSVTCTV*

*SGVSLPDYGVSWIRQPPGKGLEWIGVIWGSETTYYNPSLKSRVTISVDTSKNQVSLKLSSVTA*

*ADTAVYYCAKHYYYGGSYAMDYWGQGTSVTVSS*<u>GGGGSGGGGSGGGGSGGGGS</u>*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*<u>GGGG</u>

<u>SGGGGSGGGGSGGGGSGGGGSGGGGS</u>*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*<u>TPLGDTTHTSGRHGDEDTYYLQVRGRENFEILMK</u>

<u>LKESLELMELVPQPLVDSYRQQQQLLQRP</u><u>GGSGGA</u>

FIG. 29A

*hFMC63 VH-1b-(G₄S)₆-VL-2-(G₄S)₄-hC825 V_H-(G₄S)₆-hC825 V_L-spacer-linker-p53*

*tetramerization domain-spacer-H6 (SEQ ID NO: 54)*

MGWSCIILFLVATATG*QVQLQESGPGLVKPSETLSVTCTVSGVSLPDYGVSWIRQPPGKG*

*LEWIGVIWGSETTYYNPSLKSRVTISVDTSKNQVSLKLSSVTAADTAVYYCAKHYYYGGSYA*

*MDYWGQGTSVTVSS*GGGGSGGGGSGGGGSGGGGSGGGGSGGGGS*DIQMTQSPSSL*

*SASVGDRVTITCQASQDISKYLNWYQQKPGKAVKLLIYHTSRLHSGVPSRFSGSGSGTDYTL*

*TISSLQPEDIATYFCQQGNTLPYTFGGGTKLEITR*GGGGSGGGGSGGGGSGGGGS*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*GGGG

SGGGGSGGGGSGGGGSGGGGSGGGGS*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*TPLGDTTHTSGKPLDGEYFTLQIRGRERFEMFREL

NEALELKDAQAGKEPGGSGGA**PHHHHHH

FIG. 29B

*hFMC63 VH-1b-(G₄S)₆-VL-2-(G₄S)₄-hC825 V_H-(G₄S)₆-hC825 V_L-spacer-linker-p53*

*tetramerization domain-spacer (SEQ ID NO: 55)*

MGWSCIILFLVATATG*QVQLQESGPGLVKPSETLSVTCTVSGVSLPDYGVSWIRQPPGKG*

*LEWIGVIWGSETTYYNPSLKSRVTISVDTSKNQVSLKLSSVTAADTAVYYCAKHYYYGGSYA*

*MDYWGQGTSVTVSS*GGGGSGGGGSGGGGSGGGGSGGGGSGGGGS*DIQMTQSPSSL*

*SASVGDRVTITCQASQDISKYLNWYQQKPGKAVKLLIYHTSRLHSGVPSRFSGSGSGTDYTL*

*TISSLQPEDIATYFCQQGNTLPYTFGGGTKLEITR*GGGGSGGGGSGGGGSGGGGS*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS***GGGG*

*SGGGGSGGGGSGGGGSGGGGSGGGGS*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG***TPLGDTTHTSGKPLDGEYFTLQIRGRERFEMFREL*

NEALELKDAQAGKEPGGSGGA

FIG. 30A

*hFMC63 VH-1b-(G₄S)₆-VL-2-(G₄S)₄-hC825 V_H-(G₄S)₆-hC825 V_L-spacer-linker-p63*

*tetramerization domain-spacer-H6 (SEQ ID NO: 56)*

<u>MGWSCIILFLVATATG</u>*QVQLQESGPGLVKPSETLSVTCTVSGVSLPDYGVSWIRQPPGKG*

*LEWIGVIWGSETTYYNPSLKSRVTISVDTSKNQVSLKLSSVTAADTAVYYCAKHYYYGGSYA*

*MDYWGQGTSVTVSS*GGGGSGGGGSGGGGSGGGGSGGGGSGGGGS*DIQMTQSPSSL*

*SASVGDRVTITCQASQDISKYLNWYQQKPGKAVKLLIYHTSRLHSGVPSRFSGSGSGTDYTL*

*TISSLQPEDIATYFCQQGNTLPYTFGGGTKLEITR*GGGGSGGGGSGGGGSGGGGS*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*GGGG

SGGGGSGGGGSGGGGSGGGGSGGGGS*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*TPLGDTTHTSGRSPDDELLYLPVRGRETYEMLLKI

KESLELMQYLPQHTIETYRQQQQQQHQHLLQKQ<u>GGSGGAP</u>HHHHHH

FIG. 30B

*hFMC63 VH-1b-(G₄S)₆-VL-2-(G₄S)₄-hC825 V_H-(G₄S)₆-hC825 V_L-spacer-linker-p63*

*tetramerization domain-spacer (SEQ ID NO: 57)*

MGWSCIILFLVATATG*QVQLQESGPGLVKPSETLSVTCTVSGVSLPDYGVSWIRQPPGKG*

*LEWIGVIWGSETTYYNPSLKSRVTISVDTSKNQVSLKLSSVTAADTAVYYCAKHYYYGGSYA*

*MDYWGQGTSVTVSS*GGGGSGGGGSGGGGSGGGGSGGGGSGGGGS*DIQMTQSPSSL*

*SASVGDRVTITCQASQDISKYLNWYQQKPGKAVKLLIYHTSRLHSGVPSRFSGSGSGTDYTL*

*TISSLQPEDIATYFCQQGNTLPYTFGGGTKLEITR*GGGGSGGGGSGGGGSGGGGS*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*GGGG

SGGGGSGGGGSGGGGSGGGGSGGGGS*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*TPLGDTTHTSGRSPDDELLYLPVRGRETYEMLLKI

KESLELMQYLPQHTIETYRQQQQQQHQHLLQKQGGSGGA

FIG. 31A

*hFMC63 VH-1b-(G₄S)₆-VL-2-(G₄S)₄-hC825 Vₕ-(G₄S)₆-hC825 Vₗ-spacer-linker-p73*

*tetramerization domain-spacer-H6 (SEQ ID NO: 58)*

<u>MGWSCIILFLVATATG</u>*QVQLQESGPGLVKPSETLSVTCTVSGVSLPDYGVSWIRQPPGKG*

*LEWIGVIWGSETTYYNPSLKSRVTISVDTSKNQVSLKLSSVTAADTAVYYCAKHYYYGGSYA*

*MDYWGQGTSVTVSS*__GGGGSGGGGSGGGGSGGGGSGGGGSGGGGS__*DIQMTQSPSSL*

*SASVGDRVTITCQASQDISKYLNWYQQKPGKAVKLLIYHTSRLHSGVPSRFSGSGSGTDYTL*

*TISSLQPEDIATYFCQQGNTLPYTFGGGTKLEITR*__GGGGSGGGGSGGGGSGGGGS__*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*__GGGG__

__SGGGGSGGGGSGGGGSGGGGSGGGGS__*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*__TPLGDTTHTSGRHGDEDTYYLQVRGRENFEILMK__

__LKESLELMELVPQPLVDSYRQQQQLLQRP__<u>GGSGGAP</u>HHHHHH

FIG. 31B

*hFMC63 VH-1b-(G₄S)₆-VL-2-(G₄S)₄-hC825 V_H-(G₄S)₆-hC825 V_L-spacer-linker-p73*

*tetramerization domain-spacer (SEQ ID NO: 59)*

MGWSCIILFLVATATG*QVQLQESGPGLVKPSETLSVTCTVSGVSLPDYGVSWIRQPPGKG*

*LEWIGVIWGSETTYYNPSLKSRVTISVDTSKNQVSLKLSSVTAADTAVYYCAKHYYYGGSYA*

*MDYWGQGTSVTVSS*GGGGSGGGGSGGGGSGGGGSGGGGSGGGGS*DIQMTQSPSSL*

*SASVGDRVTITCQASQDISKYLNWYQQKPGKAVKLLIYHTSRLHSGVPSRFSGSGSGTDYTL*

*TISSLQPEDIATYFCQQGNTLPYTFGGGTKLEITR*GGGGSGGGGSGGGGSGGGGS*HVQ*

*LVESGGGLVQPGGSLRLSCAASGFSLTDYGVHWVRQAPGKGLEWLGVIWSGGGTAYNTA*

*LISRFTISRDNSKNTLYLQMNSLRAEDTAVYYCARRGSYPYNYFDAWGCGTLVTVSS*GGGG

SGGGGSGGGGSGGGGSGGGGSGGGGS*QAVVTQEPSLTVSPGGTVTLTCGSSTGAVT*

*ASNYANWVQQKPGQCPRGLIGGHNNRPPGVPARFSGSLLGGKAALTLLGAQPEDEAEYY*

*CALWYSDHWVIGGGTKLTVLG*TPLGDTTHTSGRHGDEDTYYLQVRGRENFEILMK

LKESLELMELVPQPLVDSYRQQQQLLQRPGGSGGA

| | clone # | mean fluorescent intensity (MFI) | | | | FACS | stability (40C) | | | | |
|---|---|---|---|---|---|---|---|---|---|---|---|
| | | IM9 0.1ug/ml | BV173 0.1ug/ml | BA25 0.1ug/ml | NALM6 0.025ug/ml | NALM6 EC50 ug/ml | d0 | d7 | d14 | d21 | d28 |
| chimeric | chimeric | 258 | 282 | 232 | 6872 | 0.04 | 100 | 99 | 97 | 85 | 81 |
| L1+H1b | 1 | 186 | 591 | 228 | 4428 | 0.13 | 99 | 98 | 92 | 84 | 82 |
| L1+H2b | 2 | 59.7 | 398 | 167 | 2943 | 0.23 | 99 | 98 | 97 | 82 | 65 |
| L1+H3 | 3 | 46.7 | 394 | 143 | 2115 | 0.37 | 99 | 99 | 98 | 89 | 81 |
| L1+H4 | 4 | 46.3 | 651 | 147 | 2319 | 0.25 | 99 | 99 | 97 | 89 | 77 |
| L1+H5b | 5 | 181 | 208 | 219 | 3260 | 0.18 | 99 | 99 | 98 | 98 | 92 |
| L1+H6b | 6 | 58.3 | 632 | 180 | 4746 | 0.08 | 99 | 99 | 97 | 97 | 88 |
| L1+H7b | 7 | 62.4 | 616 | 166 | 5247 | 0.07 | 99 | 99 | 98 | 88 | 86 |
| L1+H8b | 8 | 33.2 | 286 | 154 | 3596 | 0.13 | 99 | 99 | 97 | 91 | 89 |
| L2+H1b | 9 | 179 | 659 | 222 | 4421 | 0.10 | 99 | 99 | 98 | 94 | 83 |
| L2+H2b | 10 | 39.2 | 562 | 137 | 2675 | 0.17 | 100 | 99 | 99 | 93 | 91 |
| L2+H3 | 11 | 33.5 | 328 | 126 | 1756 | 0.41 | 99 | 99 | 97 | 89 | 87 |
| L2+H4 | 12 | 32.9 | 501 | 126 | 2006 | 0.27 | 100 | 99 | 97 | 83 | 66 |
| L2+H5b | 13 | 161 | 1013 | 214 | 2810 | 0.19 | 99 | 98 | 91 | 83 | 72 |
| L2+H6b | 14 | 48.4 | 809 | 169 | 4028 | 0.08 | 99 | 98 | 91 | 84 | 72 |
| L2+H7b | 15 | 50.5 | 802 | 159 | 4964 | 0.06 | 100 | 99 | 97 | 89 | 83 |
| L2+H8b | 16 | 28.9 | 852 | 133 | 3343 | 0.10 | 99 | 98 | 81 | 62 | 57 |
| L3+H1b | 17 | 169 | 1347 | 219 | 2657 | 0.19 | 99 | 99 | 98 | 98 | 83 |
| L3+H2b | 18 | 28.3 | 804 | 123 | 1750 | 0.28 | 100 | 99 | 98 | 89 | 86 |
| L3+H3 | 19 | 25.3 | 590 | 107 | 1179 | 0.64 | 100 | 99 | 99 | 98 | 92 |
| L3+H4 | 20 | 28.3 | 506 | 131 | 1511 | 0.42 | 99 | 99 | 98 | 89 | 84 |
| L3+H5b | 21 | 34.9 | 659 | 212 | 2076 | 0.28 | 99 | 99 | 98 | 86 | 78 |
| L3+H6b | 22 | 47.2 | 799 | 162 | 3003 | 0.13 | 99 | 99 | 98 | 98 | 93 |
| L3+H7b | 23 | 45.8 | 721 | 170 | 4121 | 0.08 | 99 | 99 | 99 | 98 | 92 |
| L3+H8b | 24 | 28.6 | 574 | 126 | 2396 | 0.19 | 99 | 99 | 99 | 98 | 90 |

FIG. 32

Log EC50

BC250: -4.172

BC258: -3.68

Max kill: 60.57
vs 59.85

Log EC50

BC250: -11.38

BC258: -9.315

Max kill: 73.77
vs 65.6

Log EC50

BC250: -3.855

BC258: -3.357

Max kill: 41.51
vs 41.83

```
                        SEQUENCE LISTING

<160> NUMBER OF SEQ ID NOS: 90

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
```

-continued

```
        50              55              60

Ser Arg Leu Thr Ile Ile Lys Asp Asn Ser Lys Ser Gln Val Phe Leu
65                  70              75              80

Lys Met Asn Ser Leu Gln Thr Asp Asp Thr Ala Ile Tyr Tyr Cys Ala
                85              90              95

Lys His Tyr Tyr Tyr Gly Gly Ser Tyr Ala Met Asp Tyr Trp Gly Gln
                100             105             110

Gly Thr Ser Val Thr Val Ser Ser
        115             120

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Val Ser Leu Pro Asp Tyr Gly
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Trp Gly Ser Glu Thr Thr
1               5

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys His Tyr Tyr Tyr Gly Gly Ser Tyr Ala Met Asp Tyr
1               5                   10

<210> SEQ ID NO 5
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Pro Gly Leu Val Lys Pro Ser Glu
1               5                   10                  15

Thr Leu Ser Val Thr Cys Thr Val Ser Gly Val Ser Leu Pro Asp Tyr
                20              25              30

Gly Val Ser Trp Ile Arg Gln Pro Pro Gly Lys Gly Leu Glu Trp Ile
            35              40              45

Gly Val Ile Trp Gly Ser Glu Thr Thr Tyr Tyr Asn Pro Ser Leu Lys
    50              55              60
```

```
Ser Arg Val Thr Ile Ser Val Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
                20                  25                  30

Gly Val Ser Trp Ile Arg Gln Pro Pro Gly Lys Gly Leu Glu Trp Leu
            35                  40                  45

Gly Val Ile Trp Gly Ser Glu Thr Thr Asn Tyr Asn Pro Ser Leu Lys
        50                  55                  60

Ser Arg Val Thr Ile Ser Lys Asp Thr Ser Lys Asn Gln Phe Ser Leu
65                  70                  75                  80

Lys Leu Ser Ser Leu Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
                20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Asn Tyr Asn Pro Ser Leu Lys
        50                  55                  60

Ser Arg Leu Thr Ile Ser Val Asp Thr Ser Lys Asn Gln Phe Ser Leu
65                  70                  75                  80

Lys Met Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110
```

```
Gly Thr Ser Val Thr Val Ser Ser
        115                 120

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Asn Tyr Asn Pro Ser Leu Lys
    50                  55                  60

Ser Arg Val Thr Ile Ser Val Asp Asn Ser Lys Asn Gln Phe Ser Leu
65                  70                  75                  80

Lys Leu Ser Ser Leu Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser
        115                 120

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Asn Tyr Asn Pro Ser Leu Lys
    50                  55                  60

Ser Arg Val Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser
        115                 120

<210> SEQ ID NO 10
<211> LENGTH: 120
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 10

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Pro Ser Leu Lys
    50                  55                  60

Ser Arg Val Thr Ile Ser Val Asp Asn Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120
```

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 11

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Pro Ser Leu Lys
    50                  55                  60

Ser Arg Val Thr Ile Ser Lys Asp Thr Ser Lys Ser Gln Phe Ser Leu
65                  70                  75                  80

Lys Met Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120
```

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 12

```
Gln Val Gln Leu Gln Glu Ser Gly Pro Gly Leu Val Lys Pro Ser Glu
1               5                   10                  15

Thr Leu Ser Val Thr Cys Thr Val Ser Gly Val Ser Leu Pro Asp Tyr
```

-continued

```
            20              25              30

Gly Val Ser Trp Ile Arg Gln Pro Pro Gly Lys Gly Leu Glu Trp Ile
        35              40              45

Gly Val Ile Trp Gly Ser Glu Thr Thr Tyr Tyr Asn Pro Ser Leu Lys
    50              55              60

Ser Arg Leu Thr Ile Ser Lys Asp Thr Ser Lys Asn Gln Phe Ser Leu
65              70              75              80

Lys Leu Ser Ser Val Thr Ala Ala Asp Thr Ala Val Tyr Tyr Cys Ala
                85              90              95

Lys His Tyr Tyr Tyr Gly Gly Ser Tyr Ala Met Asp Tyr Trp Gly Gln
                100             105             110

Gly Thr Ser Val Thr Val Ser Ser
        115             120

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Thr Thr Ser Ser Leu Ser Ala Ser Leu Gly
1               5               10              15

Asp Arg Val Thr Ile Ser Cys Arg Ala Ser Gln Asp Ile Ser Lys Tyr
                20              25              30

Leu Asn Trp Tyr Gln Gln Lys Pro Asp Gly Thr Val Lys Leu Leu Ile
        35              40              45

Tyr His Thr Ser Arg Leu His Ser Gly Val Pro Ser Arg Phe Ser Gly
    50              55              60

Ser Gly Ser Gly Thr Asp Tyr Ser Leu Thr Ile Ser Asn Leu Glu Gln
65              70              75              80

Glu Asp Ile Ala Thr Tyr Phe Cys Gln Gln Gly Asn Thr Leu Pro Tyr
                85              90              95

Thr Phe Gly Gly Gly Thr Lys Leu Glu Ile Thr
            100             105

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Asp Ile Ser Lys Tyr
1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Thr Ser
1
```

```
<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Gly Asn Thr Leu Pro Tyr Thr
1               5

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
                20                  25                  30

Leu Asn Trp Tyr Gln Gln Lys Pro Gly Lys Ala Val Lys Leu Leu Ile
            35                  40                  45

Tyr His Thr Ser Arg Leu His Thr Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Lys Tyr
                20                  25                  30

Leu Asn Trp Tyr Gln Gln Lys Pro Gly Lys Ala Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105
```

-continued

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Thr Ser Ser Leu Ser Ala Ser Val Gly
1               5                   10                  15

Asp Arg Val Thr Ile Thr Cys Arg Ala Ser Gln Asp Ile Ser Lys Tyr
                20                  25                  30

Leu Asn Trp Tyr Gln Gln Lys Pro Gly Lys Ala Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 20
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Trp Ser Cys Ile Ile Leu Phe Leu Val Ala Thr Ala Thr Gly
1               5                   10                  15

Asp Ile Gln Met Thr Gln Thr Thr Ser Ser Leu Ser Ala Ser Leu Gly
                20                  25                  30

Asp Arg Val Thr Ile Ser Cys Arg Ala Ser Gln Asp Ile Ser Lys Tyr
            35                  40                  45

Leu Asn Trp Tyr Gln Gln Lys Pro Asp Gly Thr Val Lys Leu Leu Ile
        50                  55                  60

Tyr His Thr Ser Arg Leu His Ser Gly Val Pro Ser Arg Phe Ser Gly
65                  70                  75                  80

Ser Gly Ser Gly Thr Asp Tyr Ser Leu Thr Ile Ser Asn Leu Glu Gln
                85                  90                  95

Glu Asp Ile Ala Thr Tyr Phe Cys Gln Gln Gly Asn Thr Leu Pro Tyr
                100                 105                 110

Thr Phe Gly Gly Gly Thr Lys Leu Glu Ile Thr Arg Thr Val Ala Ala
            115                 120                 125

Pro Ser Val Phe Ile Phe Pro Pro Ser Asp Glu Gln Leu Lys Ser Gly
            130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
                180                 185                 190

```
Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
        210                 215                 220

Phe Asn Arg Gly Glu Cys Thr Ser Gly Gly Gly Ser Gly Gly Gly
225                 230                 235                 240

Gly Ser Gly Gly Gly Gly Ser Gln Val Gln Leu Val Gln Ser Gly Gly
                245                 250                 255

Gly Val Val Gln Pro Gly Arg Ser Leu Arg Leu Ser Cys Lys Ala Ser
                260                 265                 270

Gly Tyr Thr Phe Thr Arg Tyr Thr Met His Trp Val Arg Gln Ala Pro
                275                 280                 285

Gly Lys Cys Leu Glu Trp Ile Gly Tyr Ile Asn Pro Ser Arg Gly Tyr
        290                 295                 300

Thr Asn Tyr Asn Gln Lys Phe Lys Asp Arg Phe Thr Ile Ser Arg Asp
305                 310                 315                 320

Asn Ser Lys Asn Thr Ala Phe Leu Gln Met Asp Ser Leu Arg Pro Glu
                325                 330                 335

Asp Thr Gly Val Tyr Phe Cys Ala Arg Tyr Tyr Asp Asp His Tyr Ser
                340                 345                 350

Leu Asp Tyr Trp Gly Gln Gly Thr Pro Val Thr Val Ser Ser Gly Gly
                355                 360                 365

Gly Gly Ser Gly Gly Gly Gly Ser Gly Gly Gly Gly Ser Gly Gly Gly
        370                 375                 380

Gly Ser Gly Gly Gly Gly Ser Gly Gly Gly Gly Ser Asp Ile Gln Met
385                 390                 395                 400

Thr Gln Ser Pro Ser Ser Leu Ser Ala Ser Val Gly Asp Arg Val Thr
                405                 410                 415

Ile Thr Cys Ser Ala Ser Ser Val Ser Tyr Met Asn Trp Tyr Gln
                420                 425                 430

Gln Thr Pro Gly Lys Ala Pro Lys Arg Trp Ile Tyr Asp Thr Ser Lys
        435                 440                 445

Leu Ala Ser Gly Val Pro Ser Arg Phe Ser Gly Ser Gly Ser Gly Thr
        450                 455                 460

Asp Tyr Thr Phe Thr Ile Ser Ser Leu Gln Pro Glu Asp Ile Ala Thr
465                 470                 475                 480

Tyr Tyr Cys Gln Gln Trp Ser Ser Asn Pro Phe Thr Phe Gly Cys Gly
                485                 490                 495

Thr Lys Leu Gln Ile Thr Arg
        500
```

```
<210> SEQ ID NO 21
<211> LENGTH: 1512
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgggctggt cctgcatcat cctgttcctg gtggccaccg ccaccggcga cattcagatg      60
actcagacta cttcttcact gtccgcctca ctgggggatc gggtcactat ttcctgccgc     120
gcaagccagg atatttctaa gtacctgaac tggtatcagc agaagcccga cggcaccgtg     180
aagctgctga tctaccacac aagcaggctg cactccggcg tgcctagccg gttcagcggc     240
```

```
tccggatctg gcaccgacta cagcctgaca atctccaatc tggagcagga ggatatcgcc      300
acctattttt gtcagcaggg gaatactctg ccatacacct ttggagggg aactaaactg      360 gaaatcaccc ggaccgtggc cgcccctcc gtgttcatct tcccccctc cgacgagcag       420 ctgaagtccg gcaccgcctc cgtggtgtgc ctgctgaaca acttctaccc ccgggaggcc      480
aaggtgcagt ggaaggtgga caacgccctg cagtccggca actcccagga gtccgtgacc      540
gagcaggact ccaaggactc cacctactcc ctgtcctcca ccctgaccct gtccaaggcc      600
gactacgaga agcacaaggt gtacgcctgc gaggtgaccc accagggcct gtcctccccc      660
gtgaccaagt ccttcaaccg gggcgagtgc actagtggcg gcggaggatc tggcggaggt      720
ggaagtgggg gaggcggatc tcaggtgcag ctggtgcaga gtggtggcgg agtggtgcag      780
cctggcagat ccctgagact gtcttgcaag gccagcggct acaccttcac ccggtacacc      840
atgcactggg tgcgacaggc ccctggcaag tgcctggaat ggatcggcta catcaacccc      900 tcccgggggct acaccaacta caaccagaag ttcaaggacc ggttcaccat cagccgggac      960
aactccaaga acaccgcctt tctgcagatg gactccctgc ggcctgagga taccggcgtg      1020
tacttttgcg cccggtacta cgacgaccac tacagcctgg actactgggg ccagggaacc      1080
cctgtgacag tgtctagcgg agggggaggt tcaggtggcg gtggatcagg gggcggagga      1140
agtggcgggg gaggtagtgg tggtggtgga agcggaggtg cggctccga tatccagatg       1200 acccagtccc cctccagcct gtctgcctct gtggagaca gagtgacaat tacatgctcc       1260
gccagctcca gcgtgtccta catgaattgg tatcagcaga cccctggcaa ggctcccaag      1320
cggtggatct acgacacctc caagctggcc tccggcgtgc cctccagatt ttctggcagc      1380
ggctccggca cagactatac ctttacaatc agctccctgc agcccgaaga tatcgccacc      1440
tactactgcc agcagtggtc ctccaacccc ttcaccttcg gctgcggcac aaagctgcag      1500
atcaccagat ag                                                        1512
```

<210> SEQ ID NO 22
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Gly Trp Ser Cys Ile Ile Leu Phe Leu Val Ala Thr Ala Thr Gly
1               5                   10                  15

Glu Val Lys Leu Gln Glu Ser Gly Pro Gly Leu Val Ala Pro Ser Gln
                20                  25                  30

Ser Leu Ser Val Thr Cys Thr Val Ser Gly Val Ser Leu Pro Asp Tyr
            35                  40                  45

Gly Val Ser Trp Ile Arg Gln Pro Pro Arg Lys Gly Leu Glu Trp Leu
        50                  55                  60

Gly Val Ile Trp Gly Ser Glu Thr Thr Tyr Tyr Asn Ser Ala Leu Lys
65                  70                  75                  80

Ser Arg Leu Thr Ile Ile Lys Asp Asn Ser Lys Ser Gln Val Phe Leu
                85                  90                  95

Lys Met Asn Ser Leu Gln Thr Asp Asp Thr Ala Ile Tyr Tyr Cys Ala
                100                 105                 110

Lys His Tyr Tyr Tyr Gly Gly Ser Tyr Ala Met Asp Tyr Trp Gly Gln
            115                 120                 125
```

```
Gly Thr Ser Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Ala Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465
```

<210> SEQ ID NO 23
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atgggctggt cctgcatcat cctgttcctg gtggccaccg ccaccggcga ggtgaaactg      60

```
caggaatccg ggcctggact ggtcgctcca agtcagtcac tgagcgtgac ttgtaccgtc      120
agtggcgtgt cactgcccga ttacggggtc agctggatca ggcagccacc tcgaaagggc      180
ctggagtggc tgggcgtgat ctggggaagc gaaaccacat actataatag cgcactgaaa      240
tccaggctga ccatcattaa ggacaactcc aaatctcagg tgtttctgaa gatgaacagc      300
ctgcagacag acgatactgc catctactat tgcgctaaac actactatta cggcgggtcc      360
tatgcaatgg attactgggg ccagggacc tctgtcacag tgtctagtgc ctccaccaag      420
ggcccatcgg tcttcccct ggcaccctcc tccaagagca cctctggggg cacagcggcc      480
ctgggctgcc tggtcaagga ctacttcccc gaaccggtga cggtgtcgtg gaactcaggc      540
gccctgacca gcggcgtgca caccttcccg gccgtcctac agtcctcagg actctactcc      600
ctcagcagcg tggtgaccgt gccctccagc agcttgggca cccagaccta catctgcaac      660
gtgaatcaca agcccagcaa caccaaggtg gacaagagag ttgagcccaa atcttgtgac      720
aaaactcaca catgcccacc gtgcccagca cctgaactcc tggggggacc gtcagtcttc      780 ctcttcccc caaaacccaa ggacaccctc atgatctccc ggacccctga ggtcacatgc      840
gtggtggtgg acgtgagcca cgaagaccct gaggtcaagt tcaactggta cgtggacggc      900
gtggaggtgc ataatgccaa gacaaagccg cgggaggagc agtacgccag cacgtaccgt      960
gtggtcagcg tcctcaccgt cctgcaccag gactggctga atggcaagga gtacaagtgc     1020
aaggtctcca acaaagccct cccagccccc atcgagaaa ccatctccaa agccaaaggg     1080
cagccccgag aaccacaggt gtacaccctg cccccatccc gggatgagct gaccaagaac     1140
caggtcagcc tgacctgcct ggtcaaaggc ttctatccca gcgacatcgc cgtggagtgg     1200
gagagcaatg ggcagccgga gaacaactac aagaccacgc ctcccgtgct ggactccgac     1260
ggctccttct tcctctacag caagctcacc gtggacaaga gcaggtggca gcaggggaac     1320
gtcttctcat gctccgtgat gcatgaggct ctgcacaacc actacacgca gaagagcctc     1380
tccctgtctc cgggtaaatg a                                              1401
```

```
<210> SEQ ID NO 24
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Trp Ser Cys Ile Ile Leu Phe Leu Val Ala Thr Ala Thr Gly
1               5                   10                  15

Asp Ile Gln Met Thr Gln Ser Pro Ser Ser Leu Ser Ala Ser Val Gly
                20                  25                  30

Asp Arg Val Thr Ile Thr Cys Gln Ala Ser Gln Asp Ile Ser Lys Tyr
            35                  40                  45

Leu Asn Trp Tyr Gln Gln Lys Pro Gly Lys Ala Val Lys Leu Leu Ile
        50                  55                  60

Tyr His Thr Ser Arg Leu His Ser Gly Val Pro Ser Arg Phe Ser Gly
65                  70                  75                  80

Ser Gly Ser Gly Thr Asp Tyr Thr Leu Thr Ile Ser Ser Leu Gln Pro
                85                  90                  95

Glu Asp Ile Ala Thr Tyr Phe Cys Gln Gln Gly Asn Thr Leu Pro Tyr
            100                 105                 110

Thr Phe Gly Gly Gly Thr Lys Leu Glu Ile Thr Arg Thr Val Ala Ala
```

```
              115                     120                     125

Pro Ser Val Phe Ile Phe Pro Pro Ser Asp Glu Gln Leu Lys Ser Gly
    130                     135                     140

Thr Ala Ser Val Val Cys Leu Leu Asn Asn Phe Tyr Pro Arg Glu Ala
145                     150                     155                     160

Lys Val Gln Trp Lys Val Asp Asn Ala Leu Gln Ser Gly Asn Ser Gln
                165                     170                     175

Glu Ser Val Thr Glu Gln Asp Ser Lys Asp Ser Thr Tyr Ser Leu Ser
                180                     185                     190

Ser Thr Leu Thr Leu Ser Lys Ala Asp Tyr Glu Lys His Lys Val Tyr
                195                     200                     205

Ala Cys Glu Val Thr His Gln Gly Leu Ser Ser Pro Val Thr Lys Ser
    210                     215                     220

Phe Asn Arg Gly Glu Cys Thr Ser Gly Gly Gly Ser Gly Gly Gly
225                     230                     235                     240

Gly Ser Gly Gly Gly Gly Ser Gln Val Gln Leu Val Gln Ser Gly Gly
                245                     250                     255

Gly Val Val Gln Pro Gly Arg Ser Leu Arg Leu Ser Cys Lys Ala Ser
                260                     265                     270

Gly Tyr Thr Phe Thr Arg Tyr Thr Met His Trp Val Arg Gln Ala Pro
                275                     280                     285

Gly Lys Cys Leu Glu Trp Ile Gly Tyr Ile Asn Pro Ser Arg Gly Tyr
    290                     295                     300

Thr Asn Tyr Asn Gln Lys Phe Lys Asp Arg Phe Thr Ile Ser Arg Asp
305                     310                     315                     320

Asn Ser Lys Asn Thr Ala Phe Leu Gln Met Asp Ser Leu Arg Pro Glu
                325                     330                     335

Asp Thr Gly Val Tyr Phe Cys Ala Arg Tyr Tyr Asp Asp His Tyr Ser
                340                     345                     350

Leu Asp Tyr Trp Gly Gln Gly Thr Pro Val Thr Val Ser Ser Gly Gly
                355                     360                     365

Gly Gly Ser Gly Gly Gly Gly Ser Gly Gly Gly Gly Ser Gly Gly Gly
    370                     375                     380

Gly Ser Gly Gly Gly Gly Ser Gly Gly Gly Gly Ser Asp Ile Gln Met
385                     390                     395                     400

Thr Gln Ser Pro Ser Ser Leu Ser Ala Ser Val Gly Asp Arg Val Thr
                405                     410                     415

Ile Thr Cys Ser Ala Ser Ser Ser Val Ser Tyr Met Asn Trp Tyr Gln
                420                     425                     430

Gln Thr Pro Gly Lys Ala Pro Lys Arg Trp Ile Tyr Asp Thr Ser Lys
                435                     440                     445

Leu Ala Ser Gly Val Pro Ser Arg Phe Ser Gly Ser Gly Ser Gly Thr
    450                     455                     460

Asp Tyr Thr Phe Thr Ile Ser Ser Leu Gln Pro Glu Asp Ile Ala Thr
465                     470                     475                     480

Tyr Tyr Cys Gln Gln Trp Ser Ser Asn Pro Phe Thr Phe Gly Cys Gly
                485                     490                     495

Thr Lys Leu Gln Ile Thr Arg
            500
```

<210> SEQ ID NO 25
<211> LENGTH: 1512
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atgggctggt cctgcatcat cctgttcctg gtggccaccg ccaccggcga catccagatg      60
acccagtctc caagctccct gtccgcctct gtgggcgaca gggtgaccat cacatgccag     120
gccagccagg atatctccaa gtacctgaac tggtatcagc agaagccagg caaggccgtg     180
aagctgctga tctaccacac atctcggctg cacagcggag tgccatccag attcagcggc     240
tccggctctg gcaccgacta taccctgaca atctctagcc tgcagcccga ggatatcgcc     300
acatacttct gtcagcaggg caataccctg ccttatacat ttggcggcgg caccaagctg     360
gagatcacac ggaccgtggc cgccccctcc gtgttcatct ccccccctc cgacgagcag     420 ctgaagtccg gcaccgcctc cgtggtgtgc ctgctgaaca acttctaccc ccgggaggcc     480
aaggtgcagt ggaaggtgga caacgccctg cagtccggca actcccagga gtccgtgacc     540
gagcaggact ccaaggactc cacctactcc ctgtcctcca ccctgaccct gtccaaggcc     600
gactacgaga agcacaaggt gtacgcctgc gaggtgaccc accagggcct gtcctccccc     660
gtgaccaagt ccttcaaccg gggcgagtgc actagtggcg gcggaggatc tggcggaggt     720
ggaagtgggg gaggcggatc tcaggtgcag ctggtgcaga gtggtggcgg agtggtgcag     780
cctggcagat ccctgagact gtcttgcaag gccagcggct acaccttcac ccggtacacc     840
atgcactggg tgcgacaggc ccctggcaag tgcctggaat ggatcggcta catcaacccc     900
tcccggggct acaccaacta caaccagaag ttcaaggacc ggttcaccat cagccgggac     960
aactccaaga caccgccctt tctgcagatg gactccctgc ggcctgagga taccggcgtg    1020 tactttgcg cccggtacta cgacgaccac tacagcctgg actactgggg ccagggaacc    1080
cctgtgacag tgtctagcgg aggggaggt tcaggtggcg gtggatcagg gggcggagga    1140
agtggcgggg gaggtagtgg tggtggtgga agcggaggtg gcggctccga tatccagatg    1200
acccagtccc cctccagcct gtctgcctct gtgggagaca gagtgacaat tacatgctcc    1260
gccagctcca gcgtgtccta catgaattgg tatcagcaga cccctggcaa ggctcccaag    1320
cggtggatct acgacacctc caagctggcc tccggcgtgc cctccagatt ttctggcagc    1380
ggctccggca cagactatac ctttacaatc agctccctgc agcccgaaga tatcgccacc    1440
tactactgcc agcagtggtc ctccaacccc ttcaccttcg gctgcggcac aaagctgcag    1500
atcaccagat ag                                                         1512

<210> SEQ ID NO 26
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gly Trp Ser Cys Ile Ile Leu Phe Leu Val Ala Thr Ala Thr Gly
1               5                   10                  15

Gln Val Gln Leu Gln Glu Ser Gly Pro Gly Leu Val Lys Pro Ser Glu
            20                  25                  30

Thr Leu Ser Val Thr Cys Thr Val Ser Gly Val Ser Leu Pro Asp Tyr
        35                  40                  45

Gly Val Ser Trp Ile Arg Gln Pro Pro Gly Lys Gly Leu Glu Trp Ile

-continued

```
            50              55              60

Gly Val Ile Trp Gly Ser Glu Thr Thr Tyr Tyr Asn Pro Ser Leu Lys
65                  70              75                  80

Ser Arg Val Thr Ile Ser Val Asp Thr Ser Lys Asn Gln Val Ser Leu
                85              90              95

Lys Leu Ser Ser Val Thr Ala Ala Asp Thr Ala Val Tyr Tyr Cys Ala
            100             105             110

Lys His Tyr Tyr Tyr Gly Gly Ser Tyr Ala Met Asp Tyr Trp Gly Gln
        115             120             125

Gly Thr Ser Val Thr Val Ser Ser Ala Ser Thr Lys Gly Pro Ser Val
    130             135             140

Phe Pro Leu Ala Pro Ser Ser Lys Ser Thr Ser Gly Gly Thr Ala Ala
145             150             155             160

Leu Gly Cys Leu Val Lys Asp Tyr Phe Pro Glu Pro Val Thr Val Ser
            165             170             175

Trp Asn Ser Gly Ala Leu Thr Ser Gly Val His Thr Phe Pro Ala Val
        180             185             190

Leu Gln Ser Ser Gly Leu Tyr Ser Leu Ser Ser Val Val Thr Val Pro
        195             200             205

Ser Ser Ser Leu Gly Thr Gln Thr Tyr Ile Cys Asn Val Asn His Lys
    210             215             220

Pro Ser Asn Thr Lys Val Asp Lys Arg Val Glu Pro Lys Ser Cys Asp
225             230             235             240

Lys Thr His Thr Cys Pro Pro Cys Pro Ala Pro Glu Leu Leu Gly Gly
            245             250             255

Pro Ser Val Phe Leu Phe Pro Pro Lys Pro Lys Asp Thr Leu Met Ile
            260             265             270

Ser Arg Thr Pro Glu Val Thr Cys Val Val Val Asp Val Ser His Glu
        275             280             285

Asp Pro Glu Val Lys Phe Asn Trp Tyr Val Asp Gly Val Glu Val His
    290             295             300

Asn Ala Lys Thr Lys Pro Arg Glu Glu Gln Tyr Ala Ser Thr Tyr Arg
305             310             315             320

Val Val Ser Val Leu Thr Val Leu His Gln Asp Trp Leu Asn Gly Lys
            325             330             335

Glu Tyr Lys Cys Lys Val Ser Asn Lys Ala Leu Pro Ala Pro Ile Glu
            340             345             350

Lys Thr Ile Ser Lys Ala Lys Gly Gln Pro Arg Glu Pro Gln Val Tyr
            355             360             365

Thr Leu Pro Pro Ser Arg Asp Glu Leu Thr Lys Asn Gln Val Ser Leu
        370             375             380

Thr Cys Leu Val Lys Gly Phe Tyr Pro Ser Asp Ile Ala Val Glu Trp
385             390             395             400

Glu Ser Asn Gly Gln Pro Glu Asn Asn Tyr Lys Thr Thr Pro Pro Val
            405             410             415

Leu Asp Ser Asp Gly Ser Phe Phe Leu Tyr Ser Lys Leu Thr Val Asp
            420             425             430

Lys Ser Arg Trp Gln Gln Gly Asn Val Phe Ser Cys Ser Val Met His
        435             440             445

Glu Ala Leu His Asn His Tyr Thr Gln Lys Ser Leu Ser Leu Ser Pro
    450             455             460

Gly Lys
465
```

<210> SEQ ID NO 27
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atgggctggt cctgcatcat cctgttcctg gtggccaccg ccaccggcca ggtgcagctg      60
caggagtccg gcccaggcct ggtgaagcca tctgagaccc tgagcgtgac ctgcacagtg     120
tccggcgtgt ctctgcctga ctatggcgtg tcttggatca gacagccacc tggcaagggc     180
ctggagtgga tcggcgtgat ctggggcagc gagaccacat actataaccc cagcctgaag     240
tccagagtga ccatctccgt ggacacatct aagaatcagg tgtctctgaa gctgagctcc     300
gtgaccgccg ccgatacagc cgtgtactat tgtgccaagc actactatta cggcggcagc     360
tatgctatgg actactgggg ccaggcacc tccgtgacag tgtctagcgc ctccaccaag     420
ggcccatcgg tcttcccct ggcaccctcc tccaagagca cctctggggg cacagcggcc     480
ctgggctgcc tggtcaagga ctacttcccc gaaccggtga cggtgtcgtg gaactcaggc     540
gccctgacca gcggcgtgca caccttcccg gccgtcctac agtcctcagg actctactcc     600
ctcagcagcg tggtgaccgt gccctccagc agcttgggca cccagaccta catctgcaac     660
gtgaatcaca agcccagcaa caccaaggtg gacaagagag ttgagcccaa atcttgtgac     720
aaaactcaca catgcccacc gtgcccagca cctgaactcc tggggggacc gtcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccg cgggaggagc agtacgccag cacgtaccgt     960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtacaccctg cccccatccc gggatgagct gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaatg a                                            1401
```

<210> SEQ ID NO 28
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Gly Trp Ser Cys Ile Ile Leu Phe Leu Val Ala Thr Ala Thr Gly
1               5                   10                  15

Asp Ile Gln Met Thr Gln Thr Thr Ser Ser Leu Ser Ala Ser Leu Gly
                20                  25                  30

Asp Arg Val Thr Ile Ser Cys Arg Ala Ser Gln Asp Ile Ser Lys Tyr
        35                  40                  45
```

```
Leu Asn Trp Tyr Gln Gln Lys Pro Asp Gly Thr Val Lys Leu Leu Ile
    50              55              60

Tyr His Thr Ser Arg Leu His Ser Gly Val Pro Ser Arg Phe Ser Gly
65              70              75              80

Ser Gly Ser Gly Thr Asp Tyr Ser Leu Thr Ile Ser Asn Leu Glu Gln
                85              90              95

Glu Asp Ile Ala Thr Tyr Phe Cys Gln Gln Gly Asn Thr Leu Pro Tyr
            100             105             110

Thr Phe Gly Gly Gly Thr Lys Leu Glu Ile Thr Arg Thr Val Ala Ala
        115             120             125

Pro Ser Val Phe Ile Phe Pro Pro Ser Asp Glu Gln Leu Lys Ser Gly
    130             135             140

Thr Ala Ser Val Val Cys Leu Leu Asn Asn Phe Tyr Pro Arg Glu Ala
145             150             155             160

Lys Val Gln Trp Lys Val Asp Asn Ala Leu Gln Ser Gly Asn Ser Gln
            165             170             175

Glu Ser Val Thr Glu Gln Asp Ser Lys Asp Ser Thr Tyr Ser Leu Ser
            180             185             190

Ser Thr Leu Thr Leu Ser Lys Ala Asp Tyr Glu Lys His Lys Val Tyr
        195             200             205

Ala Cys Glu Val Thr His Gln Gly Leu Ser Ser Pro Val Thr Lys Ser
    210             215             220

Phe Asn Arg Gly Glu Cys Thr Ser Gly Gly Gly Ser Gly Gly Gly
225             230             235             240

Gly Ser Gly Gly Gly Gly Ser His Val Lys Leu Gln Glu Ser Gly Pro
            245             250             255

Gly Leu Val Gln Pro Ser Gln Ser Leu Ser Leu Thr Cys Thr Val Ser
            260             265             270

Gly Phe Ser Leu Thr Asp Tyr Gly Val His Trp Val Arg Gln Ser Pro
        275             280             285

Gly Lys Gly Leu Glu Trp Leu Gly Val Ile Trp Ser Gly Gly Gly Thr
    290             295             300

Ala Tyr Asn Thr Ala Leu Ile Ser Arg Leu Asn Ile Tyr Arg Asp Asn
305             310             315             320

Ser Lys Asn Gln Val Phe Leu Glu Met Asn Ser Leu Gln Ala Glu Asp
            325             330             335

Thr Ala Met Tyr Tyr Cys Ala Arg Arg Gly Ser Tyr Pro Tyr Asn Tyr
            340             345             350

Phe Asp Ala Trp Gly Cys Gly Thr Thr Val Thr Val Ser Ser Gly Gly
        355             360             365

Gly Gly Ser Gly Gly Gly Gly Ser Gly Gly Gly Gly Ser Gly Gly Gly
    370             375             380

Gly Ser Gly Gly Gly Gly Ser Gly Gly Gly Gly Ser Gln Ala Val Val
385             390             395             400

Ile Gln Glu Ser Ala Leu Thr Thr Pro Pro Gly Glu Thr Val Thr Leu
            405             410             415

Thr Cys Gly Ser Ser Thr Gly Ala Val Thr Ala Ser Asn Tyr Ala Asn
            420             425             430

Trp Val Gln Glu Lys Pro Asp His Cys Phe Thr Gly Leu Ile Gly Gly
        435             440             445

His Asn Asn Arg Pro Pro Gly Val Pro Ala Arg Phe Ser Gly Ser Leu
    450             455             460
```

```
Ile Gly Asp Lys Ala Ala Leu Thr Ile Ala Gly Thr Gln Thr Glu Asp
465                 470                 475                 480

Glu Ala Ile Tyr Phe Cys Ala Leu Trp Tyr Ser Asp His Trp Val Ile
                485                 490                 495

Gly Gly Gly Thr Arg Leu Thr Val Leu Gly
                500                 505

<210> SEQ ID NO 29
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Trp Ser Cys Ile Ile Leu Phe Leu Val Ala Thr Ala Thr Gly
1               5                   10                  15

Glu Val Lys Leu Gln Glu Ser Gly Pro Gly Leu Val Ala Pro Ser Gln
                20                  25                  30

Ser Leu Ser Val Thr Cys Thr Val Ser Gly Val Ser Leu Pro Asp Tyr
            35                  40                  45

Gly Val Ser Trp Ile Arg Gln Pro Pro Arg Lys Gly Leu Glu Trp Leu
        50                  55                  60

Gly Val Ile Trp Gly Ser Glu Thr Thr Tyr Tyr Asn Ser Ala Leu Lys
65                  70                  75                  80

Ser Arg Leu Thr Ile Ile Lys Asp Asn Ser Lys Ser Gln Val Phe Leu
                85                  90                  95

Lys Met Asn Ser Leu Gln Thr Asp Asp Thr Ala Ile Tyr Tyr Cys Ala
                100                 105                 110

Lys His Tyr Tyr Tyr Gly Gly Ser Tyr Ala Met Asp Tyr Trp Gly Gln
            115                 120                 125

Gly Thr Ser Val Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
        210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
        290                 295                 300

Asn Ala Lys Thr Lys Pro Arg Glu Glu Gln Tyr Ala Ser Thr Tyr Arg
305                 310                 315                 320
```

-continued

```
Val Val Ser Val Leu Thr Val Leu His Gln Asp Trp Leu Asn Gly Lys
            325                 330                 335

Glu Tyr Lys Cys Ala Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 30
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Gly Trp Ser Cys Ile Ile Leu Phe Leu Val Ala Thr Ala Thr Gly
1               5                   10                  15

Asp Ile Gln Met Thr Gln Thr Thr Ser Ser Leu Ser Ala Ser Leu Gly
            20                  25                  30

Asp Arg Val Thr Ile Ser Cys Arg Ala Ser Gln Asp Ile Ser Lys Tyr
            35                  40                  45

Leu Asn Trp Tyr Gln Gln Lys Pro Asp Gly Thr Val Lys Leu Leu Ile
    50                  55                  60

Tyr His Thr Ser Arg Leu His Ser Gly Val Pro Ser Arg Phe Ser Gly
65                  70                  75                  80

Ser Gly Ser Gly Thr Asp Tyr Ser Leu Thr Ile Ser Asn Leu Glu Gln
                85                  90                  95

Glu Asp Ile Ala Thr Tyr Phe Cys Gln Gln Gly Asn Thr Leu Pro Tyr
            100                 105                 110

Thr Phe Gly Gly Gly Thr Lys Leu Glu Ile Thr Arg Thr Val Ala Ala
            115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
```

-continued

```
            195                 200                 205

Ala Cys Glu Val Thr His Gln Gly Leu Ser Ser Pro Val Thr Lys Ser
    210                 215                 220

Phe Asn Arg Gly Glu Cys Thr Ser Gly Gly Gly Ser Gly Gly Gly
225                 230                 235                 240

Gly Ser Gly Gly Gly Gly Ser His Val Gln Leu Val Glu Ser Gly Gly
                245                 250                 255

Gly Leu Val Gln Pro Gly Gly Ser Leu Arg Leu Ser Cys Ala Ala Ser
                260                 265                 270

Gly Phe Ser Leu Thr Asp Tyr Gly Val His Trp Val Arg Gln Ala Pro
                275                 280                 285

Gly Lys Gly Leu Glu Trp Leu Gly Val Ile Trp Ser Gly Gly Thr
                290                 295                 300

Ala Tyr Asn Thr Ala Leu Ile Ser Arg Phe Thr Ile Ser Arg Asp Asn
305                 310                 315                 320

Ser Lys Asn Thr Leu Tyr Leu Gln Met Asn Ser Leu Arg Ala Glu Asp
                325                 330                 335

Thr Ala Val Tyr Tyr Cys Ala Arg Arg Gly Ser Tyr Pro Tyr Asn Tyr
                340                 345                 350

Phe Asp Ala Trp Gly Cys Gly Thr Leu Val Thr Val Ser Ser Gly Gly
                355                 360                 365

Gly Gly Ser Gly Gly Gly Gly Ser Gly Gly Gly Gly Ser Gly Gly Gly
                370                 375                 380

Gly Ser Gly Gly Gly Gly Ser Gly Gly Gly Gly Ser Gln Ala Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ala Ser Asn Tyr Ala Asn
                420                 425                 430

Trp Val Gln Gln Lys Pro Gly Gln Cys Pro Arg Gly Leu Ile Gly Gly
                435                 440                 445

His Asn Asn Arg Pro Pro Gly Val Pro Ala Arg Phe Ser Gly Ser Leu
    450                 455                 460

Leu Gly Gly Lys Ala Ala Leu Thr Leu Leu Gly Ala Gln Pro Glu Asp
465                 470                 475                 480

Glu Ala Glu Tyr Tyr Cys Ala Leu Trp Tyr Ser Asp His Trp Val Ile
                485                 490                 495

Gly Gly Gly Thr Lys Leu Thr Val Leu Gly
                500                 505
```

<210> SEQ ID NO 31
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Met Gly Trp Ser Cys Ile Ile Leu Phe Leu Val Ala Thr Ala Thr Gly
1               5                   10                  15

Glu Val Lys Leu Gln Glu Ser Gly Pro Gly Leu Val Ala Pro Ser Gln
                20                  25                  30

Ser Leu Ser Val Thr Cys Thr Val Ser Gly Val Ser Leu Pro Asp Tyr
            35                  40                  45
```

```
Gly Val Ser Trp Ile Arg Gln Pro Pro Arg Lys Gly Leu Glu Trp Leu
    50              55              60

Gly Val Ile Trp Gly Ser Glu Thr Thr Tyr Tyr Asn Ser Ala Leu Lys
65              70              75              80

Ser Arg Leu Thr Ile Ile Lys Asp Asn Ser Lys Ser Gln Val Phe Leu
            85              90              95

Lys Met Asn Ser Leu Gln Thr Asp Asp Thr Ala Ile Tyr Tyr Cys Ala
        100             105             110

Lys His Tyr Tyr Tyr Gly Gly Ser Tyr Ala Met Asp Tyr Trp Gly Gln
        115             120             125

Gly Thr Ser Val Thr Val Ser Ser Ala Ser Thr Lys Gly Pro Ser Val
    130             135             140

Phe Pro Leu Ala Pro Ser Ser Lys Ser Thr Ser Gly Gly Thr Ala Ala
145             150             155             160

Leu Gly Cys Leu Val Lys Asp Tyr Phe Pro Glu Pro Val Thr Val Ser
            165             170             175

Trp Asn Ser Gly Ala Leu Thr Ser Gly Val His Thr Phe Pro Ala Val
            180             185             190

Leu Gln Ser Ser Gly Leu Tyr Ser Leu Ser Ser Val Val Thr Val Pro
        195             200             205

Ser Ser Ser Leu Gly Thr Gln Thr Tyr Ile Cys Asn Val Asn His Lys
    210             215             220

Pro Ser Asn Thr Lys Val Asp Lys Arg Val Glu Pro Lys Ser Cys Asp
225             230             235             240

Lys Thr His Thr Cys Pro Pro Cys Pro Ala Pro Glu Leu Leu Gly Gly
            245             250             255

Pro Ser Val Phe Leu Phe Pro Pro Lys Pro Lys Asp Thr Leu Met Ile
            260             265             270

Ser Arg Thr Pro Glu Val Thr Cys Val Val Val Asp Val Ser His Glu
        275             280             285

Asp Pro Glu Val Lys Phe Asn Trp Tyr Val Asp Gly Val Glu Val His
        290             295             300

Asn Ala Lys Thr Lys Pro Arg Glu Glu Gln Tyr Ala Ser Thr Tyr Arg
305             310             315             320

Val Val Ser Val Leu Thr Val Leu His Gln Asp Trp Leu Asn Gly Lys
            325             330             335

Glu Tyr Lys Cys Ala Val Ser Asn Lys Ala Leu Pro Ala Pro Ile Glu
        340             345             350

Lys Thr Ile Ser Lys Ala Lys Gly Gln Pro Arg Glu Pro Gln Val Tyr
        355             360             365

Thr Leu Pro Pro Ser Arg Asp Glu Leu Thr Lys Asn Gln Val Ser Leu
    370             375             380

Thr Cys Leu Val Lys Gly Phe Tyr Pro Ser Asp Ile Ala Val Glu Trp
385             390             395             400

Glu Ser Asn Gly Gln Pro Glu Asn Asn Tyr Lys Thr Thr Pro Pro Val
            405             410             415

Leu Asp Ser Asp Gly Ser Phe Phe Leu Tyr Ser Lys Leu Thr Val Asp
            420             425             430

Lys Ser Arg Trp Gln Gln Gly Asn Val Phe Ser Cys Ser Val Met His
        435             440             445

Glu Ala Leu His Asn His Tyr Thr Gln Lys Ser Leu Ser Leu Ser Pro
    450             455             460

Gly Lys
```

465

<210> SEQ ID NO 32
<211> LENGTH: 616
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Gly Trp Ser Cys Ile Ile Leu Phe Leu Val Ala Thr Ala Thr Gly
1               5                   10                  15

Asp Ile Gln Met Thr Gln Thr Thr Ser Ser Leu Ser Ala Ser Leu Gly
                20                  25                  30

Asp Arg Val Thr Ile Ser Cys Arg Ala Ser Gln Asp Ile Ser Lys Tyr
            35                  40                  45

Leu Asn Trp Tyr Gln Gln Lys Pro Asp Gly Thr Val Lys Leu Leu Ile
        50                  55                  60

Tyr His Thr Ser Arg Leu His Ser Gly Val Pro Ser Arg Phe Ser Gly
65                  70                  75                  80

Ser Gly Ser Gly Thr Asp Tyr Ser Leu Thr Ile Ser Asn Leu Glu Gln
                85                  90                  95

Glu Asp Ile Ala Thr Tyr Phe Cys Gln Gln Gly Asn Thr Leu Pro Tyr
                100                 105                 110

Thr Phe Gly Gly Gly Thr Lys Leu Glu Ile Thr Arg Gly Gly Gly Gly
            115                 120                 125

Ser Gly Gly Gly Gly Ser Gly Gly Gly Gly Ser Gly Gly Gly Gly Ser
        130                 135                 140

Gly Gly Gly Gly Ser Gly Gly Gly Gly Ser Glu Val Lys Leu Gln Glu
145                 150                 155                 160

Ser Gly Pro Gly Leu Val Ala Pro Ser Gln Ser Leu Ser Val Thr Cys
                165                 170                 175

Thr Val Ser Gly Val Ser Leu Pro Asp Tyr Gly Val Ser Trp Ile Arg
                180                 185                 190

Gln Pro Pro Arg Lys Gly Leu Glu Trp Leu Gly Val Ile Trp Gly Ser
            195                 200                 205

Glu Thr Thr Tyr Tyr Asn Ser Ala Leu Lys Ser Arg Leu Thr Ile Ile
        210                 215                 220

Lys Asp Asn Ser Lys Ser Gln Val Phe Leu Lys Met Asn Ser Leu Gln
225                 230                 235                 240

Thr Asp Asp Thr Ala Ile Tyr Tyr Cys Ala Lys His Tyr Tyr Tyr Gly
                245                 250                 255

Gly Ser Tyr Ala Met Asp Tyr Trp Gly Gln Gly Thr Ser Val Thr Val
                260                 265                 270

Ser Ser Gly Gly Gly Gly Ser Gly Gly Gly Gly Ser Gly Gly Gly Gly
            275                 280                 285

Ser Gly Gly Gly Gly Ser His Val Gln Leu Val Glu Ser Gly Gly Gly
        290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
                325                 330                 335

Lys Gly Leu Glu Trp Leu Gly Val Ile Trp Ser Gly Gly Thr Ala
            340                 345                 350

```
Tyr Asn Thr Ala Leu Ile Ser Arg Phe Thr Ile Ser Arg Asp Asn Ser
        355                 360                 365

Lys Asn Thr Leu Tyr Leu Gln Met Asn Ser Leu Arg Ala Glu Asp Thr
    370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
                405                 410                 415

Gly Ser Gly Gly Gly Gly Ser Gly Gly Gly Gly Ser Gly Gly Gly Gly
                420                 425                 430

Ser Gly Gly Gly Gly Ser Gly Gly Gly Gly Ser Gln Ala Val Val Thr
            435                 440                 445

Gln Glu Pro Ser Leu Thr Val Ser Pro Gly Gly Thr Val Thr Leu Thr
    450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly Gly His
                485                 490                 495

Asn Asn Arg Pro Pro Gly Val Pro Ala Arg Phe Ser Gly Ser Leu Leu
                500                 505                 510

Gly Gly Lys Ala Ala Leu Thr Leu Leu Gly Ala Gln Pro Glu Asp Glu
            515                 520                 525

Ala Glu Tyr Tyr Cys Ala Leu Trp Tyr Ser Asp His Trp Val Ile Gly
    530                 535                 540

Gly Gly Thr Lys Leu Thr Val Leu Gly Thr Pro Leu Gly Asp Thr Thr
545                 550                 555                 560

His Thr Ser Gly Lys Pro Leu Asp Gly Glu Tyr Phe Thr Leu Gln Ile
                565                 570                 575

Arg Gly Arg Glu Arg Phe Glu Met Phe Arg Glu Leu Asn Glu Ala Leu
                580                 585                 590

Glu Leu Lys Asp Ala Gln Ala Gly Lys Glu Pro Gly Gly Ser Gly Gly
            595                 600                 605

Ala Pro His His His His His His
    610                 615

<210> SEQ ID NO 33
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Gly Trp Ser Cys Ile Ile Leu Phe Leu Val Ala Thr Ala Thr Gly
1               5                   10                  15

Asp Ile Gln Met Thr Gln Thr Thr Ser Ser Leu Ser Ala Ser Leu Gly
                20                  25                  30

Asp Arg Val Thr Ile Ser Cys Arg Ala Ser Gln Asp Ile Ser Lys Tyr
            35                  40                  45

Leu Asn Trp Tyr Gln Gln Lys Pro Asp Gly Thr Val Lys Leu Leu Ile
    50                  55                  60

Tyr His Thr Ser Arg Leu His Ser Gly Val Pro Ser Arg Phe Ser Gly
65                  70                  75                  80

Ser Gly Ser Gly Thr Asp Tyr Ser Leu Thr Ile Ser Asn Leu Glu Gln
                85                  90                  95
```

-continued

```
Glu Asp Ile Ala Thr Tyr Phe Cys Gln Gln Gly Asn Thr Leu Pro Tyr
            100                 105                 110

Thr Phe Gly Gly Gly Thr Lys Leu Glu Ile Thr Arg Gly Gly Gly Gly
            115                 120                 125

Ser Gly Gly Gly Gly Ser Gly Gly Gly Ser Gly Gly Gly Gly Ser
            130                 135                 140

Gly Gly Gly Gly Ser Gly Gly Gly Ser Glu Val Lys Leu Gln Glu
145                 150                 155                 160

Ser Gly Pro Gly Leu Val Ala Pro Ser Gln Ser Leu Ser Val Thr Cys
                165                 170                 175

Thr Val Ser Gly Val Ser Leu Pro Asp Tyr Gly Val Ser Trp Ile Arg
            180                 185                 190

Gln Pro Pro Arg Lys Gly Leu Glu Trp Leu Gly Val Ile Trp Gly Ser
            195                 200                 205

Glu Thr Thr Tyr Tyr Asn Ser Ala Leu Lys Ser Arg Leu Thr Ile Ile
            210                 215                 220

Lys Asp Asn Ser Lys Ser Gln Val Phe Leu Lys Met Asn Ser Leu Gln
225                 230                 235                 240

Thr Asp Asp Thr Ala Ile Tyr Tyr Cys Ala Lys His Tyr Tyr Tyr Gly
                245                 250                 255

Gly Ser Tyr Ala Met Asp Tyr Trp Gly Gln Gly Thr Ser Val Thr Val
                260                 265                 270

Ser Ser Gly Gly Gly Gly Ser Gly Gly Gly Gly Ser Gly Gly Gly Gly
            275                 280                 285

Ser Gly Gly Gly Gly Ser His Val Gln Leu Val Glu Ser Gly Gly Gly
            290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
                325                 330                 335

Lys Gly Leu Glu Trp Leu Gly Val Ile Trp Ser Gly Gly Gly Thr Ala
            340                 345                 350

Tyr Asn Thr Ala Leu Ile Ser Arg Phe Thr Ile Ser Arg Asp Asn Ser
            355                 360                 365

Lys Asn Thr Leu Tyr Leu Gln Met Asn Ser Leu Arg Ala Glu Asp Thr
            370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
                405                 410                 415

Gly Ser Gly Gly Gly Gly Ser Gly Gly Gly Gly Ser Gly Gly Gly Gly
            420                 425                 430

Ser Gly Gly Gly Gly Ser Gly Gly Gly Gly Ser Gln Ala Val Val Thr
            435                 440                 445

Gln Glu Pro Ser Leu Thr Val Ser Pro Gly Gly Thr Val Thr Leu Thr
            450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly Gly His
                485                 490                 495

Asn Asn Arg Pro Pro Gly Val Pro Ala Arg Phe Ser Gly Ser Leu Leu
                500                 505                 510
```

-continued

```
Gly Gly Lys Ala Ala Leu Thr Leu Leu Gly Ala Gln Pro Glu Asp Glu
        515             520             525

Ala Glu Tyr Tyr Cys Ala Leu Trp Tyr Ser Asp His Trp Val Ile Gly
        530             535             540

Gly Gly Thr Lys Leu Thr Val Leu Gly Thr Pro Leu Gly Asp Thr Thr
545             550             555             560

His Thr Ser Gly Lys Pro Leu Asp Gly Glu Tyr Phe Thr Leu Gln Ile
                565             570             575

Arg Gly Arg Glu Arg Phe Glu Met Phe Arg Glu Leu Asn Glu Ala Leu
            580             585             590

Glu Leu Lys Asp Ala Gln Ala Gly Lys Glu Pro Gly Gly Ser Gly Gly
        595             600             605

Ala

<210> SEQ ID NO 34
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Gly Trp Ser Cys Ile Ile Leu Phe Leu Val Ala Thr Ala Thr Gly
1               5               10              15

Asp Ile Gln Met Thr Gln Thr Thr Ser Ser Leu Ser Ala Ser Leu Gly
                20              25              30

Asp Arg Val Thr Ile Ser Cys Arg Ala Ser Gln Asp Ile Ser Lys Tyr
            35              40              45

Leu Asn Trp Tyr Gln Gln Lys Pro Asp Gly Thr Val Lys Leu Leu Ile
        50              55              60

Tyr His Thr Ser Arg Leu His Ser Gly Val Pro Ser Arg Phe Ser Gly
65              70              75              80

Ser Gly Ser Gly Thr Asp Tyr Ser Leu Thr Ile Ser Asn Leu Glu Gln
                85              90              95

Glu Asp Ile Ala Thr Tyr Phe Cys Gln Gln Gly Asn Thr Leu Pro Tyr
            100             105             110

Thr Phe Gly Gly Gly Thr Lys Leu Glu Ile Thr Arg Gly Gly Gly Gly
        115             120             125

Ser Gly Gly Gly Gly Ser Gly Gly Gly Ser Gly Gly Gly Gly Ser
    130             135             140

Gly Gly Gly Gly Ser Gly Gly Gly Ser Glu Val Lys Leu Gln Glu
145             150             155             160

Ser Gly Pro Gly Leu Val Ala Pro Ser Gln Ser Leu Ser Val Thr Cys
                165             170             175

Thr Val Ser Gly Val Ser Leu Pro Asp Tyr Gly Val Ser Trp Ile Arg
            180             185             190

Gln Pro Pro Arg Lys Gly Leu Glu Trp Leu Gly Val Ile Trp Gly Ser
        195             200             205

Glu Thr Thr Tyr Tyr Asn Ser Ala Leu Lys Ser Arg Leu Thr Ile Ile
    210             215             220

Lys Asp Asn Ser Lys Ser Gln Val Phe Leu Lys Met Asn Ser Leu Gln
225             230             235             240

Thr Asp Asp Thr Ala Ile Tyr Tyr Cys Ala Lys His Tyr Tyr Tyr Gly
                245             250             255
```

```
Gly Ser Tyr Ala Met Asp Tyr Trp Gly Gln Gly Thr Ser Val Thr Val
            260                 265                 270

Ser Ser Gly Gly Gly Gly Ser Gly Gly Gly Gly Ser Gly Gly Gly Gly
            275                 280                 285

Ser Gly Gly Gly Gly Ser His Val Gln Leu Val Glu Ser Gly Gly Gly
            290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
            325                 330                 335

Lys Gly Leu Glu Trp Leu Gly Val Ile Trp Ser Gly Gly Thr Ala
            340                 345                 350

Tyr Asn Thr Ala Leu Ile Ser Arg Phe Thr Ile Ser Arg Asp Asn Ser
            355                 360                 365

Lys Asn Thr Leu Tyr Leu Gln Met Asn Ser Leu Arg Ala Glu Asp Thr
            370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
            405                 410                 415

Gly Ser Gly Gly Gly Gly Ser Gly Gly Gly Gly Ser Gly Gly Gly Gly
            420                 425                 430

Ser Gly Gly Gly Gly Ser Gly Gly Gly Gly Ser Gln Ala Val Val Thr
            435                 440                 445

Gln Glu Pro Ser Leu Thr Val Ser Pro Gly Gly Thr Val Thr Leu Thr
            450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly His
            485                 490                 495

Asn Asn Arg Pro Pro Gly Val Pro Ala Arg Phe Ser Gly Ser Leu Leu
            500                 505                 510

Gly Gly Lys Ala Ala Leu Thr Leu Leu Gly Ala Gln Pro Glu Asp Glu
            515                 520                 525

Ala Glu Tyr Tyr Cys Ala Leu Trp Tyr Ser Asp His Trp Val Ile Gly
            530                 535                 540

Gly Gly Thr Lys Leu Thr Val Leu Gly Thr Pro Leu Gly Asp Thr Thr
545                 550                 555                 560

His Thr Ser Gly Arg Ser Pro Asp Asp Glu Leu Leu Tyr Leu Pro Val
            565                 570                 575

Arg Gly Arg Glu Thr Tyr Glu Met Leu Leu Lys Ile Lys Glu Ser Leu
            580                 585                 590

Glu Leu Met Gln Tyr Leu Pro Gln His Thr Ile Glu Thr Tyr Arg Gln
            595                 600                 605

Gln Gln Gln Gln Gln His Gln His Leu Leu Gln Lys Gln Gly Gly Ser
            610                 615                 620

Gly Gly Ala Pro His His His His His His
625                 630
```

<210> SEQ ID NO 35
<211> LENGTH: 627
<212> TYPE: PRT
<213> ORGANISM: Artificial Sequence
<220> FEATURE:
<223> OTHER INFORMATION: Description of Artificial Sequence: Synthetic -continued

```
     polypeptide

<400> SEQUENCE: 35

Met Gly Trp Ser Cys Ile Ile Leu Phe Leu Val Ala Thr Ala Thr Gly
1               5                   10                  15

Asp Ile Gln Met Thr Gln Thr Thr Ser Ser Leu Ser Ala Ser Leu Gly
            20                  25                  30

Asp Arg Val Thr Ile Ser Cys Arg Ala Ser Gln Asp Ile Ser Lys Tyr
        35                  40                  45

Leu Asn Trp Tyr Gln Gln Lys Pro Asp Gly Thr Val Lys Leu Leu Ile
    50                  55                  60

Tyr His Thr Ser Arg Leu His Ser Gly Val Pro Ser Arg Phe Ser Gly
65                  70                  75                  80

Ser Gly Ser Gly Thr Asp Tyr Ser Leu Thr Ile Ser Asn Leu Glu Gln
                85                  90                  95

Glu Asp Ile Ala Thr Tyr Phe Cys Gln Gln Gly Asn Thr Leu Pro Tyr
            100                 105                 110

Thr Phe Gly Gly Gly Thr Lys Leu Glu Ile Thr Arg Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Gly Ser Glu Val Lys Leu Gln Glu
145                 150                 155                 160

Ser Gly Pro Gly Leu Val Ala Pro Ser Gln Ser Leu Ser Val Thr Cys
                165                 170                 175

Thr Val Ser Gly Val Ser Leu Pro Asp Tyr Gly Val Ser Trp Ile Arg
            180                 185                 190

Gln Pro Pro Arg Lys Gly Leu Glu Trp Leu Gly Val Ile Trp Gly Ser
            195                 200                 205

Glu Thr Thr Tyr Tyr Asn Ser Ala Leu Lys Ser Arg Leu Thr Ile Ile
        210                 215                 220

Lys Asp Asn Ser Lys Ser Gln Val Phe Leu Lys Met Asn Ser Leu Gln
225                 230                 235                 240

Thr Asp Asp Thr Ala Ile Tyr Tyr Cys Ala Lys His Tyr Tyr Tyr Gly
            245                 250                 255

Gly Ser Tyr Ala Met Asp Tyr Trp Gly Gln Gly Thr Ser Val Thr Val
            260                 265                 270

Ser Ser Gly Gly Gly Gly Ser Gly Gly Gly Gly Ser Gly Gly Gly Gly
        275                 280                 285

Ser Gly Gly Gly Gly Ser His Val Gln Leu Val Glu Ser Gly Gly Gly
    290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
            325                 330                 335

Lys Gly Leu Glu Trp Leu Gly Val Ile Trp Ser Gly Gly Gly Thr Ala
            340                 345                 350

Tyr Asn Thr Ala Leu Ile Ser Arg Phe Thr Ile Ser Arg Asp Asn Ser
        355                 360                 365

Lys Asn Thr Leu Tyr Leu Gln Met Asn Ser Leu Arg Ala Glu Asp Thr
    370                 375                 380

Ala Val Tyr Tyr Cys Ala Arg Arg Gly Ser Tyr Pro Tyr Asn Tyr Phe
385                 390                 395                 400
```

-continued

```
Asp Ala Trp Gly Cys Gly Thr Leu Val Thr Val Ser Ser Gly Gly Gly
            405                 410                 415

Gly Ser Gly Gly Gly Gly Ser Gly Gly Gly Gly Ser Gly Gly Gly Gly
            420                 425                 430

Ser Gly Gly Gly Gly Ser Gly Gly Gly Gly Ser Gln Ala Val Val Thr
            435                 440                 445

Gln Glu Pro Ser Leu Thr Val Ser Pro Gly Gly Thr Val Thr Leu Thr
    450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly Gly His
            485                 490                 495

Asn Asn Arg Pro Pro Gly Val Pro Ala Arg Phe Ser Gly Ser Leu Leu
            500                 505                 510

Gly Gly Lys Ala Ala Leu Thr Leu Leu Gly Ala Gln Pro Glu Asp Glu
            515                 520                 525

Ala Glu Tyr Tyr Cys Ala Leu Trp Tyr Ser Asp His Trp Val Ile Gly
    530                 535                 540

Gly Gly Thr Lys Leu Thr Val Leu Gly Thr Pro Leu Gly Asp Thr Thr
545                 550                 555                 560

His Thr Ser Gly Arg Ser Pro Asp Asp Glu Leu Leu Tyr Leu Pro Val
            565                 570                 575

Arg Gly Arg Glu Thr Tyr Glu Met Leu Leu Lys Ile Lys Glu Ser Leu
            580                 585                 590

Glu Leu Met Gln Tyr Leu Pro Gln His Thr Ile Glu Thr Tyr Arg Gln
            595                 600                 605

Gln Gln Gln Gln Gln His Gln His Leu Leu Gln Lys Gln Gly Gly Ser
    610                 615                 620

Gly Gly Ala
625

<210> SEQ ID NO 36
<211> LENGTH: 629
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Gly Trp Ser Cys Ile Ile Leu Phe Leu Val Ala Thr Ala Thr Gly
1               5                   10                  15

Asp Ile Gln Met Thr Gln Thr Thr Ser Ser Leu Ser Ala Ser Leu Gly
            20                  25                  30

Asp Arg Val Thr Ile Ser Cys Arg Ala Ser Gln Asp Ile Ser Lys Tyr
            35                  40                  45

Leu Asn Trp Tyr Gln Gln Lys Pro Asp Gly Thr Val Lys Leu Leu Ile
    50                  55                  60

Tyr His Thr Ser Arg Leu His Ser Gly Val Pro Ser Arg Phe Ser Gly
65                  70                  75                  80

Ser Gly Ser Gly Thr Asp Tyr Ser Leu Thr Ile Ser Asn Leu Glu Gln
            85                  90                  95

Glu Asp Ile Ala Thr Tyr Phe Cys Gln Gln Gly Asn Thr Leu Pro Tyr
            100                 105                 110

Thr Phe Gly Gly Gly Thr Lys Leu Glu Ile Thr Arg Gly Gly Gly Gly
            115                 120                 125
```

-continued

```
Ser Gly Gly Gly Gly Ser Gly Gly Gly Ser Gly Gly Gly Gly Ser
    130             135             140

Gly Gly Gly Gly Ser Gly Gly Gly Ser Glu Val Lys Leu Gln Glu
145             150             155             160

Ser Gly Pro Gly Leu Val Ala Pro Ser Gln Ser Leu Ser Val Thr Cys
            165             170             175

Thr Val Ser Gly Val Ser Leu Pro Asp Tyr Gly Val Ser Trp Ile Arg
            180             185             190

Gln Pro Pro Arg Lys Gly Leu Glu Trp Leu Gly Val Ile Trp Gly Ser
        195             200             205

Glu Thr Thr Tyr Tyr Asn Ser Ala Leu Lys Ser Arg Leu Thr Ile Ile
    210             215             220

Lys Asp Asn Ser Lys Ser Gln Val Phe Leu Lys Met Asn Ser Leu Gln
225             230             235             240

Thr Asp Asp Thr Ala Ile Tyr Tyr Cys Ala Lys His Tyr Tyr Tyr Gly
            245             250             255

Gly Ser Tyr Ala Met Asp Tyr Trp Gly Gln Gly Thr Ser Val Thr Val
            260             265             270

Ser Ser Gly Gly Gly Gly Ser Gly Gly Gly Gly Ser Gly Gly Gly Gly
        275             280             285

Ser Gly Gly Gly Gly Ser His Val Gln Leu Val Glu Ser Gly Gly Gly
    290             295             300

Leu Val Gln Pro Gly Gly Ser Leu Arg Leu Ser Cys Ala Ala Ser Gly
305             310             315             320

Phe Ser Leu Thr Asp Tyr Gly Val His Trp Val Arg Gln Ala Pro Gly
            325             330             335

Lys Gly Leu Glu Trp Leu Gly Val Ile Trp Ser Gly Gly Gly Thr Ala
        340             345             350

Tyr Asn Thr Ala Leu Ile Ser Arg Phe Thr Ile Ser Arg Asp Asn Ser
    355             360             365

Lys Asn Thr Leu Tyr Leu Gln Met Asn Ser Leu Arg Ala Glu Asp Thr
370             375             380

Ala Val Tyr Tyr Cys Ala Arg Arg Gly Ser Tyr Pro Tyr Asn Tyr Phe
385             390             395             400

Asp Ala Trp Gly Cys Gly Thr Leu Val Thr Val Ser Ser Gly Gly Gly
            405             410             415

Gly Ser Gly Gly Gly Gly Ser Gly Gly Gly Gly Ser Gly Gly Gly Gly
        420             425             430

Ser Gly Gly Gly Gly Ser Gly Gly Gly Gly Ser Gln Ala Val Val Thr
        435             440             445

Gln Glu Pro Ser Leu Thr Val Ser Pro Gly Gly Thr Val Thr Leu Thr
    450             455             460

Cys Gly Ser Ser Thr Gly Ala Val Thr Ala Ser Asn Tyr Ala Asn Trp
465             470             475             480

Val Gln Gln Lys Pro Gly Gln Cys Pro Arg Gly Leu Ile Gly Gly His
            485             490             495

Asn Asn Arg Pro Pro Gly Val Pro Ala Arg Phe Ser Gly Ser Leu Leu
        500             505             510

Gly Gly Lys Ala Ala Leu Thr Leu Leu Gly Ala Gln Pro Glu Asp Glu
        515             520             525

Ala Glu Tyr Tyr Cys Ala Leu Trp Tyr Ser Asp His Trp Val Ile Gly
    530             535             540
```

-continued

```
Gly Gly Thr Lys Leu Thr Val Leu Gly Thr Pro Leu Gly Asp Thr Thr
545             550             555             560

His Thr Ser Gly Arg His Gly Asp Glu Asp Thr Tyr Tyr Leu Gln Val
                565             570             575

Arg Gly Arg Glu Asn Phe Glu Ile Leu Met Lys Leu Lys Glu Ser Leu
            580             585             590

Glu Leu Met Glu Leu Val Pro Gln Pro Leu Val Asp Ser Tyr Arg Gln
        595             600             605

Gln Gln Gln Leu Leu Gln Arg Pro Gly Gly Ser Gly Gly Ala Pro His
    610             615             620

His His His His His
625
```

```
<210> SEQ ID NO 37
<211> LENGTH: 622
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Gly Trp Ser Cys Ile Ile Leu Phe Leu Val Ala Thr Ala Thr Gly
1               5               10              15

Asp Ile Gln Met Thr Gln Thr Thr Ser Ser Leu Ser Ala Ser Leu Gly
            20              25              30

Asp Arg Val Thr Ile Ser Cys Arg Ala Ser Gln Asp Ile Ser Lys Tyr
        35              40              45

Leu Asn Trp Tyr Gln Gln Lys Pro Asp Gly Thr Val Lys Leu Leu Ile
    50              55              60

Tyr His Thr Ser Arg Leu His Ser Gly Val Pro Ser Arg Phe Ser Gly
65              70              75              80

Ser Gly Ser Gly Thr Asp Tyr Ser Leu Thr Ile Ser Asn Leu Glu Gln
            85              90              95

Glu Asp Ile Ala Thr Tyr Phe Cys Gln Gln Gly Asn Thr Leu Pro Tyr
        100             105             110

Thr Phe Gly Gly Gly Thr Lys Leu Glu Ile Thr Arg Gly Gly Gly Gly
        115             120             125

Ser Gly Gly Gly Gly Ser Gly Gly Gly Gly Ser Gly Gly Gly Gly Ser
    130             135             140

Gly Gly Gly Gly Ser Gly Gly Gly Gly Ser Glu Val Lys Leu Gln Glu
145             150             155             160

Ser Gly Pro Gly Leu Val Ala Pro Ser Gln Ser Leu Ser Val Thr Cys
            165             170             175

Thr Val Ser Gly Val Ser Leu Pro Asp Tyr Gly Val Ser Trp Ile Arg
            180             185             190

Gln Pro Pro Arg Lys Gly Leu Glu Trp Leu Gly Val Ile Trp Gly Ser
        195             200             205

Glu Thr Thr Tyr Tyr Asn Ser Ala Leu Lys Ser Arg Leu Thr Ile Ile
        210             215             220

Lys Asp Asn Ser Lys Ser Gln Val Phe Leu Lys Met Asn Ser Leu Gln
225             230             235             240

Thr Asp Asp Thr Ala Ile Tyr Tyr Cys Ala Lys His Tyr Tyr Tyr Gly
            245             250             255

Gly Ser Tyr Ala Met Asp Tyr Trp Gly Gln Gly Thr Ser Val Thr Val
        260             265             270
```

```
Ser Ser Gly Gly Gly Gly Ser Gly Gly Gly Gly Ser Gly Gly Gly Gly
        275             280             285

Ser Gly Gly Gly Gly Ser His Val Gln Leu Val Glu Ser Gly Gly Gly
    290             295             300

Leu Val Gln Pro Gly Gly Ser Leu Arg Leu Ser Cys Ala Ala Ser Gly
305             310             315             320

Phe Ser Leu Thr Asp Tyr Gly Val His Trp Val Arg Gln Ala Pro Gly
            325             330             335

Lys Gly Leu Glu Trp Leu Gly Val Ile Trp Ser Gly Gly Thr Ala
        340             345             350

Tyr Asn Thr Ala Leu Ile Ser Arg Phe Thr Ile Ser Arg Asp Asn Ser
        355             360             365

Lys Asn Thr Leu Tyr Leu Gln Met Asn Ser Leu Arg Ala Glu Asp Thr
    370             375             380

Ala Val Tyr Tyr Cys Ala Arg Arg Gly Ser Tyr Pro Tyr Asn Tyr Phe
385             390             395             400

Asp Ala Trp Gly Cys Gly Thr Leu Val Thr Val Ser Ser Gly Gly Gly
            405             410             415

Gly Ser Gly Gly Gly Gly Ser Gly Gly Gly Gly Ser Gly Gly Gly Gly
        420             425             430

Ser Gly Gly Gly Gly Ser Gly Gly Gly Gly Ser Gln Ala Val Val Thr
        435             440             445

Gln Glu Pro Ser Leu Thr Val Ser Pro Gly Gly Thr Val Thr Leu Thr
    450             455             460

Cys Gly Ser Ser Thr Gly Ala Val Thr Ala Ser Asn Tyr Ala Asn Trp
465             470             475             480

Val Gln Gln Lys Pro Gly Gln Cys Pro Arg Gly Leu Ile Gly Gly His
            485             490             495

Asn Asn Arg Pro Pro Gly Val Pro Ala Arg Phe Ser Gly Ser Leu Leu
        500             505             510

Gly Gly Lys Ala Ala Leu Thr Leu Leu Gly Ala Gln Pro Glu Asp Glu
        515             520             525

Ala Glu Tyr Tyr Cys Ala Leu Trp Tyr Ser Asp His Trp Val Ile Gly
    530             535             540

Gly Gly Thr Lys Leu Thr Val Leu Gly Thr Pro Leu Gly Asp Thr Thr
545             550             555             560

His Thr Ser Gly Arg His Gly Asp Glu Asp Thr Tyr Tyr Leu Gln Val
            565             570             575

Arg Gly Arg Glu Asn Phe Glu Ile Leu Met Lys Leu Lys Glu Ser Leu
        580             585             590

Glu Leu Met Glu Leu Val Pro Gln Pro Leu Val Asp Ser Tyr Arg Gln
        595             600             605

Gln Gln Gln Leu Leu Gln Arg Pro Gly Gly Ser Gly Gly Ala
    610             615             620
```

<210> SEQ ID NO 38
<211> LENGTH: 616
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Gly Trp Ser Cys Ile Ile Leu Phe Leu Val Ala Thr Ala Thr Gly
```

-continued

```
1               5                    10                   15

Glu Val Lys Leu Gln Glu Ser Gly Pro Gly Leu Val Ala Pro Ser Gln
            20                  25                  30

Ser Leu Ser Val Thr Cys Thr Val Ser Gly Val Ser Leu Pro Asp Tyr
            35                  40                  45

Gly Val Ser Trp Ile Arg Gln Pro Pro Arg Lys Gly Leu Glu Trp Leu
    50                  55                  60

Gly Val Ile Trp Gly Ser Glu Thr Thr Tyr Tyr Asn Ser Ala Leu Lys
65                  70                  75                  80

Ser Arg Leu Thr Ile Ile Lys Asp Asn Ser Lys Ser Gln Val Phe Leu
                85                  90                  95

Lys Met Asn Ser Leu Gln Thr Asp Asp Thr Ala Ile Tyr Tyr Cys Ala
            100                 105                 110

Lys His Tyr Tyr Tyr Gly Gly Ser Tyr Ala Met Asp Tyr Trp Gly Gln
            115                 120                 125

Gly Thr Ser Val Thr Val Ser Ser Gly Gly Gly Ser Gly Gly Gly
            130                 135                 140

Gly Ser Gly Gly Gly Gly Ser Gly Gly Gly Ser Gly Gly Gly Gly
145                 150                 155                 160

Ser Gly Gly Gly Gly Ser Asp Ile Gln Met Thr Gln Thr Thr Ser Ser
                165                 170                 175

Leu Ser Ala Ser Leu Gly Asp Arg Val Thr Ile Ser Cys Arg Ala Ser
            180                 185                 190

Gln Asp Ile Ser Lys Tyr Leu Asn Trp Tyr Gln Gln Lys Pro Asp Gly
            195                 200                 205

Thr Val Lys Leu Leu Ile Tyr His Thr Ser Arg Leu His Ser Gly Val
    210                 215                 220

Pro Ser Arg Phe Ser Gly Ser Gly Ser Gly Thr Asp Tyr Ser Leu Thr
225                 230                 235                 240

Ile Ser Asn Leu Glu Gln Glu Asp Ile Ala Thr Tyr Phe Cys Gln Gln
            245                 250                 255

Gly Asn Thr Leu Pro Tyr Thr Phe Gly Gly Gly Thr Lys Leu Glu Ile
            260                 265                 270

Thr Arg Gly Gly Gly Gly Ser Gly Gly Gly Gly Ser Gly Gly Gly Gly
    275                 280                 285

Ser Gly Gly Gly Gly Ser His Val Gln Leu Val Glu Ser Gly Gly Gly
    290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
                325                 330                 335

Lys Gly Leu Glu Trp Leu Gly Val Ile Trp Ser Gly Gly Gly Thr Ala
            340                 345                 350

Tyr Asn Thr Ala Leu Ile Ser Arg Phe Thr Ile Ser Arg Asp Asn Ser
            355                 360                 365

Lys Asn Thr Leu Tyr Leu Gln Met Asn Ser Leu Arg Ala Glu Asp Thr
            370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
                405                 410                 415

Gly Ser Gly Gly Gly Gly Ser Gly Gly Gly Gly Ser Gly Gly Gly Gly
            420                 425                 430
```

-continued

```
Ser Gly Gly Gly Gly Ser Gly Gly Gly Gly Ser Gln Ala Val Val Thr
        435                 440                 445

Gln Glu Pro Ser Leu Thr Val Ser Pro Gly Gly Thr Val Thr Leu Thr
    450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly Gly His
                485                 490                 495

Asn Asn Arg Pro Pro Gly Val Pro Ala Arg Phe Ser Gly Ser Leu Leu
                500                 505                 510

Gly Gly Lys Ala Ala Leu Thr Leu Leu Gly Ala Gln Pro Glu Asp Glu
                515                 520                 525

Ala Glu Tyr Tyr Cys Ala Leu Trp Tyr Ser Asp His Trp Val Ile Gly
    530                 535                 540

Gly Gly Thr Lys Leu Thr Val Leu Gly Thr Pro Leu Gly Asp Thr Thr
545                 550                 555                 560

His Thr Ser Gly Lys Pro Leu Asp Gly Glu Tyr Phe Thr Leu Gln Ile
                565                 570                 575

Arg Gly Arg Glu Arg Phe Glu Met Phe Arg Glu Leu Asn Glu Ala Leu
                580                 585                 590

Glu Leu Lys Asp Ala Gln Ala Gly Lys Glu Pro Gly Gly Ser Gly Gly
                595                 600                 605

Ala Pro His His His His His His
    610                 615
```

```
<210> SEQ ID NO 39
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gly Trp Ser Cys Ile Ile Leu Phe Leu Val Ala Thr Ala Thr Gly
1               5                   10                  15

Glu Val Lys Leu Gln Glu Ser Gly Pro Gly Leu Val Ala Pro Ser Gln
                20                  25                  30

Ser Leu Ser Val Thr Cys Thr Val Ser Gly Val Ser Leu Pro Asp Tyr
            35                  40                  45

Gly Val Ser Trp Ile Arg Gln Pro Pro Arg Lys Gly Leu Glu Trp Leu
    50                  55                  60

Gly Val Ile Trp Gly Ser Glu Thr Thr Tyr Tyr Asn Ser Ala Leu Lys
65                  70                  75                  80

Ser Arg Leu Thr Ile Ile Lys Asp Asn Ser Lys Ser Gln Val Phe Leu
                85                  90                  95

Lys Met Asn Ser Leu Gln Thr Asp Asp Thr Ala Ile Tyr Tyr Cys Ala
                100                 105                 110

Lys His Tyr Tyr Tyr Gly Gly Ser Tyr Ala Met Asp Tyr Trp Gly Gln
                115                 120                 125

Gly Thr Ser Val Thr Val Ser Ser Gly Gly Gly Gly Ser Gly Gly Gly
                130                 135                 140

Gly Ser Gly Gly Gly Gly Ser Gly Gly Gly Gly Ser Gly Gly Gly Gly
145                 150                 155                 160

Ser Gly Gly Gly Gly Ser Asp Ile Gln Met Thr Gln Thr Thr Ser Ser
```

```
                  165                    170                    175

Leu Ser Ala Ser Leu Gly Asp Arg Val Thr Ile Ser Cys Arg Ala Ser
            180                    185                    190

Gln Asp Ile Ser Lys Tyr Leu Asn Trp Tyr Gln Gln Lys Pro Asp Gly
        195                    200                    205

Thr Val Lys Leu Leu Ile Tyr His Thr Ser Arg Leu His Ser Gly Val
    210                    215                    220

Pro Ser Arg Phe Ser Gly Ser Gly Ser Gly Thr Asp Tyr Ser Leu Thr
225                    230                    235                    240

Ile Ser Asn Leu Glu Gln Glu Asp Ile Ala Thr Tyr Phe Cys Gln Gln
                245                    250                    255

Gly Asn Thr Leu Pro Tyr Thr Phe Gly Gly Gly Thr Lys Leu Glu Ile
            260                    265                    270

Thr Arg Gly Gly Gly Gly Ser Gly Gly Gly Gly Ser Gly Gly Gly Gly
        275                    280                    285

Ser Gly Gly Gly Gly Ser His Val Gln Leu Val Glu Ser Gly Gly Gly
    290                    295                    300

Leu Val Gln Pro Gly Gly Ser Leu Arg Leu Ser Cys Ala Ala Ser Gly
305                    310                    315                    320

Phe Ser Leu Thr Asp Tyr Gly Val His Trp Val Arg Gln Ala Pro Gly
                325                    330                    335

Lys Gly Leu Glu Trp Leu Gly Val Ile Trp Ser Gly Gly Thr Ala
            340                    345                    350

Tyr Asn Thr Ala Leu Ile Ser Arg Phe Thr Ile Ser Arg Asp Asn Ser
        355                    360                    365

Lys Asn Thr Leu Tyr Leu Gln Met Asn Ser Leu Arg Ala Glu Asp Thr
    370                    375                    380

Ala Val Tyr Tyr Cys Ala Arg Arg Gly Ser Tyr Pro Tyr Asn Tyr Phe
385                    390                    395                    400

Asp Ala Trp Gly Cys Gly Thr Leu Val Thr Val Ser Ser Gly Gly Gly
                405                    410                    415

Gly Ser Gly Gly Gly Gly Ser Gly Gly Gly Gly Ser Gly Gly Gly Gly
            420                    425                    430

Ser Gly Gly Gly Gly Ser Gly Gly Gly Gly Ser Gln Ala Val Val Thr
        435                    440                    445

Gln Glu Pro Ser Leu Thr Val Ser Pro Gly Gly Thr Val Thr Leu Thr
    450                    455                    460

Cys Gly Ser Ser Thr Gly Ala Val Thr Ala Ser Asn Tyr Ala Asn Trp
465                    470                    475                    480

Val Gln Gln Lys Pro Gly Gln Cys Pro Arg Gly Leu Ile Gly Gly His
                485                    490                    495

Asn Asn Arg Pro Pro Gly Val Pro Ala Arg Phe Ser Gly Ser Leu Leu
            500                    505                    510

Gly Gly Lys Ala Ala Leu Thr Leu Leu Gly Ala Gln Pro Glu Asp Glu
        515                    520                    525

Ala Glu Tyr Tyr Cys Ala Leu Trp Tyr Ser Asp His Trp Val Ile Gly
    530                    535                    540

Gly Gly Thr Lys Leu Thr Val Leu Gly Thr Pro Leu Gly Asp Thr Thr
545                    550                    555                    560

His Thr Ser Gly Lys Pro Leu Asp Gly Glu Tyr Phe Thr Leu Gln Ile
                565                    570                    575

Arg Gly Arg Glu Arg Phe Glu Met Phe Arg Glu Leu Asn Glu Ala Leu
            580                    585                    590
```

```
Glu Leu Lys Asp Ala Gln Ala Gly Lys Glu Pro Gly Gly Ser Gly Gly
        595                 600                 605

Ala

<210> SEQ ID NO 40
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Gly Trp Ser Cys Ile Ile Leu Phe Leu Val Ala Thr Ala Thr Gly
1               5                   10                  15

Glu Val Lys Leu Gln Glu Ser Gly Pro Gly Leu Val Ala Pro Ser Gln
            20                  25                  30

Ser Leu Ser Val Thr Cys Thr Val Ser Gly Val Ser Leu Pro Asp Tyr
        35                  40                  45

Gly Val Ser Trp Ile Arg Gln Pro Pro Arg Lys Gly Leu Glu Trp Leu
    50                  55                  60

Gly Val Ile Trp Gly Ser Glu Thr Thr Tyr Tyr Asn Ser Ala Leu Lys
65                  70                  75                  80

Ser Arg Leu Thr Ile Ile Lys Asp Asn Ser Lys Ser Gln Val Phe Leu
                85                  90                  95

Lys Met Asn Ser Leu Gln Thr Asp Asp Thr Ala Ile Tyr Tyr Cys Ala
            100                 105                 110

Lys His Tyr Tyr Tyr Gly Gly Ser Tyr Ala Met Asp Tyr Trp Gly Gln
        115                 120                 125

Gly Thr Ser Val Thr Val Ser Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Gly Gly Gly Gly Ser Asp Ile Gln Met Thr Gln Thr Thr Ser Ser
                165                 170                 175

Leu Ser Ala Ser Leu Gly Asp Arg Val Thr Ile Ser Cys Arg Ala Ser
            180                 185                 190

Gln Asp Ile Ser Lys Tyr Leu Asn Trp Tyr Gln Gln Lys Pro Asp Gly
        195                 200                 205

Thr Val Lys Leu Leu Ile Tyr His Thr Ser Arg Leu His Ser Gly Val
    210                 215                 220

Pro Ser Arg Phe Ser Gly Ser Gly Ser Gly Thr Asp Tyr Ser Leu Thr
225                 230                 235                 240

Ile Ser Asn Leu Glu Gln Glu Asp Ile Ala Thr Tyr Phe Cys Gln Gln
                245                 250                 255

Gly Asn Thr Leu Pro Tyr Thr Phe Gly Gly Gly Thr Lys Leu Glu Ile
            260                 265                 270

Thr Arg Gly Gly Gly Gly Ser Gly Gly Gly Gly Ser Gly Gly Gly Gly
        275                 280                 285

Ser Gly Gly Gly Gly Ser His Val Gln Leu Val Glu Ser Gly Gly Gly
        290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
                325                 330                 335
```

```
Lys Gly Leu Glu Trp Leu Gly Val Ile Trp Ser Gly Gly Thr Ala
        340                 345                 350

Tyr Asn Thr Ala Leu Ile Ser Arg Phe Thr Ile Ser Arg Asp Asn Ser
        355                 360                 365

Lys Asn Thr Leu Tyr Leu Gln Met Asn Ser Leu Arg Ala Glu Asp Thr
        370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
                405                 410                 415

Gly Ser Gly Gly Gly Gly Ser Gly Gly Gly Gly Ser Gly Gly Gly Gly
                420                 425                 430

Ser Gly Gly Gly Gly Ser Gly Gly Gly Gly Ser Gln Ala Val Val Thr
                435                 440                 445

Gln Glu Pro Ser Leu Thr Val Ser Pro Gly Gly Thr Val Thr Leu Thr
        450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly Gly His
                485                 490                 495

Asn Asn Arg Pro Pro Gly Val Pro Ala Arg Phe Ser Gly Ser Leu Leu
                500                 505                 510

Gly Gly Lys Ala Ala Leu Thr Leu Leu Gly Ala Gln Pro Glu Asp Glu
                515                 520                 525

Ala Glu Tyr Tyr Cys Ala Leu Trp Tyr Ser Asp His Trp Val Ile Gly
        530                 535                 540

Gly Gly Thr Lys Leu Thr Val Leu Gly Thr Pro Leu Gly Asp Thr Thr
545                 550                 555                 560

His Thr Ser Gly Arg Ser Pro Asp Asp Glu Leu Leu Tyr Leu Pro Val
                565                 570                 575

Arg Gly Arg Glu Thr Tyr Glu Met Leu Leu Lys Ile Lys Glu Ser Leu
                580                 585                 590

Glu Leu Met Gln Tyr Leu Pro Gln His Thr Ile Glu Thr Tyr Arg Gln
        595                 600                 605

Gln Gln Gln Gln Gln His Gln His Leu Leu Gln Lys Gln Gly Gly Ser
        610                 615                 620

Gly Gly Ala Pro His His His His His His
625                 630

<210> SEQ ID NO 41
<211> LENGTH: 627
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gly Trp Ser Cys Ile Ile Leu Phe Leu Val Ala Thr Ala Thr Gly
1               5                   10                  15

Glu Val Lys Leu Gln Glu Ser Gly Pro Gly Leu Val Ala Pro Ser Gln
            20                  25                  30

Ser Leu Ser Val Thr Cys Thr Val Ser Gly Val Ser Leu Pro Asp Tyr
        35                  40                  45

Gly Val Ser Trp Ile Arg Gln Pro Pro Arg Lys Gly Leu Glu Trp Leu
```

-continued

```
            50                  55                  60

Gly Val Ile Trp Gly Ser Glu Thr Thr Tyr Tyr Asn Ser Ala Leu Lys
65                  70                  75                  80

Ser Arg Leu Thr Ile Ile Lys Asp Asn Ser Lys Ser Gln Val Phe Leu
                85                  90                  95

Lys Met Asn Ser Leu Gln Thr Asp Asp Thr Ala Ile Tyr Tyr Cys Ala
                100                 105                 110

Lys His Tyr Tyr Tyr Gly Gly Ser Tyr Ala Met Asp Tyr Trp Gly Gln
                115                 120                 125

Gly Thr Ser Val Thr Val Ser Ser Gly Gly Gly Ser Gly Gly Gly
                130                 135                 140

Gly Ser Gly Gly Gly Gly Ser Gly Gly Gly Ser Gly Gly Gly Gly
145                 150                 155                 160

Ser Gly Gly Gly Gly Ser Asp Ile Gln Met Thr Gln Thr Thr Ser Ser
                165                 170                 175

Leu Ser Ala Ser Leu Gly Asp Arg Val Thr Ile Ser Cys Arg Ala Ser
                180                 185                 190

Gln Asp Ile Ser Lys Tyr Leu Asn Trp Tyr Gln Gln Lys Pro Asp Gly
                195                 200                 205

Thr Val Lys Leu Leu Ile Tyr His Thr Ser Arg Leu His Ser Gly Val
                210                 215                 220

Pro Ser Arg Phe Ser Gly Ser Gly Ser Gly Thr Asp Tyr Ser Leu Thr
225                 230                 235                 240

Ile Ser Asn Leu Glu Gln Glu Asp Ile Ala Thr Tyr Phe Cys Gln Gln
                245                 250                 255

Gly Asn Thr Leu Pro Tyr Thr Phe Gly Gly Gly Thr Lys Leu Glu Ile
                260                 265                 270

Thr Arg Gly Gly Gly Gly Ser Gly Gly Gly Gly Ser Gly Gly Gly Gly
                275                 280                 285

Ser Gly Gly Gly Gly Ser His Val Gln Leu Val Glu Ser Gly Gly Gly
                290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
                325                 330                 335

Lys Gly Leu Glu Trp Leu Gly Val Ile Trp Ser Gly Gly Thr Ala
                340                 345                 350

Tyr Asn Thr Ala Leu Ile Ser Arg Phe Thr Ile Ser Arg Asp Asn Ser
                355                 360                 365

Lys Asn Thr Leu Tyr Leu Gln Met Asn Ser Leu Arg Ala Glu Asp Thr
                370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
                405                 410                 415

Gly Ser Gly Gly Gly Gly Ser Gly Gly Gly Ser Gly Gly Gly Gly
                420                 425                 430

Ser Gly Gly Gly Gly Ser Gly Gly Gly Gly Ser Gln Ala Val Val Thr
                435                 440                 445

Gln Glu Pro Ser Leu Thr Val Ser Pro Gly Gly Thr Val Thr Leu Thr
                450                 455                 460

Cys Gly Ser Ser Thr Gly Ala Val Thr Ala Ser Asn Tyr Ala Asn Trp
465                 470                 475                 480
```

```
Val Gln Gln Lys Pro Gly Gln Cys Pro Arg Gly Leu Ile Gly Gly His
              485             490             495

Asn Asn Arg Pro Pro Gly Val Pro Ala Arg Phe Ser Gly Ser Leu Leu
              500             505             510

Gly Gly Lys Ala Ala Leu Thr Leu Leu Gly Ala Gln Pro Glu Asp Glu
              515             520             525

Ala Glu Tyr Tyr Cys Ala Leu Trp Tyr Ser Asp His Trp Val Ile Gly
              530             535             540

Gly Gly Thr Lys Leu Thr Val Leu Gly Thr Pro Leu Gly Asp Thr Thr
545             550             555             560

His Thr Ser Gly Arg Ser Pro Asp Asp Glu Leu Leu Tyr Leu Pro Val
              565             570             575

Arg Gly Arg Glu Thr Tyr Glu Met Leu Leu Lys Ile Lys Glu Ser Leu
              580             585             590

Glu Leu Met Gln Tyr Leu Pro Gln His Thr Ile Glu Thr Tyr Arg Gln
              595             600             605

Gln Gln Gln Gln His Gln His Leu Leu Gln Lys Gln Gly Gly Ser
      610             615             620

Gly Gly Ala
625
```

```
<210> SEQ ID NO 42
<211> LENGTH: 629
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42
```

```
Met Gly Trp Ser Cys Ile Ile Leu Phe Leu Val Ala Thr Ala Thr Gly
1               5               10              15

Glu Val Lys Leu Gln Glu Ser Gly Pro Gly Leu Val Ala Pro Ser Gln
              20              25              30

Ser Leu Ser Val Thr Cys Thr Val Ser Gly Val Ser Leu Pro Asp Tyr
              35              40              45

Gly Val Ser Trp Ile Arg Gln Pro Pro Arg Lys Gly Leu Glu Trp Leu
      50              55              60

Gly Val Ile Trp Gly Ser Glu Thr Thr Tyr Tyr Asn Ser Ala Leu Lys
65              70              75              80

Ser Arg Leu Thr Ile Ile Lys Asp Asn Ser Lys Ser Gln Val Phe Leu
              85              90              95

Lys Met Asn Ser Leu Gln Thr Asp Asp Thr Ala Ile Tyr Tyr Cys Ala
              100             105             110

Lys His Tyr Tyr Tyr Gly Gly Ser Tyr Ala Met Asp Tyr Trp Gly Gln
              115             120             125

Gly Thr Ser Val Thr Val Ser Ser Gly Gly Gly Ser Gly Gly Gly Gly
              130             135             140

Gly Ser Gly Gly Gly Gly Ser Gly Gly Gly Ser Gly Gly Gly Gly
145             150             155             160

Ser Gly Gly Gly Gly Ser Asp Ile Gln Met Thr Gln Thr Thr Ser Ser
              165             170             175

Leu Ser Ala Ser Leu Gly Asp Arg Val Thr Ile Ser Cys Arg Ala Ser
              180             185             190

Gln Asp Ile Ser Lys Tyr Leu Asn Trp Tyr Gln Gln Lys Pro Asp Gly
```

-continued

```
              195                 200                 205
Thr Val Lys Leu Leu Ile Tyr His Thr Ser Arg Leu His Ser Gly Val
    210                 215                 220

Pro Ser Arg Phe Ser Gly Ser Gly Ser Gly Thr Asp Tyr Ser Leu Thr
225                 230                 235                 240

Ile Ser Asn Leu Glu Gln Glu Asp Ile Ala Thr Tyr Phe Cys Gln Gln
                245                 250                 255

Gly Asn Thr Leu Pro Tyr Thr Phe Gly Gly Gly Thr Lys Leu Glu Ile
                260                 265                 270

Thr Arg Gly Gly Gly Gly Ser Gly Gly Gly Gly Ser Gly Gly Gly Gly
                275                 280                 285

Ser Gly Gly Gly Gly Ser His Val Gln Leu Val Glu Ser Gly Gly Gly
    290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
                325                 330                 335

Lys Gly Leu Glu Trp Leu Gly Val Ile Trp Ser Gly Gly Thr Ala
                340                 345                 350

Tyr Asn Thr Ala Leu Ile Ser Arg Phe Thr Ile Ser Arg Asp Asn Ser
                355                 360                 365

Lys Asn Thr Leu Tyr Leu Gln Met Asn Ser Leu Arg Ala Glu Asp Thr
    370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
                405                 410                 415

Gly Ser Gly Gly Gly Gly Ser Gly Gly Gly Gly Ser Gly Gly Gly Gly
                420                 425                 430

Ser Gly Gly Gly Gly Ser Gly Gly Gly Gly Ser Gln Ala Val Val Thr
                435                 440                 445

Gln Glu Pro Ser Leu Thr Val Ser Pro Gly Gly Thr Val Thr Leu Thr
    450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly Gly His
                485                 490                 495

Asn Asn Arg Pro Pro Gly Val Pro Ala Arg Phe Ser Gly Ser Leu Leu
                500                 505                 510

Gly Gly Lys Ala Ala Leu Thr Leu Leu Gly Ala Gln Pro Glu Asp Glu
                515                 520                 525

Ala Glu Tyr Tyr Cys Ala Leu Trp Tyr Ser Asp His Trp Val Ile Gly
    530                 535                 540

Gly Gly Thr Lys Leu Thr Val Leu Gly Thr Pro Leu Gly Asp Thr Thr
545                 550                 555                 560

His Thr Ser Gly Arg His Gly Asp Glu Asp Thr Tyr Tyr Leu Gln Val
                565                 570                 575

Arg Gly Arg Glu Asn Phe Glu Ile Leu Met Lys Leu Lys Glu Ser Leu
                580                 585                 590

Glu Leu Met Glu Leu Val Pro Gln Pro Leu Val Asp Ser Tyr Arg Gln
                595                 600                 605

Gln Gln Gln Leu Leu Gln Arg Pro Gly Gly Ser Gly Gly Ala Pro His
    610                 615                 620
```

```
His His His His His
625

<210> SEQ ID NO 43
<211> LENGTH: 622
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Trp Ser Cys Ile Ile Leu Phe Leu Val Ala Thr Ala Thr Gly
1               5                   10                  15

Glu Val Lys Leu Gln Glu Ser Gly Pro Gly Leu Val Ala Pro Ser Gln
            20                  25                  30

Ser Leu Ser Val Thr Cys Thr Val Ser Gly Val Ser Leu Pro Asp Tyr
        35                  40                  45

Gly Val Ser Trp Ile Arg Gln Pro Pro Arg Lys Gly Leu Glu Trp Leu
    50                  55                  60

Gly Val Ile Trp Gly Ser Glu Thr Thr Tyr Tyr Asn Ser Ala Leu Lys
65                  70                  75                  80

Ser Arg Leu Thr Ile Ile Lys Asp Asn Ser Lys Ser Gln Val Phe Leu
            85                  90                  95

Lys Met Asn Ser Leu Gln Thr Asp Asp Thr Ala Ile Tyr Tyr Cys Ala
            100                 105                 110

Lys His Tyr Tyr Tyr Gly Gly Ser Tyr Ala Met Asp Tyr Trp Gly Gln
        115                 120                 125

Gly Thr Ser Val Thr Val Ser Ser Gly Gly Gly Gly Ser Gly Gly Gly
    130                 135                 140

Gly Ser Gly Gly Gly Gly Ser Gly Gly Gly Ser Gly Gly Gly Gly
145                 150                 155                 160

Ser Gly Gly Gly Gly Ser Asp Ile Gln Met Thr Gln Thr Thr Ser Ser
            165                 170                 175

Leu Ser Ala Ser Leu Gly Asp Arg Val Thr Ile Ser Cys Arg Ala Ser
            180                 185                 190

Gln Asp Ile Ser Lys Tyr Leu Asn Trp Tyr Gln Gln Lys Pro Asp Gly
        195                 200                 205

Thr Val Lys Leu Leu Ile Tyr His Thr Ser Arg Leu His Ser Gly Val
    210                 215                 220

Pro Ser Arg Phe Ser Gly Ser Gly Ser Gly Thr Asp Tyr Ser Leu Thr
225                 230                 235                 240

Ile Ser Asn Leu Glu Gln Glu Asp Ile Ala Thr Tyr Phe Cys Gln Gln
            245                 250                 255

Gly Asn Thr Leu Pro Tyr Thr Phe Gly Gly Gly Thr Lys Leu Glu Ile
            260                 265                 270

Thr Arg Gly Gly Gly Gly Ser Gly Gly Gly Gly Ser Gly Gly Gly Gly
        275                 280                 285

Ser Gly Gly Gly Gly Ser His Val Gln Leu Val Glu Ser Gly Gly Gly
    290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
            325                 330                 335

Lys Gly Leu Glu Trp Leu Gly Val Ile Trp Ser Gly Gly Gly Thr Ala
```

-continued

```
              340                 345                 350
Tyr Asn Thr Ala Leu Ile Ser Arg Phe Thr Ile Ser Arg Asp Asn Ser
         355                 360                 365
Lys Asn Thr Leu Tyr Leu Gln Met Asn Ser Leu Arg Ala Glu Asp Thr
     370                 375                 380
Ala Val Tyr Tyr Cys Ala Arg Arg Gly Ser Tyr Pro Tyr Asn Tyr Phe
385                 390                 395                 400
Asp Ala Trp Gly Cys Gly Thr Leu Val Thr Val Ser Ser Gly Gly Gly
                 405                 410                 415
Gly Ser Gly Gly Gly Gly Ser Gly Gly Gly Ser Gly Gly Gly Gly
                 420                 425                 430
Ser Gly Gly Gly Gly Ser Gly Gly Gly Gly Ser Gln Ala Val Val Thr
             435                 440                 445
Gln Glu Pro Ser Leu Thr Val Ser Pro Gly Gly Thr Val Thr Leu Thr
         450                 455                 460
Cys Gly Ser Ser Thr Gly Ala Val Thr Ala Ser Asn Tyr Ala Asn Trp
465                 470                 475                 480
Val Gln Gln Lys Pro Gly Gln Cys Pro Arg Gly Leu Ile Gly Gly His
                 485                 490                 495
Asn Asn Arg Pro Pro Gly Val Pro Ala Arg Phe Ser Gly Ser Leu Leu
                 500                 505                 510
Gly Gly Lys Ala Ala Leu Thr Leu Leu Gly Ala Gln Pro Glu Asp Glu
             515                 520                 525
Ala Glu Tyr Tyr Cys Ala Leu Trp Tyr Ser Asp His Trp Val Ile Gly
         530                 535                 540
Gly Gly Thr Lys Leu Thr Val Leu Gly Thr Pro Leu Gly Asp Thr Thr
545                 550                 555                 560
His Thr Ser Gly Arg His Gly Asp Glu Asp Thr Tyr Tyr Leu Gln Val
                 565                 570                 575
Arg Gly Arg Glu Asn Phe Glu Ile Leu Met Lys Leu Lys Glu Ser Leu
                 580                 585                 590
Glu Leu Met Glu Leu Val Pro Gln Pro Leu Val Asp Ser Tyr Arg Gln
             595                 600                 605
Gln Gln Gln Leu Leu Gln Arg Pro Gly Gly Ser Gly Gly Ala
     610                 615                 620
```

```
<210> SEQ ID NO 44
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Gly Trp Ser Cys Ile Ile Leu Phe Leu Val Ala Thr Ala Thr Gly
1               5                  10                  15
Asp Ile Gln Met Thr Gln Ser Pro Ser Ser Leu Ser Ala Ser Val Gly
             20                  25                  30
Asp Arg Val Thr Ile Thr Cys Gln Ala Ser Gln Asp Ile Ser Lys Tyr
         35                  40                  45
Leu Asn Trp Tyr Gln Gln Lys Pro Gly Lys Ala Val Lys Leu Leu Ile
     50                  55                  60
Tyr His Thr Ser Arg Leu His Ser Gly Val Pro Ser Arg Phe Ser Gly
65                  70                  75                  80
```

-continued

```
Ser Gly Ser Gly Thr Asp Tyr Thr Leu Thr Ile Ser Ser Leu Gln Pro
                85              90                  95

Glu Asp Ile Ala Thr Tyr Phe Cys Gln Gln Gly Asn Thr Leu Pro Tyr
            100             105             110

Thr Phe Gly Gly Gly Thr Lys Leu Glu Ile Thr Arg Thr Val Ala Ala
        115             120             125

Pro Ser Val Phe Ile Phe Pro Pro Ser Asp Glu Gln Leu Lys Ser Gly
    130             135             140

Thr Ala Ser Val Val Cys Leu Leu Asn Asn Phe Tyr Pro Arg Glu Ala
145             150             155             160

Lys Val Gln Trp Lys Val Asp Asn Ala Leu Gln Ser Gly Asn Ser Gln
                165             170             175

Glu Ser Val Thr Glu Gln Asp Ser Lys Asp Ser Thr Tyr Ser Leu Ser
            180             185             190

Ser Thr Leu Thr Leu Ser Lys Ala Asp Tyr Glu Lys His Lys Val Tyr
        195             200             205

Ala Cys Glu Val Thr His Gln Gly Leu Ser Ser Pro Val Thr Lys Ser
    210             215             220

Phe Asn Arg Gly Glu Cys Thr Ser Gly Gly Gly Ser Gly Gly Gly
225             230             235             240

Gly Ser Gly Gly Gly Gly Ser His Val Lys Leu Gln Glu Ser Gly Pro
        245             250             255

Gly Leu Val Gln Pro Ser Gln Ser Leu Ser Leu Thr Cys Thr Val Ser
        260             265             270

Gly Phe Ser Leu Thr Asp Tyr Gly Val His Trp Val Arg Gln Ser Pro
        275             280             285

Gly Lys Gly Leu Glu Trp Leu Gly Val Ile Trp Ser Gly Gly Gly Thr
    290             295             300

Ala Tyr Asn Thr Ala Leu Ile Ser Arg Leu Asn Ile Tyr Arg Asp Asn
305             310             315             320

Ser Lys Asn Gln Val Phe Leu Glu Met Asn Ser Leu Gln Ala Glu Asp
            325             330             335

Thr Ala Met Tyr Tyr Cys Ala Arg Arg Gly Ser Tyr Pro Tyr Asn Tyr
            340             345             350

Phe Asp Ala Trp Gly Cys Gly Thr Thr Val Thr Val Ser Ser Gly Gly
        355             360             365

Gly Gly Ser Gly Gly Gly Gly Ser Gly Gly Gly Gly Ser Gly Gly Gly
    370             375             380

Gly Ser Gly Gly Gly Gly Ser Gly Gly Gly Gly Ser Gln Ala Val Val
385             390             395             400

Ile Gln Glu Ser Ala Leu Thr Thr Pro Pro Gly Glu Thr Val Thr Leu
            405             410             415

Thr Cys Gly Ser Ser Thr Gly Ala Val Thr Ala Ser Asn Tyr Ala Asn
            420             425             430

Trp Val Gln Glu Lys Pro Asp His Cys Phe Thr Gly Leu Ile Gly Gly
            435             440             445

His Asn Asn Arg Pro Pro Gly Val Pro Ala Arg Phe Ser Gly Ser Leu
    450             455             460

Ile Gly Asp Lys Ala Ala Leu Thr Ile Ala Gly Thr Gln Thr Glu Asp
465             470             475             480

Glu Ala Ile Tyr Phe Cys Ala Leu Trp Tyr Ser Asp His Trp Val Ile
            485             490             495

Gly Gly Gly Thr Arg Leu Thr Val Leu Gly
```

-continued

```
                    500                    505

<210> SEQ ID NO 45
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly Trp Ser Cys Ile Ile Leu Phe Leu Val Ala Thr Ala Thr Gly
1               5                   10                  15

Gln Val Gln Leu Gln Glu Ser Gly Pro Gly Leu Val Lys Pro Ser Glu
                20                  25                  30

Thr Leu Ser Val Thr Cys Thr Val Ser Gly Val Ser Leu Pro Asp Tyr
            35                  40                  45

Gly Val Ser Trp Ile Arg Gln Pro Pro Gly Lys Gly Leu Glu Trp Ile
        50                  55                  60

Gly Val Ile Trp Gly Ser Glu Thr Thr Tyr Tyr Asn Pro Ser Leu Lys
65                  70                  75                  80

Ser Arg Val Thr Ile Ser Val Asp Thr Ser Lys Asn Gln Val Ser Leu
                85                  90                  95

Lys Leu Ser Ser Val Thr Ala Ala Asp Thr Ala Val Tyr Tyr Cys Ala
                100                 105                 110

Lys His Tyr Tyr Tyr Gly Gly Ser Tyr Ala Met Asp Tyr Trp Gly Gln
            115                 120                 125

Gly Thr Ser Val Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
        210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
            290                 295                 300

Asn Ala Lys Thr Lys Pro Arg Glu Glu Gln Tyr Ala Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Ala Val Ser Asn Lys Ala Leu Pro Ala Pro Ile Glu
                340                 345                 350
```

```
Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

```
<210> SEQ ID NO 46
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Gly Trp Ser Cys Ile Ile Leu Phe Leu Val Ala Thr Ala Thr Gly
1               5                   10                  15

Asp Ile Gln Met Thr Gln Ser Pro Ser Ser Leu Ser Ala Ser Val Gly
                20                  25                  30

Asp Arg Val Thr Ile Thr Cys Gln Ala Ser Gln Asp Ile Ser Lys Tyr
            35                  40                  45

Leu Asn Trp Tyr Gln Gln Lys Pro Gly Lys Ala Val Lys Leu Leu Ile
    50                  55                  60

Tyr His Thr Ser Arg Leu His Ser Gly Val Pro Ser Arg Phe Ser Gly
65                  70                  75                  80

Ser Gly Ser Gly Thr Asp Tyr Thr Leu Thr Ile Ser Ser Leu Gln Pro
                85                  90                  95

Glu Asp Ile Ala Thr Tyr Phe Cys Gln Gln Gly Asn Thr Leu Pro Tyr
                100                 105                 110

Thr Phe Gly Gly Gly Thr Lys Leu Glu Ile Thr Arg Thr Val Ala Ala
        115                 120                 125

Pro Ser Val Phe Ile Phe Pro Pro Ser Asp Glu Gln Leu Lys Ser Gly
        130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
                180                 185                 190

Ser Thr Leu Thr Leu Ser Lys Ala Asp Tyr Glu Lys His Lys Val Tyr
            195                 200                 205

Ala Cys Glu Val Thr His Gln Gly Leu Ser Ser Pro Val Thr Lys Ser
    210                 215                 220

Phe Asn Arg Gly Glu Cys Thr Ser Gly Gly Gly Gly Ser Gly Gly Gly
225                 230                 235                 240
```

-continued

```
Gly Ser Gly Gly Gly Gly Ser His Val Gln Leu Val Glu Ser Gly Gly
                245                 250                 255

Gly Leu Val Gln Pro Gly Gly Ser Leu Arg Leu Ser Cys Ala Ala Ser
                260                 265                 270

Gly Phe Ser Leu Thr Asp Tyr Gly Val His Trp Val Arg Gln Ala Pro
                275                 280                 285

Gly Lys Gly Leu Glu Trp Leu Gly Val Ile Trp Ser Gly Gly Gly Thr
        290                 295                 300

Ala Tyr Asn Thr Ala Leu Ile Ser Arg Phe Thr Ile Ser Arg Asp Asn
305                 310                 315                 320

Ser Lys Asn Thr Leu Tyr Leu Gln Met Asn Ser Leu Arg Ala Glu Asp
                325                 330                 335

Thr Ala Val Tyr Tyr Cys Ala Arg Arg Gly Ser Tyr Pro Tyr Asn Tyr
                340                 345                 350

Phe Asp Ala Trp Gly Cys Gly Thr Leu Val Thr Val Ser Ser Gly Gly
                355                 360                 365

Gly Gly Ser Gly Gly Gly Gly Ser Gly Gly Gly Gly Ser Gly Gly Gly
        370                 375                 380

Gly Ser Gly Gly Gly Gly Ser Gly Gly Gly Gly Ser Gln Ala Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ala Ser Asn Tyr Ala Asn
                420                 425                 430

Trp Val Gln Gln Lys Pro Gly Gln Cys Pro Arg Gly Leu Ile Gly Gly
        435                 440                 445

His Asn Asn Arg Pro Pro Gly Val Pro Ala Arg Phe Ser Gly Ser Leu
        450                 455                 460

Leu Gly Gly Lys Ala Ala Leu Thr Leu Leu Gly Ala Gln Pro Glu Asp
465                 470                 475                 480

Glu Ala Glu Tyr Tyr Cys Ala Leu Trp Tyr Ser Asp His Trp Val Ile
                485                 490                 495

Gly Gly Gly Thr Lys Leu Thr Val Leu Gly
                500                 505
```

<210> SEQ ID NO 47
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Met Gly Trp Ser Cys Ile Ile Leu Phe Leu Val Ala Thr Ala Thr Gly
1                   5                   10                  15

Gln Val Gln Leu Gln Glu Ser Gly Pro Gly Leu Val Lys Pro Ser Glu
                20                  25                  30

Thr Leu Ser Val Thr Cys Thr Val Ser Gly Val Ser Leu Pro Asp Tyr
        35                  40                  45

Gly Val Ser Trp Ile Arg Gln Pro Pro Gly Lys Gly Leu Glu Trp Ile
        50                  55                  60

Gly Val Ile Trp Gly Ser Glu Thr Thr Tyr Tyr Asn Pro Ser Leu Lys
65                  70                  75                  80

Ser Arg Val Thr Ile Ser Val Asp Thr Ser Lys Asn Gln Val Ser Leu
```

-continued

```
              85                    90                    95

Lys Leu Ser Ser Val Thr Ala Ala Asp Thr Ala Val Tyr Tyr Cys Ala
             100                   105                   110

Lys His Tyr Tyr Tyr Gly Gly Ser Tyr Ala Met Asp Tyr Trp Gly Gln
             115                   120                   125

Gly Thr Ser Val Thr Val Ser Ser Ala Ser Thr Lys Gly Pro Ser Val
         130                   135                   140

Phe Pro Leu Ala Pro Ser Ser Lys Ser Thr Ser Gly Gly Thr Ala Ala
145                   150                   155                   160

Leu Gly Cys Leu Val Lys Asp Tyr Phe Pro Glu Pro Val Thr Val Ser
             165                   170                   175

Trp Asn Ser Gly Ala Leu Thr Ser Gly Val His Thr Phe Pro Ala Val
             180                   185                   190

Leu Gln Ser Ser Gly Leu Tyr Ser Leu Ser Ser Val Val Thr Val Pro
             195                   200                   205

Ser Ser Ser Leu Gly Thr Gln Thr Tyr Ile Cys Asn Val Asn His Lys
         210                   215                   220

Pro Ser Asn Thr Lys Val Asp Lys Arg Val Glu Pro Lys Ser Cys Asp
225                   230                   235                   240

Lys Thr His Thr Cys Pro Pro Cys Pro Ala Pro Glu Leu Leu Gly Gly
             245                   250                   255

Pro Ser Val Phe Leu Phe Pro Pro Lys Pro Lys Asp Thr Leu Met Ile
             260                   265                   270

Ser Arg Thr Pro Glu Val Thr Cys Val Val Val Asp Val Ser His Glu
             275                   280                   285

Asp Pro Glu Val Lys Phe Asn Trp Tyr Val Asp Gly Val Glu Val His
         290                   295                   300

Asn Ala Lys Thr Lys Pro Arg Glu Glu Gln Tyr Ala Ser Thr Tyr Arg
305                   310                   315                   320

Val Val Ser Val Leu Thr Val Leu His Gln Asp Trp Leu Asn Gly Lys
             325                   330                   335

Glu Tyr Lys Cys Ala Val Ser Asn Lys Ala Leu Pro Ala Pro Ile Glu
             340                   345                   350

Lys Thr Ile Ser Lys Ala Lys Gly Gln Pro Arg Glu Pro Gln Val Tyr
             355                   360                   365

Thr Leu Pro Pro Ser Arg Asp Glu Leu Thr Lys Asn Gln Val Ser Leu
         370                   375                   380

Thr Cys Leu Val Lys Gly Phe Tyr Pro Ser Asp Ile Ala Val Glu Trp
385                   390                   395                   400

Glu Ser Asn Gly Gln Pro Glu Asn Asn Tyr Lys Thr Thr Pro Pro Val
             405                   410                   415

Leu Asp Ser Asp Gly Ser Phe Phe Leu Tyr Ser Lys Leu Thr Val Asp
             420                   425                   430

Lys Ser Arg Trp Gln Gln Gly Asn Val Phe Ser Cys Ser Val Met His
             435                   440                   445

Glu Ala Leu His Asn His Tyr Thr Gln Lys Ser Leu Ser Leu Ser Pro
         450                   455                   460

Gly Lys
465
```

```
<210> SEQ ID NO 48
<211> LENGTH: 616
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 48

Met Gly Trp Ser Cys Ile Ile Leu Phe Leu Val Ala Thr Ala Thr Gly
1               5                   10                  15

Asp Ile Gln Met Thr Gln Ser Pro Ser Ser Leu Ser Ala Ser Val Gly
                20                  25                  30

Asp Arg Val Thr Ile Thr Cys Gln Ala Ser Gln Asp Ile Ser Lys Tyr
            35                  40                  45

Leu Asn Trp Tyr Gln Gln Lys Pro Gly Lys Ala Val Lys Leu Leu Ile
        50                  55                  60

Tyr His Thr Ser Arg Leu His Ser Gly Val Pro Ser Arg Phe Ser Gly
65                  70                  75                  80

Ser Gly Ser Gly Thr Asp Tyr Thr Leu Thr Ile Ser Ser Leu Gln Pro
                85                  90                  95

Glu Asp Ile Ala Thr Tyr Phe Cys Gln Gln Gly Asn Thr Leu Pro Tyr
            100                 105                 110

Thr Phe Gly Gly Gly Thr Lys Leu Glu Ile Thr Arg Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Gln Val Gln Leu Gln Glu
145                 150                 155                 160

Ser Gly Pro Gly Leu Val Lys Pro Ser Glu Thr Leu Ser Val Thr Cys
                165                 170                 175

Thr Val Ser Gly Val Ser Leu Pro Asp Tyr Gly Val Ser Trp Ile Arg
                180                 185                 190

Gln Pro Pro Gly Lys Gly Leu Glu Trp Ile Gly Val Ile Trp Gly Ser
            195                 200                 205

Glu Thr Thr Tyr Tyr Asn Pro Ser Leu Lys Ser Arg Val Thr Ile Ser
    210                 215                 220

Val Asp Thr Ser Lys Asn Gln Val Ser Leu Lys Leu Ser Ser Val Thr
225                 230                 235                 240

Ala Ala Asp Thr Ala Val Tyr Tyr Cys Ala Lys His Tyr Tyr Tyr Gly
            245                 250                 255

Gly Ser Tyr Ala Met Asp Tyr Trp Gly Gln Gly Thr Ser Val Thr Val
            260                 265                 270

Ser Ser Gly Gly Gly Gly Ser Gly Gly Gly Gly Ser Gly Gly Gly Gly
        275                 280                 285

Ser Gly Gly Gly Gly Ser His Val Gln Leu Val Glu Ser Gly Gly Gly
    290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
            325                 330                 335

Lys Gly Leu Glu Trp Leu Gly Val Ile Trp Ser Gly Gly Thr Ala
            340                 345                 350

Tyr Asn Thr Ala Leu Ile Ser Arg Phe Thr Ile Ser Arg Asp Asn Ser
            355                 360                 365

Lys Asn Thr Leu Tyr Leu Gln Met Asn Ser Leu Arg Ala Glu Asp Thr
    370                 375                 380

Ala Val Tyr Tyr Cys Ala Arg Arg Gly Ser Tyr Pro Tyr Asn Tyr Phe

-continued

```
385                 390                 395                 400

Asp Ala Trp Gly Cys Gly Thr Leu Val Thr Val Ser Ser Gly Gly Gly
            405                 410                 415

Gly Ser Gly Gly Gly Gly Ser Gly Gly Gly Gly Ser Gly Gly Gly Gly
            420                 425                 430

Ser Gly Gly Gly Gly Ser Gly Gly Gly Ser Gln Ala Val Val Thr
            435                 440                 445

Gln Glu Pro Ser Leu Thr Val Ser Pro Gly Gly Thr Val Thr Leu Thr
    450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly His
            485                 490                 495

Asn Asn Arg Pro Pro Gly Val Pro Ala Arg Phe Ser Gly Ser Leu Leu
            500                 505                 510

Gly Gly Lys Ala Ala Leu Thr Leu Leu Gly Ala Gln Pro Glu Asp Glu
            515                 520                 525

Ala Glu Tyr Tyr Cys Ala Leu Trp Tyr Ser Asp His Trp Val Ile Gly
    530                 535                 540

Gly Gly Thr Lys Leu Thr Val Leu Gly Thr Pro Leu Gly Asp Thr Thr
545                 550                 555                 560

His Thr Ser Gly Lys Pro Leu Asp Gly Glu Tyr Phe Thr Leu Gln Ile
            565                 570                 575

Arg Gly Arg Glu Arg Phe Glu Met Phe Arg Glu Leu Asn Glu Ala Leu
            580                 585                 590

Glu Leu Lys Asp Ala Gln Ala Gly Lys Glu Pro Gly Gly Ser Gly Gly
            595                 600                 605

Ala Pro His His His His His His
    610                 615

<210> SEQ ID NO 49
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Gly Trp Ser Cys Ile Ile Leu Phe Leu Val Ala Thr Ala Thr Gly
1                   5                   10                  15

Asp Ile Gln Met Thr Gln Ser Pro Ser Ser Leu Ser Ala Ser Val Gly
            20                  25                  30

Asp Arg Val Thr Ile Thr Cys Gln Ala Ser Gln Asp Ile Ser Lys Tyr
            35                  40                  45

Leu Asn Trp Tyr Gln Gln Lys Pro Gly Lys Ala Val Lys Leu Leu Ile
    50                  55                  60

Tyr His Thr Ser Arg Leu His Ser Gly Val Pro Ser Arg Phe Ser Gly
65                  70                  75                  80

Ser Gly Ser Gly Thr Asp Tyr Thr Leu Thr Ile Ser Ser Leu Gln Pro
            85                  90                  95

Glu Asp Ile Ala Thr Tyr Phe Cys Gln Gln Gly Asn Thr Leu Pro Tyr
            100                 105                 110

Thr Phe Gly Gly Gly Thr Lys Leu Glu Ile Thr Arg Gly Gly Gly Gly
            115                 120                 125
```

-continued

```
Ser Gly Gly Gly Gly Ser Gly Gly Gly Ser Gly Gly Gly Ser
    130             135             140

Gly Gly Gly Gly Ser Gly Gly Gly Ser Gln Val Gln Leu Gln Glu
145             150             155             160

Ser Gly Pro Gly Leu Val Lys Pro Ser Glu Thr Leu Ser Val Thr Cys
            165             170             175

Thr Val Ser Gly Val Ser Leu Pro Asp Tyr Gly Val Ser Trp Ile Arg
            180             185             190

Gln Pro Pro Gly Lys Gly Leu Glu Trp Ile Gly Val Ile Trp Gly Ser
        195             200             205

Glu Thr Thr Tyr Tyr Asn Pro Ser Leu Lys Ser Arg Val Thr Ile Ser
    210             215             220

Val Asp Thr Ser Lys Asn Gln Val Ser Leu Lys Leu Ser Ser Val Thr
225             230             235             240

Ala Ala Asp Thr Ala Val Tyr Tyr Cys Ala Lys His Tyr Tyr Tyr Gly
            245             250             255

Gly Ser Tyr Ala Met Asp Tyr Trp Gly Gln Gly Thr Ser Val Thr Val
            260             265             270

Ser Ser Gly Gly Gly Gly Ser Gly Gly Gly Gly Ser Gly Gly Gly Gly
            275             280             285

Ser Gly Gly Gly Gly Ser His Val Gln Leu Val Glu Ser Gly Gly Gly
        290             295             300

Leu Val Gln Pro Gly Gly Ser Leu Arg Leu Ser Cys Ala Ala Ser Gly
305             310             315             320

Phe Ser Leu Thr Asp Tyr Gly Val His Trp Val Arg Gln Ala Pro Gly
            325             330             335

Lys Gly Leu Glu Trp Leu Gly Val Ile Trp Ser Gly Gly Gly Thr Ala
            340             345             350

Tyr Asn Thr Ala Leu Ile Ser Arg Phe Thr Ile Ser Arg Asp Asn Ser
            355             360             365

Lys Asn Thr Leu Tyr Leu Gln Met Asn Ser Leu Arg Ala Glu Asp Thr
    370             375             380

Ala Val Tyr Tyr Cys Ala Arg Arg Gly Ser Tyr Pro Tyr Asn Tyr Phe
385             390             395             400

Asp Ala Trp Gly Cys Gly Thr Leu Val Thr Val Ser Ser Gly Gly Gly
            405             410             415

Gly Ser Gly Gly Gly Gly Ser Gly Gly Gly Gly Ser Gly Gly Gly Gly
            420             425             430

Ser Gly Gly Gly Gly Ser Gly Gly Gly Gly Ser Gln Ala Val Val Thr
            435             440             445

Gln Glu Pro Ser Leu Thr Val Ser Pro Gly Gly Thr Val Thr Leu Thr
    450             455             460

Cys Gly Ser Ser Thr Gly Ala Val Thr Ala Ser Asn Tyr Ala Asn Trp
465             470             475             480

Val Gln Gln Lys Pro Gly Gln Cys Pro Arg Gly Leu Ile Gly Gly His
            485             490             495

Asn Asn Arg Pro Pro Gly Val Pro Ala Arg Phe Ser Gly Ser Leu Leu
            500             505             510

Gly Gly Lys Ala Ala Leu Thr Leu Leu Gly Ala Gln Pro Glu Asp Glu
            515             520             525

Ala Glu Tyr Tyr Cys Ala Leu Trp Tyr Ser Asp His Trp Val Ile Gly
    530             535             540

Gly Gly Thr Lys Leu Thr Val Leu Gly Thr Pro Leu Gly Asp Thr Thr
```

-continued

```
545              550              555              560

His Thr Ser Gly Lys Pro Leu Asp Gly Glu Tyr Phe Thr Leu Gln Ile
             565              570              575

Arg Gly Arg Glu Arg Phe Glu Met Phe Arg Glu Leu Asn Glu Ala Leu
             580              585              590

Glu Leu Lys Asp Ala Gln Ala Gly Lys Glu Pro Gly Gly Ser Gly Gly
             595              600              605

Ala
```

```
<210> SEQ ID NO 50
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Gly Trp Ser Cys Ile Ile Leu Phe Leu Val Ala Thr Ala Thr Gly
1               5               10              15

Asp Ile Gln Met Thr Gln Ser Pro Ser Ser Leu Ser Ala Ser Val Gly
             20              25              30

Asp Arg Val Thr Ile Thr Cys Gln Ala Ser Gln Asp Ile Ser Lys Tyr
             35              40              45

Leu Asn Trp Tyr Gln Gln Lys Pro Gly Lys Ala Val Lys Leu Leu Ile
      50              55              60

Tyr His Thr Ser Arg Leu His Ser Gly Val Pro Ser Arg Phe Ser Gly
65              70              75              80

Ser Gly Ser Gly Thr Asp Tyr Thr Leu Thr Ile Ser Ser Leu Gln Pro
             85              90              95

Glu Asp Ile Ala Thr Tyr Phe Cys Gln Gln Gly Asn Thr Leu Pro Tyr
             100             105             110

Thr Phe Gly Gly Gly Thr Lys Leu Glu Ile Thr Arg Gly Gly Gly Gly
             115             120             125

Ser Gly Gly Gly Gly Ser Gly Gly Gly Gly Ser Gly Gly Gly Gly Ser
      130             135             140

Gly Gly Gly Gly Ser Gly Gly Gly Gly Ser Gln Val Gln Leu Gln Glu
145             150             155             160

Ser Gly Pro Gly Leu Val Lys Pro Ser Glu Thr Leu Ser Val Thr Cys
             165             170             175

Thr Val Ser Gly Val Ser Leu Pro Asp Tyr Gly Val Ser Trp Ile Arg
             180             185             190

Gln Pro Pro Gly Lys Gly Leu Glu Trp Ile Gly Val Ile Trp Gly Ser
             195             200             205

Glu Thr Thr Tyr Tyr Asn Pro Ser Leu Lys Ser Arg Val Thr Ile Ser
      210             215             220

Val Asp Thr Ser Lys Asn Gln Val Ser Leu Lys Leu Ser Ser Val Thr
225             230             235             240

Ala Ala Asp Thr Ala Val Tyr Tyr Cys Ala Lys His Tyr Tyr Tyr Gly
             245             250             255

Gly Ser Tyr Ala Met Asp Tyr Trp Gly Gln Gly Thr Ser Val Thr Val
             260             265             270

Ser Ser Gly Gly Gly Gly Ser Gly Gly Gly Gly Ser Gly Gly Gly Gly
      275             280             285

Ser Gly Gly Gly Gly Ser His Val Gln Leu Val Glu Ser Gly Gly Gly
```

-continued

```
            290                 295                 300
Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
                325                 330                 335

Lys Gly Leu Glu Trp Leu Gly Val Ile Trp Ser Gly Gly Thr Ala
                340                 345                 350

Tyr Asn Thr Ala Leu Ile Ser Arg Phe Thr Ile Ser Arg Asp Asn Ser
            355                 360                 365

Lys Asn Thr Leu Tyr Leu Gln Met Asn Ser Leu Arg Ala Glu Asp Thr
            370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
                405                 410                 415

Gly Ser Gly Gly Gly Gly Ser Gly Gly Gly Gly Ser Gly Gly Gly Gly
                420                 425                 430

Ser Gly Gly Gly Gly Ser Gly Gly Gly Gly Ser Gln Ala Val Val Thr
            435                 440                 445

Gln Glu Pro Ser Leu Thr Val Ser Pro Gly Gly Thr Val Thr Leu Thr
            450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly Gly His
                485                 490                 495

Asn Asn Arg Pro Pro Gly Val Pro Ala Arg Phe Ser Gly Ser Leu Leu
                500                 505                 510

Gly Gly Lys Ala Ala Leu Thr Leu Leu Gly Ala Gln Pro Glu Asp Glu
                515                 520                 525

Ala Glu Tyr Tyr Cys Ala Leu Trp Tyr Ser Asp His Trp Val Ile Gly
            530                 535                 540

Gly Gly Thr Lys Leu Thr Val Leu Gly Thr Pro Leu Gly Asp Thr Thr
545                 550                 555                 560

His Thr Ser Gly Arg Ser Pro Asp Asp Glu Leu Leu Tyr Leu Pro Val
                565                 570                 575

Arg Gly Arg Glu Thr Tyr Glu Met Leu Leu Lys Ile Lys Glu Ser Leu
                580                 585                 590

Glu Leu Met Gln Tyr Leu Pro Gln His Thr Ile Glu Thr Tyr Arg Gln
            595                 600                 605

Gln Gln Gln Gln Gln His Gln His Leu Leu Gln Lys Gln Gly Gly Ser
            610                 615                 620

Gly Gly Ala Pro His His His His His His
625                 630
```

<210> SEQ ID NO 51
<211> LENGTH: 627
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Met Gly Trp Ser Cys Ile Ile Leu Phe Leu Val Ala Thr Ala Thr Gly
1                   5                   10                  15
```

-continued

```
Asp Ile Gln Met Thr Gln Ser Pro Ser Ser Leu Ser Ala Ser Val Gly
            20                  25                  30

Asp Arg Val Thr Ile Thr Cys Gln Ala Ser Gln Asp Ile Ser Lys Tyr
            35                  40                  45

Leu Asn Trp Tyr Gln Gln Lys Pro Gly Lys Ala Val Lys Leu Leu Ile
        50                  55                  60

Tyr His Thr Ser Arg Leu His Ser Gly Val Pro Ser Arg Phe Ser Gly
65                  70                  75                  80

Ser Gly Ser Gly Thr Asp Tyr Thr Leu Thr Ile Ser Ser Leu Gln Pro
                85                  90                  95

Glu Asp Ile Ala Thr Tyr Phe Cys Gln Gln Gly Asn Thr Leu Pro Tyr
            100                 105                 110

Thr Phe Gly Gly Gly Thr Lys Leu Glu Ile Thr Arg Gly Gly Gly Gly
            115                 120                 125

Ser Gly Gly Gly Gly Ser Gly Gly Gly Ser Gly Gly Gly Gly Ser
        130                 135                 140

Gly Gly Gly Gly Ser Gly Gly Gly Gly Ser Gln Val Gln Leu Gln Glu
145                 150                 155                 160

Ser Gly Pro Gly Leu Val Lys Pro Ser Glu Thr Leu Ser Val Thr Cys
                165                 170                 175

Thr Val Ser Gly Val Ser Leu Pro Asp Tyr Gly Val Ser Trp Ile Arg
            180                 185                 190

Gln Pro Pro Gly Lys Gly Leu Glu Trp Ile Gly Val Ile Trp Gly Ser
            195                 200                 205

Glu Thr Thr Tyr Tyr Asn Pro Ser Leu Lys Ser Arg Val Thr Ile Ser
        210                 215                 220

Val Asp Thr Ser Lys Asn Gln Val Ser Leu Lys Leu Ser Ser Val Thr
225                 230                 235                 240

Ala Ala Asp Thr Ala Val Tyr Tyr Cys Ala Lys His Tyr Tyr Tyr Gly
                245                 250                 255

Gly Ser Tyr Ala Met Asp Tyr Trp Gly Gln Gly Thr Ser Val Thr Val
            260                 265                 270

Ser Ser Gly Gly Gly Gly Ser Gly Gly Gly Gly Ser Gly Gly Gly Gly
            275                 280                 285

Ser Gly Gly Gly Gly Ser His Val Gln Leu Val Glu Ser Gly Gly Gly
        290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
                325                 330                 335

Lys Gly Leu Glu Trp Leu Gly Val Ile Trp Ser Gly Gly Gly Thr Ala
            340                 345                 350

Tyr Asn Thr Ala Leu Ile Ser Arg Phe Thr Ile Ser Arg Asp Asn Ser
            355                 360                 365

Lys Asn Thr Leu Tyr Leu Gln Met Asn Ser Leu Arg Ala Glu Asp Thr
        370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
                405                 410                 415

Gly Ser Gly Gly Gly Gly Ser Gly Gly Gly Gly Ser Gly Gly Gly Gly
            420                 425                 430

Ser Gly Gly Gly Gly Ser Gly Gly Gly Gly Ser Gln Ala Val Val Thr
```

-continued

```
          435                  440                  445
Gln Glu Pro Ser Leu Thr Val Ser Pro Gly Gly Thr Val Thr Leu Thr
    450                  455                  460

Cys Gly Ser Ser Thr Gly Ala Val Thr Ala Ser Asn Tyr Ala Asn Trp
465                  470                  475                  480

Val Gln Gln Lys Pro Gly Gln Cys Pro Arg Gly Leu Ile Gly Gly His
                485                  490                  495

Asn Asn Arg Pro Pro Gly Val Pro Ala Arg Phe Ser Gly Ser Leu Leu
            500                  505                  510

Gly Gly Lys Ala Ala Leu Thr Leu Leu Gly Ala Gln Pro Glu Asp Glu
            515                  520                  525

Ala Glu Tyr Tyr Cys Ala Leu Trp Tyr Ser Asp His Trp Val Ile Gly
    530                  535                  540

Gly Gly Thr Lys Leu Thr Val Leu Gly Thr Pro Leu Gly Asp Thr Thr
545                  550                  555                  560

His Thr Ser Gly Arg Ser Pro Asp Asp Glu Leu Leu Tyr Leu Pro Val
                565                  570                  575

Arg Gly Arg Glu Thr Tyr Glu Met Leu Leu Lys Ile Lys Glu Ser Leu
            580                  585                  590

Glu Leu Met Gln Tyr Leu Pro Gln His Thr Ile Glu Thr Tyr Arg Gln
            595                  600                  605

Gln Gln Gln Gln Gln His Gln His Leu Leu Gln Lys Gln Gly Gly Ser
    610                  615                  620

Gly Gly Ala
625
```

<210> SEQ ID NO 52
<211> LENGTH: 629
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Met Gly Trp Ser Cys Ile Ile Leu Phe Leu Val Ala Thr Ala Thr Gly
1                5                  10                  15

Asp Ile Gln Met Thr Gln Ser Pro Ser Ser Leu Ser Ala Ser Val Gly
            20                  25                  30

Asp Arg Val Thr Ile Thr Cys Gln Ala Ser Gln Asp Ile Ser Lys Tyr
            35                  40                  45

Leu Asn Trp Tyr Gln Gln Lys Pro Gly Lys Ala Val Lys Leu Leu Ile
    50                  55                  60

Tyr His Thr Ser Arg Leu His Ser Gly Val Pro Ser Arg Phe Ser Gly
65                  70                  75                  80

Ser Gly Ser Gly Thr Asp Tyr Thr Leu Thr Ile Ser Ser Leu Gln Pro
                85                  90                  95

Glu Asp Ile Ala Thr Tyr Phe Cys Gln Gln Gly Asn Thr Leu Pro Tyr
            100                 105                 110

Thr Phe Gly Gly Gly Thr Lys Leu Glu Ile Thr Arg Gly Gly Gly Gly
            115                 120                 125

Ser Gly Gly Gly Gly Ser Gly Gly Gly Ser Gly Gly Gly Gly Ser
    130                 135                 140

Gly Gly Gly Gly Ser Gly Gly Gly Gly Ser Gln Val Gln Leu Gln Glu
145                 150                 155                 160
```

```
Ser Gly Pro Gly Leu Val Lys Pro Ser Glu Thr Leu Ser Val Thr Cys
            165                 170                 175

Thr Val Ser Gly Val Ser Leu Pro Asp Tyr Gly Val Ser Trp Ile Arg
            180                 185                 190

Gln Pro Pro Gly Lys Gly Leu Glu Trp Ile Gly Val Ile Trp Gly Ser
            195                 200                 205

Glu Thr Thr Tyr Tyr Asn Pro Ser Leu Lys Ser Arg Val Thr Ile Ser
    210                 215                 220

Val Asp Thr Ser Lys Asn Gln Val Ser Leu Lys Leu Ser Ser Val Thr
225                 230                 235                 240

Ala Ala Asp Thr Ala Val Tyr Tyr Cys Ala Lys His Tyr Tyr Tyr Gly
            245                 250                 255

Gly Ser Tyr Ala Met Asp Tyr Trp Gly Gln Gly Thr Ser Val Thr Val
            260                 265                 270

Ser Ser Gly Gly Gly Gly Ser Gly Gly Gly Gly Ser Gly Gly Gly Gly
            275                 280                 285

Ser Gly Gly Gly Gly Ser His Val Gln Leu Val Glu Ser Gly Gly Gly
            290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
            325                 330                 335

Lys Gly Leu Glu Trp Leu Gly Val Ile Trp Ser Gly Gly Gly Thr Ala
            340                 345                 350

Tyr Asn Thr Ala Leu Ile Ser Arg Phe Thr Ile Ser Arg Asp Asn Ser
            355                 360                 365

Lys Asn Thr Leu Tyr Leu Gln Met Asn Ser Leu Arg Ala Glu Asp Thr
    370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
            405                 410                 415

Gly Ser Gly Gly Gly Gly Ser Gly Gly Gly Gly Ser Gly Gly Gly Gly
            420                 425                 430

Ser Gly Gly Gly Gly Ser Gly Gly Gly Gly Ser Gln Ala Val Val Thr
            435                 440                 445

Gln Glu Pro Ser Leu Thr Val Ser Pro Gly Gly Thr Val Thr Leu Thr
    450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly Gly His
            485                 490                 495

Asn Asn Arg Pro Pro Gly Val Pro Ala Arg Phe Ser Gly Ser Leu Leu
            500                 505                 510

Gly Gly Lys Ala Ala Leu Thr Leu Leu Gly Ala Gln Pro Glu Asp Glu
            515                 520                 525

Ala Glu Tyr Tyr Cys Ala Leu Trp Tyr Ser Asp His Trp Val Ile Gly
            530                 535                 540

Gly Gly Thr Lys Leu Thr Val Leu Gly Thr Pro Leu Gly Asp Thr Thr
545                 550                 555                 560

His Thr Ser Gly Arg His Gly Asp Glu Asp Thr Tyr Tyr Leu Gln Val
            565                 570                 575

Arg Gly Arg Glu Asn Phe Glu Ile Leu Met Lys Leu Lys Glu Ser Leu
```

-continued

```
                  580                    585                    590
Glu Leu Met Glu Leu Val Pro Gln Pro Leu Val Asp Ser Tyr Arg Gln
             595                    600                    605

Gln Gln Gln Leu Leu Gln Arg Pro Gly Gly Ser Gly Gly Ala Pro His
         610                    615                    620

His His His His His
625
```

```
<210> SEQ ID NO 53
<211> LENGTH: 622
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Gly Trp Ser Cys Ile Ile Leu Phe Leu Val Ala Thr Ala Thr Gly
1               5                  10                  15

Asp Ile Gln Met Thr Gln Ser Pro Ser Ser Leu Ser Ala Ser Val Gly
             20                  25                  30

Asp Arg Val Thr Ile Thr Cys Gln Ala Ser Gln Asp Ile Ser Lys Tyr
         35                  40                  45

Leu Asn Trp Tyr Gln Gln Lys Pro Gly Lys Ala Val Lys Leu Leu Ile
     50                  55                  60

Tyr His Thr Ser Arg Leu His Ser Gly Val Pro Ser Arg Phe Ser Gly
65                  70                  75                  80

Ser Gly Ser Gly Thr Asp Tyr Thr Leu Thr Ile Ser Ser Leu Gln Pro
                 85                  90                  95

Glu Asp Ile Ala Thr Tyr Phe Cys Gln Gln Gly Asn Thr Leu Pro Tyr
             100                 105                 110

Thr Phe Gly Gly Gly Thr Lys Leu Glu Ile Thr Arg Gly Gly Gly Gly
         115                 120                 125

Ser Gly Gly Gly Gly Ser Gly Gly Gly Ser Gly Gly Gly Gly Ser
     130                 135                 140

Gly Gly Gly Gly Ser Gly Gly Gly Gly Ser Gln Val Gln Leu Gln Glu
145                 150                 155                 160

Ser Gly Pro Gly Leu Val Lys Pro Ser Glu Thr Leu Ser Val Thr Cys
                 165                 170                 175

Thr Val Ser Gly Val Ser Leu Pro Asp Tyr Gly Val Ser Trp Ile Arg
             180                 185                 190

Gln Pro Pro Gly Lys Gly Leu Glu Trp Ile Gly Val Ile Trp Gly Ser
         195                 200                 205

Glu Thr Thr Tyr Tyr Asn Pro Ser Leu Lys Ser Arg Val Thr Ile Ser
     210                 215                 220

Val Asp Thr Ser Lys Asn Gln Val Ser Leu Lys Leu Ser Ser Val Thr
225                 230                 235                 240

Ala Ala Asp Thr Ala Val Tyr Tyr Cys Ala Lys His Tyr Tyr Tyr Gly
             245                 250                 255

Gly Ser Tyr Ala Met Asp Tyr Trp Gly Gln Gly Thr Ser Val Thr Val
             260                 265                 270

Ser Ser Gly Gly Gly Gly Ser Gly Gly Gly Ser Gly Gly Gly Gly
         275                 280                 285

Ser Gly Gly Gly Gly Ser His Val Gln Leu Val Glu Ser Gly Gly Gly
     290                 295                 300
```

```
Leu Val Gln Pro Gly Gly Ser Leu Arg Leu Ser Cys Ala Ala Ser Gly
305             310             315             320

Phe Ser Leu Thr Asp Tyr Gly Val His Trp Val Arg Gln Ala Pro Gly
                325             330             335

Lys Gly Leu Glu Trp Leu Gly Val Ile Trp Ser Gly Gly Gly Thr Ala
            340             345             350

Tyr Asn Thr Ala Leu Ile Ser Arg Phe Thr Ile Ser Arg Asp Asn Ser
            355             360             365

Lys Asn Thr Leu Tyr Leu Gln Met Asn Ser Leu Arg Ala Glu Asp Thr
    370             375             380

Ala Val Tyr Tyr Cys Ala Arg Arg Gly Ser Tyr Pro Tyr Asn Tyr Phe
385             390             395             400

Asp Ala Trp Gly Cys Gly Thr Leu Val Thr Val Ser Ser Gly Gly Gly
            405             410             415

Gly Ser Gly Gly Gly Gly Ser Gly Gly Gly Ser Gly Gly Gly Gly
            420             425             430

Ser Gly Gly Gly Gly Ser Gly Gly Gly Ser Gln Ala Val Val Thr
            435             440             445

Gln Glu Pro Ser Leu Thr Val Ser Pro Gly Gly Thr Val Thr Leu Thr
    450             455             460

Cys Gly Ser Ser Thr Gly Ala Val Thr Ala Ser Asn Tyr Ala Asn Trp
465             470             475             480

Val Gln Gln Lys Pro Gly Gln Cys Pro Arg Gly Leu Ile Gly Gly His
            485             490             495

Asn Asn Arg Pro Pro Gly Val Pro Ala Arg Phe Ser Gly Ser Leu Leu
            500             505             510

Gly Gly Lys Ala Ala Leu Thr Leu Leu Gly Ala Gln Pro Glu Asp Glu
            515             520             525

Ala Glu Tyr Tyr Cys Ala Leu Trp Tyr Ser Asp His Trp Val Ile Gly
    530             535             540

Gly Gly Thr Lys Leu Thr Val Leu Gly Thr Pro Leu Gly Asp Thr Thr
545             550             555             560

His Thr Ser Gly Arg His Gly Asp Glu Asp Thr Tyr Tyr Leu Gln Val
            565             570             575

Arg Gly Arg Glu Asn Phe Glu Ile Leu Met Lys Leu Lys Glu Ser Leu
            580             585             590

Glu Leu Met Glu Leu Val Pro Gln Pro Leu Val Asp Ser Tyr Arg Gln
            595             600             605

Gln Gln Gln Leu Leu Gln Arg Pro Gly Gly Ser Gly Gly Ala
    610             615             620
```

```
<210> SEQ ID NO 54
<211> LENGTH: 616
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54
```

```
Met Gly Trp Ser Cys Ile Ile Leu Phe Leu Val Ala Thr Ala Thr Gly
1               5               10              15

Gln Val Gln Leu Gln Glu Ser Gly Pro Gly Leu Val Lys Pro Ser Glu
            20              25              30

Thr Leu Ser Val Thr Cys Thr Val Ser Gly Val Ser Leu Pro Asp Tyr
            35              40              45
```

```
Gly Val Ser Trp Ile Arg Gln Pro Pro Gly Lys Gly Leu Glu Trp Ile
    50              55              60
Gly Val Ile Trp Gly Ser Glu Thr Thr Tyr Tyr Asn Pro Ser Leu Lys
65              70              75              80
Ser Arg Val Thr Ile Ser Val Asp Thr Ser Lys Asn Gln Val Ser Leu
                85              90              95
Lys Leu Ser Ser Val Thr Ala Ala Asp Thr Ala Val Tyr Tyr Cys Ala
            100             105             110
Lys His Tyr Tyr Tyr Gly Gly Ser Tyr Ala Met Asp Tyr Trp Gly Gln
            115             120             125
Gly Thr Ser Val Thr Val Ser Ser Gly Gly Gly Gly Ser Gly Gly Gly
    130             135             140
Gly Ser Gly Gly Gly Gly Ser Gly Gly Gly Gly Ser Gly Gly Gly Gly
145             150             155             160
Ser Gly Gly Gly Gly Ser Asp Ile Gln Met Thr Gln Ser Pro Ser Ser
            165             170             175
Leu Ser Ala Ser Val Gly Asp Arg Val Thr Ile Thr Cys Gln Ala Ser
            180             185             190
Gln Asp Ile Ser Lys Tyr Leu Asn Trp Tyr Gln Gln Lys Pro Gly Lys
            195             200             205
Ala Val Lys Leu Leu Ile Tyr His Thr Ser Arg Leu His Ser Gly Val
    210             215             220
Pro Ser Arg Phe Ser Gly Ser Gly Ser Gly Thr Asp Tyr Thr Leu Thr
225             230             235             240
Ile Ser Ser Leu Gln Pro Glu Asp Ile Ala Thr Tyr Phe Cys Gln Gln
            245             250             255
Gly Asn Thr Leu Pro Tyr Thr Phe Gly Gly Gly Thr Lys Leu Glu Ile
            260             265             270
Thr Arg Gly Gly Gly Gly Ser Gly Gly Gly Gly Ser Gly Gly Gly Gly
            275             280             285
Ser Gly Gly Gly Gly Ser His Val Gln Leu Val Glu Ser Gly Gly Gly
    290             295             300
Leu Val Gln Pro Gly Gly Ser Leu Arg Leu Ser Cys Ala Ala Ser Gly
305             310             315             320
Phe Ser Leu Thr Asp Tyr Gly Val His Trp Val Arg Gln Ala Pro Gly
            325             330             335
Lys Gly Leu Glu Trp Leu Gly Val Ile Trp Ser Gly Gly Gly Thr Ala
            340             345             350
Tyr Asn Thr Ala Leu Ile Ser Arg Phe Thr Ile Ser Arg Asp Asn Ser
            355             360             365
Lys Asn Thr Leu Tyr Leu Gln Met Asn Ser Leu Arg Ala Glu Asp Thr
            370             375             380
Ala Val Tyr Tyr Cys Ala Arg Arg Gly Ser Tyr Pro Tyr Asn Tyr Phe
385             390             395             400
Asp Ala Trp Gly Cys Gly Thr Leu Val Thr Val Ser Ser Gly Gly Gly
            405             410             415
Gly Ser Gly Gly Gly Gly Ser Gly Gly Gly Gly Ser Gly Gly Gly Gly
            420             425             430
Ser Gly Gly Gly Gly Ser Gly Gly Gly Gly Ser Gln Ala Val Val Thr
            435             440             445
Gln Glu Pro Ser Leu Thr Val Ser Pro Gly Gly Thr Val Thr Leu Thr
    450             455             460
```

-continued

```
Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly Gly His
                485                 490                 495

Asn Asn Arg Pro Pro Gly Val Pro Ala Arg Phe Ser Gly Ser Leu Leu
            500                 505                 510

Gly Gly Lys Ala Ala Leu Thr Leu Leu Gly Ala Gln Pro Glu Asp Glu
            515                 520                 525

Ala Glu Tyr Tyr Cys Ala Leu Trp Tyr Ser Asp His Trp Val Ile Gly
        530                 535                 540

Gly Gly Thr Lys Leu Thr Val Leu Gly Thr Pro Leu Gly Asp Thr Thr
545                 550                 555                 560

His Thr Ser Gly Lys Pro Leu Asp Gly Glu Tyr Phe Thr Leu Gln Ile
                565                 570                 575

Arg Gly Arg Glu Arg Phe Glu Met Phe Arg Glu Leu Asn Glu Ala Leu
            580                 585                 590

Glu Leu Lys Asp Ala Gln Ala Gly Lys Glu Pro Gly Gly Ser Gly Gly
            595                 600                 605

Ala Pro His His His His His His
        610                 615
```

```
<210> SEQ ID NO 55
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55
```

```
Met Gly Trp Ser Cys Ile Ile Leu Phe Leu Val Ala Thr Ala Thr Gly
1               5                   10                  15

Gln Val Gln Leu Gln Glu Ser Gly Pro Gly Leu Val Lys Pro Ser Glu
                20                  25                  30

Thr Leu Ser Val Thr Cys Thr Val Ser Gly Val Ser Leu Pro Asp Tyr
            35                  40                  45

Gly Val Ser Trp Ile Arg Gln Pro Pro Gly Lys Gly Leu Glu Trp Ile
        50                  55                  60

Gly Val Ile Trp Gly Ser Glu Thr Thr Tyr Tyr Asn Pro Ser Leu Lys
65                  70                  75                  80

Ser Arg Val Thr Ile Ser Val Asp Thr Ser Lys Asn Gln Val Ser Leu
                85                  90                  95

Lys Leu Ser Ser Val Thr Ala Ala Asp Thr Ala Val Tyr Tyr Cys Ala
            100                 105                 110

Lys His Tyr Tyr Tyr Gly Gly Ser Tyr Ala Met Asp Tyr Trp Gly Gln
            115                 120                 125

Gly Thr Ser Val Thr Val Ser Ser Gly Gly Gly Gly Ser Gly Gly Gly
        130                 135                 140

Gly Ser Gly Gly Gly Gly Ser Gly Gly Gly Gly Ser Gly Gly Gly Gly
145                 150                 155                 160

Ser Gly Gly Gly Gly Ser Asp Ile Gln Met Thr Gln Ser Pro Ser Ser
                165                 170                 175

Leu Ser Ala Ser Val Gly Asp Arg Val Thr Ile Thr Cys Gln Ala Ser
            180                 185                 190

Gln Asp Ile Ser Lys Tyr Leu Asn Trp Tyr Gln Gln Lys Pro Gly Lys
            195                 200                 205
```

```
Ala Val Lys Leu Leu Ile Tyr His Thr Ser Arg Leu His Ser Gly Val
    210             215             220
Pro Ser Arg Phe Ser Gly Ser Gly Ser Gly Thr Asp Tyr Thr Leu Thr
225             230             235             240
Ile Ser Ser Leu Gln Pro Glu Asp Ile Ala Thr Tyr Phe Cys Gln Gln
            245             250             255
Gly Asn Thr Leu Pro Tyr Thr Phe Gly Gly Gly Thr Lys Leu Glu Ile
            260             265             270
Thr Arg Gly Gly Gly Gly Ser Gly Gly Gly Ser Gly Gly Gly Gly
        275             280             285
Ser Gly Gly Gly Gly Ser His Val Gln Leu Val Glu Ser Gly Gly Gly
    290             295             300
Leu Val Gln Pro Gly Gly Ser Leu Arg Leu Ser Cys Ala Ala Ser Gly
305             310             315             320
Phe Ser Leu Thr Asp Tyr Gly Val His Trp Val Arg Gln Ala Pro Gly
            325             330             335
Lys Gly Leu Glu Trp Leu Gly Val Ile Trp Ser Gly Gly Thr Ala
            340             345             350
Tyr Asn Thr Ala Leu Ile Ser Arg Phe Thr Ile Ser Arg Asp Asn Ser
    355             360             365
Lys Asn Thr Leu Tyr Leu Gln Met Asn Ser Leu Arg Ala Glu Asp Thr
    370             375             380
Ala Val Tyr Tyr Cys Ala Arg Arg Gly Ser Tyr Pro Tyr Asn Tyr Phe
385             390             395             400
Asp Ala Trp Gly Cys Gly Thr Leu Val Thr Val Ser Ser Gly Gly Gly
            405             410             415
Gly Ser Gly Gly Gly Gly Ser Gly Gly Gly Gly Ser Gly Gly Gly Gly
            420             425             430
Ser Gly Gly Gly Gly Ser Gly Gly Gly Gly Ser Gln Ala Val Val Thr
        435             440             445
Gln Glu Pro Ser Leu Thr Val Ser Pro Gly Gly Thr Val Thr Leu Thr
    450             455             460
Cys Gly Ser Ser Thr Gly Ala Val Thr Ala Ser Asn Tyr Ala Asn Trp
465             470             475             480
Val Gln Gln Lys Pro Gly Gln Cys Pro Arg Gly Leu Ile Gly Gly His
            485             490             495
Asn Asn Arg Pro Pro Gly Val Pro Ala Arg Phe Ser Gly Ser Leu Leu
            500             505             510
Gly Gly Lys Ala Ala Leu Thr Leu Leu Gly Ala Gln Pro Glu Asp Glu
        515             520             525
Ala Glu Tyr Tyr Cys Ala Leu Trp Tyr Ser Asp His Trp Val Ile Gly
    530             535             540
Gly Gly Thr Lys Leu Thr Val Leu Gly Thr Pro Leu Gly Asp Thr Thr
545             550             555             560
His Thr Ser Gly Lys Pro Leu Asp Gly Glu Tyr Phe Thr Leu Gln Ile
            565             570             575
Arg Gly Arg Glu Arg Phe Glu Met Phe Arg Glu Leu Asn Glu Ala Leu
            580             585             590
Glu Leu Lys Asp Ala Gln Ala Gly Lys Glu Pro Gly Gly Ser Gly Gly
        595             600             605
Ala
```

<210> SEQ ID NO 56
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Met Gly Trp Ser Cys Ile Ile Leu Phe Leu Val Ala Thr Ala Thr Gly
1               5                   10                  15

Gln Val Gln Leu Gln Glu Ser Gly Pro Gly Leu Val Lys Pro Ser Glu
            20                  25                  30

Thr Leu Ser Val Thr Cys Thr Val Ser Gly Val Ser Leu Pro Asp Tyr
            35                  40                  45

Gly Val Ser Trp Ile Arg Gln Pro Pro Gly Lys Gly Leu Glu Trp Ile
        50                  55                  60

Gly Val Ile Trp Gly Ser Glu Thr Thr Tyr Tyr Asn Pro Ser Leu Lys
65                  70                  75                  80

Ser Arg Val Thr Ile Ser Val Asp Thr Ser Lys Asn Gln Val Ser Leu
                85                  90                  95

Lys Leu Ser Ser Val Thr Ala Ala Asp Thr Ala Val Tyr Tyr Cys Ala
            100                 105                 110

Lys His Tyr Tyr Tyr Gly Gly Ser Tyr Ala Met Asp Tyr Trp Gly Gln
            115                 120                 125

Gly Thr Ser Val Thr Val Ser Ser Gly Gly Gly Ser Gly Gly Gly
            130                 135                 140

Gly Ser Gly Gly Gly Gly Ser Gly Gly Gly Ser Gly Gly Gly Gly
145                 150                 155                 160

Ser Gly Gly Gly Gly Ser Asp Ile Gln Met Thr Gln Ser Pro Ser Ser
                165                 170                 175

Leu Ser Ala Ser Val Gly Asp Arg Val Thr Ile Thr Cys Gln Ala Ser
            180                 185                 190

Gln Asp Ile Ser Lys Tyr Leu Asn Trp Tyr Gln Gln Lys Pro Gly Lys
            195                 200                 205

Ala Val Lys Leu Leu Ile Tyr His Thr Ser Arg Leu His Ser Gly Val
            210                 215                 220

Pro Ser Arg Phe Ser Gly Ser Gly Ser Gly Thr Asp Tyr Thr Leu Thr
225                 230                 235                 240

Ile Ser Ser Leu Gln Pro Glu Asp Ile Ala Thr Tyr Phe Cys Gln Gln
            245                 250                 255

Gly Asn Thr Leu Pro Tyr Thr Phe Gly Gly Gly Thr Lys Leu Glu Ile
            260                 265                 270

Thr Arg Gly Gly Gly Gly Ser Gly Gly Gly Gly Ser Gly Gly Gly Gly
            275                 280                 285

Ser Gly Gly Gly Gly Ser His Val Gln Leu Val Glu Ser Gly Gly Gly
            290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
            325                 330                 335

Lys Gly Leu Glu Trp Leu Gly Val Ile Trp Ser Gly Gly Thr Ala
            340                 345                 350

Tyr Asn Thr Ala Leu Ile Ser Arg Phe Thr Ile Ser Arg Asp Asn Ser
            355                 360                 365
```

```
Lys Asn Thr Leu Tyr Leu Gln Met Asn Ser Leu Arg Ala Glu Asp Thr
    370             375             380

Ala Val Tyr Tyr Cys Ala Arg Arg Gly Ser Tyr Pro Tyr Asn Tyr Phe
385             390             395             400

Asp Ala Trp Gly Cys Gly Thr Leu Val Thr Val Ser Ser Gly Gly Gly
            405             410             415

Gly Ser Gly Gly Gly Gly Ser Gly Gly Gly Ser Gly Gly Gly Gly
            420             425             430

Ser Gly Gly Gly Gly Ser Gly Gly Gly Gly Ser Gln Ala Val Val Thr
            435             440             445

Gln Glu Pro Ser Leu Thr Val Ser Pro Gly Gly Thr Val Thr Leu Thr
    450             455             460

Cys Gly Ser Ser Thr Gly Ala Val Thr Ala Ser Asn Tyr Ala Asn Trp
465             470             475             480

Val Gln Gln Lys Pro Gly Gln Cys Pro Arg Gly Leu Ile Gly His
            485             490             495

Asn Asn Arg Pro Pro Gly Val Pro Ala Arg Phe Ser Gly Ser Leu Leu
            500             505             510

Gly Gly Lys Ala Ala Leu Thr Leu Leu Gly Ala Gln Pro Glu Asp Glu
            515             520             525

Ala Glu Tyr Tyr Cys Ala Leu Trp Tyr Ser Asp His Trp Val Ile Gly
    530             535             540

Gly Gly Thr Lys Leu Thr Val Leu Gly Thr Pro Leu Gly Asp Thr Thr
545             550             555             560

His Thr Ser Gly Arg Ser Pro Asp Asp Glu Leu Leu Tyr Leu Pro Val
            565             570             575

Arg Gly Arg Glu Thr Tyr Glu Met Leu Leu Lys Ile Lys Glu Ser Leu
            580             585             590

Glu Leu Met Gln Tyr Leu Pro Gln His Thr Ile Glu Thr Tyr Arg Gln
            595             600             605

Gln Gln Gln Gln Gln His Gln His Leu Leu Gln Lys Gln Gly Gly Ser
    610             615             620

Gly Gly Ala Pro His His His His His His
625             630
```

```
<210> SEQ ID NO 57
<211> LENGTH: 627
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gly Trp Ser Cys Ile Ile Leu Phe Leu Val Ala Thr Ala Thr Gly
1               5               10              15

Gln Val Gln Leu Gln Glu Ser Gly Pro Gly Leu Val Lys Pro Ser Glu
            20              25              30

Thr Leu Ser Val Thr Cys Thr Val Ser Gly Val Ser Leu Pro Asp Tyr
            35              40              45

Gly Val Ser Trp Ile Arg Gln Pro Pro Gly Lys Gly Leu Glu Trp Ile
    50              55              60

Gly Val Ile Trp Gly Ser Glu Thr Thr Tyr Tyr Asn Pro Ser Leu Lys
65              70              75              80

Ser Arg Val Thr Ile Ser Val Asp Thr Ser Lys Asn Gln Val Ser Leu
            85              90              95
```

```
Lys Leu Ser Ser Val Thr Ala Ala Asp Thr Ala Val Tyr Tyr Cys Ala
            100                 105                 110

Lys His Tyr Tyr Tyr Gly Gly Ser Tyr Ala Met Asp Tyr Trp Gly Gln
            115                 120                 125

Gly Thr Ser Val Thr Val Ser Ser Gly Gly Gly Gly Ser Gly Gly Gly
            130                 135                 140

Gly Ser Gly Gly Gly Gly Ser Gly Gly Gly Gly Ser Gly Gly Gly Gly
    145                 150                 155                 160

Ser Gly Gly Gly Gly Ser Asp Ile Gln Met Thr Gln Ser Pro Ser Ser
                165                 170                 175

Leu Ser Ala Ser Val Gly Asp Arg Val Thr Ile Thr Cys Gln Ala Ser
            180                 185                 190

Gln Asp Ile Ser Lys Tyr Leu Asn Trp Tyr Gln Gln Lys Pro Gly Lys
            195                 200                 205

Ala Val Lys Leu Leu Ile Tyr His Thr Ser Arg Leu His Ser Gly Val
            210                 215                 220

Pro Ser Arg Phe Ser Gly Ser Gly Ser Gly Thr Asp Tyr Thr Leu Thr
225                 230                 235                 240

Ile Ser Ser Leu Gln Pro Glu Asp Ile Ala Thr Tyr Phe Cys Gln Gln
            245                 250                 255

Gly Asn Thr Leu Pro Tyr Thr Phe Gly Gly Gly Thr Lys Leu Glu Ile
            260                 265                 270

Thr Arg Gly Gly Gly Gly Ser Gly Gly Gly Gly Ser Gly Gly Gly Gly
            275                 280                 285

Ser Gly Gly Gly Gly Ser His Val Gln Leu Val Glu Ser Gly Gly Gly
            290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
                325                 330                 335

Lys Gly Leu Glu Trp Leu Gly Val Ile Trp Ser Gly Gly Thr Ala
            340                 345                 350

Tyr Asn Thr Ala Leu Ile Ser Arg Phe Thr Ile Ser Arg Asp Asn Ser
            355                 360                 365

Lys Asn Thr Leu Tyr Leu Gln Met Asn Ser Leu Arg Ala Glu Asp Thr
            370                 375                 380

Ala Val Tyr Tyr Cys Ala Arg Arg Gly Ser Tyr Pro Tyr Asn Tyr Phe
385                 390                 395                 400

Asp Ala Trp Gly Cys Gly Thr Leu Val Thr Val Ser Ser Gly Gly Gly
                405                 410                 415

Gly Ser Gly Gly Gly Gly Ser Gly Gly Gly Gly Ser Gly Gly Gly Gly
            420                 425                 430

Ser Gly Gly Gly Gly Ser Gly Gly Gly Gly Ser Gln Ala Val Val Thr
            435                 440                 445

Gln Glu Pro Ser Leu Thr Val Ser Pro Gly Gly Thr Val Thr Leu Thr
            450                 455                 460

Cys Gly Ser Ser Thr Gly Ala Val Thr Ala Ser Asn Tyr Ala Asn Trp
465                 470                 475                 480

Val Gln Gln Lys Pro Gly Gln Cys Pro Arg Gly Leu Ile Gly His
                485                 490                 495

Asn Asn Arg Pro Pro Gly Val Pro Ala Arg Phe Ser Gly Ser Leu Leu
            500                 505                 510
```

-continued

```
Gly Gly Lys Ala Ala Leu Thr Leu Leu Gly Ala Gln Pro Glu Asp Glu
        515                 520                 525

Ala Glu Tyr Tyr Cys Ala Leu Trp Tyr Ser Asp His Trp Val Ile Gly
        530                 535                 540

Gly Gly Thr Lys Leu Thr Val Leu Gly Thr Pro Leu Gly Asp Thr Thr
545                 550                 555                 560

His Thr Ser Gly Arg Ser Pro Asp Asp Glu Leu Leu Tyr Leu Pro Val
                565                 570                 575

Arg Gly Arg Glu Thr Tyr Glu Met Leu Leu Lys Ile Lys Glu Ser Leu
                580                 585                 590

Glu Leu Met Gln Tyr Leu Pro Gln His Thr Ile Glu Thr Tyr Arg Gln
        595                 600                 605

Gln Gln Gln Gln Gln His Gln His Leu Leu Gln Lys Gln Gly Gly Ser
        610                 615                 620

Gly Gly Ala
625
```

<210> SEQ ID NO 58
<211> LENGTH: 629
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Met Gly Trp Ser Cys Ile Ile Leu Phe Leu Val Ala Thr Ala Thr Gly
1               5                   10                  15

Gln Val Gln Leu Gln Glu Ser Gly Pro Gly Leu Val Lys Pro Ser Glu
                20                  25                  30

Thr Leu Ser Val Thr Cys Thr Val Ser Gly Val Ser Leu Pro Asp Tyr
            35                  40                  45

Gly Val Ser Trp Ile Arg Gln Pro Pro Gly Lys Gly Leu Glu Trp Ile
        50                  55                  60

Gly Val Ile Trp Gly Ser Glu Thr Thr Tyr Tyr Asn Pro Ser Leu Lys
65                  70                  75                  80

Ser Arg Val Thr Ile Ser Val Asp Thr Ser Lys Asn Gln Val Ser Leu
                85                  90                  95

Lys Leu Ser Ser Val Thr Ala Ala Asp Thr Ala Val Tyr Tyr Cys Ala
            100                 105                 110

Lys His Tyr Tyr Tyr Gly Gly Ser Tyr Ala Met Asp Tyr Trp Gly Gln
        115                 120                 125

Gly Thr Ser Val Thr Val Ser Ser Gly Gly Gly Gly Ser Gly Gly Gly
        130                 135                 140

Gly Ser Gly Gly Gly Gly Ser Gly Gly Gly Ser Gly Gly Gly Gly
145                 150                 155                 160

Ser Gly Gly Gly Gly Ser Asp Ile Gln Met Thr Gln Ser Pro Ser Ser
                165                 170                 175

Leu Ser Ala Ser Val Gly Asp Arg Val Thr Ile Thr Cys Gln Ala Ser
            180                 185                 190

Gln Asp Ile Ser Lys Tyr Leu Asn Trp Tyr Gln Gln Lys Pro Gly Lys
        195                 200                 205

Ala Val Lys Leu Leu Ile Tyr His Thr Ser Arg Leu His Ser Gly Val
        210                 215                 220

Pro Ser Arg Phe Ser Gly Ser Gly Ser Gly Thr Asp Tyr Thr Leu Thr
225                 230                 235                 240
```

-continued

```
Ile Ser Ser Leu Gln Pro Glu Asp Ile Ala Thr Tyr Phe Cys Gln Gln
            245             250             255

Gly Asn Thr Leu Pro Tyr Thr Phe Gly Gly Thr Lys Leu Glu Ile
            260             265             270

Thr Arg Gly Gly Gly Gly Ser Gly Gly Gly Gly Ser Gly Gly Gly Gly
            275             280             285

Ser Gly Gly Gly Gly Ser His Val Gln Leu Val Glu Ser Gly Gly Gly
            290             295             300

Leu Val Gln Pro Gly Gly Ser Leu Arg Leu Ser Cys Ala Ala Ser Gly
305             310             315             320

Phe Ser Leu Thr Asp Tyr Gly Val His Trp Val Arg Gln Ala Pro Gly
            325             330             335

Lys Gly Leu Glu Trp Leu Gly Val Ile Trp Ser Gly Gly Thr Ala
            340             345             350

Tyr Asn Thr Ala Leu Ile Ser Arg Phe Thr Ile Ser Arg Asp Asn Ser
            355             360             365

Lys Asn Thr Leu Tyr Leu Gln Met Asn Ser Leu Arg Ala Glu Asp Thr
            370             375             380

Ala Val Tyr Tyr Cys Ala Arg Arg Gly Ser Tyr Pro Tyr Asn Tyr Phe
385             390             395             400

Asp Ala Trp Gly Cys Gly Thr Leu Val Thr Val Ser Ser Gly Gly Gly
            405             410             415

Gly Ser Gly Gly Gly Gly Ser Gly Gly Gly Gly Ser Gly Gly Gly Gly
            420             425             430

Ser Gly Gly Gly Gly Ser Gly Gly Gly Gly Ser Gln Ala Val Val Thr
            435             440             445

Gln Glu Pro Ser Leu Thr Val Ser Pro Gly Gly Thr Val Thr Leu Thr
            450             455             460

Cys Gly Ser Ser Thr Gly Ala Val Thr Ala Ser Asn Tyr Ala Asn Trp
465             470             475             480

Val Gln Gln Lys Pro Gly Gln Cys Pro Arg Gly Leu Ile Gly Gly His
            485             490             495

Asn Asn Arg Pro Pro Gly Val Pro Ala Arg Phe Ser Gly Ser Leu Leu
            500             505             510

Gly Gly Lys Ala Ala Leu Thr Leu Leu Gly Ala Gln Pro Glu Asp Glu
            515             520             525

Ala Glu Tyr Tyr Cys Ala Leu Trp Tyr Ser Asp His Trp Val Ile Gly
            530             535             540

Gly Gly Thr Lys Leu Thr Val Leu Gly Thr Pro Leu Gly Asp Thr Thr
545             550             555             560

His Thr Ser Gly Arg His Gly Asp Glu Asp Thr Tyr Tyr Leu Gln Val
            565             570             575

Arg Gly Arg Glu Asn Phe Glu Ile Leu Met Lys Leu Lys Glu Ser Leu
            580             585             590

Glu Leu Met Glu Leu Val Pro Gln Pro Leu Val Asp Ser Tyr Arg Gln
            595             600             605

Gln Gln Gln Leu Leu Gln Arg Pro Gly Gly Ser Gly Gly Ala Pro His
            610             615             620

His His His His His
625
```

<210> SEQ ID NO 59
<211> LENGTH: 622

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Met Gly Trp Ser Cys Ile Ile Leu Phe Leu Val Ala Thr Ala Thr Gly
1               5                   10                  15

Gln Val Gln Leu Gln Glu Ser Gly Pro Gly Leu Val Lys Pro Ser Glu
            20                  25                  30

Thr Leu Ser Val Thr Cys Thr Val Ser Gly Val Ser Leu Pro Asp Tyr
        35                  40                  45

Gly Val Ser Trp Ile Arg Gln Pro Pro Gly Lys Gly Leu Glu Trp Ile
    50                  55                  60

Gly Val Ile Trp Gly Ser Glu Thr Thr Tyr Tyr Asn Pro Ser Leu Lys
65                  70                  75                  80

Ser Arg Val Thr Ile Ser Val Asp Thr Ser Lys Asn Gln Val Ser Leu
            85                  90                  95

Lys Leu Ser Ser Val Thr Ala Ala Asp Thr Ala Val Tyr Tyr Cys Ala
            100                 105                 110

Lys His Tyr Tyr Tyr Gly Gly Ser Tyr Ala Met Asp Tyr Trp Gly Gln
            115                 120                 125

Gly Thr Ser Val Thr Val Ser Ser Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Gly Gly Gly Gly Ser Asp Ile Gln Met Thr Gln Ser Pro Ser Ser
            165                 170                 175

Leu Ser Ala Ser Val Gly Asp Arg Val Thr Ile Thr Cys Gln Ala Ser
            180                 185                 190

Gln Asp Ile Ser Lys Tyr Leu Asn Trp Tyr Gln Gln Lys Pro Gly Lys
            195                 200                 205

Ala Val Lys Leu Leu Ile Tyr His Thr Ser Arg Leu His Ser Gly Val
    210                 215                 220

Pro Ser Arg Phe Ser Gly Ser Gly Ser Gly Thr Asp Tyr Thr Leu Thr
225                 230                 235                 240

Ile Ser Ser Leu Gln Pro Glu Asp Ile Ala Thr Tyr Phe Cys Gln Gln
            245                 250                 255

Gly Asn Thr Leu Pro Tyr Thr Phe Gly Gly Gly Thr Lys Leu Glu Ile
            260                 265                 270

Thr Arg Gly Gly Gly Gly Ser Gly Gly Gly Gly Ser Gly Gly Gly Gly
            275                 280                 285

Ser Gly Gly Gly Gly Ser His Val Gln Leu Val Glu Ser Gly Gly Gly
    290                 295                 300

Leu Val Gln Pro Gly Gly Ser Leu Arg Leu Ser Cys Ala Ala Ser Gly
305                 310                 315                 320

Phe Ser Leu Thr Asp Tyr Gly Val His Trp Val Arg Gln Ala Pro Gly
            325                 330                 335

Lys Gly Leu Glu Trp Leu Gly Val Ile Trp Ser Gly Gly Thr Ala
            340                 345                 350

Tyr Asn Thr Ala Leu Ile Ser Arg Phe Thr Ile Ser Arg Asp Asn Ser
            355                 360                 365

Lys Asn Thr Leu Tyr Leu Gln Met Asn Ser Leu Arg Ala Glu Asp Thr
    370                 375                 380
```

```
Ala Val Tyr Tyr Cys Ala Arg Arg Gly Ser Tyr Pro Tyr Asn Tyr Phe
385                 390             395             400

Asp Ala Trp Gly Cys Gly Thr Leu Val Thr Val Ser Ser Gly Gly Gly
                405             410             415

Gly Ser Gly Gly Gly Gly Ser Gly Gly Gly Ser Gly Gly Gly Gly
                420             425             430

Ser Gly Gly Gly Gly Ser Gly Gly Gly Gly Ser Gln Ala Val Val Thr
                435             440             445

Gln Glu Pro Ser Leu Thr Val Ser Pro Gly Gly Thr Val Thr Leu Thr
        450             455             460

Cys Gly Ser Ser Thr Gly Ala Val Thr Ala Ser Asn Tyr Ala Asn Trp
465             470             475             480

Val Gln Gln Lys Pro Gly Gln Cys Pro Arg Gly Leu Ile Gly Gly His
                485             490             495

Asn Asn Arg Pro Pro Gly Val Pro Ala Arg Phe Ser Gly Ser Leu Leu
                500             505             510

Gly Gly Lys Ala Ala Leu Thr Leu Leu Gly Ala Gln Pro Glu Asp Glu
                515             520             525

Ala Glu Tyr Tyr Cys Ala Leu Trp Tyr Ser Asp His Trp Val Ile Gly
        530             535             540

Gly Gly Thr Lys Leu Thr Val Leu Gly Thr Pro Leu Gly Asp Thr Thr
545             550             555             560

His Thr Ser Gly Arg His Gly Asp Glu Asp Thr Tyr Tyr Leu Gln Val
                565             570             575

Arg Gly Arg Glu Asn Phe Glu Ile Leu Met Lys Leu Lys Glu Ser Leu
                580             585             590

Glu Leu Met Glu Leu Val Pro Gln Pro Leu Val Asp Ser Tyr Arg Gln
        595             600             605

Gln Gln Gln Leu Leu Gln Arg Pro Gly Gly Ser Gly Gly Ala
        610             615             620
```

```
<210> SEQ ID NO 60
<211> LENGTH: 556
<212> TYPE: PRT
<213> ORGANISM: Homo sapiens

<400> SEQUENCE: 60
```

```
Met Pro Pro Pro Arg Leu Leu Phe Phe Leu Leu Phe Leu Thr Pro Met
1               5               10              15

Glu Val Arg Pro Glu Glu Pro Leu Val Val Lys Val Glu Glu Gly Asp
                20              25              30

Asn Ala Val Leu Gln Cys Leu Lys Gly Thr Ser Asp Gly Pro Thr Gln
        35              40              45

Gln Leu Thr Trp Ser Arg Glu Ser Pro Leu Lys Pro Phe Leu Lys Leu
        50              55              60

Ser Leu Gly Leu Pro Gly Leu Gly Ile His Met Arg Pro Leu Ala Ile
65              70              75              80

Trp Leu Phe Ile Phe Asn Val Ser Gln Gln Met Gly Gly Phe Tyr Leu
                85              90              95

Cys Gln Pro Gly Pro Pro Ser Glu Lys Ala Trp Gln Pro Gly Trp Thr
                100             105             110

Val Asn Val Glu Gly Ser Gly Glu Leu Phe Arg Trp Asn Val Ser Asp
        115             120             125

Leu Gly Gly Leu Gly Cys Gly Leu Lys Asn Arg Ser Ser Glu Gly Pro
```

```
          130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555
```

-continued

```
<210> SEQ ID NO 61
<211> LENGTH: 557
<212> TYPE: PRT
<213> ORGANISM: Homo sapiens

<400> SEQUENCE: 61

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
            325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
    355                 360                 365

Ala Gly Leu Gly Gly Thr Ala Pro Ser Tyr Gly Asn Pro Ser Ser Asp
```

-continued

```
      370            375            380
Val Gln Ala Asp Gly Ala Leu Gly Ser Arg Ser Pro Pro Gly Val Gly
385                390            395                400

Pro Glu Glu Glu Glu Gly Glu Gly Tyr Glu Glu Pro Asp Ser Glu Glu
              405            410            415

Asp Ser Glu Phe Tyr Glu Asn Asp Ser Asn Leu Gly Gln Asp Gln Leu
              420            425            430

Ser Gln Asp Gly Ser Gly Tyr Glu Asn Pro Glu Asp Glu Pro Leu Gly
          435            440            445

Pro Glu Asp Glu Asp Ser Phe Ser Asn Ala Glu Ser Tyr Glu Asn Glu
          450            455            460

Asp Glu Glu Leu Thr Gln Pro Val Ala Arg Thr Met Asp Phe Leu Ser
465            470            475            480

Pro His Gly Ser Ala Trp Asp Pro Ser Arg Glu Ala Thr Ser Leu Ala
              485            490            495

Gly Ser Gln Ser Tyr Glu Asp Met Arg Gly Ile Leu Tyr Ala Ala Pro
          500            505            510

Gln Leu Arg Ser Ile Arg Gly Gln Pro Gly Pro Asn His Glu Glu Asp
          515            520            525

Ala Asp Ser Tyr Glu Asn Met Asp Asn Pro Asp Gly Pro Asp Pro Ala
          530            535            540

Trp Gly Gly Gly Gly Arg Met Gly Thr Trp Ser Thr Arg
545            550            555

<210> SEQ ID NO 62
<211> LENGTH: 468
<212> TYPE: PRT
<213> ORGANISM: Homo sapiens

<400> SEQUENCE: 62

Met Pro Pro Pro Arg Leu Leu Phe Phe Leu Leu Phe Leu Thr Pro Met
1               5              10              15

Glu Val Arg Pro Glu Glu Pro Leu Val Val Lys Val Glu Gly Glu Leu
              20              25              30

Phe Arg Trp Asn Val Ser Asp Leu Gly Gly Leu Gly Cys Gly Leu Lys
          35              40              45

Asn Arg Ser Ser Glu Gly Pro Ser Ser Pro Ser Gly Lys Leu Met Ser
          50              55              60

Pro Lys Leu Tyr Val Trp Ala Lys Asp Arg Pro Glu Ile Trp Glu Gly
65              70              75              80

Glu Pro Pro Cys Leu Pro Pro Arg Asp Ser Leu Asn Gln Ser Leu Ser
              85              90              95

Gln Asp Leu Thr Met Ala Pro Gly Ser Thr Leu Trp Leu Ser Cys Gly
          100            105            110

Val Pro Pro Asp Ser Val Ser Arg Gly Pro Leu Ser Trp Thr His Val
          115            120            125

His Pro Lys Gly Pro Lys Ser Leu Leu Ser Leu Glu Leu Lys Asp Asp
          130            135            140

Arg Pro Ala Arg Asp Met Trp Val Met Glu Thr Gly Leu Leu Leu Pro
145            150            155            160

Arg Ala Thr Ala Gln Asp Ala Gly Lys Tyr Tyr Cys His Arg Gly Asn
              165            170            175

Leu Thr Met Ser Phe His Leu Glu Ile Thr Ala Arg Pro Val Leu Trp
              180            185            190
```

```
His Trp Leu Leu Arg Thr Gly Gly Trp Lys Val Ser Ala Val Thr Leu
        195                 200                 205

Ala Tyr Leu Ile Phe Cys Leu Cys Ser Leu Val Gly Ile Leu His Leu
        210                 215                 220

Gln Arg Ala Leu Val Leu Arg Arg Lys Arg Lys Arg Met Thr Asp Pro
225                 230                 235                 240

Thr Arg Arg Phe Phe Lys Val Thr Pro Pro Pro Gly Ser Gly Pro Gln
                245                 250                 255

Asn Gln Tyr Gly Asn Val Leu Ser Leu Pro Thr Pro Thr Ser Gly Leu
                260                 265                 270

Gly Arg Ala Gln Arg Trp Ala Ala Gly Leu Gly Gly Thr Ala Pro Ser
        275                 280                 285

Tyr Gly Asn Pro Ser Ser Asp Val Gln Ala Asp Gly Ala Leu Gly Ser
        290                 295                 300

Arg Ser Pro Pro Gly Val Gly Pro Glu Glu Glu Glu Gly Glu Gly Tyr
305                 310                 315                 320

Glu Glu Pro Asp Ser Glu Glu Asp Ser Glu Phe Tyr Glu Asn Asp Ser
                325                 330                 335

Asn Leu Gly Gln Asp Gln Leu Ser Gln Asp Gly Ser Gly Tyr Glu Asn
                340                 345                 350

Pro Glu Asp Glu Pro Leu Gly Pro Glu Asp Glu Asp Ser Phe Ser Asn
        355                 360                 365

Ala Glu Ser Tyr Glu Asn Glu Asp Glu Glu Leu Thr Gln Pro Val Ala
        370                 375                 380

Arg Thr Met Asp Phe Leu Ser Pro His Gly Ser Ala Trp Asp Pro Ser
385                 390                 395                 400

Arg Glu Ala Thr Ser Leu Ala Gly Ser Gln Ser Tyr Glu Asp Met Arg
                405                 410                 415

Gly Ile Leu Tyr Ala Ala Pro Gln Leu Arg Ser Ile Arg Gly Gln Pro
                420                 425                 430

Gly Pro Asn His Glu Glu Asp Ala Asp Ser Tyr Glu Asn Met Asp Asn
        435                 440                 445

Pro Asp Gly Pro Asp Pro Ala Trp Gly Gly Gly Gly Arg Met Gly Thr
        450                 455                 460

Trp Ser Thr Arg
465
```

```
<210> SEQ ID NO 63
<211> LENGTH: 467
<212> TYPE: PRT
<213> ORGANISM: Homo sapiens

<400> SEQUENCE: 63
```

```
Met Pro Pro Pro Arg Leu Leu Phe Phe Leu Leu Phe Leu Thr Pro Met
1                   5                   10                  15

Glu Val Arg Pro Glu Glu Pro Leu Val Val Lys Val Glu Gly Glu Leu
                20                  25                  30

Phe Arg Trp Asn Val Ser Asp Leu Gly Gly Leu Gly Cys Gly Leu Lys
        35                  40                  45

Asn Arg Ser Ser Glu Gly Pro Ser Ser Pro Ser Gly Lys Leu Met Ser
        50                  55                  60

Pro Lys Leu Tyr Val Trp Ala Lys Asp Arg Pro Glu Ile Trp Glu Gly
65                  70                  75                  80

Glu Pro Pro Cys Leu Pro Pro Arg Asp Ser Leu Asn Gln Ser Leu Ser
                85                  90                  95
```

```
Gln Asp Leu Thr Met Ala Pro Gly Ser Thr Leu Trp Leu Ser Cys Gly
            100                 105                 110

Val Pro Pro Asp Ser Val Ser Arg Gly Pro Leu Ser Trp Thr His Val
            115                 120                 125

His Pro Lys Gly Pro Lys Ser Leu Leu Ser Leu Glu Leu Lys Asp Asp
            130                 135                 140

Arg Pro Ala Arg Asp Met Trp Val Met Glu Thr Gly Leu Leu Leu Pro
145                 150                 155                 160

Arg Ala Thr Ala Gln Asp Ala Gly Lys Tyr Tyr Cys His Arg Gly Asn
                165                 170                 175

Leu Thr Met Ser Phe His Leu Glu Ile Thr Ala Arg Pro Val Leu Trp
                180                 185                 190

His Trp Leu Leu Arg Thr Gly Gly Trp Lys Val Ser Ala Val Thr Leu
                195                 200                 205

Ala Tyr Leu Ile Phe Cys Leu Cys Ser Leu Val Gly Ile Leu His Leu
            210                 215                 220

Gln Arg Ala Leu Val Leu Arg Arg Lys Arg Lys Arg Met Thr Asp Pro
225                 230                 235                 240

Thr Arg Arg Phe Phe Lys Val Thr Pro Pro Pro Gly Ser Gly Pro Gln
                245                 250                 255

Asn Gln Tyr Gly Asn Val Leu Ser Leu Pro Thr Pro Thr Ser Gly Leu
                260                 265                 270

Gly Arg Ala Gln Arg Trp Ala Ala Gly Leu Gly Gly Thr Ala Pro Ser
                275                 280                 285

Tyr Gly Asn Pro Ser Ser Asp Val Gln Ala Asp Gly Ala Leu Gly Ser
            290                 295                 300

Arg Ser Pro Pro Gly Val Gly Pro Glu Glu Glu Glu Gly Glu Gly Tyr
305                 310                 315                 320

Glu Glu Pro Asp Ser Glu Glu Asp Ser Glu Phe Tyr Glu Asn Asp Ser
                325                 330                 335

Asn Leu Gly Gln Asp Gln Leu Ser Gln Asp Gly Ser Gly Tyr Glu Asn
                340                 345                 350

Pro Glu Asp Glu Pro Leu Gly Pro Glu Asp Glu Asp Ser Phe Ser Asn
            355                 360                 365

Ala Glu Ser Tyr Glu Asn Glu Asp Glu Glu Leu Thr Gln Pro Val Ala
            370                 375                 380

Arg Thr Met Asp Phe Leu Ser Pro His Gly Ser Ala Trp Asp Pro Ser
385                 390                 395                 400

Arg Glu Ala Thr Ser Leu Gly Ser Gln Ser Tyr Glu Asp Met Arg Gly
                405                 410                 415

Ile Leu Tyr Ala Ala Pro Gln Leu Arg Ser Ile Arg Gly Gln Pro Gly
                420                 425                 430

Pro Asn His Glu Glu Asp Ala Asp Ser Tyr Glu Asn Met Asp Asn Pro
            435                 440                 445

Asp Gly Pro Asp Pro Ala Trp Gly Gly Gly Gly Arg Met Gly Thr Trp
            450                 455                 460

Ser Thr Arg
465
```

```
<210> SEQ ID NO 64
<211> LENGTH: 282
<212> TYPE: PRT
<213> ORGANISM: Homo sapiens
```

<400> SEQUENCE: 64

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Ala Pro Ser Pro
    275                 280

<210> SEQ ID NO 65
<211> LENGTH: 384
<212> TYPE: PRT
<213> ORGANISM: Homo sapiens

<400> SEQUENCE: 65

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
            35                  40                  45

Gln Pro Gln Arg Thr Phe Pro Glu Ile Gln Arg Arg Asp Ser Tyr Tyr
        50                  55                  60

Met Thr Ser Ser Gln Leu Ser Thr Pro Leu Gln Gln Trp Arg Gln Gly
65                  70                  75                  80

-continued

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
            115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
            195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
            245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
            325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
    370                 375                 380

<210> SEQ ID NO 66
<211> LENGTH: 330
<212> TYPE: PRT
<213> ORGANISM: Homo sapiens

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

-continued

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 67
<211> LENGTH: 326
<212> TYPE: PRT
<213> ORGANISM: Homo sapiens

<400> SEQUENCE: 67

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp

-continued

```
            115                 120                 125
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 68
<211> LENGTH: 377
<212> TYPE: PRT
<213> ORGANISM: Homo sapiens

<400> SEQUENCE: 68

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160
```

-continued

```
Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 69
<211> LENGTH: 452
<212> TYPE: PRT
<213> ORGANISM: Homo sapiens

<400> SEQUENCE: 69

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
            85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
        130                 135                 140

Gln Val Ser Trp Leu Arg Glu Gly Lys Gln Val Gly Ser Gly Val Thr
145                 150                 155                 160
```

-continued

```
Thr Asp Gln Val Gln Ala Glu Ala Lys Glu Ser Gly Pro Thr Thr Tyr
            165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
            195                 200                 205

Asn Ala Ser Ser Met Cys Val Pro Asp Gln Asp Thr Ala Ile Arg Val
            210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
            245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
            275                 280                 285

Ser Ile Cys Glu Asp Asp Trp Asn Ser Gly Glu Arg Phe Thr Cys Thr
            290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
            325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
            370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
            405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
            435                 440                 445

Gly Thr Cys Tyr
    450

<210> SEQ ID NO 70
<211> LENGTH: 327
<212> TYPE: PRT
<213> ORGANISM: Homo sapiens

<400> SEQUENCE: 70

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
```

```
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 71
<211> LENGTH: 353
<212> TYPE: PRT
<213> ORGANISM: Homo sapiens

<400> SEQUENCE: 71

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
                20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
                100                 105                 110
```

```
Ser Thr Pro Pro Thr Pro Ser Pro Ser Cys Cys His Pro Arg Leu Ser
        115             120             125

Leu His Arg Pro Ala Leu Glu Asp Leu Leu Leu Gly Ser Glu Ala Asn
    130             135             140

Leu Thr Cys Thr Leu Thr Gly Leu Arg Asp Ala Ser Gly Val Thr Phe
145             150             155             160

Thr Trp Thr Pro Ser Ser Gly Lys Ser Ala Val Gln Gly Pro Pro Glu
            165             170             175

Arg Asp Leu Cys Gly Cys Tyr Ser Val Ser Ser Val Leu Pro Gly Cys
        180             185             190

Ala Glu Pro Trp Asn His Gly Lys Thr Phe Thr Cys Thr Ala Ala Tyr
        195             200             205

Pro Glu Ser Lys Thr Pro Leu Thr Ala Thr Leu Ser Lys Ser Gly Asn
    210             215             220

Thr Phe Arg Pro Glu Val His Leu Leu Pro Pro Ser Glu Glu Leu
225             230             235             240

Ala Leu Asn Glu Leu Val Thr Leu Thr Cys Leu Ala Arg Gly Phe Ser
            245             250             255

Pro Lys Asp Val Leu Val Arg Trp Leu Gln Gly Ser Gln Glu Leu Pro
            260             265             270

Arg Glu Lys Tyr Leu Thr Trp Ala Ser Arg Gln Glu Pro Ser Gln Gly
        275             280             285

Thr Thr Thr Phe Ala Val Thr Ser Ile Leu Arg Val Ala Ala Glu Asp
    290             295             300

Trp Lys Lys Gly Asp Thr Phe Ser Cys Met Val Gly His Glu Ala Leu
305             310             315             320

Pro Leu Ala Phe Thr Gln Lys Thr Ile Asp Arg Leu Ala Gly Lys Pro
            325             330             335

Thr His Val Asn Val Ser Val Val Met Ala Glu Val Asp Gly Thr Cys
            340             345             350

Tyr
```

```
<210> SEQ ID NO 72
<211> LENGTH: 340
<212> TYPE: PRT
<213> ORGANISM: Homo sapiens

<400> SEQUENCE: 72

Ala Ser Pro Thr Ser Pro Lys Val Phe Pro Leu Ser Leu Asp Ser Thr
1               5               10              15

Pro Gln Asp Gly Asn Val Val Val Ala Cys Leu Val Gln Gly Phe Phe
            20              25              30

Pro Gln Glu Pro Leu Ser Val Thr Trp Ser Glu Ser Gly Gln Asn Val
        35              40              45

Thr Ala Arg Asn Phe Pro Pro Ser Gln Asp Ala Ser Gly Asp Leu Tyr
    50              55              60

Thr Thr Ser Ser Gln Leu Thr Leu Pro Ala Thr Gln Cys Pro Asp Gly
65              70              75              80

Lys Ser Val Thr Cys His Val Lys His Tyr Thr Asn Pro Ser Gln Asp
            85              90              95

Val Thr Val Pro Cys Pro Val Pro Pro Pro Pro Cys Cys His Pro
            100             105             110

Arg Leu Ser Leu His Arg Pro Ala Leu Glu Asp Leu Leu Leu Gly Ser
        115             120             125
```

-continued

```
Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
                180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
                260                 265                 270

Ser Gln Gly Thr Thr Thr Phe Ala Val Thr Ser Ile Leu Arg Val Ala
            275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
                340

<210> SEQ ID NO 73
<211> LENGTH: 106
<212> TYPE: PRT
<213> ORGANISM: Homo sapiens

<400> SEQUENCE: 73

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 74
<211> LENGTH: 39
<212> TYPE: PRT
<213> ORGANISM: Homo sapiens

<400> SEQUENCE: 74
```

Lys Pro Leu Asp Gly Glu Tyr Phe Thr Leu Gln Ile Arg Gly Arg Glu
1               5                   10                  15

Arg Phe Glu Met Phe Arg Glu Leu Asn Glu Ala Leu Glu Leu Lys Asp
            20                  25                  30

Ala Gln Ala Gly Lys Glu Pro
        35

<210> SEQ ID NO 75
<211> LENGTH: 57
<212> TYPE: PRT
<213> ORGANISM: Homo sapiens

<400> SEQUENCE: 75

Arg Ser Pro Asp Asp Glu Leu Leu Tyr Leu Pro Val Arg Gly Arg Glu
1               5                   10                  15

Thr Tyr Glu Met Leu Leu Lys Ile Lys Glu Ser Leu Glu Leu Met Gln
            20                  25                  30

Tyr Leu Pro Gln His Thr Ile Glu Thr Tyr Arg Gln Gln Gln Gln Gln
        35                  40                  45

Gln His Gln His Leu Leu Gln Lys Gln
        50                  55

<210> SEQ ID NO 76
<211> LENGTH: 52
<212> TYPE: PRT
<213> ORGANISM: Homo sapiens

<400> SEQUENCE: 76

Arg His Gly Asp Glu Asp Thr Tyr Tyr Leu Gln Val Arg Gly Arg Glu
1               5                   10                  15

Asn Phe Glu Ile Leu Met Lys Leu Lys Glu Ser Leu Glu Leu Met Glu
            20                  25                  30

Leu Val Pro Gln Pro Leu Val Asp Ser Tyr Arg Gln Gln Gln Gln Leu
        35                  40                  45

Leu Gln Arg Pro
    50

<210> SEQ ID NO 77
<211> LENGTH: 27
<212> TYPE: PRT
<213> ORGANISM: Homo sapiens

<400> SEQUENCE: 77

Gln Ala Ile Lys Lys Glu Leu Thr Gln Ile Lys Gln Lys Val Asp Ser
1               5                   10                  15

Leu Leu Glu Asn Leu Glu Lys Ile Glu Lys Glu
            20                  25

<210> SEQ ID NO 78
<211> LENGTH: 54
<212> TYPE: PRT
<213> ORGANISM: Homo sapiens

<400> SEQUENCE: 78

Ser Thr Arg Arg Ile Leu Gly Leu Ala Ile Glu Ser Gln Asp Ala Gly
1               5                   10                  15

Ile Lys Thr Ile Thr Met Leu Asp Glu Gln Lys Glu Gln Leu Asn Arg
            20                  25                  30

Ile Glu Glu Gly Leu Asp Gln Ile Asn Lys Asp Met Arg Glu Thr Glu
        35                  40                  45

```
Lys Thr Leu Thr Glu Leu
    50

<210> SEQ ID NO 79
<211> LENGTH: 97
<212> TYPE: PRT
<213> ORGANISM: Homo sapiens

<400> SEQUENCE: 79

Met Cys Gly Ala Pro Ser Ala Thr Gln Pro Ala Thr Ala Glu Thr Gln
1               5                   10                  15

His Ile Ala Asp Gln Val Arg Ser Gln Leu Glu Glu Lys Glu Asn Lys
            20                  25                  30

Lys Phe Pro Val Phe Lys Ala Val Ser Phe Lys Ser Gln Val Val Ala
        35                  40                  45

Gly Thr Asn Tyr Phe Ile Lys Val His Val Gly Asp Glu Asp Phe Val
    50                  55                  60

His Leu Arg Val Phe Gln Ser Leu Pro His Glu Asn Lys Pro Leu Thr
65                  70                  75                  80

Leu Ser Asn Tyr Gln Thr Asn Lys Ala Lys His Asp Glu Leu Thr Tyr
                85                  90                  95

Phe

<210> SEQ ID NO 80
<211> LENGTH: 30
<212> TYPE: PRT
<213> ORGANISM: Unknown
<220> FEATURE:
<223> OTHER INFORMATION: Description of Unknown:
      KCNQ4 sequence

<400> SEQUENCE: 80

Asp Glu Ile Ser Met Met Gly Arg Val Val Lys Val Glu Lys Gln Val
1               5                   10                  15

Gln Ser Ile Glu His Lys Leu Asp Leu Leu Leu Gly Phe Tyr
            20                  25                  30

<210> SEQ ID NO 81
<211> LENGTH: 60
<212> TYPE: PRT
<213> ORGANISM: Unknown
<220> FEATURE:
<223> OTHER INFORMATION: Description of Unknown:
      CBFA2T1 sequence

<400> SEQUENCE: 81

Thr Val Ala Glu Ala Lys Arg Gln Ala Ala Glu Asp Ala Leu Ala Val
1               5                   10                  15

Ile Asn Gln Gln Glu Asp Ser Ser Glu Ser Cys Trp Asn Cys Gly Arg
            20                  25                  30

Lys Ala Ser Glu Thr Cys Ser Gly Cys Asn Thr Ala Arg Tyr Cys Gly
        35                  40                  45

Ser Phe Cys Gln His Lys Asp Trp Glu Lys His His
    50                  55                  60

<210> SEQ ID NO 82
<211> LENGTH: 90
<212> TYPE: PRT
<213> ORGANISM: Homo sapiens

<400> SEQUENCE: 82
```

```
Glu Glu Gly Asp Asn Ala Val Leu Gln Cys Leu Lys Gly Thr Ser Asp
1               5                   10                  15

Gly Pro Thr Gln Gln Leu Thr Trp Ser Arg Glu Ser Pro Leu Lys Pro
                20                  25                  30

Phe Leu Lys Leu Ser Leu Gly Leu Pro Gly Leu Gly Ile His Met Arg
            35                  40                  45

Pro Leu Ala Ile Trp Leu Phe Ile Phe Asn Val Ser Gln Gln Met Gly
        50                  55                  60

Gly Phe Tyr Leu Cys Gln Pro Gly Pro Pro Ser Glu Lys Ala Trp Gln
65                  70                  75                  80

Pro Gly Trp Thr Val Asn Val Glu Gly Ser
                85                  90
```

<210> SEQ ID NO 83
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
                20                  25                  30
```

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

```
Thr Pro Leu Gly Asp Thr Thr His Thr
1               5
```

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Gly Gly Gly Gly Ser Gly Gly Gly Gly Ser Gly Gly Gly Gly Ser
```

-continued

```
1               5               10              15
```

```
<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Gly Gly Gly Ser
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 88

His His His His His His
1               5

<210> SEQ ID NO 89
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(75)
<223> OTHER INFORMATION: This sequence may encompass 1-15 "Gly Gly Gly
      Gly Ser" repeating units
<220> FEATURE:
<223> OTHER INFORMATION: See specification as filed for detailed
      description of substitutions and preferred embodiments

<400> SEQUENCE: 89

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
          20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
      50                  55                  60

Ser Gly Gly Gly Gly Ser Gly Gly Gly Gly Ser
65                  70                  75

<210> SEQ ID NO 90
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-20, 25 or 30 "Gly
      Gly Gly Gly Ser" repeating units
<220> FEATURE:
<223> OTHER INFORMATION: See specification as filed for detailed
```

-continued

```
description of substitutions and preferred embodiments

<400> SEQUENCE: 90

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
            85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser
145                 150
```

CD19 ANTIBODIES AND METHODS OF USING THE SAME

CROSS-REFERENCE TO RELATED APPLICATIONS

This application is a U.S. National Stage Application under 35 U.S.C. § 371 of International Patent Application No. PCT/US2020/027071, filed on Apr. 7, 2020, which claims the benefit of and priority to U.S. Provisional Patent Application No. 62/831,123, filed Apr. 8, 2019, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on May 5, 2020, is named 115872-0779 SL.txt and is 262,688 bytes in size.

TECHNICAL FIELD

The present technology relates generally to the preparation of immunoglobulin-related compositions (e.g., antibodies or antigen binding fragments thereof) that specifically bind CD19 protein and uses of the same. In particular, the present technology relates to the preparation of CD19 binding antibodies and their use in detecting and treating CD19-associated cancers and CD19-associated autoimmune diseases.

BACKGROUND

The following description of the background of the present technology is provided simply as an aid in understanding the present technology and is not admitted to describe or constitute prior art to the present technology.

Non-Hodgkin lymphoma (NHLs) is a heterogeneous disease comprising more than 30 types of B lymphocyte and T lymphocyte malignancies, and 4.3% of all cancers diagnosed in the US. B-cell malignancies include non-Hodgkin lymphomas (NHL), chronic lymphocytic leukemia (CLL), and acute lymphocytic leukemia (ALL). B-cell lymphomas constitute 85% of all NHL; 30% being diffuse large B-cell lymphoma (DLBCL) and 20% follicular lymphoma (20%), resulting in almost 19,000 deaths. In the US, CLL accounts for one third of leukemias and responsible for 4600 deaths annually. (Jemal et al., *J Natl Cancer Inst* 109(9), djx030 (2017).

SUMMARY OF THE PRESENT TECHNOLOGY

In one aspect, the present disclosure provides an antibody or antigen binding fragment thereof comprising a heavy chain immunoglobulin variable domain ($V_H$) and a light chain immunoglobulin variable domain ($V_L$), wherein: (a) the $V_H$ comprises an amino acid sequence selected from the group consisting of: SEQ ID NOs: 5, 6, 7, 8, 9, 10, 11, and 12; and/or (b) the $V_L$ comprises an amino acid sequence selected from the group consisting of: SEQ ID NO: 17, SEQ ID NO: 18, and SEQ ID NO: 19. The antibody may further comprise an Fc domain of an isotype selected from the group consisting of IgG1, IgG2, IgG3, IgG4, IgA1, IgA2, IgM, IgD, and IgE. In some embodiments, the antibody comprises an IgG1 constant region comprising one or more amino acid substitutions selected from the group consisting of N297A and K322A. Additionally or alternatively, in some embodiments, the antibody comprises an IgG4 constant region comprising a S228P mutation. In certain embodiments, the antigen binding fragment is selected from the group consisting of Fab, F(ab')$_2$, Fab', scF$_v$, and F$_v$. In some embodiments, the antibody is a monoclonal antibody, chimeric antibody, humanized antibody, or a bispecific antibody.

Additionally or alternatively, in some embodiments, the antibody or antigen binding fragment binds to a CD19 polypeptide including an Ig-like C2 loop that comprises the amino acid sequence EE GDNAVLQCLK GTSDGPTQQL TWSRESPLKP FLKLSLGLPG LGIHMRPLAI WLFIFNVSQQ MGGFYLCQPG PPSEKAWQPG WTVN-VEGS (SEQ ID NO: 82) (corresponding to the amino acid residues at positions 29-118 of SEQ ID NO: 60 or SEQ ID NO: 61). Additionally or alternatively, in certain embodiments, the antibody or antigen binding fragment binds to a conformational epitope comprising the amino acid residues corresponding to positions 29-118 of SEQ ID NO: 60 or SEQ ID NO: 61.

In one aspect, the present disclosure provides an antibody comprising a heavy chain (HC) comprising amino acid sequence comprising SEQ ID NO: 22, SEQ ID NO: 26, SEQ ID NO: 29, SEQ ID NO: 31, SEQ ID NO: 45, SEQ ID NO: 47, ora variant thereof having one or more conservative amino acid substitutions, and/or a light chain (LC) amino acid sequence comprising SEQ ID NO: 20, SEQ ID NO: 24, SEQ ID NO: 28, SEQ ID NO: 30, SEQ ID NO: 44, SEQ ID NO: 46, or a variant thereof having one or more conservative amino acid substitutions.

In some embodiments, the antibody comprises a HC amino acid sequence and a LC amino acid sequence selected from the group consisting of: SEQ ID NO: 22 and SEQ ID NO: 20 (chFMC63×CD3 BsAb); SEQ ID NO: 26 and SEQ ID NO: 24 (BC250-hFMC63 VL-2/VH-1b×CD3 BsAb); SEQ ID NO: 29 and SEQ ID NO: 28 (mFMC63×mC825 BsAb); SEQ ID NO: 31 and SEQ ID NO: 30 (mFMC63×hC825 BsAb); SEQ ID NO: 45 and SEQ ID NO: 44 (hFMC63 VL-2VH-1b×mC825); and SEQ ID NO: 47 and SEQ ID NO: 46 (hFMC63 VL-2VH-1b×hC825), respectively.

In one aspect, the present disclosure provides an antibody comprising (a) a light chain immunoglobulin variable domain sequence that is at least 80%, at least 85%, at least 90%, at least 95%, or at least 99% identical to the light chain immunoglobulin variable domain sequence present in any one of SEQ ID NOs: 17, 18, or 19; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: 5, 6, 7, 8, 9, 10, 11, or 12.

In another aspect, the present disclosure provides an antibody comprising (a) a LC sequence that is at least 80%, at least 85%, at least 90%, at least 95%, or at least 99% identical to the LC sequence present in any one of SEQ ID NOs: 20, 24, 28, 30, 44, or 46; and/or (b) a HC sequence that is at least 80%, at least 85%, at least 90%, at least 95%, or at least 99% identical to the HC sequence present in any one of SEQ ID NOs: 22, 26, 29, 31, 45, or 47.

In any of the above embodiments, the antibody is a chimeric antibody, a humanized antibody, or a bispecific antibody. Additionally or alternatively, in some embodiments, the antibody comprises an IgG1 constant region comprising one or more amino acid substitutions selected from the group consisting of N297A and K322A. In certain embodiments, the antibody of the present technology comprises an IgG4 constant region comprising a S228P mutation. In any of the above embodiments, the antibody or antigen binding fragment binds to a CD19 polypeptide including an Ig-like C2 loop that comprises the amino acid sequence EE GDNAVLQCLK GTSDGPTQQL TWSRE-SPLKP FLKLSLGLPG LGIHMRPLAI WLFIFNVSQQ MGGFYLCQPG PPSEKAWQPG WTVNVEGS (SEQ ID NO: 82) (corresponding to the amino acid residues at positions 29-118 of SEQ ID NO: 60 or SEQ ID NO: 61). Additionally or alternatively, in certain embodiments, the antibody or antigen binding fragment binds to a conformational epitope comprising the amino acid residues corresponding to positions 29-118 of SEQ ID NO: 60 or SEQ ID NO: 61.

Additionally or alternatively, in some embodiments, the antibody of the present technology lacks α-1,6-fucose modifications.

In one aspect, the present disclosure provides a bispecific antibody or antigen binding fragment comprising an amino acid sequence that is at least 95% identical to an amino acid sequence selected from any one of SEQ ID NOs: 32-43, or 48-59. In certain embodiments, the bispecific antibody or antigen binding fragment comprises an amino acid sequence selected from any one of SEQ ID NOs: 32-43, or 48-59.

In one aspect, the present disclosure provides a bispecific antigen binding fragment comprising a first polypeptide chain, wherein: the first polypeptide chain comprises in the N-terminal to C-terminal direction: (i) a heavy chain variable domain of a first immunoglobulin that is capable of specifically binding to a first epitope; (ii) a flexible peptide linker comprising the amino acid sequence (GGGGS)$_6$ (SEQ ID NO: 83); (iii) a light chain variable domain of the first immunoglobulin; (iv) a flexible peptide linker comprising the amino acid sequence (GGGGS)$_4$ (SEQ ID NO: 84); (v) a heavy chain variable domain of a second immunoglobulin that is capable of specifically binding to a second epitope; (vi) a flexible peptide linker comprising the amino acid sequence (GGGGS)$_6$ (SEQ ID NO: 83); (vii) a light chain variable domain of the second immunoglobulin; (viii) a flexible peptide linker sequence comprising the amino acid sequence TPLGDTTHT (SEQ ID NO: 85); and (ix) a self-assembly disassembly (SADA) polypeptide, wherein the heavy chain variable domain of the first immunoglobulin is selected from the group consisting of: SEQ ID NOs: 5, 6, 7, 8, 9, 10, 11, and 12; and/or the light chain variable domain of the first immunoglobulin is selected from the group consisting of: SEQ ID NO: 17, SEQ ID NO: 18, and SEQ ID NO: 19.

In another aspect, the present disclosure provides a bispecific antigen binding fragment comprising a first polypeptide chain, wherein: the first polypeptide chain comprises in the N-terminal to C-terminal direction: (i) a light chain variable domain of a first immunoglobulin that is capable of specifically binding to a first epitope; (ii) a flexible peptide linker comprising the amino acid sequence (GGGGS)$_6$ (SEQ ID NO: 83); (iii) a heavy chain variable domain of the first immunoglobulin; (iv) a flexible peptide linker comprising the amino acid sequence (GGGGS)$_4$ (SEQ ID NO: 84); (v) a heavy chain variable domain of a second immunoglobulin that is capable of specifically binding to a second epitope; (vi) a flexible peptide linker comprising the amino acid sequence (GGGGS)$_6$ (SEQ ID NO: 83); (vii) a light chain variable domain of the second immunoglobulin; (viii) a flexible peptide linker sequence comprising the amino acid sequence TPLGDTTHT (SEQ ID NO: 85); and (ix) a self-assembly disassembly (SADA) polypeptide, wherein the heavy chain variable domain of the first immunoglobulin is selected from the group consisting of: SEQ ID NOs: 5, 6, 7, 8, 9, 10, 11, and 12; and/or the light chain variable domain of the first immunoglobulin is selected from the group consisting of: SEQ ID NO: 17, SEQ ID NO: 18, and SEQ ID NO: 19.

In certain embodiments of the bispecific antigen binding fragments disclosed herein, the SADA polypeptide comprises a tetramerization, pentamerization, or hexamerization domain. In some embodiments, the SADA polypeptide comprises a tetramerization domain of any one of p53, p63, p'73, hnRNPC, SNA-23, Stefin B, KCNQ4, and CBFA2T1. Additionally or alternatively, in some embodiments, the bispecific antigen binding fragment comprises an amino acid sequence selected from SEQ ID NOs: 32-43, or 48-59.

In one aspect, the present disclosure provides a bispecific antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein: (a) each of the first polypeptide chain and the fourth polypeptide chain comprises in the N-terminal to C-terminal direction: (i) a light chain variable domain of a first immunoglobulin that is capable of specifically binding to a first epitope; (ii) a light chain constant domain of the first immunoglobulin; (iii) a flexible peptide linker comprising the amino acid sequence (GGGGS)$_3$ (SEQ ID NO: 86); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin are capable of specifically binding to a second epitope, and are linked together via a flexible peptide linker comprising the amino acid sequence (GGGGS)$_6$ (SEQ ID NO: 83) to form a single-chain variable fragment; and (b) each of the second polypeptide chain and the third polypeptide chain comprises in the N-terminal to C-terminal direction: (i) a heavy chain variable domain of the first immunoglobulin that is capable of specifically binding to the first epitope; and (ii) a heavy chain constant domain of the first immunoglobulin; and wherein the heavy chain variable domain of the first immunoglobulin is selected from the group consisting of: SEQ ID NOs: 5, 6, 7, 8, 9, 10, 11, and 12; and/or the light chain variable domain of the first immunoglobulin is selected from the group consisting of: SEQ ID NO: 17, SEQ ID NO: 18, and SEQ ID NO: 19. In certain embodiments, the second immunoglobulin binds to CD3, CD4, CD8, CD20, CD19, CD21, CD23, CD46, CD80, HLA-DR, CD74, CD19, CD14, CD15, CD16, CD123, TCR gamma/delta, NKp46, KIR, or a small molecule DOTA hapten.

In one aspect, the present disclosure provides a recombinant nucleic acid sequence encoding any of the antibodies or antigen binding fragments described herein. In some embodiments, the recombinant nucleic acid sequence is selected from the group consisting of: SEQ ID NOs: 21, 23, 25, and 27.

In another aspect, the present disclosure provides a host cell or vector comprising any of the recombinant nucleic acid sequences disclosed herein.

In one aspect, the present disclosure provides a composition comprising an antibody or antigen binding fragment of the present technology and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof In some embodiments of the bispecific antibody or antigen binding fragment of the present technology, the bispecific antibody binds to T cells, B-cells, myeloid cells, plasma cells, or mast-cells. Additionally or alternatively, in some embodiments, the bispecific antibody or antigen binding fragment binds to CD3, CD4, CD8, CD20, CD19, CD21, CD23, CD46, CD80, HLA-DR, CD74, CD19, CD14, CD15, CD16, CD123, TCR gamma/delta, NKp46, KIR, or a small molecule DOTA hapten. The small molecule DOTA hapten may be selected from the group consisting of DOTA, DOTA-Bn, DOTA-desferrioxamine, DOTA-Phe-Lys(HSG)-D-Tyr-Lys(HSG)-NH$_2$, Ac-Lys(HSG)D-Tyr-Lys(HSG)-Lys (Tscg-Cys)-NH$_2$, DOTA-D-Asp-D-Lys(HSG)-D-Asp-D-Lys(HSG)-NH$_2$; DOTA-D-Glu-D-Lys(HSG)-D-Glu-D-Lys (HSG)-NH$_2$, DOTA-D-Tyr-D-Lys(HSG)-D-Glu-D-Lys (HSG)-NH$_2$, DOTA-D-Ala-D-Lys(HSG)-D-Glu-D-Lys (HSG)-NH$_2$, DOTA-D-Phe-D-Lys(HSG)-D-Tyr-D-Lys (HSG)-NH$_2$, Ac-D-Phe-D-Lys(DOTA)-D-Tyr-D-Lys (DOTA)-NH$_2$, Ac-D-Phe-D-Lys(DTPA)-D-Tyr-D-Lys (DTPA)-NH$_2$, Ac-D-Phe-D-Lys(Bz-DTPA)-D-Tyr-D-Lys (Bz-DTPA)-NH$_2$, Ac-D-Lys(HSG)-D-Tyr-D-Lys(HSG)-D-Lys(Tscg-Cys)-NH$_2$, DOTA-D-Phe-D-Lys(HSG)-D-Tyr-D-Lys(HSG)-D-Lys(Tscg-Cys)-NH$_2$, (Tscg-Cys)-D-Phe-D-Lys(HSG)-D-Tyr-D-Lys(HSG)-D-Lys(DOTA)-NH$_2$, Tscg-D-Cys-D-Glu-D-Lys(HSG)-D-Glu-D-Lys(HSG)-NH$_2$, (Tscg-Cys)-D-Glu-D-Lys(HSG)-D-Glu-D-Lys(HSG)-NH$_2$, Ac-D-Cys-D-Lys(DOTA)-D-Tyr-D-Ala-D-Lys(DOTA)-D-Cys-NH$_2$, Ac-D-Cys-D-Lys(DTPA)-D-Tyr-D-Lys(DTPA)-NH$_2$, Ac-D-Lys(DTPA)-D-Tyr-D-Lys(DTPA)-D-Lys(Tscg-Cys)-NH$_2$, and Ac-D-Lys(DOTA)-D-Tyr-D-Lys(DOTA)-D-Lys(Tscg-Cys)-NH$_2$.

In another aspect, the present disclosure provides a method for treating a CD19-associated cancer, or a CD19-associated autoimmune disease in a subject in need thereof, comprising administering to the subject an effective amount of any one of the antibodies or antigen binding fragments disclosed herein. In certain embodiments, the antibody comprises a HC amino acid sequence and a LC amino acid sequence selected from the group consisting of: SEQ ID NO: 22 and SEQ ID NO: 20 (chFMC63×CD3 BsAb); SEQ ID NO: 26 and SEQ ID NO: 24 (BC250-hFMC63 VL-2/VH-1b×CD3 BsAb); SEQ ID NO: 29 and SEQ ID NO: 28 (mFMC63×mC825 BsAb); SEQ ID NO: 31 and SEQ ID NO: 30 (mFMC63×hC825 BsAb); SEQ ID NO: 45 and SEQ ID NO: 44 (hFMC63 VL-2VH-1b×mC825); and SEQ ID NO: 47 and SEQ ID NO: 46 (hFMC63 VL-2VH-1b×hC825), respectively, wherein the antibody specifically binds to CD19. In some embodiments, the antibody or antigen binding fragment comprises an amino acid sequence selected from any one of SEQ ID NOs: 32-43, or 48-59.

Examples of CD19-associated cancer include acute myeloid leukemia, myelodysplastic syndrome, chronic Myeloid Leukemia, Chronic Lymphocytic Leukemia, Non-Hodgkin Lymphoma, multiple myeloma, Plasmacytoma, Monoclonal gammopathy of undetermined significance, Waldenstrom's macroglobulinemia (lymphoplasmacytic lymphoma), Heavy chain disease, primary amyloidosis, Post-transplant lymphoproliferative disorder, Hodgkin lymphoma, MALT lymphoma, B cell Lymphoma, mantle cell lymphoma, (germinal center-like) diffuse large cell lymphoma, Burkitt's lymphoma, Bilineage leukemia, biphenotypic leukemia, Hairy cell leukemia, Precursor B acute lymphoblastic leukemia/lymphoma, Primary cutaneous follicle center lymphoma, follicular lymphoma, or Marginal Zone B-cell Non-Hodgkin's Lymphoma.

Examples of CD19-associated autoimmune disease include multiple sclerosis (MS), rheumatoid arthritis (RA), systemic lupus erythematosus, paraneoplastic syndromes, Pemphigus Vulgaris, type 2 diabetes, or graft-versus-host disease.

Additionally or alternatively, in some embodiments of the method, the antibody or antigen binding fragment is administered to the subject separately, sequentially or simultaneously with an additional therapeutic agent. Examples of additional therapeutic agents for treating cancer include one or more of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents. Examples of additional therapeutic agents for treating autoimmune disease include one or more of non-steroidal anti-inflammatory drugs (NSAIDs), glucocorticoids, disease-modifying antirheumatic drugs (DMARD5), anti-TNF biologics, abatacept, tocilizumab, anakinra, and rituximab.

In another aspect, the present disclosure provides a method for detecting a tumor in a subject in vivo comprising (a) administering to the subject an effective amount of an antibody or antigen binding fragment of the present technology, wherein the antibody or antigen binding fragment is configured to localize to a tumor expressing CD19 and is labeled with a radioisotope; and (b) detecting the presence of a tumor in the subject by detecting radioactive levels emitted by the antibody or antigen binding fragment that are higher than a reference value. In some embodiments, the subject is diagnosed with or is suspected of having cancer. Radioactive levels emitted by the antibody or antigen binding fragment may be detected using positron emission tomography or single photon emission computed tomography.

Additionally or alternatively, in some embodiments, the method further comprises administering to the subject an effective amount of an immunoconjugate comprising an antibody or antigen binding fragment of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}$Y, $^{90}$Y, $^{89}$Sr, $^{165}$Dy, $^{186}$Re, $^{188}$Re, $^{177}$Lu, and $^{67}$Cu. In some embodiments of the method, nonspecific FcR-dependent binding in normal tissues is eliminated or reduced (e.g., via N297A mutation in Fc region, which results in aglycosylation).

Also disclosed herein are kits for the detection and/or treatment of CD19-associated cancers, or CD19-associated autoimmune diseases, comprising at least one immunoglobulin-related composition of the present technology (e.g., any antibody or antigen binding fragment described herein), or a functional variant (e.g., substitutional variant) thereof and instructions for use. In certain embodiments, the immunoglobulin-related composition is coupled to one or more detectable labels. In one embodiment, the one or more detectable labels comprise a radioactive label, a fluorescent label, or a chromogenic label.

Additionally or alternatively, in some embodiments, the kit further comprises a secondary antibody that specifically binds to an anti-CD19 immunoglobulin-related composition described herein. In some embodiments, the secondary antibody is coupled to at least one detectable label selected from the group consisting of a radioactive label, a fluorescent label, or a chromogenic label.

In another aspect, the present disclosure provides a method for selecting a subject for pretargeted radioimmunotherapy comprising (a) administering to the subject an effective amount of a complex comprising a radiolabeled DOTA hapten and a bispecific antibody or antigen binding fragment of the present technology that binds to the radiolabeled DOTA hapten and a CD19 antigen, wherein the complex is configured to localize to a tumor expressing the CD19 antigen recognized by the bispecific antibody or antigen binding fragment of the complex; (b) detecting radioactive levels emitted by the complex; and (c) selecting the subject for pretargeted radioimmunotherapy when the radioactive levels emitted by the complex are higher than a reference value.

In one aspect, the present disclosure provides a method for increasing tumor sensitivity to radiation therapy in a subject diagnosed with a CD19-associated cancer comprising administering to the subject an effective amount of a complex comprising a radiolabeled-DOTA hapten and a bispecific antibody or antigen binding fragment of the present technology that recognizes and binds to the radiolabeled-DOTA hapten and a CD19 antigen target, wherein the complex is configured to localize to a tumor expressing the CD19 antigen target recognized by the bispecific antibody or antigen binding fragment of the complex.

In another aspect, the present disclosure provides a method for treating cancer in a subject in need thereof comprising administering to the subject an effective amount of a complex comprising a radiolabeled-DOTA hapten and a bispecific antibody or antigen binding fragment of the present technology that recognizes and binds to the radiolabeled-DOTA hapten and a CD19 antigen target, wherein the complex is configured to localize to a tumor expressing the CD19 antigen target recognized by the bispecific antibody or antigen binding fragment of the complex.

In any of the above embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally, intratumorally, or intranasally. In some embodiments of the methods disclosed herein, the subject is human. Additionally or alternatively, in any of the above embodiments of the methods disclosed herein, the radiolabeled-DOTA hapten comprises $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu, and optionally comprises an alpha particle-emitting isotope, a beta particle-emitting isotope, or an Auger-emitter.

In one aspect, the present disclosure provides a method for increasing tumor sensitivity to radiation therapy in a subject diagnosed with a CD19-associated cancer comprising (a) administering an effective amount of an anti-DOTA bispecific antibody or antigen binding fragment of the present technology to the subject, wherein the anti-DOTA bispecific antibody or antigen binding fragment is configured to localize to a tumor expressing a CD19 antigen target; and (b) administering an effective amount of a radiolabeled-DOTA hapten to the subject, wherein the radiolabeled-DOTA hapten is configured to bind to the anti-DOTA bispecific antibody or antigen binding fragment. In another aspect, the present disclosure provides a method for treating cancer in a subject in need thereof comprising (a) administering an effective amount of an anti-DOTA bispecific antibody or antigen binding fragment of the present technology to the subject, wherein the anti-DOTA bispecific antibody or antigen binding fragment is configured to localize to a tumor expressing a CD19 antigen target; and (b) administering an effective amount of a radiolabeled-DOTA hapten to the subject, wherein the radiolabeled-DOTA hapten is configured to bind to the anti-DOTA bispecific antibody or antigen binding fragment. In some embodiments, the methods of the present technology further comprise administering an effective amount of a clearing agent to the subject prior to administration of the radiolabeled-DOTA hapten.

Additionally or alternatively, in any of the above embodiments of the methods disclosed herein, the radiolabeled-DOTA hapten comprises $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu, and optionally comprises an alpha particle-emitting isotope, a beta particle-emitting isotope, or an Auger-emitter. In any of the above embodiments of the methods disclosed herein, the subject is human.

BRIEF DESCRIPTION OF THE DRAWINGS

As shown in FIG. 4, binding of some antibodies resisted repeated washing, demonstrating that those antibodies had high affinity to their target. There was a spectrum of affinities from low to high for these humanized clones. Since the humanized $V_H$ and $V_L$ sequences had CDR sequences that were identical to those of the FMC63 parent, these data demonstrate that the affinity of the humanized CD19 antibodies could be modulated by changing the sequence of the antibody framework regions, while retaining the CDR sequences of the parent antibody.

FIG. 5C shows a comparison of the $EC_{50}$ of different anti-CD19 BsAbs against their corresponding affinity towards CD19. The potency of the anti CD19-BsAbs correlates with their affinity to CD19, with BC250 (VL-2, VH-1b) showing the highest cytotoxic potency.

FIG. 6A shows leukemia progression as monitored by BLI. FIG. 6B shows a plot of total luminous flux from the mice as a function of the number of days post-injection of the NALM6-luciferase ALL cells. FIG. 6C shows the percentage survival of the mice as a function of time post-injection of the NALM6-luciferase ALL cells.

FIG. 7A shows lymphoma progression as monitored by BLI. FIG. 7B shows a plot of total luminous flux from the mice as a function of the number of days post-injection of the Daudi cells. FIG. 7C shows photographs of the kidney of a representative mouse from the different treatment groups (top panel) and the corresponding flow cytometry images of the kidney homogenates stained with anti-CD19 and anti-human CD45 antibodies (bottom panel). The population of cells along the diagonal are Daudi cells.

FIG. 8A shows leukemia progression as monitored by BLI. FIG. 8B shows the percentage survival of the mice as a function of time post-injection of the BV173-luciferase cells. FIG. 8C shows a plot of total luminous flux from the mice as a function of the number of days post-injection of the BV173 cells. FIG. 8D shows photographs of the liver of a representative mouse from the different treatment groups (top panel) and the corresponding flow cytometry images of the liver homogenates stained with anti-CD19 and anti-human CD45 antibodies (bottom panel). The livers of mice from the groups that did not receive BC250 had multiple visible metastases, while mice that were treated with ATC/BC250 showed no liver metastasis.

FIG. 9A shows lymphoma progression as monitored by BLI. FIG. 9B shows a plot of total luminous flux from the mice as a function of the number of days post-injection of Raji cells.

FIG. 10A shows the in vitro cytotoxicity of increasing doses of the CD19-BsAb (BC250) BsAb, and Blinatumomab. FIG. 10B shows the in vivo efficacy of CD19-BsAb (BC250) and Blinatumomab against NALM6 cells in a xenograft mouse model. NSG mice were intravenously injected with 1 million NALM6-luciferase-expressing ALL cells on day 0. After 3 days, the mice were imaged (bioluminescent imaging, BLI) and were separated into 7 treatment groups: (1) T cells only, (2) T cells plus 5 femtomoles BC250, (3) T cells plus 50 femtomoles BC250, (4) T cells plus 500 femtomoles BC250, (5) T cells plus 10 femtomoles Blinatumomab, (6) T cells plus 100 femtomoles Blinatumomab, and (7) T cells plus 1000 femtomoles Blinatumomab. Treatment was initiated at day 4, once the leukemia was established. For three weeks, mice received 3 injections of 10 million activated T cells on days 4, 11, and 18. BsAb was administered 5 days/week. After the last dose of activated T cells, antibody was administered for 8 more doses and then stopped. To support T cell survival in vivo, 1000 IU IL2 was administered subcutaneously twice per week. Leukemia progression was monitored by BLI.

FIG. 11A shows a plot of total luminous flux as a function of time in mice treated with ATC alone, or ATC in combination with 10 femtomole Blinatumomab or 5 femtomole BC250. FIG. 11B shows the percent survival of mice treated with ATC alone, or ATC in combination with 10 femtomole Blinatumomab or 5 femtomole BC250. FIG. 11C shows a plot of total luminous flux as a function of time in mice treated with ATC alone, or ATC in combination with 100 femtomole Blinatumomab or 50 femtomole BC250. Administration of 50 femtomole/dose of BC250 reduced leukemia burden 11-fold and 68-fold more at days 11 and 17, respectively, compared to 100 femtomole/dose of Blinatumomab. FIG. 11D shows the percent survival of mice treated with ATC alone, or ATC in combination with 100 femtomole Blinatumomab or 50 femtomole BC250. FIG. 11E shows a plot of total luminous flux as a function of time in mice treated with ATC alone, or ATC in combination with 1000 femtomole Blinatumomab or 500 femtomole BC250. FIG. 11F shows the percent survival of mice treated with ATC alone, or ATC in combination with 1000 femtomole Blinatumomab or 500 femtomole BC250. The indicated p-values in FIGS. 11A, 11C and 11E are based on the statistical difference between: ATC/Blinatumomab vs. ATC/BC250 at day 11 and day 17. The indicated p-values in FIGS. 11B, 11D and 11F are based on the statistical difference between: ATC/Blinatumomab vs. ATC/BC250.

FIG. 12 shows amino acid sequences of murine and humanized FMC63 heavy chain variable domains (SEQ ID NOs: 1 and 5-12). CDR sequences are indicated in underlined boldface font. The amino acid sequences of the V_{H}CDR1, V_{H}CDR2, and V_{H}CDR3 regions of murine FMC63 V_{H} domain are GVSLPDYG (SEQ ID NO: 2), IWGSETT (SEQ ID NO: 3), and AKHYYYGGSYAMDY (SEQ ID NO: 4), respectively. VH-1b (SEQ ID NO: 5), VH-2b (SEQ ID NO: 6), VH-3 (SEQ ID NO: 7), VH-4 (SEQ ID NO: 8), VH-5b (SEQ ID NO: 9), VH-6b (SEQ ID NO: 10), VH-7b (SEQ ID NO: 11) and VH-8b (SEQ ID NO: 12) are humanized versions of the murine FMC63 V_{H} domain.

FIG. 13 shows the amino acid sequences of the murine and humanized FMC63 light chain variable domains (SEQ ID NOs: 13 and 17-19). CDR sequences are indicated in underlined boldface font. The amino acid sequences of the V_{L}CDR1, V_{L}CDR2, and V_{L}CDR3 regions of murine FMC63 V_{L} domain are QDISKY (SEQ ID NO: 14), HTS (SEQ ID NO: 15), and QQGNTLPYT (SEQ ID NO: 16), respectively. VL-1 (SEQ ID NO: 17), VL-2 (SEQ ID NO: 18), and VL-3 (SEQ ID NO: 19) are humanized versions of the murine FMC63 V_{L} domain.

FIGS. 14A and 14B show the amino acid and nucleotide sequences of the light chain of the chimeric BsAb (chFMC63), represented as SEQ ID NOs: 20 and 21, respectively. FIGS. 14C and 14D show the amino acid and nucleotide sequences of the heavy chain of the chimeric BsAb (chFMC63), represented as SEQ ID NOs: 22 and 23, respectively. The signal peptide is underlined, the variable domains of the chimeric anti-CD19 antibody are italicized, and linker sequences are boldfaced and underlined.

FIG. 15A-15B show the amino acid and nucleotide sequences of the light chain of BsAb BC250 (hFMC63 L2HC1b), represented as SEQ ID NOs: 24 and 25, respectively. FIG. 15C-15D show the amino acid and nucleotide sequences of the heavy chain of BsAb BC250 (hFMC63 L2HC1b), represented as SEQ ID NOs: 26 and 27, respectively. The signal peptide is underlined, the variable domains of the anti-CD19 BsAb BC250 (hFMC63 L2HC1b) are italicized, and linker sequences are boldfaced and underlined.

FIGS. 16A-16B show the amino acid sequences of the light chain and heavy chain of a murine FMC63× murine C825 (anti-DOTA) BsAb, represented as SEQ ID NOs: 28 and 29, respectively. The signal peptide is underlined, the variable domains of the murine FMC63× murine C825 (anti-DOTA) BsAb are italicized, and linker sequences are boldfaced and underlined.

FIGS. 17A-17B show the amino acid sequences of the light chain and heavy chain of a murine FMC63× humanized C825 (anti-DOTA) BsAb, represented as SEQ ID NOs: 30 and 31, respectively. The signal peptide is underlined, the variable domains of the murine FMC63× humanized C825 (anti-DOTA) BsAb are italicized, and linker sequences are boldfaced and underlined.

FIGS. 18A-18B show the amino acid sequences of two murine FMC63× humanized C825 (anti-DOTA) single-chain bispecific tandem fragment variable (scBsTaFv) immunoglobulin-related compositions of the present technology (SEQ ID NOs: 32 and 33). The signal peptide is underlined, the variable domains of the murine FMC63× humanized C825 (anti-DOTA) scBsTaFvs are italicized, linker or spacer sequences are indicated in boldfaced, underlined font, and p53 tetramerization domains are boldfaced.

FIGS. 19A-19B show the amino acid sequences of two murine FMC63× humanized C825 (anti-DOTA) single-chain bispecific tandem fragment variable (scBsTaFv) immunoglobulin-related compositions of the present technology (SEQ ID NOs: 34 and 35). The signal peptide is underlined, the variable domains of the murine FMC63× humanized C825 (anti-DOTA) scBsTaFvs are italicized, linker or spacer sequences are indicated in boldfaced, underlined font, and p63 tetramerization domains are boldfaced.

FIGS. 20A-20B show the amino acid sequences of two murine FMC63× humanized C825 (anti-DOTA) single-chain bispecific tandem fragment variable (scBsTaFv) immunoglobulin-related compositions of the present technology (SEQ ID NOs: 36 and 37). The signal peptide is underlined, the variable domains of the murine FMC63× humanized C825 (anti-DOTA) scBsTaFvs are italicized, linker or spacer sequences are indicated in boldfaced, underlined font, and p73 tetramerization domains are boldfaced.

FIGS. 21A-21B show the amino acid sequences of two murine FMC63× humanized C825 (anti-DOTA) single-chain bispecific tandem fragment variable (scBsTaFv) immunoglobulin-related compositions of the present technology (SEQ ID NOs: 38 and 39). The signal peptide is underlined, the variable domains of the murine FMC63× humanized C825 (anti-DOTA) scBsTaFvs are italicized, linker or spacer sequences are indicated in boldfaced, underlined font, and p53 tetramerization domains are boldfaced.

FIGS. 22A-22B show the amino acid sequences of two murine FMC63× humanized C825 (anti-DOTA) single-chain bispecific tandem fragment variable (scBsTaFv) immunoglobulin-related compositions of the present technology (SEQ ID NOs: 40 and 41). The signal peptide is underlined, the variable domains of the murine FMC63× humanized C825 (anti-DOTA) scBsTaFvs are italicized, linker or spacer sequences are indicated in boldfaced, underlined font, and p63 tetramerization domains are boldfaced.

FIGS. 23A-23B show the amino acid sequences of two murine FMC63× humanized C825 (anti-DOTA) single-chain bispecific tandem fragment variable (scBsTaFv) immunoglobulin-related compositions of the present technology (SEQ ID NOs: 42 and 43). The signal peptide is underlined, the variable domains of the murine FMC63× humanized C825 (anti-DOTA) scBsTaFvs are italicized, linker or spacer sequences are indicated in boldfaced, underlined font, and p73 tetramerization domains are boldfaced.

FIGS. 24A-24B show the amino acid sequences of the light chain and the heavy chain of a humanized FMC63× murine C825 (anti-DOTA) IgG-scFv BsAb, represented as SEQ ID NOs: 44 and 45 respectively. The signal peptide is underlined, the variable domains of the humanized FMC63× murine C825 (anti-DOTA) BsAb are italicized, and linker sequences are boldfaced and underlined.

FIGS. 25A-25B show the amino acid sequences of the light chain and the heavy chain of a humanized FMC63× humanized C825 (anti-DOTA) IgG-scFv BsAb, represented as SEQ ID NOs: 46 and 47 respectively. The signal peptide is underlined, the variable domains of the humanized FMC63× humanized C825 (anti-DOTA) BsAb are italicized, and linker sequences are boldfaced and underlined.

FIGS. 26A-26B show the amino acid sequences of two humanized FMC63× humanized C825 (anti-DOTA) single-chain bispecific tandem fragment variable (scBsTaFv) immunoglobulin-related compositions of the present technology (SEQ ID NOs:48 and 49). The signal peptide is underlined, the variable domains of the humanized FMC63× humanized C825 (anti-DOTA) scBsTaFvs are italicized, linker or spacer sequences are indicated in boldfaced, underlined font, and p53 tetramerization domains are boldfaced.

FIGS. 27A-27B show the amino acid sequences of two humanized FMC63× humanized C825 (anti-DOTA) single-chain bispecific tandem fragment variable (scBsTaFv) immunoglobulin-related compositions of the present technology (SEQ ID NOs: 50 and 51). The signal peptide is underlined, the variable domains of the humanized FMC63× humanized C825 (anti-DOTA) scBsTaFvs are italicized, linker or spacer sequences are indicated in boldfaced, underlined font, and p63 tetramerization domains are boldfaced.

FIGS. 28A-28B show the amino acid sequences of two humanized FMC63× humanized C825 (anti-DOTA) single-chain bispecific tandem fragment variable (scBsTaFv) immunoglobulin-related compositions of the present technology (SEQ ID NOs: 52 and 53). The signal peptide is underlined, the variable domains of the humanized FMC63× humanized C825 (anti-DOTA) scBsTaFvs are italicized, linker or spacer sequences are indicated in boldfaced, underlined font, and p73 tetramerization domains are boldfaced.

FIGS. 29A-29B show the amino acid sequences of two humanized FMC63× humanized C825 (anti-DOTA) single-chain bispecific tandem fragment variable (scBsTaFv) immunoglobulin-related compositions of the present technology (SEQ ID NOs: 54 and 55). The signal peptide is underlined, the variable domains of the humanized FMC63× humanized C825 (anti-DOTA) scBsTaFvs are italicized, linker or spacer sequences are indicated in boldfaced, underlined font, and p53 tetramerization domains are boldfaced.

FIGS. 30A-30B show the amino acid sequences of two humanized FMC63× humanized C825 (anti-DOTA) single-chain bispecific tandem fragment variable (scBsTaFv) immunoglobulin-related compositions of the present technology (SEQ ID NOs: 56 and 57). The signal peptide is underlined, the variable domains of the humanized FMC63× humanized C825 (anti-DOTA) scBsTaFvs are italicized, linker or spacer sequences are indicated in boldfaced, underlined font, and p63 tetramerization domains are boldfaced.

FIGS. 31A-31B show the amino acid sequences of two humanized FMC63× humanized C825 (anti-DOTA) single-chain bispecific tandem fragment variable (scBsTaFv) immunoglobulin-related compositions of the present technology (SEQ ID NOs: 58 and 59). The signal peptide is underlined, the variable domains of the humanized FMC63× humanized C825 (anti-DOTA) scBsTaFvs are italicized, linker or spacer sequences are indicated in boldfaced, underlined font, and p73 tetramerization domains are boldfaced.

FIG. 32 shows the stability data, EC50 data, and MFI data against several cell lines for each of the CD19-CD3 IgG-scFv bispecific antibody clones.

DETAILED DESCRIPTION

Figure 1A:
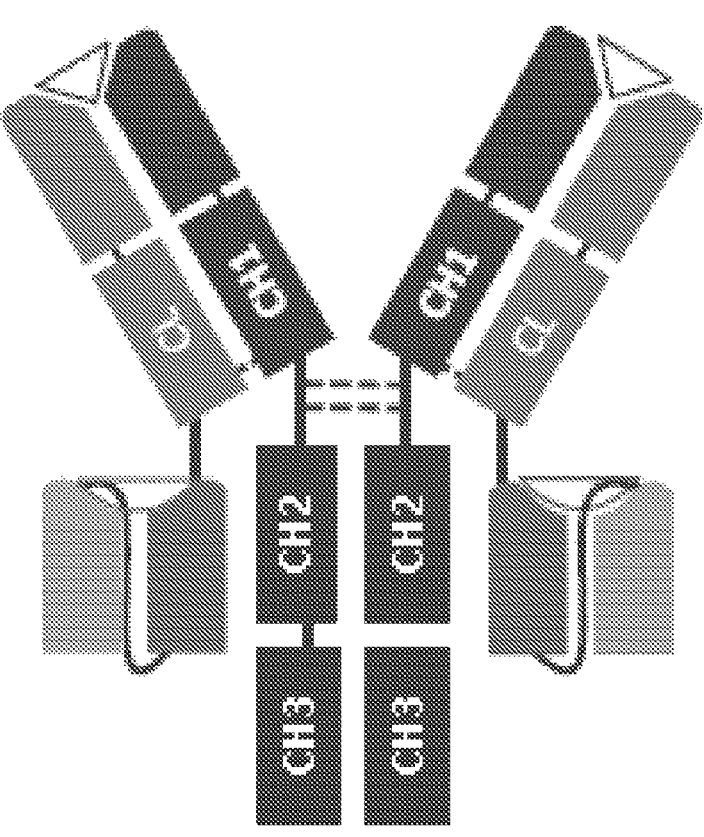
FIG. 1A shows a schematic diagram showing the structure of modular IgG-scFv CD19-BsAb. CH1 through CH3 are constant domains of the heavy chain of a first antibody. CL is the constant domain of the light chain of the first antibody. The C-terminus of the CL is fused to a single chain Fv fragment (scFv) derived from a second antibody.

It is to be appreciated that certain aspects, modes, embodiments, variations and features of the present methods are described below in various levels of detail in order to provide a substantial understanding of the present technology.

The present disclosure generally provides immunoglobulin-related compositions (e.g., antibodies or antigen binding fragments thereof), which can specifically bind to CD19 polypeptides. The immunoglobulin-related compositions of the present technology are useful in methods for detecting or treating CD19-associated cancers or CD19-associated autoimmune diseases in a subject in need thereof. Accordingly, the various aspects of the present methods relate to the preparation, characterization, and manipulation of anti-CD19 antibodies. The immunoglobulin-related compositions of the present technology are useful alone or in combination with additional therapeutic agents for treating cancer. In some embodiments, the immunoglobulin-related composition is a humanized antibody, a chimeric antibody, or a bispecific antibody.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) PCR 1: *A Practical Approach* (IRL Press at Oxford University Press); MacPherson et al. (1995) PCR 2: *A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.* Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics,* Second Edition. (John Wiley and Sons, Inc., NY, 1999)).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, intratumorally or topically. Administration includes self-administration and the administration by another.

An "adjuvant" refers to one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4 M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, $3^{rd}$ Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda ($\lambda$) and kappa ($\kappa$). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a $\beta$-sheet conformation and the CDRs form loops which connect, and in some cases form part of, the $\beta$-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds CD19 protein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Immunoglobulin-related compositions" as used herein, refers to antibodies (including monoclonal antibodies, polyclonal antibodies, humanized antibodies, chimeric antibodies, recombinant antibodies, multispecific antibodies, bispecific antibodies, etc.,) as well as antibody fragments. An antibody or antigen binding fragment thereof specifically binds to an antigen.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods, e.g., but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR). As such "antibody fragments" or "antigen binding fragments" can comprise a portion of a full length antibody, generally the antigen binding or variable region thereof. Examples of antibody fragments or antigen binding fragments include Fab, Fab', F(ab')$_2$, and Fv fragments; diabodies; linear antibodies; single-chain antibody molecules; and multi specific antibodies formed from antibody fragments.

"Bispecific antibody" or "BsAb", as used herein, refers to an antibody that can bind simultaneously to two targets that have a distinct structure, e.g., two different target antigens, two different epitopes on the same target antigen, or a hapten and a target antigen or epitope on a target antigen. A variety of different bispecific antibody structures are known in the art. In some embodiments, each antigen binding moiety in a bispecific antibody includes $V_H$ and/or $V_L$ regions; in some such embodiments, the $V_H$ and/or $V_L$ regions are those found in a particular monoclonal antibody. In some embodiments, the bispecific antibody contains two antigen binding moieties, each including $V_H$ and/or $V_L$ regions from different monoclonal antibodies. In some embodiments, the bispecific antibody contains two antigen binding moieties, wherein one of the two antigen binding moieties includes an immunoglobulin molecule having $V_H$ and/or $V_L$ regions that contain CDRs from a first monoclonal antibody, and the other antigen binding moiety includes an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

As used herein, a "clearing agent" is an agent that binds to excess bispecific antibody that is present in the blood compartment of a subject to facilitate rapid clearance via kidneys. The use of the clearing agent prior to hapten administration (e.g., DOTA) facilitates better tumor-to-background ratios in pretargeted radioimmunotherapy (PRIT) systems. Examples of clearing agents include 500 kD-dextran-DOTA-Bn(Y) (Orcutt et al., *Mol Cancer Ther.* 11(6): 1365-1372 (2012)), 500 kD aminodextran-DOTA conjugate, antibodies against the pretargeting antibody, etc.

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404, 097; WO 93/11161; and Hollinger et al., *Proc. Natl. Acad. Sci. USA,* 90: 6444-6448 (1993).

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain $F_v$ (scF$_v$)). Bird et al. (1988) *Science* 242:423-426 and Huston et al. (1988) Proc. Natl. Acad Sci. USA 85:5879-5883. Such single-chain antibodies can be prepared by recombinant techniques or enzymatic or chemical cleavage of intact antibodies.

Any of the above-noted antibody fragments are obtained using conventional techniques known to those of skill in the art, and the fragments are screened for binding specificity and neutralization activity in the same manner as are intact antibodies.

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be a polypeptide (e.g., a CD19 polypeptide). An antigen may also be administered to an animal to generate an immune response in the animal.

The term "antigen binding fragment" refers to a fragment of the whole immunoglobulin structure which possesses a part of a polypeptide responsible for binding to antigen.

Examples of the antigen binding fragment useful in the present technology include scFv, (scFv)$_2$, scFvFc, Fab, Fab' and F(ab')$_2$, but are not limited thereto.

By "binding affinity" is meant the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_D$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a blood sample or a sample derived from bone marrow aspiration and biopsy.

As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 0125, 023; Better et al., *Science* 240: 1041-1043, 1988; Liu et al., *Proc. Natl. Acad. Sci. USA* 84: 3439-3443, 1987; Liu et al., *J. Immunol* 139: 3521-3526, 1987; Sun et al., *Proc. Natl. Acad. Sci. USA* 84: 214-218, 1987; Nishimura et al., *Cancer Res* 47: 999-1005, 1987; Wood et al., *Nature* 314: 446-449, 1885; and Shaw et al., *J. Natl. Cancer Inst.* 80: 1553-1559, 1988.

As used herein, the term "consensus FR" means a framework (FR) antibody region in a consensus immunoglobulin sequence. The FR regions of an antibody do not contact the antigen.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. In some embodiments, an "epitope" of the CD19 protein is a region of the protein to which the anti-CD19 antibodies of the present technology specifically bind. In some embodiments, the epitope is a conformational epitope or a non-conformational epitope. To screen for anti-CD19 antibodies which bind to an epitope, a routine cross-blocking assay such as that described in Antibodies, A Laboratory Manual, Cold Spring Harbor Laboratory, Ed Harlow and David Lane (1988), can be performed. This assay can be used to determine if an anti-CD19 antibody binds the same site or epitope as an anti-CD19 antibody of the present technology. Alternatively, or additionally, epitope mapping can be performed by methods known in the art. For example, the antibody sequence can be mutagenized such as by alanine scanning, to identify contact residues. In a different method, peptides corresponding to different regions of CD19 protein can be used in competition assays with the test antibodies or with a test antibody and an antibody with a characterized or known epitope.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues.

Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', F(ab')$_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immuno-globulin. For further details, see Jones et al., *Nature* 321: 522-525 (1986); Reichmann et al., *Nature* 332:323-329 (1988); and Presta, *Curr. Op. Struct. Biol.* 2:593-596 (1992). See e.g., Ahmed & Cheung, *FEBS Letters* 588(2):288-297 (2014).

As used herein, the term "hypervariable region" refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the V$_L$, and around about 31-35B (H1), 50-65 (H2) and 95-102 (H3) in the V$_H$ (Kabat et al., *Sequences of Proteins of Immunological Interest,* 5th Ed. Public Health Service, National Institutes of Health, Bethesda, MD. (1991)) and/or those residues from a "hypervariable loop" (e.g., residues 26-32 (L1), 50-52 (L2) and 91-96 (L3) in the V$_L$, and 26-32 (H1), 52A-55 (H2) and 96-101 (H3) in the V$_H$ (Chothia and Lesk *J. Mol. Biol.* 196:901-917 (1987)).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein)), when compared and aligned for maximum correspondence over a comparison window or designated region as measured using a BLAST or BLAST 2.0 sequence comparison algorithms with default parameters described below, or by manual alignment and visual inspection (e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, the term "intact antibody" or "intact immunoglobulin" means an antibody that has at least two heavy (H) chain polypeptides and two light (L) chain polypeptides interconnected by disulfide bonds. Each heavy chain is comprised of a heavy chain variable region (abbreviated herein as HCVR or V$_H$) and a heavy chain constant region. The heavy chain constant region is comprised of three domains, CH$_1$, CH$_2$ and CH$_3$. Each light chain is comprised of a light chain variable region (abbreviated herein as LCVR or V$_L$) and a light chain constant region. The light chain constant region is comprised of one domain, C$_L$. The V$_H$ and V$_L$ regions can be further subdivided into regions of hypervariability, termed complementarity determining regions (CDR), interspersed with regions that are more conserved, termed framework regions (FR). Each V$_H$ and V$_L$ is composed of three CDRs and four FRs, arranged from amino-terminus to carboxyl-terminus in the following order: FR$_1$, CDR$_1$, FR$_2$, CDR$_2$, FR$_3$, CDR$_3$, FR$_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the terms "individual", "patient", or "subject" can be an individual organism, a vertebrate, a mammal, or a human. In some embodiments, the individual, patient or subject is a human.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., *Nature* 256:495 (1975), or may be made by recombinant DNA methods (See, e.g., U.S. Pat. No. 4,816, 567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20th edition, ed. A. Gennaro, 2000, Lippincott, Williams & Wilkins, Philadelphia, Pa.).

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the terms "polypeptide," "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, "PRIT" or "pretargeted radioimmuno-therapy" refers to a multistep process that resolves the slow blood clearance of tumor targeting antibodies, which contributes to undesirable toxicity to normal tissues such as bone marrow. In pre-targeting, a radionuclide or other diagnostic or therapeutic agent is attached to a small hapten. A pre-targeting bispecific antibody, which has binding sites for the hapten as well as a target antigen, is administered first. Unbound antibody is then allowed to clear from circulation and the hapten is subsequently administered.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, "specifically binds" refers to a molecule (e.g., an antibody or antigen binding fragment thereof) which recognizes and binds another molecule (e.g., an antigen), but that does not substantially recognize and bind other molecules. The terms "specific binding," "specifically binds to," or is "specific for" a particular molecule (e.g., a polypeptide, or an epitope on a polypeptide), as used herein, can be exhibited, for example, by a molecule having a $K_D$ for the molecule to which it binds to of about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. The term "specifically binds" may also refer to binding where a molecule (e.g., an antibody or antigen binding fragment thereof) binds to a particular polypeptide (e.g., a CD19 polypeptide), or an epitope on a particular polypeptide, without substantially binding to any other polypeptide, or polypeptide epitope.

As used herein, the term "simultaneous" therapeutic use refers to the administration of at least two active ingredients by the same route and at the same time or at substantially the same time.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Amino acid sequence modification(s) of the anti-CD19 antibodies described herein are contemplated. For example, it may be desirable to improve the binding affinity and/or other biological properties of the antibody. Amino acid sequence variants of an anti-CD19 antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated. "Conservative substitutions" are shown in the Table below.

TABLE 1

| Amino Acid Substitutions | | |
| --- | --- | --- |
| Original Residue | Exemplary Substitutions | Conservative Substitutions |
| Ala (A) | val; leu; ile | val |
| Arg (R) | lys; gln; asn | lys |
| Asn (N) | gln; his; asp, lys; arg | gln |

27

TABLE 1-continued

Amino Acid Substitutions

| Original Residue | Exemplary Substitutions | Conservative Substitutions |
|---|---|---|
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development.

CD19

CD19 (also known as Cluster of Differentiation 19, B-Lymphocyte Surface Antigen B4 (or simply B4), T-Cell Surface Antigen Leu-12, or common variable immunodeficiency-3 (CVID3)) is a central positive response regulator in B cells. Human CD19 is about 556 amino acids in length and is encoded by the 7.41 kilobase CD19 gene located on the short arm of chromosome 16. The CD19 gene contains at least fifteen exons, that encode an extracellular domain, a transmembrane domain, and a cytoplasmic domain. At least five isoforms of CD19 protein exist in nature. The amino acid sequence of human CD19 isoform 2 precursor (NCBI Reference Sequence: NP_001761.3; SEQ ID NO: 60) is provided below:

```
  1 MPPPRLLFFL LFLTPMEVRP EEPLVVKVEE GDNAVLQCLK GTSDGPTQQL TWSRESPLKP

61 FLKLSLGLPG LGIHMRPLAI WLFIFNVSQQ MGGFYLCQPG PPSEKAWQPG WTVNVEGSGE

121 LFRWNVSDLG GLGCGLKNRS SEGPSSPSGK LMSPKLYVWA KDRPEIWEGE PPCLPPRDSL

181 NQSLSQDLTM APGSTLWLSC GVPPDSVSRG PLSWTHVHPK GPKSLLSLEL KDDRPARDMW

241 VMETGLLLPR ATAQDAGKYY CHRGNLTMSF HLEITARPVL WHWLLRTGGW KVSAVTLAYL

301 IFCLCSLVGI LHLQRALVLR RKRKRMTDPT RRFFKVTPPP GSGPQNQYGN VLSLPTPTSG

361 LGRAQRWAAG LGGTAPSYGN PSSDVQADGA LGSRSPPGVG PEEEEGEGYE EPDSEEDSEF

421 YENDSNLGQD QLSQDGSGYE NPEDEPLGPE DEDSFSNAES YENEDEELTQ PVARTMDFLS

481 PHGSAWDPSR EATSLGSQSY EDMRGILYAA PQLRSIRGQP GPNHEEDADS YENMDNPDGP

541 DPAWGGGGRM GTWSTR
```

The amino acid sequence of human CD19 isoform 1 precursor (NCBI Reference Sequence: NP_001171569.1; SEQ ID NO: 61) is provided below:

```
  1 MPPPRLLFFL LFLTPMEVRP EEPLVVKVEE GDNAVLQCLK GTSDGPTQQL TWSRESPLKP

61 FLKLSLGLPG LGIHMRPLAI WLFIFNVSQQ MGGFYLCQPG PPSEKAWQPG WTVNVEGSGE

121 LFRWNVSDLG GLGCGLKNRS SEGPSSPSGK LMSPKLYVWA KDRPEIWEGE PPCLPPRDSL

181 NQSLSQDLTM APGSTLWLSC GVPPDSVSRG PLSWTHVHPK GPKSLLSLEL KDDRPARDMW

241 VMETGLLLPR ATAQDAGKYY CHRGNLTMSF HLEITARPVL WHWLLRTGGW KVSAVTLAYL

301 IFCLCSLVGI LHLQRALVLR RKRKRMTDPT RRFFKVTPPP GSGPQNQYGN VLSLPTPTSG

361 LGRAQRWAAG LGGTAPSYGN PSSDVQADGA LGSRSPPGVG PEEEEGEGYE EPDSEEDSEF

421 YENDSNLGQD QLSQDGSGYE NPEDEPLGPE DEDSFSNAES YENEDEELTQ PVARTMDFLS
```

28

-continued

```
481 PHGSAWDPSR EATSLAGSQS YEDMRGILYA APQLRSIRGQ PGPNHEEDAD SYENMDNPDG

541 PDPAWGGGGR MGTWSTR
```

Three additional, shorter isoforms of CD19 protein are CD19 isoform X1 (NCBI Reference Sequence: XP_006721166.1; SEQ ID NO: 62), which is 468 amino acids in length, CD19 isoform X2 (NCBI Reference Sequence: XP_016879382.1; SEQ ID NO: 63), which is 467 amino acids in length, and CD19 isoform X3 (NCBI Reference Sequence: XP_011544283.1; SEQ ID NO: 64), which is 282 amino acids in length.

CD19 is a 95 kDa Type I transmembrane glycoprotein of the immunoglobulin superfamily (IgSF) with two extracellular C2-type Ig-like domains, and a large, highly conserved cytoplasmic tail. The cytoplasmic domain is 240 amino acids in length, and includes nine conserved tyrosine residues. Upon tyrosine phosphorylation, CD19 functions as a specialized adaptor protein involved in intrinsic and antigen receptor-induced signal transduction.

CD19 is a critical co-receptor for B cell antigen receptor (BCR) signal transduction. CD19 regulates B lymphocyte activation and differentiation through modulation of BCR signaling, and optimizes immune responses by controlling antigen-independent B cell development, and immunoglobulin-induced B lymphocyte activation.

CD19 is expressed in all phases of B cell development until terminal differentiation, and in follicular dendritic cells. CD19 surface expression coincides with B cell lineage commitment from hematopoietic stem cell, during immunoglobulin (Ig) gene rearrangement. CD19 is then expressed on early pro-B cells, late pro-B cells, memory B cells, plasmablasts and some plasma cells. CD19 expression is observed in B-cell leukemia, lymphomas and other cancers. CD19 is expressed on >90% of ALL, B-NHL and CLL. CD19 has a broader expression profile than that of CD20, and is retained after CD20 downregulation or loss. Overexpression of a CD19 in mice can lead to autoimmune diseases.

Immunoglobulin-related Compositions of the Present Technology

The anti-CD19 immunoglobulin-related compositions of the present disclosure may be useful in the diagnosis, or treatment of CD19-associated cancers, and CD19-associated autoimmune diseases. Anti-CD19 immunoglobulin-related compositions within the scope of the present technology include, e.g., but are not limited to, monoclonal, chimeric, humanized, bispecific antibodies and diabodies that specifically bind the target polypeptide, a homolog, derivative or a fragment thereof. The present disclosure also provides antigen binding fragments of any of the anti-CD19 antibodies disclosed herein, wherein the antigen binding fragment is selected from the group consisting of Fab, F(ab)'2, Fab', scF$_v$, and F$_v$. The present technology discloses anti-CD19 bispecific antibody formats that address existing issues of inferior tumor antigen binding avidity, short in vivo half-life and toxicity. In one aspect, the present technology provides chimeric and humanized variants of FMC63, including multispecific immunoglobulin-related compositions (e.g., bispecific antibody agents).

In one aspect, the present disclosure provides an antibody or antigen binding fragment thereof comprising a heavy chain immunoglobulin variable domain ($V_H$) and a light chain immunoglobulin variable domain ($V_L$), wherein: (a) the $V_H$ comprises an amino acid sequence selected from the group consisting of: SEQ ID NOs: 5, 6, 7, 8, 9, 10, 11, and 12; and/or (b) the $V_L$ comprises an amino acid sequence selected from the group consisting of: SEQ ID NO: 17, SEQ ID NO: 18, and SEQ ID NO: 19. In some embodiments, the antibody further comprises a Fc domain of any isotype, e.g., but are not limited to, IgG (including IgG1, IgG2, IgG3, and IgG4), IgA (including IgA$_1$ and IgA$_2$), IgD, IgE, or IgM, and IgY. Non-limiting examples of constant region sequences include:

```
Human IgD constant region, Uniprot: P01880
                                   (SEQ ID NO: 65)
APTKAPDVFPIISGCRHPKDNSPVVLACLITGYHPTSVTVTWYMGTQSQPQRT

FPEIQRRDSYYMTSSQLSTPLQQWRQGEYKCVVQHTASKSKKEIFRWPESPKAQASSVP

TAQPQAEGSLAKATTAPATTRNTGRGGEEKKKEKEKEEQEERETKTPECPSHTQPLGVY

LLTPAVQDLWLRDKATFTCFVVGSDLKDAHLTWEVAGKVPTGGVEEGLLERHSNGSQS

QHSRLTLPRSLWNAGTSVTCTLNHPSLPPQRLMALREPAAQAPVKLSLNLLASSDPPEA

ASWLLCEVSGFSPPNILLMWLEDQREVNTSGFAPARPPPQPGSTTFWAWSVLRVPAPPSP

QPATYTCVVSHEDSRTLLNASRSLEVSYVTDHGPMK

Human IgG1 constant region, Uniprot: P01857
                                   (SEQ ID NO: 66)
ASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGK
```

-continued

Human IgG2 constant region, Uniprot: P01859

(SEQ ID NO: 67)

ASTKGPSVFPLAPCSRSTSESTAALGCLVKDYFPEPVTVSWNSGALTSGVHTF

PAVLQSSGLYSLSSVVTVPSSNFGTQTYTCNVDHKPSNTKVDKTVERKCCVECPPCPAPP

VAGPSVFLFPPKPKDTLMISRTPEVTCVVVDVSHEDPEVQFNWYVDGVEVHNAKTKPR

EEQFNSTFRVVSVLTVVHQDWLNGKEYKCKVSNKGLPAPIEKTISKTKGQPREPQVYTL

PPSREEMTKNQVSLTCLVKGFYPSDISVEWESNGQPENNYKTTPPMLDSDGSFFLYSKLT

VDKSRWQQGNVFSCSVMHEALHNHYTQKSLSLSPGK

Human IgG3 constant region, Uniprot: P01860

(SEQ ID NO: 68)

ASTKGPSVFPLAPCSRSTSGGTAALGCLVKDYFPEPVTVSWNSGALTSGVHTF

PAVLQSSGLYSLSSVVTVPSSSLGTQTYTCNVNHKPSNTKVDKRVELKTPLGDTTHTCP

RCPEPKSCDTPPPCPRCPEPKSCDTPPPCPRCPEPKSCDTPPPCPRCPAPELLGGPSVFLFPP

KPKDTLMISRTPEVTCVVVDVSHEDPEVQFKWYVDGVEVHNAKTKPREEQYNSTFRVV

SVLTVLHQDWLNGKEYKCKVSNKALPAPIEKTISKTKGQPREPQVYTLPPSREEMTKNQ

VSLTCLVKGFYPSDIAVEWESSGQPENNYNTTPPMLDSDGSFFLYSKLTVDKSRWQQGN

IFSCSVMHEALHNRFTQKSLSLSPGK

Human IgM constant region, Uniprot: P01871

(SEQ ID NO: 69)

GSASAPTLFPLVSCENSPSDTSSVAVGCLAQDFLPDSITLSWKYKNNSDISSTR

GFPSVLRGGKYAATSQVLLPSKDVMQGTDEHVVCKVQHPNGNKEKNVPLPVIAELPPK

VSVFVPPRDGFFGNPRKSKLICQATGFSPRQIQVSWLREGKQVGSGVTTDQVQAEAKES

GPTTYKVTSTLTIKESDWLGQSMFTCRVDHRGLTFQQNASSMCVPDQDTAIRVFAIPPSF

ASIFLTKSTKLTCLVTDLTTYDSVTISWTRQNGEAVKTHTNISESHPNATFSAVGEASICE

DDWNSGERFTCTVTHTDLPSPLKQTISRPKGVALHRPDVYLLPPAREQLNLRESATITCL

VTGFSPADVFVQWMQRGQPLSPEKYVTSAPMPEPQAPGRYFAHSILTVSEEEWNTGETY

TCVAHEALPNRVTERTVDKSTGKPTLYNVSLVMSDTAGTCY

Human IgG4 constant region, Uniprot: P01861

(SEQ ID NO: 70)

ASTKGPSVFPLAPCSRSTSESTAALGCLVKDYFPEPVTVSWNSGALTSGVHTF

PAVLQSSGLYSLSSVVTVPSSSLGTKTYTCNVDHKPSNTKVDKRVESKYGPPCPSCPAPE

FLGGPSVFLFPPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSDGSFFLYSRLT

VDKSRWQEGNVFSCSVMHEALHNHYTQKSLSLSLGK

Human IgA1 constant region, Uniprot: P01876

(SEQ ID NO: 71)

ASPTSPKVFPLSLCSTQPDGNVVIACLVQGFFPQEPLSVTWSESGQGVTARNF

PPSQDASGDLYTTSSQLTLPATQCLAGKSVTCHVKHYTNPSQDVTVPCPVPSTPPTPSPS

TPPTPSPSCCHPRLSLHRPALEDLLLGSEANLTCTLTGLRDASGVTFTWTPSSGKSAVQG

PPERDLCGCYSVSSVLPGCAEPWNHGKTFTCTAAYPESKTPLTATLSKSGNTFRPEVHLL

PPPSEELALNELVTLTCLARGFSPKDVLVRWLQGSQELPREKYLTWASRQEPSQGTTTF

AVTSILRVAAEDWKKGDTFSCMVGHEALPLAFTQKTIDRLAGKPTHVNVSVVMAEVD

GTCY

-continued

Human IgA2 constant region, Uniprot: P01877

(SEQ ID NO: 72)

ASPTSPKVFPLSLDSTPQDGNVVVACLVQGFFPQEPLSVTWSESGQNVTARNF

PPSQDASGDLYTTSSQLTLPATQCPDGKSVTCHVKHYTNPSQDVTVPCPVPPPPPCCHPR

LSLHRPALEDLLLGSEANLTCTLTGLRDASGATFTWTPSSGKSAVQGPPERDLCGCYSVS

SVLPGCAQPWNHGETFTCTAAHPELKTPLTANITKSGNTFRPEVHLLPPPSEELALNELV

TLTCLARGFSPKDVLVRWLQGSQELPREKYLTWASRQEPSQGTTTFAVTSILRVAAEDW

KKGDTFSCMVGHEALPLAFTQKTIDRMAGKPTHVNVSVVMAEVDGTCY

Human Ig kappa constant region, Uniprot: P01834

(SEQ ID NO: 73)

TVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

In some embodiments, the immunoglobulin-related compositions of the present technology comprise a heavy chain constant region that is at least 80%, at least 85%, at least 90%, at least 95%, at least 99%, or is 100% identical to SEQ ID NOS: 65-72. Additionally or alternatively, in some embodiments, the immunoglobulin-related compositions of the present technology comprise a light chain constant region that is at least 80%, at least 85%, at least 90%, at least 95%, at least 99%, or is 100% identical to SEQ ID NO: 73. In some embodiments, the antibody or antigen binding fragment binds to a CD19 polypeptide including an Ig-like C2 loop that comprises the amino acid sequence EE GDNAVLQCLK GTSDGPTQQL TWSRESPLKP FLKLSLGLPG LGIHMRPLAI WLFIFNVSQQ MGGFYLCQPG PPSEKAWQPG WTVNVEGS (SEQ ID NO: 82) (corresponding to the amino acid residues at positions 29-118 of SEQ ID NO: 60 or SEQ ID NO: 61). Additionally or alternatively, in certain embodiments, the antibody or antigen binding fragment binds to a conformational epitope comprising the amino acid residues corresponding to positions 29-118 of SEQ ID NO: 60 or SEQ ID NO: 61.

In another aspect, the present disclosure provides an isolated immunoglobulin-related composition (e.g., an antibody or antigen binding fragment thereof) comprising a heavy chain (HC) amino acid sequence comprising SEQ ID NO: 22, SEQ ID NO: 26, SEQ ID NO: 29, SEQ ID NO: 31, SEQ ID NO: 45, SEQ ID NO: 47, or a variant thereof having one or more conservative amino acid substitutions.

Additionally or alternatively, in some embodiments, the immunoglobulin-related compositions of the present technology comprise a light chain (LC) amino acid sequence comprising SEQ ID NO: 20, SEQ ID NO: 24, SEQ ID NO: 28, SEQ ID NO: 30, SEQ ID NO: 44, SEQ ID NO: 46, or a variant thereof having one or more conservative amino acid substitutions.

In some embodiments, the immunoglobulin-related compositions of the present technology comprise a HC amino acid sequence and a LC amino acid sequence selected from the group consisting of: SEQ ID NO: 22 and SEQ ID NO: 20 (chFMC63×CD3 BsAb); SEQ ID NO: 26 and SEQ ID NO: 24 (BC250-hFMC63 VL-2/VH-1b×CD3 BsAb); SEQ ID NO: 29 and SEQ ID NO: 28 (mFMC63×mC825 BsAb); SEQ ID NO: 31 and SEQ ID NO: 30 (mFMC63×hC825 BsAb); SEQ ID NO: 45 and SEQ ID NO: 44 (hFMC63 VL-2VH-1b×mC825); and SEQ ID NO: 47 and SEQ ID NO: 46 (hFMC63 VL-2VH-1b×hC825), respectively.

In any of the above embodiments of the immunoglobulin-related compositions, the HC and LC immunoglobulin variable domain sequences form an antigen binding site that binds to a CD19 polypeptide including an Ig-like C2 loop that comprises the amino acid sequence EE GDNAVLQCLK GTSDGPTQQL TWSRESPLKP FLKLSLGLPG LGIHMRPLAI WLFIFNVSQQ MGGFYLCQPG PPSEKAWQPG WTVNVEGS (SEQ ID NO: 82) (corresponding to the amino acid residues at positions 29-118 of SEQ ID NO: 60 or SEQ ID NO: 61). In some embodiments, the epitope is a conformational epitope. Additionally or alternatively, in certain embodiments, the antibody or antigen binding fragment binds to a conformational epitope comprising the amino acid residues corresponding to positions 29-118 of SEQ ID NO: 60 or SEQ ID NO: 61.

In some embodiments, the HC and LC immunoglobulin variable domain sequences are components of the same polypeptide chain. In other embodiments, the HC and LC immunoglobulin variable domain sequences are components of different polypeptide chains. In certain embodiments, the antibody is a full-length antibody.

In some embodiments, the immunoglobulin-related compositions of the present technology bind specifically to at least one CD19 polypeptide. In some embodiments, the immunoglobulin-related compositions of the present technology bind at least one CD19 polypeptide with a dissociation constant $(K_D)$ of about $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M or $10^{-15}$ M. In certain embodiments, the immunoglobulin-related compositions are monoclonal antibodies, chimeric antibodies, humanized antibodies, or bispecific antibodies. In some embodiments, the antibodies comprise a human antibody framework region.

In certain embodiments, the immunoglobulin-related composition includes one or more of the following characteristics: (a) a light chain immunoglobulin variable domain sequence that is at least 80%, at least 85%, at least 90%, at least 95%, or at least 99% identical to the light chain immunoglobulin variable domain sequence present in any one of SEQ ID NOs: 17, 18, or 19; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: 5, 6, 7, 8, 9, 10, 11, or 12. In another aspect, one or more amino acid residues in the immunoglobulin-related compositions provided herein are substituted with another amino acid. The substitution may be a "conservative substitution" as defined herein.

In some embodiments, the immunoglobulin-related composition comprises (a) a LC sequence that is at least 80%, at least 85%, at least 90%, at least 95%, or at least 99% identical to the LC sequence present in any one of SEQ ID NOs: 20, 24, 28, 30, 44, or 46; and/or (b) a HC sequence that is at least 80%, at least 85%, at least 90%, at least 95%, or at least 99% identical to the HC sequence present in any one of SEQ ID NO: 22, 26, 29, 31, 45, or 47.

In one aspect, the present disclosure provides an immunoglobulin-related composition comprising an amino acid sequence that is at least 80%, at least 85%, at least 90%, at least 95%, or at least 99% identical to an amino acid sequence selected from SEQ ID NOs: 32-43, or 48-59. In certain embodiments, an immunoglobulin-related composition of the present disclosure comprises an amino acid sequence selected from SEQ ID NOs: 32-43, or 48-59.

In one aspect, the present disclosure provides a bispecific antigen binding fragment comprising a first polypeptide chain, wherein: the first polypeptide chain comprises in the N-terminal to C-terminal direction: (i) a heavy chain variable domain of a first immunoglobulin that is capable of specifically binding to a first epitope; (ii) a flexible peptide linker comprising the amino acid sequence (GGGGS)$_6$ (SEQ ID NO: 83); (iii) a light chain variable domain of the first immunoglobulin; (iv) a flexible peptide linker comprising the amino acid sequence (GGGGS)$_4$ (SEQ ID NO: 84); (v) a heavy chain variable domain of a second immunoglobulin that is capable of specifically binding to a second epitope; (vi) a flexible peptide linker comprising the amino acid sequence (GGGGS)$_6$ (SEQ ID NO: 83); (vii) a light chain variable domain of the second immunoglobulin; (viii) a flexible peptide linker sequence comprising the amino acid sequence TPLGDTTHT (SEQ ID NO: 85); and (ix) a self-assembly disassembly (SADA) polypeptide, wherein the heavy chain variable domain of the first immunoglobulin is selected from the group consisting of: SEQ ID NOs: 5, 6, 7, 8, 9, 10, 11, and 12; and/or the light chain variable domain of the first immunoglobulin is selected from the group consisting of: SEQ ID NO: 17, SEQ ID NO: 18, and SEQ ID NO: 19.

In another aspect, the present disclosure provides a bispecific antigen binding fragment comprising a first polypeptide chain, wherein: the first polypeptide chain comprises in the N-terminal to C-terminal direction: (i) a light chain variable domain of a first immunoglobulin that is capable of specifically binding to a first epitope; (ii) a flexible peptide linker comprising the amino acid sequence (GGGGS)$_6$ (SEQ ID NO: 83); (iii) a heavy chain variable domain of the first immunoglobulin; (iv) a flexible peptide linker comprising the amino acid sequence (GGGGS)$_4$ (SEQ ID NO: 84); (v) a heavy chain variable domain of a second immunoglobulin that is capable of specifically binding to a second epitope; (vi) a flexible peptide linker comprising the amino acid sequence (GGGGS)$_6$ (SEQ ID NO: 83); (vii) a light chain variable domain of the second immunoglobulin; (viii) a flexible peptide linker sequence comprising the amino acid sequence TPLGDTTHT (SEQ ID NO: 85); and (ix) a self-assembly disassembly (SADA) polypeptide, wherein the heavy chain variable domain of the first immunoglobulin is selected from the group consisting of: SEQ ID NOs: 5, 6, 7, 8, 9, 10, 11, and 12; and/or the light chain variable domain of the first immunoglobulin is selected from the group consisting of: SEQ ID NO: 17, SEQ ID NO: 18, and SEQ ID NO: 19.

In certain embodiments of the bispecific antigen binding fragments disclosed herein, the SADA polypeptide comprises a tetramerization, pentamerization, or hexamerization domain. In some embodiments, the SADA polypeptide comprises a tetramerization domain of any one of p53, p63, p'73, hnRNPC, SNA-23, Stefin B, KCNQ4, and CBFA2T1. Additionally or alternatively, in some embodiments, the bispecific antigen binding fragment comprises an amino acid sequence selected from SEQ ID NOs: 32-43, or 48-59.

In one aspect, the present disclosure provides a bispecific antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein: (a) each of the first polypeptide chain and the fourth polypeptide chain comprises in the N-terminal to C-terminal direction: (i) a light chain variable domain of a first immunoglobulin that is capable of specifically binding to a first epitope; (ii) a light chain constant domain of the first immunoglobulin; (iii) a flexible peptide linker comprising the amino acid sequence (GGGGS)$_3$ (SEQ ID NO: 86); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin are capable of specifically binding to a second epitope, and are linked together via a flexible peptide linker comprising the amino acid sequence (GGGGS)$_6$ (SEQ ID NO: 83) to form a single-chain variable fragment; and (b) each of the second polypeptide chain and the third polypeptide chain comprises in the N-terminal to C-terminal direction: (i) a heavy chain variable domain of the first immunoglobulin that is capable of specifically binding to the first epitope; and (ii) a heavy chain constant domain of the first immunoglobulin; and wherein the heavy chain variable domain of the first immunoglobulin is selected from the group consisting of: SEQ ID NOs: 5, 6, 7, 8, 9, 10, 11, and 12; and/or the light chain variable domain of the first immunoglobulin is selected from the group consisting of: SEQ ID NO: 17, SEQ ID NO: 18, and SEQ ID NO: 19. In certain embodiments, the second immunoglobulin binds to CD3, CD4, CD8, CD20, CD19, CD21, CD23, CD46, CD80, HLA-DR, CD74, CD19, CD14, CD15, CD16, CD123, TCR gamma/delta, NKp46, KIR, or a small molecule DOTA hapten.

In certain embodiments, the immunoglobulin-related compositions contain an IgG1 constant region comprising one or more amino acid substitutions selected from the group consisting of N297A and K322A. Additionally or alternatively, in some embodiments, the immunoglobulin-related compositions contain an IgG4 constant region comprising a S228P mutation.

In some aspects, the anti-CD19 immunoglobulin-related compositions described herein contain structural modifications to facilitate rapid binding and cell uptake and/or slow release. In some aspects, the anti-CD19 immunoglobulin-related composition of the present technology (e.g., an antibody) may contain a deletion in the CH2 constant heavy chain region to facilitate rapid binding and cell uptake and/or slow release. In some aspects, a Fab fragment is used to facilitate rapid binding and cell uptake and/or slow release. In some aspects, a F(ab)'$_2$ fragment is used to facilitate rapid binding and cell uptake and/or slow release.

In one aspect, the present technology provides a recombinant nucleic acid sequence encoding any of the immunoglobulin-related compositions described herein. In some embodiments, the nucleic acid sequence is selected from the group consisting of SEQ ID NOs: 21, 23, 25, and 27.

In another aspect, the present technology provides a host cell expressing any nucleic acid sequence encoding any of the immunoglobulin-related compositions described herein.

The immunoglobulin-related compositions of the present technology (e.g., an anti-CD19 antibody) can be monospecific, bispecific, trispecific or of greater multispecificity. Multispecific antibodies can be specific for different epitopes of one or more CD19 polypeptides or can be specific for both the CD19 polypeptide(s) as well as for heterologous compositions, such as a heterologous polypeptide or solid support material. See, e.g., WO 93/17715; WO 92/08802; WO 91/00360; WO 92/05793; Tuft et al., *J. Immunol.* 147: 60-69 (1991); U.S. Pat. Nos. 5,573,920, 4,474,893, 5,601,819, 4,714,681, 4,925,648; 6,106,835; Kostelny et al., *J. Immunol.* 148: 1547-1553 (1992). In some embodiments, the immunoglobulin-related compositions are chimeric. In certain embodiments, the immunoglobulin-related compositions are humanized.

The immunoglobulin-related compositions of the present technology can further be recombinantly fused to a heterologous polypeptide at the N- or C-terminus or chemically conjugated (including covalently and non-covalently conjugations) to polypeptides or other compositions. For example, the immunoglobulin-related compositions of the present technology can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

In any of the above embodiments of the immunoglobulin-related compositions of the present technology, the antibody or antigen binding fragment may be optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof. For a chemical bond or physical bond, a functional group on the immunoglobulin-related composition typically associates with a functional group on the agent. Alternatively, a functional group on the agent associates with a functional group on the immunoglobulin-related composition.

The functional groups on the agent and immunoglobulin-related composition can associate directly. For example, a functional group (e.g., a sulfhydryl group) on an agent can associate with a functional group (e.g., sulfhydryl group) on an immunoglobulin-related composition to form a disulfide. Alternatively, the functional groups can associate through a cross-linking agent (i.e., linker). Some examples of cross-linking agents are described below. The cross-linker can be attached to either the agent or the immunoglobulin-related composition. The number of agents or immunoglobulin-related compositions in a conjugate is also limited by the number of functional groups present on the other. For example, the maximum number of agents associated with a conjugate depends on the number of functional groups present on the immunoglobulin-related composition. Alternatively, the maximum number of immunoglobulin-related compositions associated with an agent depends on the number of functional groups present on the agent.

In yet another embodiment, the conjugate comprises one immunoglobulin-related composition associated to one agent. In one embodiment, a conjugate comprises at least one agent chemically bonded (e.g., conjugated) to at least one immunoglobulin-related composition. The agent can be chemically bonded to an immunoglobulin-related composition by any method known to those in the art. For example, a functional group on the agent may be directly attached to a functional group on the immunoglobulin-related composition. Some examples of suitable functional groups include, for example, amino, carboxyl, sulfhydryl, maleimide, isocyanate, isothiocyanate and hydroxyl.

The agent may also be chemically bonded to the immunoglobulin-related composition by means of cross-linking agents, such as dialdehydes, carbodiimides, dimaleimides, and the like. Cross-linking agents can, for example, be obtained from Pierce Biotechnology, Inc., Rockford, Ill. The Pierce Biotechnology, Inc. web-site can provide assistance. Additional cross-linking agents include the platinum cross-linking agents described in U.S. Pat. Nos. 5,580,990; 5,985, 566; and 6,133,038 of Kreatech Biotechnology, B.V., Amsterdam, The Netherlands.

Alternatively, the functional group on the agent and immunoglobulin-related composition can be the same. Homobifunctional cross-linkers are typically used to cross-link identical functional groups. Examples of homobifunctional cross-linkers include EGS (i.e., ethylene glycol bis [succinimidylsuccinate]), DSS (i.e., disuccinimidyl suberate), DMA (i.e., dimethyl adipimidate.2HCl), DTSSP (i.e., 3,3'-dithiobis[sulfosuccinimidylpropionate])), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

In other instances, it may be beneficial to cleave the agent from the immunoglobulin-related composition. The web-site of Pierce Biotechnology, Inc. described above can also provide assistance to one skilled in the art in choosing suitable cross-linkers which can be cleaved by, for example, enzymes in the cell. Thus the agent can be separated from the immunoglobulin-related composition. Examples of cleavable linkers include SMPT (i.e., 4-succinimidyloxycarbonyl-methyl-α-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e., sulfosuccinimidyl 6-(3-[2-pyridyldithio]-propionamido)hexanoate), SPDP (i.e., N-succinimidyl 3-[2-pyridyl-dithio]-propionamidohexanoate), and AEDP (i.e., 3-[(2-aminoethyl)dithio]propionic acid HCl).

In another embodiment, a conjugate comprises at least one agent physically bonded with at least one immunoglobulin-related composition. Any method known to those in the art can be employed to physically bond the agents with the immunoglobulin-related compositions. For example, the immunoglobulin-related compositions and agents can be mixed together by any method known to those in the art. The order of mixing is not important. For instance, agents can be physically mixed with immunoglobulin-related compositions by any method known to those in the art. For example, the immunoglobulin-related compositions and agents can be placed in a container and agitated, by for example, shaking the container, to mix the immunoglobulin-related compositions and agents.

The immunoglobulin-related compositions can be modified by any method known to those in the art. For instance, the immunoglobulin-related composition may be modified by means of cross-linking agents or functional groups, as described above.

A. Methods of Preparing Anti-CD19 Antibodies of the Present Technology

General Overview. Initially, a target polypeptide is chosen to which an antibody of the present technology can be raised. For example, an antibody may be raised against the full-length CD19 protein, a CD19 protein lacking the cytoplasmic domain, CD19 extracellular and transmembrane domains, or to a portion of the extracellular domain of the CD19 protein (e.g., a region comprising the two Ig-like C2 loops of CD19, or a constant region 2 (C2)-type Ig-like loop that comprises the amino acid residues corresponding to positions 29-118 of SEQ ID NO: 60 or SEQ ID NO: 61). Techniques for generating antibodies directed to such target polypeptides are well known to those skilled in the art. Examples of such techniques include, for example, but are not limited to, those involving display libraries, xeno or human mice, hybridomas, and the like. Target polypeptides within the scope of the present technology include any polypeptide derived from CD19 protein containing the extracellular domain which is capable of eliciting an immune response (e.g., the Ig-like C2 loop encoded by exon 2 of CD19).

It should be understood that recombinantly engineered antibodies and antibody fragments, e.g., antibody-related polypeptides, which are directed to CD19 protein and fragments thereof are suitable for use in accordance with the present disclosure.

Anti-CD19 antibodies that can be subjected to the techniques set forth herein include monoclonal and polyclonal antibodies, and antibody fragments such as Fab, Fab', F(ab')$_2$, Fd, scFv, diabodies, antibody light chains, antibody heavy chains and/or antibody fragments. Methods useful for the high yield production of antibody Fv-containing polypeptides, e.g., Fab' and F(ab')$_2$ antibody fragments have been described. See U.S. Pat. No. 5,648,237.

Generally, an antibody is obtained from an originating species. More particularly, the nucleic acid or amino acid sequence of the variable portion of the light chain, heavy chain or both, of an originating species antibody having specificity for a target polypeptide antigen is obtained. An originating species is any species which was useful to generate the antibody of the present technology or library of antibodies, e.g., rat, mouse, rabbit, chicken, monkey, human, and the like.

Phage or phagemid display technologies are useful techniques to derive the antibodies of the present technology. Techniques for generating and cloning monoclonal antibodies are well known to those skilled in the art. Expression of sequences encoding antibodies of the present technology, can be carried out in *E. coli.*

Due to the degeneracy of nucleic acid coding sequences, other sequences which encode substantially the same amino acid sequences as those of the naturally occurring proteins may be used in the practice of the present technology These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present technology tolerates sequence homology variations of up to 25% as calculated by standard methods ("Current Methods in Sequence Comparison and Analysis," *Macromolecule*

*Sequencing and Synthesis, Selected Methods and Applications*, pp. 127-149, 1998, Alan R. Liss, Inc.) so long as such a variant forms an operative antibody which recognizes CD19 proteins. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present technology are proteins or fragments or derivatives thereof which are differentially modified during or after translation, e.g., by glycosylation, proteolytic cleavage, linkage to an antibody molecule or other cellular ligands, etc. Additionally, an immunoglobulin encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacia), and the like.

Preparation of Polyclonal Antisera and Immunogens. Methods of generating antibodies or antibody fragments of the present technology typically include immunizing a subject (generally a non-human subject such as a mouse or rabbit) with a purified CD19 protein or fragment thereof or with a cell expressing the CD19 protein or fragment thereof. An appropriate immunogenic preparation can contain, e.g., a recombinantly-expressed CD19 protein or a chemically-synthesized CD19 peptide. The extracellular domain of the CD19 protein, or a portion or fragment thereof (e.g., a portion or fragment comprising the amino acid residues corresponding to positions 29-118 of SEQ ID NO: 60 or SEQ ID NO: 61), can be used as an immunogen to generate an anti-CD19 antibody that binds to the CD19 protein, or a portion or fragment thereof using standard techniques for polyclonal and monoclonal antibody preparation. The full-length CD19 protein or fragments thereof, are useful as fragments as immunogens. In some embodiments, a CD19 fragment comprises the amino acid residues corresponding to positions 29-118 of SEQ ID NO: 60 or SEQ ID NO: 61, such that an antibody raised against the peptide forms a specific immune complex with CD19 protein. The polypeptide encoded by exon 2 of CD19 may also be used as an immunogen.

In some embodiments, the antigenic CD19 peptide comprises at least 5, 8, 10, 15, 20, 30, 40, 50, 60, 70, 80, or 90 amino acid residues. Longer antigenic peptides are sometimes desirable over shorter antigenic peptides, depending on use and according to methods well known to those skilled in the art. Multimers of a given epitope are sometimes more effective than a monomer.

If needed, the immunogenicity of the CD19 protein (or fragment thereof) can be increased by fusion or conjugation to a hapten such as keyhole limpet hemocyanin (KLH) or ovalbumin (OVA). Many such haptens are known in the art. One can also combine the CD19 protein with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. These techniques are standard in the art.

In describing the present technology, immune responses may be described as either "primary" or "secondary" immune responses. A primary immune response, which is also described as a "protective" immune response, refers to an immune response produced in an individual as a result of some initial exposure (e.g., the initial "immunization") to a particular antigen, e.g., CD19 protein. In some embodiments, the immunization can occur as a result of vaccinating the individual with a vaccine containing the antigen. For example, the vaccine can be a CD19 vaccine comprising one or more CD19 protein-derived antigens. A primary immune response can become weakened or attenuated over time and can even disappear or at least become so attenuated that it cannot be detected. Accordingly, the present technology also relates to a "secondary" immune response, which is also described here as a "memory immune response." The term secondary immune response refers to an immune response elicited in an individual after a primary immune response has already been produced.

Thus, a secondary immune response can be elicited, e.g., to enhance an existing immune response that has become weakened or attenuated, or to recreate a previous immune response that has either disappeared or can no longer be detected. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by CD4$^+$ T cells. A first exposure to an antigen primes the immune system and additional exposure(s) results in a DTH.

Following appropriate immunization, the anti-CD19 antibody can be prepared from the subject's serum. If desired, the antibody molecules directed against the CD19 protein can be isolated from the mammal (e.g., from the blood) and further purified by well-known techniques, such as polypeptide A chromatography to obtain the IgG fraction.

Monoclonal Antibody. In one embodiment of the present technology, the antibody is an anti-CD19 monoclonal antibody. For example, in some embodiments, the anti-CD19 monoclonal antibody may be a human or a mouse anti-CD19 monoclonal antibody. For preparation of monoclonal antibodies directed towards the CD19 protein, or derivatives, fragments, analogs or homologs thereof, any technique that provides for the production of antibody molecules by continuous cell line culture can be utilized. Such techniques include, but are not limited to, the hybridoma technique (See, e.g., Kohler & Milstein, 1975. *Nature* 256: 495-497); the trioma technique; the human B-cell hybridoma technique (See, e.g., Kozbor, et al., 1983. *Immunol. Today* 4: 72) and the EBV hybridoma technique to produce human monoclonal antibodies (See, e.g., Cole, et al., 1985. In: MONOCLONAL ANTIBODIES AND CANCER THERAPY, Alan R. Liss, Inc., pp. 77-96). Human monoclonal antibodies can be utilized in the practice of the present technology and can be produced by using human hybridomas (See, e.g., Cote, et al., 1983. *Proc. Natl. Acad. Sci. USA* 80: 2026-2030) or by transforming human B-cells with Epstein Barr Virus in vitro (See, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then DNAs encoding antibodies or fragments thereof, such as variable domains, are reconstructed from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the CD19 protein. Alternatively, hybridomas expressing anti-CD19 monoclonal antibodies can be prepared by immunizing a subject and then isolating hybridomas from the subject's spleen using routine methods. See, e.g., Milstein et al., (Galfre and Milstein, Methods Enzymol (1981) 73: 3-46). Screening the hybridomas using standard methods will produce monoclonal antibodies of varying specificity (i.e., for different epitopes) and affinity. A selected monoclonal antibody with the desired properties, e.g., CD19 binding, can be used as expressed by the hybridoma, it can be bound to a molecule such as polyethylene glycol (PEG) to alter its properties, or a cDNA encoding it can be isolated, sequenced and manipulated in various ways. Synthetic dendromeric trees can be added to reactive amino acid side chains, e.g., lysine, to enhance the immunogenic properties of CD19 protein. Also, CPG-dinucleotide techniques can be used to enhance the immunogenic properties of the CD19 protein. Other manipulations include substituting or deleting particular amino acyl residues that contribute to instability of the antibody during storage or after administration to a subject, and affinity maturation techniques to improve affinity of the antibody of the CD19 protein.

Hybridoma Technique. In some embodiments, the antibody of the present technology is an anti-CD19 monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, NY, 349 (1988); Hammerling et al., *Monoclonal Antibodies And T-Cell Hybridomas*, 563-681 (1981). Other methods for producing hybridomas and monoclonal antibodies are well known to those of skill in the art.

Phage Display Technique. As noted above, the antibodies of the present technology can be produced through the application of recombinant DNA and phage display technology. For example, anti-CD19 antibodies, can be prepared using various phage display methods known in the art. In phage display methods, functional antibody domains are displayed on the surface of a phage particle which carries polynucleotide sequences encoding them. Phages with a desired binding property are selected from a repertoire or combinatorial antibody library (e.g., human or murine) by selecting directly with an antigen, typically an antigen bound or captured to a solid surface or bead. Phages used in these methods are typically filamentous phage including fd and M13 with Fab, Fv or disulfide stabilized Fv antibody domains that are recombinantly fused to either the phage gene III or gene VIII protein. In addition, methods can be adapted for the construction of Fab expression libraries (See, e.g., Huse, et al., Science 246: 1275-1281, 1989) to allow rapid and effective identification of monoclonal Fab fragments with the desired specificity for a CD19 polypeptide, e.g., a polypeptide or derivatives, fragments, analogs or homologs thereof. Other examples of phage display methods that can be used to make the antibodies of the present technology include those disclosed in Huston et al., *Proc.* *Natl. Acad. Sci U.S.A.,* 85: 5879-5883, 1988; Chaudhary et al., *Proc. Natl. Acad. Sci U.S.A.,* 87: 1066-1070, 1990; Brinkman et al., *J. Immunol. Methods* 182: 41-50, 1995; Ames et al., *J. Immunol. Methods* 184: 177-186, 1995; Kettleborough et al., *Eur. J. Immunol.* 24: 952-958, 1994; Persic et al., Gene 187: 9-18, 1997; Burton et al., *Advances in Immunology* 57: 191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintain good binding activity, because the antibody or antibody fragment will be present on the surface of the phage or phagemid particle. See, e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Anti-CD19 Antibodies. As noted above, the antibodies of the present technology can be produced through the application of recombinant DNA technology. Recombinant polynucleotide constructs encoding an anti-CD19 antibody of the present technology typically include an expression control sequence operably-linked to the coding sequences of anti-CD19 antibody chains, including naturally-associated or heterologous promoter regions. As such, another aspect of the technology includes vectors containing one or more nucleic acid sequences encoding an anti-CD19 antibody of the present technology. For recombinant expression of one or more of the polypeptides of the present technology, the nucleic acid containing all or a portion of the nucleotide sequence encoding the anti-CD19 antibody is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160 and 6,680,192.

In general, expression vectors useful in recombinant DNA techniques are often in the form of plasmids. In the present disclosure, "plasmid" and "vector" can be used interchangeably as the plasmid is the most commonly used form of vector. However, the present technology is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression of a construct in that subject. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the anti-CD19 antibody, and the collection and purification of the anti-CD19 antibody, e.g., cross-reacting anti-CD19 antibodies. See generally, U.S. 2002/0199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the present technology comprise a nucleic acid encoding a protein with CD19 binding properties in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., anti-CD19 antibody), include, e.g., but are not limited to, promoters of 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding an anti-CD19 antibody of the present technology is operably-linked to an ara B promoter and expressible in a host cell. See U.S. Pat. No. 5,028,530. The expression vectors of the present technology can be introduced into host cells to thereby produce polypeptides or peptides, including fusion polypeptides, encoded by nucleic acids as described herein (e.g., anti-CD19 antibody, etc.).

Another aspect of the present technology pertains to anti-CD19 antibody-expressing host cells, which contain a nucleic acid encoding one or more anti-CD19 antibodies. The recombinant expression vectors of the present technology can be designed for expression of an anti-CD19 antibody in prokaryotic or eukaryotic cells. For example, an anti-CD19 antibody can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif (1990). Alternatively, the recombinant expression vector can be transcribed and translated in vitro, e.g., using T7 promoter regulatory sequences and T7 polymerase. Methods useful for the preparation and screening of polypeptides having a predetermined property, e.g., anti-CD19 antibody, via expression of stochastically generated polynucleotide sequences has been previously described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene* 69: 301-315) and pET 11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., an anti-CD19 antibody, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (See, e.g., Wada, et al., 1992. *Nucl. Acids Res.* 20: 2111-2118). Such alteration of nucleic acid sequences of the present technology can be carried out by standard DNA synthesis techniques.

In another embodiment, the anti-CD19 antibody expression vector is a yeast expression vector. Examples of vectors for expression in yeast *Saccharomyces cerevisiae* include pYepSec1 (Baldari, et al., 1987. *EMBO J.* 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif.), and picZ (Invitrogen Corp, San Diego, Calif.). Alternatively, an anti-CD19 antibody can be expressed in insect cells using baculovirus expression vectors. Baculovirus vectors available for expression of polypeptides, e.g., anti-CD19 antibody, in cultured insect cells (e.g., SF9 cells) include the pAc series (Smith, et al., *Mol. Cell. Biol.* 3:2156-2165, 1983) and the pVL series (Lucklow and Summers, 1989. *Virology* 170: 31-39).

In yet another embodiment, a nucleic acid encoding an anti-CD19 antibody of the present technology is expressed in mammalian cells using a mammalian expression vector. Examples of mammalian expression vectors include, e.g., but are not limited to, pCDM8 (Seed, *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells that are useful for expression of the anti-CD19 antibody of the present technology, see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), promoters of T cell receptors (Winoto and Baltimore, *EMBO J.* 8: 729-733, 1989) and immunoglobulins (Banerji, et al., 1983. *Cell* 33: 729-740; Queen and Baltimore, Cell 33: 741-748, 1983.), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the a-fetoprotein promoter (Campes and Tilghman, *Genes Dev.* 3: 537-546, 1989).

Another aspect of the present methods pertains to host cells into which a recombinant expression vector of the present technology has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an anti-CD19 antibody can be expressed in bacterial cells such as E. coli, insect cells, yeast or mammalian cells. Mammalian cells are a suitable host for expressing nucleotide segments encoding immunoglobulins or fragments thereof. See Winnacker, From Genes To Clones, (VCH Publishers, NY, 1987). A number of suitable host cell lines capable of secreting intact heterologous proteins have been developed in the art, and include Chinese hamster ovary (CHO) cell lines, various COS cell lines, HeLa cells, L cells and myeloma cell lines. In some embodiments, the cells are non-human. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., Immunol. Rev. 89: 49, 1986. Illustrative expression control sequences are promoters derived from endogenous genes, cytomegalovirus, SV40, adenovirus, bovine papillomavirus, and the like. Co et al., J. Immunol. 148: 1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, biolistics or viral-based transfection. Other methods used to transform mammalian cells include the use of polybrene, protoplast fusion, liposomes, electroporation, and microinjection (See generally, Sambrook et al., Molecular Cloning). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well-known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the anti-CD19 antibody or can be introduced on a separate vector. Cells stably transfected with the introduced nucleic acid can be identified by drug selection (e.g., cells that have incorporated the selectable marker gene will survive, while the other cells die).

A host cell that includes an anti-CD19 antibody of the present technology, such as a prokaryotic or eukaryotic host cell in culture, can be used to produce (i.e., express) recombinant anti-CD19 antibody. In one embodiment, the method comprises culturing the host cell (into which a recombinant expression vector encoding the anti-CD19 antibody has been introduced) in a suitable medium such that the anti-CD19 antibody is produced. In another embodiment, the method further comprises the step of isolating the anti-CD19 antibody from the medium or the host cell. Once expressed, collections of the anti-CD19 antibody, e.g., the anti-CD19 antibodies or the anti-CD19 antibody-related polypeptides are purified from culture media and host cells. The anti-CD19 antibody can be purified according to standard procedures of the art, including HPLC purification, column chromatography, gel electrophoresis and the like. In one embodiment, the anti-CD19 antibody is produced in a host organism by the method of Boss et al., U.S. Pat. No. 4,816,397. Usually, anti-CD19 antibody chains are expressed with signal sequences and are thus released to the culture media. However, if the anti-CD19 antibody chains are not naturally secreted by host cells, the anti-CD19 antibody chains can be released by treatment with mild detergent. Purification of recombinant polypeptides is well known in the art and includes ammonium sulfate precipitation, affinity chromatography purification technique, column chromatography, ion exchange purification technique, gel electrophoresis and the like (See generally Scopes, Protein Purification (Springer-Verlag, N.Y., 1982).

Polynucleotides encoding anti-CD19 antibodies, e.g., the anti-CD19 antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be micro-injected into fertilized oocytes, or can be incorporated into the genome of embryonic stem cells, and the nuclei of such cells transferred into enucleated oocytes.

Single-Chain Antibodies. In one embodiment, the anti-CD19 antibody of the present technology is a single-chain anti-CD19 antibody. According to the present technology, techniques can be adapted for the production of single-chain antibodies specific to a CD19 protein (See, e.g., U.S. Pat. No. 4,946,778). Examples of techniques which can be used to produce single-chain Fvs and antibodies of the present technology include those described in U.S. Pat. Nos. 4,946, 778 and 5,258,498; Huston et al., Methods in Enzymology, 203: 46-88, 1991; Shu, L. et al., Proc. Natl. Acad. Sci. USA, 90: 7995-7999, 1993; and Skerra et al., Science 240: 1038-1040, 1988.

Chimeric and Humanized Antibodies. In one embodiment, the anti-CD19 antibody of the present technology is a chimeric anti-CD19 antibody. In one embodiment, the anti-CD19 antibody of the present technology is a humanized anti-CD19 antibody. In one embodiment of the present technology, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-CD19 antibodies, such as chimeric and humanized monoclonal antibodies, comprising both human and non-human portions, can be made using standard recombinant DNA techniques, and are within the scope of the present technology. For some uses, including in vivo use of the anti-CD19 antibody of the present technology in humans as well as use of these agents in in vitro detection assays, it is possible to use chimeric or humanized anti-CD19 antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187; European Patent No. 171496; European Pat. No. 173494; PCT International Publication No. WO 86/01533; U.S. Pat. Nos. 4,816,567; 5,225,539; European Patent No. 125023; Better, et al., 1988. *Science* 240: 1041-1043; Liu, et al., 1987. *Proc. Natl. Acad. Sci. USA* 84: 3439-3443; Liu, et al., 1987. *J. Immunol.* 139: 3521-3526; Sun, et al., 1987. *Proc. Natl. Acad. Sci. USA* 84: 214-218; Nishimura, et al., 1987. *Cancer Res.* 47: 999-1005; Wood, et al., 1985. *Nature* 314: 446-449; Shaw, et al., 1988. *J. Natl. Cancer Inst.* 80: 1553-1559; Morrison (1985) *Science* 229: 1202-1207; Oi, et al. (1986) *BioTechniques* 4: 214; Jones, et al., 1986. *Nature* 321: 552-525; Verhoeyan, et al., 1988. *Science* 239: 1534; Morrison, *Science* 229: 1202, 1985; Oi et al., *BioTechniques* 4: 214, 1986; Gillies et al., *J. Immunol. Methods,* 125: 191-202, 1989; U.S. Pat. No. 5,807,715; and Beidler, et al., 1988. *J. Immunol.* 141: 4053-4060. For example, antibodies can be humanized using a variety of techniques including CDR-grafting (EP 0 239 400; WO 91/09967; U.S. Pat. Nos. 5,530,101; 5,585,089; 5,859,205; 6,248,516; EP460167), veneering or resurfacing (EP 0 592 106; EP 0 519 596; Padlan E. A., *Molecular Immunology,* 28: 489-498, 1991; Studnicka et al., *Protein Engineering* 7: 805-814, 1994; Roguska et al., *PNAS* 91: 969-973, 1994), and chain shuffling (U.S. Pat. No. 5,565, 332). In one embodiment, a cDNA encoding a murine anti-CD19 monoclonal antibody is digested with a restriction enzyme selected specifically to remove the sequence encoding the Fc constant region, and the equivalent portion of a cDNA encoding a human Fc constant region is substituted (See Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al. (1988) *Science* 240: 1041-1043; Liu et al. (1987) *Proc. Natl. Acad. Sci. USA* 84: 3439-3443; Liu et al. (1987) *J Immunol* 139: 3521-3526; Sun et al. (1987) *Proc. Natl. Acad. Sci. USA* 84: 214-218; Nishimura et al. (1987) *Cancer Res* 47: 999-1005; Wood et al. (1985) *Nature* 314: 446-449; and Shaw et al. (1988) *J. Natl. Cancer Inst.* 80: 1553-1559; U.S. Pat. Nos. 6,180,370; 6,300,064; 6,696,248; 6,706,484; 6,828,422.

In one embodiment, the present technology provides the construction of humanized anti-CD19 antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present technology provides for a humanized anti-CD19 antibodies, heavy and light chain immunoglobulins.

CDR Antibodies. In some embodiments, the anti-CD19 antibody of the present technology is an anti-CD19 CDR antibody. Generally the donor and acceptor antibodies used to generate the anti-CD19 CDR antibody are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently, all three CDRs in all variable domains of the acceptor antibody will be replaced with the corresponding donor CDRs, though one needs to replace only as many as necessary to permit adequate binding of the resulting CDR-grafted antibody to CD19 protein. Methods for generating CDR-grafted and humanized antibodies are taught by Queen et al. U.S. Pat. Nos. 5,585,089; 5,693,761; 5,693,762; and Winter 5,225,539; and EP 0682040. Methods useful to prepare $V_H$ and $V_L$ polypeptides are taught by Winter et al., U.S. Pat. Nos. 4,816,397; 6,291,158; 6,291, 159; 6,291,161; 6,545,142; EP 0368684; EP0451216; and EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-CD19 CDR-grafted antibody by replacing certain residues of a given FR to make the FR more similar to the corresponding FR of the donor antibody. Suitable locations of the substitutions include amino acid residues adjacent to the CDR, or which are capable of interacting with a CDR (See, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-CD19 CDR-grafted antibody significantly compared to the same antibody with a fully human FR.

Bispecific Antibodies (BsAbs). A bispecific antibody is an antibody that can bind simultaneously to two targets that have a distinct structure, e.g., two different target antigens, two different epitopes on the same target antigen, or a hapten and a target antigen or epitope on a target antigen. BsAbs can be made, for example, by combining heavy chains and/or light chains that recognize different epitopes of the same or different antigen. In some embodiments, by molecular function, a bispecific binding agent binds one antigen (or epitope) on one of its two binding arms (one VH/VL pair), and binds a different antigen (or epitope) on its second arm (a different VH/VL pair). By this definition, a bispecific binding agent has two distinct antigen binding arms (in both specificity and CDR sequences), and is monovalent for each antigen to which it binds.

Bispecific antibodies (BsAb) and bispecific antibody fragments (BsFab) of the present technology have at least one arm that specifically binds to, for example, CD19 and at least one other arm that specifically binds to a second target antigen. In some embodiments, the second target antigen is an antigen or epitope of a B-cell, a T-cell, a myeloid cell, a plasma cell, or a mast-cell. Additionally or alternatively, in certain embodiments, the second target antigen is selected from the group consisting of CD3, CD4, CD8, CD20, CD19, CD21, CD23, CD46, CD80, HLA-DR, CD74, CD19, CD14, CD15, CD16, CD123, TCR gamma/delta, NKp46 and KIR. In certain embodiments, the BsAbs are capable of binding to tumor cells that express CD19 antigen on the cell surface. In some embodiments, the BsAbs have been engineered to facilitate killing of tumor cells by directing (or recruiting) cytotoxic T cells to a tumor site. Other exemplary BsAbs include those with a first antigen binding site specific for CD19 and a second antigen binding site specific for a small molecule hapten (e.g., DTP A, IMP288, DOTA, DOTA-Bn, DOTA-desferrioxamine, other DOTA-chelates described herein, Biotin, fluorescein, or those disclosed in Goodwin, D A. et al, 1994, *Cancer Res.* 54(22):5937-5946).

A variety of bispecific fusion proteins can be produced using molecular engineering. For example, BsAbs have been constructed that either utilize the full immunoglobulin framework (e.g., IgG), single chain variable fragment (scFv), or combinations thereof. In some embodiments, the bispecific fusion protein is divalent, comprising, for example, a scFv with a single binding site for one antigen and a Fab fragment with a single binding site for a second antigen. In some embodiments, the bispecific fusion protein is divalent, comprising, for example, an scFv with a single binding site for one antigen and another scFv fragment with a single binding site for a second antigen. In other embodiments, the bispecific fusion protein is tetravalent, comprising, for example, an immunoglobulin (e.g., IgG) with two binding sites for one antigen and two identical scFvs for a second antigen. BsAbs composed of two scFv units in tandem have been shown to be a clinically successful bispecific antibody format. In some embodiments, BsAbs comprise two single chain variable fragments (scFvs) in tandem have been designed such that an scFv that binds a tumor antigen (e.g., CD19) is linked with an scFv that engages T cells (e.g., by binding CD3). In this way, T cells are recruited to a tumor site such that they can mediate cytotoxic killing of the tumor cells. See e.g., Dreier et al., *J. Immunol.* 170:4397-4402 (2003); Bargou et al., *Science* 321:974-977 (2008)). In some embodiments, BsAbs of the present technology comprise two single chain variable fragments (scFvs) in tandem have been designed such that an scFv that binds a tumor antigen (e.g., CD19) is linked with an scFv that engages a small molecule DOTA hapten.

Recent methods for producing BsAbs include engineered recombinant monoclonal antibodies which have additional cysteine residues so that they crosslink more strongly than the more common immunoglobulin isotypes. See, e.g., FitzGerald et al., *Protein Eng.* 10(10):1221-1225 (1997). Another approach is to engineer recombinant fusion proteins linking two or more different single-chain antibody or antibody fragment segments with the needed dual specificities. See, e.g., Coloma et al., *Nature Biotech.* 15:159-163 (1997). A variety of bispecific fusion proteins can be produced using molecular engineering.

Bispecific fusion proteins linking two or more different single-chain antibodies or antibody fragments are produced in a similar manner. Recombinant methods can be used to produce a variety of fusion proteins. In some certain embodiments, a BsAb according to the present technology comprises an immunoglobulin, which immunoglobulin comprises a heavy chain and a light chain, and an scFv. In some certain embodiments, the scFv is linked to the C-terminal end of the heavy chain of any CD19 immunoglobulin disclosed herein. In some certain embodiments, scFvs are linked to the C-terminal end of the light chain of any CD19 immunoglobulin disclosed herein. In various embodiments, scFvs are linked to heavy or light chains via a linker sequence. Appropriate linker sequences necessary for the in-frame connection of the heavy chain Fd to the scFv are introduced into the $V_L$ and $V_{kappa}$ domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the $V_H$ region of a CD19 antibody. The resulting vector can be used to transfect an appropriate host cell, such as a mammalian cell for the expression of the bispecific fusion protein.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second antigen binding sites). In some embodiments, a linker is employed in a BsAb described herein based on specific properties imparted to the BsAb such as, for example, an increase in stability. In some embodiments, a BsAb of the present technology comprises a G45 linker (SEQ ID NO: 87). In some certain embodiments, a BsAb of the present technology comprises a $(G_4S)_n$ linker (SEQ ID NO: 89), wherein n is 1, 2, 3, 4, 5, 6, 7, 8, 9, 10, 1 1, 12, 13, 14, 15 or more.

Self assembly disassembly (SADA) Conjugates. In some embodiments, the anti-CD19 antibodies of the present technology comprise one or more SADA domains. SADA domains can be designed and/or tailored to achieve environmentally-dependent multimerization with beneficial kinetic, thermodynamic, and/or pharmacologic properties. For example, it is recognized that SADA domains may be part of a conjugate that permit effective delivery of a payload to a target site of interest while minimizing the risk of off-target interactions. The anti-CD19 antibodies of the present technology may comprise a SADA domain linked to one or more binding domains. In some embodiments, such conjugates are characterized in that they multimerize to form a complex of a desired size under relevant conditions (e.g., in a solution in which the conjugate is present above a threshold concentration or pH and/or when present at a target site characterized by a relevant level or density of receptors for the payload), and disassemble to a smaller form under other conditions (e.g., absent the relevant environmental multimerization trigger).

A SADA conjugate may have improved characteristics compared to a conjugate without a SADA domain. In some embodiments, improved characteristics of a multimeric conjugate include: increased avidity/binding to a target, increased specificity for target cells or tissues, and/or extended initial serum half-life. In some embodiments, improved characteristics include that through dissociation to smaller states (e.g., dimeric or monomeric), a SADA conjugate exhibits reduced non-specific binding, decreased toxicity, and/or improved renal clearance. In some embodiments, a SADA conjugate comprises a SADA polypeptide having an amino acid sequence that shows at least 75% identity with that of a human homo-multimerizing polypeptide and is characterized by one or more multimerization dissociation constants ($K_D$).

In some embodiments, a SADA conjugate is constructed and arranged so that it adopts a first multimerization state and one or more higher-order multimerization states. In some embodiments, a first multimerization state is less than about ~70 kDa in size. In some embodiments, a first multimerization state is an unmultimerized state (e.g., a monomer or a dimer). In some embodiments, a first multimerization state is a monomer. In some embodiments, a first multimerization state is a dimer. In some embodiments, a first multimerization state is a multimerized state (e.g., a trimer or a tetramer). In some embodiments, a higher-order multimerization states is a homo-tetramer or higher-order homo-multimer greater than 150 kDa in size. In some embodiments, a higher-order homo-multimerized conjugate is stable in aqueous solution when the conjugate is present at a concentration above the SADA polypeptide $K_D$. In some embodiments, a SADA conjugate transitions from a higher-order multimerization state(s) to a first multimerization state under physiological conditions when the concentration of the conjugate is below the SADA polypeptide $K_D$.

In some embodiments, a SADA polypeptide is covalently linked to a binding domain via a linker. Any suitable linker known in the art can be used. In some embodiments, a SADA polypeptide is linked to a binding domain via a polypeptide linker. In some embodiments, a polypeptide linker is a Gly-Ser linker. In some embodiments, a polypeptide linker is or comprises a sequence of (GGGGS)n (SEQ ID NO: 90), where n represents the number of repeating GGGGS (SEQ ID NO: 87) units and is 1, 2, 3, 4, 5, 6, 7, 8, 9, 10, 11, 12, 13, 14, 15, 16, 17, 18, 19, 20, 25, 30 or more. In some embodiments, a binding domain is directly fused to a SADA polypeptide.

In some embodiments, a SADA domain is a human polypeptide or a fragment and/or derivative thereof. In some embodiments, a SADA domain is substantially non-immunogenic in a human. In some embodiments, a SADA polypeptide is stable as a multimer. In some embodiments, a SADA polypeptide lacks unpaired cysteine residues. In some embodiments, a SADA polypeptide does not have large exposed hydrophobic surfaces. In some embodiments, a SADA domain has or is predicted to have a structure comprising helical bundles that can associate in a parallel or anti-parallel orientation. In some embodiments, a SADA polypeptide is capable of reversible multimerization. In some embodiments, a SADA domain is a tetramerization domain, a heptamerization domain, a hexamerization domain or an octamerization domain. In certain embodiments, a SADA domain is a tetramerization domain. In some embodiments, a SADA domain is composed of a multimerization domains which are each composed of helical bundles that associate in a parallel or anti-parallel orientation. In some embodiments, a SADA domain is selected from the group of one of the following human proteins: p53, p63, p73, heterogeneous nuclear Ribonucleoprotein C (hnRNPC), N-terminal domain of Synaptosomal-associated protein 23 (SNAP-23), Stefin B (Cystatin B), Potassium voltage-gated channel subfamily KQT member 4 (KCNQ4), or Cyclin-D-related protein (CBFA2T1). Examples of suitable SA.DA domains are described in PCT/US2018/031235, which is hereby incorporated by reference in its entirety. Provided below are polypeptide sequences for exemplary SADA domains.

```
Human p53 tetramerization domain amino acid sequence (321-359)
                                              (SEQ ID NO: 74)
KPLDGEYFTLQIRGRERFEMFRELNEALELKDAQAGKEP Human p63 tetramerization domain amino acid sequence (396-450)
                                              (SEQ ID NO: 75)
RSPDDELLYLPVRGRETYEMLLKIKESLELMQYLPQHTIETYRQQQQQQHQHLLQKQ Human p73 tetramerization domain amino acid sequence (348-399)
                                              (SEQ ID NO: 76)
RHGDEDTYYLQVRGRENFEILMKLKESLELMELVPQPLVDSYRQQQQLLQRP.

Human HNRNPC tetramerization domain amino acid sequence (194-220)
                                              (SEQ ID NO: 77)
QAIKKELTQIKQKVDSLLENLEKIEKE Human SNAP-23 tetramerization domain amino acid sequence (23-76)
                                              (SEQ ID NO: 78)
STRRILGLAIESQDAGIKTITMLDEQKEQLNRIEEGLDQINKDMRETEKTLTEL Human Stefin B tetramerizaiton domain amino acid sequence (2-98)
                                              (SEQ ID NO: 79)
MCGAPSATQPATAETQHIADQVRSQLEEKENKKFPVFKAVSFKSQVVAGTNYFIKVHV

GDEDFVHLRVFQSLPHENKPLTLSNYQTNKAKHDELTYF

KCNQ4 tetramerizaiton domain amino acid sequence (611-640)
                                              (SEQ ID NO: 80)
DEISMMGRVVKVEKQVQSIEHKLDLLLGFY
```

-continued

CBFA2T1 tetramerizaiton domain amino acid sequence (462-521)
(SEQ ID NO: 81)

TVAEAKRQAAEDALAVINQQEDSSESCWNCGRKASETCSGCNTARYCGSFCQHKDWE

KHH

In some embodiments, a SADA polypeptide is or comprises a tetramerization domain of p53, p63, p73, heterogeneous nuclear Ribonucleoprotein C (hnRNPC), N-terminal domain of Synaptosomal-associated protein 23 (SNAP-23), Stefin B (Cystatin B), Potassium voltage-gated channel subfamily KQT member 4 (KCNQ4), or Cyclin-D-related protein (CBFA2T1). In some embodiments, a SADA polypeptide is or comprises a sequence that is at least 75%, 80%, 85%, 90%, 91%, 92%, 93%, 94%, 95%, 96%, 97%, 98%, 99% or 100% identical to a sequence as set forth in any one of SEQ ID NOs: 74-81.

Fc Modifications. In some embodiments, the anti-CD19 antibodies of the present technology comprise a variant Fc region, wherein said variant Fc region comprises at least one amino acid modification relative to a wild-type Fc region (or the parental Fc region), such that said molecule has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al., *Nature,* 406:267-273 (2000). Examples of positions within the Fc region that make a direct contact with an Fc receptor such as an FcγR, include amino acids 234-239 (hinge region), amino acids 265-269 (B/C loop), amino acids 297-299 (C7E loop), and amino acids 327-332 (F/G) loop.

In some embodiments, an anti-CD19 antibody of the present technology has an altered affinity for activating and/or inhibitory receptors, having a variant Fc region with one or more amino acid modifications, wherein said one or more amino acid modification is a N297 substitution with alanine, or a K322 substitution with alanine.

Glycosylation Modifications. In some embodiments, anti-CD19 antibodies of the present technology have an Fc region with variant glycosylation as compared to a parent Fc region. In some embodiments, variant glycosylation includes the absence of fucose; in some embodiments, variant glycosylation results from expression in GnT1-deficient CHO cells.

In some embodiments, the antibodies of the present technology, may have a modified glycosylation site relative to an appropriate reference antibody that binds to an antigen of interest (e.g., CD19), without altering the functionality of the antibody, e.g., binding activity to the antigen. As used herein, "glycosylation sites" include any specific amino acid sequence in an antibody to which an oligosaccharide (i.e., carbohydrates containing two or more simple sugars linked together) will specifically and covalently attach.

Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform (hCD19-IgGln) that lacks certain oligosaccharides including fucose and terminal N-acetylglucosamine may be produced in special CHO cells and exhibit enhanced ADCC effector function.

In some embodiments, the carbohydrate content of an immunoglobulin-related composition disclosed herein is modified by adding or deleting a glycosylation site. Methods for modifying the carbohydrate content of antibodies are well known in the art and are included within the present technology, see, e.g., U.S. Pat. No. 6,218,149; EP 0359096B1; U.S. Patent Publication No. US 2002/0028486; International Patent Application Publication WO 03/035835; U.S. Patent Publication No. 2003/0115614; U.S. Pat. Nos. 6,218,149; 6,472,511; all of which are incorporated herein by reference in their entirety. In some embodiments, the carbohydrate content of an antibody (or relevant portion or component thereof) is modified by deleting one or more endogenous carbohydrate moieties of the antibody. In some certain embodiments, the present technology includes deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by coexpression with one or more enzymes, for example N-acetylglucosaminyltransferase III (GnTIII), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, *Nat. Biotechnol.* 17: 176-180; Davies et al., 2001, *Biotechnol. Bioeng.* 74:288-294; Shields et al., 2002, *J. Biol. Chem.* 277:26733-26740; Shinkawa et al., 2003, *J. Biol. Chem.* 278:3466-3473; U.S. Pat. No. 6,602,684; U.S. patent application Ser. No. 10/277, 370; U.S. patent application Ser. No. 10/113,929; International Patent Application Publications WO 00/61739A1; WO 01/292246A1; WO 02/311140A1; WO 02/30954A1; POTILLEGENT™ technology (Biowa, Inc. Princeton, N.J.); GLYCOMAB™ glycosylation engineering technology (GLYCART biotechnology AG, Zurich, Switzerland); each of which is incorporated herein by reference in its entirety. See, e.g., International Patent Application Publication WO 00/061739; U.S. Patent Application Publication No. 2003/0115614; Okazaki et al., 2004, *JMB,* 336: 1239-49.

Fusion Proteins. In one embodiment, the anti-CD19 antibody of the present technology is a fusion protein. The anti-CD19 antibodies of the present technology, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present technology can also be engineered to improve characteristics of the anti-CD19 antibodies. For instance, a region of additional amino acids, particularly charged amino acids, can be added to the N-terminus of the anti-CD19 antibody to improve stability and persistence during purification from the host cell or subsequent handling and storage. Also, peptide moieties can be added to an anti-CD19 antibody to facilitate purification. Such regions can be removed prior to final preparation of the anti-CD19 antibody. The addition of peptide moieties to facilitate handling of polypeptides are familiar and routine techniques in the art. The anti-CD19 antibody of the present technology can be fused to marker sequences, such as a peptide which facilitates purification of the fused polypeptide. In select embodiments, the marker amino acid sequence is a hexa-histidine peptide (SEQ ID NO: 88), such as the tag provided in a pQE vector (QIA-GEN, Inc., Chatsworth, Calif), among others, many of which are commercially available. As described in Gentz et al., *Proc. Natl. Acad. Sci. USA* 86: 821-824, 1989, for instance, hexa-histidine (SEQ ID NO: 88) provides for convenient purification of the fusion protein. Another peptide tag useful for purification, the "HA" tag, corresponds to an epitope derived from the influenza hemagglutinin protein. Wilson et al., *Cell* 37: 767, 1984.

Thus, any of these above fusion proteins can be engineered using the polynucleotides or the polypeptides of the present technology. Also, in some embodiments, the fusion proteins described herein show an increased half-life in vivo.

Fusion proteins having disulfide-linked dimeric structures (due to the IgG) can be more efficient in binding and neutralizing other molecules compared to the monomeric secreted protein or protein fragment alone. Fountoulakis et al., *J. Biochem.* 270: 3958-3964, 1995.

Similarly, EP-A-0 464 533 (Canadian counterpart 2045869) discloses fusion proteins comprising various portions of constant region of immunoglobulin molecules together with another human protein or a fragment thereof. In many cases, the Fc part in a fusion protein is beneficial in therapy and diagnosis, and thus can result in, e.g., improved pharmacokinetic properties. See EP-A 0232 262. Alternatively, deleting or modifying the Fc part after the fusion protein has been expressed, detected, and purified, may be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8: 52-58, 1995; Johanson et al., *J. Biol. Chem.,* 270: 9459-9471, 1995.

Labeled Anti-CD19 antibodies. In one embodiment, the anti-CD19 antibody of the present technology is coupled with a label moiety, i.e., detectable group. The particular label or detectable group conjugated to the anti-CD19 antibody is not a critical aspect of the technology, so long as it does not significantly interfere with the specific binding of the anti-CD19 antibody of the present technology to the CD19 protein. The detectable group can be any material having a detectable physical or chemical property. Such detectable labels have been well-developed in the field of immunoassays and imaging. In general, almost any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^3$H, $^{14}$C, $^{35}$S, $^{125}$I, $^{131}$I, $^{112}$In, $^{99}$mTc), other imaging agents such as microbubbles (for ultrasound imaging), $^{18}$F, $^{11}$, $^{15}$O, (for Positron emission tomography), $^{99m}$TC, $^{111}$In (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277, 437; 4,275,149; and 4,366,241, each incorporated herein by reference in their entirety and for all purposes. See also Handbook of Fluorescent Probes and Research Chemicals (6$^{th}$ Ed., Molecular Probes, Inc., Eugene OR.).

The label can be coupled directly or indirectly to the desired component of an assay according to methods well known in the art. As indicated above, a wide variety of labels can be used, with the choice of label depending on factors such as required sensitivity, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-CD19 antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labeling moieties, include, but are not limited to, e.g., luciferin, and 2,3-dihydrophthalazinediones, e.g., luminol. For a review of various labeling or signal-producing systems which can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally, simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-CD19 antibodies. In this case, antigen-coated particles are agglutinated by samples comprising the target antibodies. In this format, none of the components need be labeled and the presence of the target antibody is detected by simple visual inspection.

B. Identifying and Characterizing the Anti-CD19 Antibodies of the Present Technology Methods for identifying and/or screening the anti-CD19 antibodies of the present technology. Methods useful to identify and screen antibodies against CD19 polypeptides for those that possess the desired specificity to CD19 protein (e.g., those that bind to an epitope comprising the amino acid residues corresponding to positions 29-118 of SEQ ID NO: 60 or SEQ ID NO: 61, or the polypeptide encoded by exon-2 of CD19 mRNA) include any immunologically-mediated techniques known within the art. For example, flow cytometry and immunofluorescence or immunohistochemistry may be used. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A et al., *Immunity,* 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.,* 86: 4230-4, 1989); (4) mast cells can be incubated with reagents that cross-link their Fc-epsilon receptors and histamine release measured by enzyme immunoassay (Siraganian et al., TIPS, 4: 432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72: 1310-5, 1988); (3) the proliferation of peripheral blood mononuclear cells (PBMCs) in response to mitogens or mixed lymphocyte reaction can be measured using $^3$H-thymidine; (4) the phagocytic capacity of granulocytes, macrophages, and other phagocytes in PBMCs can be measured by placing PBMCs in wells together with labeled particles (Peters et al., *Blood,* 72: 1310-5, 1988); and (5) the differentiation of immune system cells can be measured by labeling PBMCs with antibodies to CD molecules such as CD4 and CD8 and measuring the fraction of the PBMCs expressing these markers.

In one embodiment, anti-CD19 antibodies of the present technology are selected using display of CD19 peptides on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. Nos. 5,871,907; 5,969,108; 6,225,447; 6,291,650; 6,492,160.

In some embodiments, anti-CD19 antibodies of the present technology are selected using display of CD19 peptides on the surface of a yeast host cell. Methods useful for the isolation of scFv polypeptides by yeast surface display have been described by Kieke et al., *Protein Eng.* 1997 November; 10(11): 1303-10.

In some embodiments, anti-CD19 antibodies of the present technology are selected using ribosome display. Methods useful for identifying ligands in peptide libraries using ribosome display have been described by Mattheakis et al., *Proc. Natl. Acad. Sci. USA* 91: 9022-26, 1994; and Hanes et al., *Proc. Natl. Acad. Sci. USA* 94: 4937-42, 1997.

In certain embodiments, anti-CD19 antibodies of the present technology are selected using tRNA display of CD19 peptides. Methods useful for in vitro selection of ligands using tRNA display have been described by Merryman et al., *Chem. Biol.,* 9: 741-46, 2002.

In one embodiment, anti-CD19 antibodies of the present technology are selected using RNA display. Methods useful for selecting peptides and proteins using RNA display libraries have been described by Roberts et al. *Proc. Natl. Acad. Sci. USA,* 94: 12297-302, 1997; and Nemoto et al., *FEBS Lett.,* 414: 405-8, 1997. Methods useful for selecting peptides and proteins using unnatural RNA display libraries have been described by Frankel et al., *Curr. Opin. Struct. Biol.,* 13: 506-12, 2003.

In some embodiments, anti-CD19 antibodies of the present technology are expressed in the periplasm of gram negative bacteria and mixed with labeled CD19 protein. See WO 02/34886. In clones expressing recombinant polypeptides with affinity for CD19 protein, the concentration of the labeled CD19 protein bound to the anti-CD19 antibodies is increased and allows the cells to be isolated from the rest of the library as described in Harvey et al., *Proc. Natl. Acad. Sci.* 22: 9193-98 2004 and U.S. Pat. Publication No. 2004/0058403.

After selection of the desired anti-CD19 antibodies, it is contemplated that said antibodies can be produced in large volume by any technique known to those skilled in the art, e.g., prokaryotic or eukaryotic cell expression and the like. The anti-CD19 antibodies which are, e.g., but not limited to, anti-CD19 hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of CD19 Binding. In some embodiments, a CD19 binding assay refers to an assay format wherein CD19 protein and an anti-CD19 antibody are mixed under conditions suitable for binding between the CD19 protein and the anti-CD19 antibody and assessing the amount of binding between the CD19 protein and the anti-CD19 antibody. The amount of binding is compared with a suitable control, which can be the amount of binding in the absence of the CD19 protein, the amount of the binding in the presence of a non-specific immunoglobulin composition, or both. The amount of binding can be assessed by any suitable method. Binding assay methods include, e.g., ELISA, radioimmunoassays, scintillation proximity assays, fluorescence energy transfer assays, liquid chromatography, membrane filtration assays, and the like. Biophysical assays for the direct measurement of CD19 protein binding to anti-CD19 antibody are, e.g., nuclear magnetic resonance, fluorescence, fluorescence polarization, surface plasmon resonance (BIA- CORE chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate anti-CD19 antibody is at least 1 percent greater than the binding observed in the absence of the candidate anti-CD19 antibody, the candidate anti-CD19 antibody is useful as an anti-CD19 antibody of the present technology. In some embodiments, the CD19 protein is a CD19 protein containing the extracellular domain (e.g., the two Ig-like C2 loops of CD19), or a CD19 polypeptide comprising the amino acid residues corresponding to positions 29-118 of SEQ ID NO: 60 or SEQ ID NO: 61.

Uses of the Anti-CD19 Antibodies of the Present Technology

General. The anti-CD19 antibodies of the present technology are useful in methods known in the art relating to the localization and/or quantitation of CD19 protein (e.g., for use in measuring levels of the CD19 protein within appropriate physiological samples, for use in diagnostic methods, for use in imaging the polypeptide, and the like). Antibodies of the present technology are useful to isolate or detect a CD19 protein by standard techniques, such as affinity chromatography, immunofluorescence, flow cytometry, immunohistochemistry, or immunoprecipitation. The anti-CD19 antibody of the present technology can facilitate the purification of natural immunoreactive CD19 proteins from biological samples, e.g., mammalian sera or cells as well as recombinantly-produced immunoreactive CD19 proteins expressed in a host system. Moreover, the anti-CD19 antibodies of present disclosure can be used to detect an immunoreactive CD19 protein (e.g., in plasma, a cellular lysate or cell supernatant) in order to evaluate the abundance and pattern of expression of the immunoreactive polypeptide. The anti-CD19 antibodies of the present technology can be used diagnostically to monitor immunoreactive CD19 protein levels in tissue as part of a clinical testing procedure, e.g., to determine the efficacy of a given treatment regimen. As noted above, the detection can be facilitated by coupling (i.e., physically linking) the anti-CD19 antibodies of the present technology to a detectable substance.

Detection of CD19 protein. An exemplary method for detecting the presence or absence of an immunoreactive CD19 protein in a biological sample involves obtaining a biological sample from a test subject and contacting the biological sample with an anti-CD19 antibody of the present technology capable of detecting an immunoreactive CD19 protein such that the presence of an immunoreactive CD19 protein is detected in the biological sample. Detection may be accomplished by means of a detectable label attached to the antibody.

The term "labeled" with regard to the anti-CD19 antibody is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

In some embodiments, the anti-CD19 antibodies disclosed herein are conjugated to one or more detectable labels. For such uses, anti-CD19 antibodies may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid. Examples of suitable enzyme labels include malate dehydrogenase, staphylococcal nuclease, 4-5-steroid isomerase, yeast-alcohol dehydrogenase, $\alpha$-glycerol phosphate dehydrogenase, triose phosphate isomerase, peroxidase, alkaline phosphatase, asparaginase, glucose oxidase, $\beta$-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is an exemplary isotope where in vivo imaging is used since its avoids the problem of dehalogenation of the $^{125}$I or $^{131}$I-labeled CD19-binding antibodies by the liver. In addition, this isotope has a more favorable gamma emission energy for imaging (Perkins et al, *Eur. J. Nucl. Med.* 70:296-301 (1985); Carasquillo et al., *J. Nucl. Med.* 25:281-287 (1987)). For example, $^{111}$In coupled to monoclonal antibodies with 1-(P-isothiocyanatobenzyl)-DPTA exhibits little uptake in non-tumorous tissues, particularly the liver, and enhances specificity of tumor localization (Esteban et al., *J. Nucl. Med.* 28:861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

The detection method of the present technology can be used to detect an immunoreactive CD19 protein in a biological sample in vitro as well as in vivo. In vitro techniques for detection of an immunoreactive CD19 protein include enzyme linked immunosorbent assays (ELISAs), flow cytometry, Western blots, immunohistochemistry, immunoprecipitations, radioimmunoassay, and immunofluorescence. Furthermore, in vivo techniques for detection of an immunoreactive CD19 protein include introducing into a subject a labeled anti-CD19 antibody. For example, the anti-CD19 antibody can be labeled with a radioactive marker whose presence and location in a subject can be detected by standard imaging techniques. In one embodiment, the biological sample contains CD19 protein molecules from the test subject.

Immunoassay and Imaging. An anti-CD19 antibody of the present technology can be used to assay immunoreactive CD19 protein levels in a biological sample (e.g., human plasma) using antibody-based techniques. For example, protein expression in tissues can be studied with classical immunohistological methods. Jalkanen, M. et al., *J. Cell. Biol.* 101: 976-985, 1985; Jalkanen, M. et al., *J. Cell. Biol.* 105: 3087-3096, 1987. Other antibody-based methods useful for detecting protein gene expression include immunoassays, such as the enzyme linked immunosorbent assay (ELISA) and the radioimmunoassay (MA). Suitable antibody assay labels are known in the art and include enzyme labels, such as, glucose oxidase, and radioisotopes or other radioactive agent, such as iodine ($^{125}$I, $^{121}$I, $^{131}$I), carbon ($^{14}$C), sulfur ($^{35}$S), tritium ($^{3}$H), indium ($^{112}$In), and technetium ($^{99}$mTc), and fluorescent labels, such as fluorescein, rhodamine, and green fluorescent protein (GFP), as well as biotin.

In addition to assaying immunoreactive CD19 protein levels in a biological sample, anti-CD19 antibodies of the present technology may be used for in vivo imaging of CD19. Antibodies useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-CD19 antibodies by labeling of nutrients for the relevant scFv clone.

An anti-CD19 antibody which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled anti-CD19 antibody will then accumulate at the location of cells which contain the specific target polypeptide. For example, labeled anti-CD19 antibodies of the present technology will accumulate within the subject in cells and tissues in which the CD19 protein has localized.

Thus, the present technology provides a diagnostic method of a medical condition, which involves: (a) assaying the expression of immunoreactive CD19 protein by measuring binding of an anti-CD19 antibody of the present technology in cells or body fluid of an individual; (b) comparing the amount of immunoreactive CD19 protein present in the sample with a standard reference, wherein an increase or decrease in immunoreactive CD19 protein levels compared to the standard is indicative of a medical condition.

Affinity Purification. The anti-CD19 antibodies of the present technology may be used to purify immunoreactive CD19 protein from a sample. In some embodiments, the antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody or polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support can also be applied for conjugation of a first support to a second support, where the first and second solid support can be the same or different.

Appropriate linkers, which can be cross-linking agents, for use for conjugating a polypeptide to a solid support include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl)propionic acid can be employed as a means for cleaving a polypeptide from a solid support. (Brown et al., *Mol. Divers, pp,* 4-12 (1995); Rothschild et al., *Nucl. Acids Res.,* 24:351-66 (1996); and U.S. Pat. No. 5,643,722). Other cross-linking reagents are well-known in the art. (See, e.g., Wong (1991), supra; and Hermanson (1996), supra).

An antibody or polypeptide can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g., to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoroacetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the polypeptide. Acid lability can also be changed. For example, trityl, monomethoxytrityl, dimethoxytrityl or trimethoxytrityl can be changed to the appropriate p-substituted, or more acid-labile tritylamine derivatives, of the polypeptide, i.e., trityl ether and tritylamine bonds can be made to the polypeptide. Accordingly, a polypeptide can be removed from a hydrophobic linker, e.g., by disrupting the hydrophobic attraction or by cleaving tritylether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest to a solid support. Using such linkers, a first solid support, e.g., a bead, can be selectively cleaved from a second solid support, without cleaving the polypeptide from the support; the polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize a polypeptide to the support. As desired, the linkage of the polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hy-droxy-aminomethane.

Noncovalent Binding Association. An antibody or poly-peptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, e.g., a polypeptide containing an attached trityl group or with a second solid support having hydrophobic character.

A solid support can also be provided with a member of a specific binding pair and, therefore, can be conjugated to a polypeptide or a second solid support containing a comple-mentary binding moiety. For example, a bead coated with avidin or with streptavidin can be bound to a polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either a polypeptide or a solid support and, conversely, avidin or other biotin binding moiety would be incorporated into the support or the polypeptide, respectively. Other specific bind-ing pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

A. Diagnostic Uses of Anti-CD19 Antibodies of the Present Technology

General. The anti-CD19 antibodies of the present tech-nology are useful in diagnostic methods. As such, the present technology provides methods using the antibodies in the diagnosis of CD19 activity in a subject. Anti-CD19 antibodies of the present technology may be selected such that they have any level of epitope binding specificity and very high binding affinity to a CD19 protein. In general, the higher the binding affinity of an antibody the more stringent wash conditions can be performed in an immunoassay to remove nonspecifically bound material without removing target polypeptide. Accordingly, anti-CD19 antibodies of the present technology useful in diagnostic assays usually have binding affinities of about $10^8$ $M^{-1}$, $10^9$ $M^{-1}$, $10^{10}$ $M^{-1}$, $10^{11}$ $M^{-1}$ or $10^{12}$ $M^{-1}$. Further, it is desirable that anti-CD19 antibodies used as diagnostic reagents have a sufficient kinetic on-rate to reach equilibrium under standard condi-tions in at least 12 h, at least five (5) h, or at least one (1) hour.

Anti-CD19 antibodies can be used to detect an immu-noreactive CD19 protein in a variety of standard assay formats. Such formats include immunoprecipitation, West-ern blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject. In certain embodiments, the subject is at an early stage of cancer. In one embodiment, the early stage of cancer is determined by the level or expression pattern of CD19 protein in a sample obtained from the subject. In certain embodiments, the sample is selected from the group consisting of urine, blood, serum, plasma, saliva, amniotic fluid, cerebrospinal fluid (CSF), and biopsied body tissue.

Immunometric or sandwich assays are one format for the diagnostic methods of the present technology. See U.S. Pat. Nos. 4,376,110, 4,486,530, 5,914,241, and 5,965,375. Such assays use one antibody, e.g., an anti-CD19 antibody or a population of anti-CD19 antibodies immobilized to a solid phase, and another anti-CD19 antibody or a population of anti-CD19 antibodies in solution. Typically, the solution anti-CD19 antibody or population of anti-CD19 antibodies is labeled. If an antibody population is used, the population can contain antibodies binding to different epitope specifici-ties within the target polypeptide. Accordingly, the same population can be used for both solid phase and solution antibody. If anti-CD19 monoclonal antibodies are used, first and second CD19 monoclonal antibodies having different binding specificities are used for the solid and solution phase. Solid phase (also referred to as "capture") and solution (also referred to as "detection") antibodies can be contacted with target antigen in either order or simultane-ously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting the CD19 protein with the anti-CD19 antibody, a sample is incubated for a period that usually varies from about 10 min to about 24 hr and is usually about 1 hr. A wash step is then performed to remove components of the sample not specifically bound to the anti-CD19 antibody being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the immunoreactive CD19 protein in samples being tested are then read by interpolation from the calibration curve (i.e., standard curve). Analyte can be measured either from the amount of labeled solution antibody bound at equilibrium or by kinetic measurements of bound labeled solution antibody at a series of time points before equilibrium is reached. The slope of such a curve is a measure of the concentration of the CD19 protein in a sample.

Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J.), and the like. Immobilization can be by absorption or by covalent attachment. Optionally, anti-CD19 antibodies can be joined to a linker molecule, such as biotin for attachment to a surface bound linker, such as avidin.

In some embodiments, the present disclosure provides an anti-CD19 antibody of the present technology conjugated to a diagnostic agent. The diagnostic agent may comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A diagnostic agent is a molecule which is administered conjugated to an antibody moiety, i.e., antibody or antibody fragment, or subfragment, and is useful in diagnosing or detecting a disease by locating the cells containing the antigen.

Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. In some embodiments, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates may be coupled to the antibodies of the present technology using standard chemistries. The chelate is normally linked to the antibody by a group which enables formation of a bond to the molecule with minimal loss of immunoreactivity and minimal aggregation and/or internal cross-linking. Other methods and reagents for conjugating chelates to antibodies are disclosed in U.S. Pat. No. 4,824,659. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MM, when used along with the CD19 antibodies of the present technology.

Macrocyclic chelates such as NOTA (1,4,7-triaza-cyclo-nonane-N,N,N"-triacetic acid), DOTA, and TETA (p-bromoacetamido-benzyl-tetraethylaminetetraacetic acid) are of use with a variety of metals and radiometals, such as radionuclides of gallium, yttrium and copper, respectively. Such metal-chelate complexes can be stabilized by tailoring the ring size to the metal of interest. Examples of other DOTA chelates include (i) DOTA-Phe-Lys(HSG)-D-Tyr-Lys(HSG)-NH$_2$; (ii) Ac-Lys(HSG)D-Tyr-Lys(HSG)-Lys (Tscg-Cys)-NH$_2$; (iii) DOTA-D-Asp-D-Lys(HSG)-D-Asp-D-Lys(HSG)-NH$_2$; (iv) DOTA-D-Glu-D-Lys(HSG)-D-Glu-D-Lys(HSG)-NH$_2$; (v) DOTA-D-Tyr-D-Lys(HSG)-D-Glu-D-Lys(HSG)-NH$_2$; (vi) DOTA-D-Ala-D-Lys(HSG)-D-Glu-D-Lys(HSG)-NH$_2$; (vii) DOTA-D-Phe-D-Lys(HSG)-D-Tyr-D-Lys(HSG)-NH$_2$; (viii) Ac-D-Phe-D-Lys(DOTA)-D-Tyr-D-Lys(DOTA)-NH$_2$; (ix) Ac-D-Phe-D-Lys(DTPA)-D-Tyr-D-Lys(DTPA)-NH$_2$; (x) Ac-D-Phe-D-Lys(Bz-DTPA)-D-Tyr-D-Lys(Bz-DTPA)-NH$_2$; (xi) Ac-D-Lys(HSG)-D-Tyr-D-Lys(HSG)-D-Lys(Tscg-Cys)-NH$_2$; (xii) DOTA-D-Phe-D-Lys(HSG)-D-Tyr-D-Lys(HSG)-D-Lys(Tscg-Cys)-NH$_2$; (xiii) (Tscg-Cys)-D-Phe-D-Lys(HSG)-D-Tyr-D-Lys(HSG)-D-Lys(DOTA)-NH$_2$; (xiv) Tscg-D-Cys-D-Glu-D-Lys (HSG)-D-Glu-D-Lys(HSG)-NH$_2$; (xv) (Tscg-Cys)-D-Glu-D-Lys(HSG)-D-Glu-D-Lys(HSG)-NH$_2$; (xvi) Ac-D-Cys-D-Lys(DOTA)-D-Tyr-D-Ala-D-Lys(DOTA)-D-Cys-NH$_2$; (xvii) Ac-D-Cys-D-Lys(DTPA)-D-Tyr-D-Lys(DTPA)-NH$_2$; (xviii) Ac-D-Lys(DTPA)-D-Tyr-D-Lys(DTPA)-D-Lys(Tscg-Cys)-NH$_2$; and (xix) Ac-D-Lys(DOTA)-D-Tyr-D-Lys (DOTA)-D-Lys(Tscg-Cys)-NH$_2$.

Other ring-type chelates such as macrocyclic polyethers, which are of interest for stably binding nuclides, such as $^{223}$Ra for RAIT are also contemplated.

B. Therapeutic Use of Anti-CD19 Antibodies of the Present Technology

The immunoglobulin-related compositions (e.g., antibodies or antigen binding fragments thereof) of the present technology are useful for the treatment of CD19-associated cancers and CD19-associated autoimmune diseases. Such treatment can be used in patients identified as having pathologically high levels of the CD19 (e.g., those diagnosed by the methods described herein) or in patients diagnosed with a disease known to be associated with such pathological levels. In one aspect, the present disclosure provides a method for treating a CD19-associated cancer or a CD19-associated autoimmune disease in a subject in need thereof, comprising administering to the subject an effective amount of an antibody (or antigen binding fragment thereof) of the present technology. Examples of cancers that can be treated by the antibodies of the present technology include, but are not limited to: acute myeloid leukemia, myelodysplastic syndrome, chronic Myeloid Leukemia, Chronic Lymphocytic Leukemia, Non-Hodgkin Lymphoma, multiple myeloma, Plasmacytoma, Monoclonal gammapathy of undetermined significance, Waldenstrom's macroglobulinemia (lymphoplasmacytic lymphoma), Heavy chain disease, primary amyloidosis, post-transplant lymphoproliferative disorder, Hodgkin lymphoma, MALT lymphoma, B cell Lymphoma, mantle cell lymphoma, (germinal center-like) diffuse large cell lymphoma, Burkitt's lymphoma, Bilineage leukemia, biphenotypic leukemia, Hairy cell leukemia, Precursor B acute lymphoblastic leukemia/lymphoma, Primary cutaneous follicle center lymphoma, follicular lymphoma, Marginal Zone B-cell Non-Hodgkins Lymphoma. Examples of autoimmune diseases that can be treated by the antibodies of the present technology include, but are not limited to: multiple sclerosis (MS), rheumatoid arthritis (RA), systemic lupus erythematosus, paraneoplastic syndromes, Pemphigus Vulgaris, type 2 diabetes, and graft-versus-host diseases.

The compositions of the present technology may be employed in conjunction with other therapeutic agents useful in the treatment of CD19-associated cancers. For example, the antibodies of the present technology may be separately, sequentially or simultaneously administered with at least one additional therapeutic agent-selected from the group consisting of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent. Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), bevacizumab, oxaliplatin, melphalan, etoposide, mechlorethamine, bleomycin, microtubule poisons, annonaceous acetogenins, or combinations thereof.

The compositions of the present technology may optionally be administered as a single bolus to a subject in need thereof. Alternatively, the dosing regimen may comprise multiple administrations performed at various times after the appearance of tumors.

Methods for treating autoimmune diseases may further comprise sequentially, separately, or simultaneously administering to the subject at least one additional therapy selected from among non-steroidal anti-inflammatory drugs (NSAIDs), glucocorticoids, disease-modifying antirheumatic drugs (DMARDs), anti-TNF biologics, abatacept, tocilizumab, anakinra, and rituximab. Examples of NSAIDs include (1) salicylic acid derivatives such as acetylsalicylic acid (aspirin), diflunisal and sulfasalazine; (2) para-aminophenol derivatives such as acetaminophen; (3) fenamates such as mefenamic acid, meclofenamate, flufenamic acid; (4) propionic acid derivatives such as ibuprofen, naproxen, fenoprofen, ketoprofen, flurbiprofen, oxaprozin; (5) enolic acid (oxicam) derivatives such as piroxicam, tenoxicam; (6) selective COX-2 inhibitors such as meloxicam, salicylate, and nimesulide; and (7) highly selective COX-2 inhibitors such as celecoxib, rofecoxib, valdecoxib, lumiracoxib, parecoxib, and etoricoxib. Examples of glucocorticoids include prednisone/prednisolone, methylprednisolone, and fluorinated glucocorticoids such as dexamethasone and betamethasone. Examples of DMARDs include methotrexate, leflunomide, gold compounds, sulfasalazine, azathioprine, cyclophosphamide, antimalarials, D-penicillamine, cyclosporine, hydroxychloroquine, and chloroquine. Examples of anti-TNF biologics include infliximab, etanercept, adalimumab, golimumab, and certolizumab pegol.

Administration can be carried out by any suitable route, including orally, intranasally, parenterally (intravenously, intramuscularly, intraperitoneally, or subcutaneously), rectally, intracranially, intratumorally, intrathecally, or topically. Administration includes self-administration and the administration by another. It is also to be appreciated that the various modes of treatment of medical conditions as described are intended to mean "substantial", which includes total but also less than total treatment, and wherein some biologically or medically relevant result is achieved.

In some embodiments, the antibodies of the present technology comprise pharmaceutical formulations which may be administered to subjects in need thereof in one or more doses. Dosage regimens can be adjusted to provide the desired response (e.g., a therapeutic response).

Typically, an effective amount of the antibody compositions of the present technology, sufficient for achieving a therapeutic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For administration of anti-CD19 antibodies, the dosage ranges from about 0.0001 to 100 mg/kg, and more usually 0.01 to 5 mg/kg every week, every two weeks or every three weeks, of the subject body weight. For example, dosages can be 1 mg/kg body weight or 10 mg/kg body weight every week, every two weeks or every three weeks or within the range of 1-10 mg/kg every week, every two weeks or every three weeks. In one embodiment, a single dosage of antibody ranges from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Anti-CD19 antibodies may be administered on multiple occasions. Intervals between single dosages can be hourly, daily, weekly, monthly or yearly. Intervals can also be irregular as indicated by measuring blood levels of the antibody in the subject. In some methods, dosage is adjusted to achieve a serum antibody concentration in the subject of from about 75 µg/mL to about 125 µg/mL, 100 µg/mL to about 150 µg/mL, from about 125 µg/mL to about 175 µg/mL, or from about 150 µg/mL to about 200 µg/mL. Alternatively, anti-CD19 antibodies can be administered as a sustained release formulation, in which case less frequent administration is required. Dosage and frequency vary depending on the half-life of the antibody in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In another aspect, the present disclosure provides a method for detecting a tumor in a subject in vivo comprising (a) administering to the subject an effective amount of an antibody (or antigen binding fragment thereof) of the present technology, wherein the antibody is configured to localize to a tumor expressing CD19 and is labeled with a radioisotope; and (b) detecting the presence of a tumor in the subject by detecting radioactive levels emitted by the antibody that are higher than a reference value. In some embodiments, the reference value is expressed as injected dose per gram (% ID/g). The reference value may be calculated by measuring the radioactive levels present in non-tumor (normal) tissues, and computing the average radioactive levels present in non-tumor (normal) tissues ±standard deviation. In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In some embodiments, the subject is diagnosed with or is suspected of having cancer. Radioactive levels emitted by the antibody may be detected using positron emission tomography or single photon emission computed tomography.

Additionally or alternatively, in some embodiments, the method further comprises administering to the subject an effective amount of an immunoconjugate comprising an antibody of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}$Y, $^{90}$Y, $^{89}$Sr, $^{165}$Dy, $^{186}$Re, $^{188}$Re, $^{177}$Lu, and $^{67}$Cu. Examples of alpha particle-emitting isotopes includes $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, and $^{255}$Fm. Examples of Auger-emitters include $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, and $^{203}$Pb. In some embodiments of the method, nonspecific FcR-dependent binding in normal tissues is eliminated or reduced (e.g., via N297A mutation in Fc region, which results in aglycosylation). The therapeutic effectiveness of such an immunoconjugate may be determined by computing the area under the curve (AUC) tumor: AUC normal tissue ratio. In some embodiments, the immunoconjugate has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

PRIT. In one aspect, the present disclosure provides a method for detecting tumors in a subject in need thereof comprising (a) administering to the subject an effective amount of a complex comprising a radiolabeled DOTA hapten and a bispecific antibody of the present technology that binds to the radiolabeled DOTA hapten and a CD19 antigen, wherein the complex is configured to localize to a tumor expressing the CD19 antigen recognized by the bispecific antibody of the complex; and (b) detecting the presence of solid tumors in the subject by detecting radioactive levels emitted by the complex that are higher than a reference value. In some embodiments, the subject is human.

In another aspect, the present disclosure provides a method for selecting a subject for pretargeted radioimmunotherapy comprising (a) administering to the subject an effective amount of a complex comprising a radiolabeled DOTA hapten and a bispecific antibody of the present technology that binds to the radiolabeled DOTA hapten and a CD19 antigen, wherein the complex is configured to localize to a tumor expressing the CD19 antigen recognized by the bispecific antibody of the complex; (b) detecting radioactive levels emitted by the complex; and (c) selecting the subject for pretargeted radioimmunotherapy when the radioactive levels emitted by the complex are higher than a reference value. In some embodiments, the subject is human.

Examples of DOTA haptens include (i) DOTA-Phe-Lys(HSG)-D-Tyr-Lys(HSG)-NH2; (ii) Ac-Lys(HSG)D-Tyr-Lys(HSG)-Lys(Tscg-Cys)-NH$_2$; (iii) DOTA-D-Asp-D-Lys(HSG)-D-Asp-D-Lys(HSG)-NH$_2$; (iv) DOTA-D-Glu-D-Lys (HSG)-D-Glu-D-Lys(HSG)-NH$_2$; (v) DOTA-D-Tyr-D-Lys(HSG)-D-Glu-D-Lys(HSG)-NH$_2$; (vi) DOTA-D-Ala-D-Lys(HSG)-D-Glu-D-Lys(HSG)-NH$_2$; (vii) DOTA-D-Phe-D-Lys(HSG)-D-Tyr-D-Lys(HSG)-NH$_2$; (viii) Ac-D-Phe-D-Lys(DOTA)-D-Tyr-D-Lys(DOTA)-NH$_2$; (ix) Ac-D-Phe-D-Lys(DTPA)-D-Tyr-D-Lys(DTPA)-NH$_2$; (x) Ac-D-Phe-D-Lys(Bz-DTPA)-D-Tyr-D-Lys(Bz-DTPA)-NH$_2$; (xi) Ac-D-Lys(HSG)-D-Tyr-D-Lys(HSG)-D-Lys(Tscg-Cys)-NH$_2$; (xii) DOTA-D-Phe-D-Lys(HSG)-D-Tyr-D-Lys(HSG)-D-Lys (Tscg-Cys)-NH$_2$; (xiii) (Tscg-Cys)-D-Phe-D-Lys(HSG)-D-Tyr-D-Lys(HSG)-D-Lys(DOTA)-NH$_2$; (xiv) Tscg-D-Cys-D-Glu-D-Lys(HSG)-D-Glu-D-Lys(HSG)-NH$_2$; (xv) (Tscg-Cys)-D-Glu-D-Lys(HSG)-D-Glu-D-Lys(HSG)-NH$_2$; (xvi) Ac-D-Cys-D-Lys(DOTA)-D-Tyr-D-Ala-D-Lys(DOTA)-D-Cys-NH$_2$; (xvii) Ac-D-Cys-D-Lys(DTPA)-D-Tyr-D-Lys (DTPA)-NH$_2$; (xviii) Ac-D-Lys(DTPA)-D-Tyr-D-Lys (DTPA)-D-Lys(Tscg-Cys)-NH$_2$; (xix) Ac-D-Lys(DOTA)-D-Tyr-D-Lys(DOTA)-D-Lys(Tscg-Cys)-NH$_2$ and (xx) DOTA. The radiolabel may be an alpha particle-emitting isotope, a beta particle-emitting isotope, or an Auger-emitter. Examples of radiolabels include $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu.

In some embodiments of the methods disclosed herein, the radioactive levels emitted by the complex are detected using positron emission tomography or single photon emission computed tomography. Additionally or alternatively, in some embodiments of the methods disclosed herein, the subject is diagnosed with, or is suspected of having a CD19 associated cancer such as acute myeloid leukemia, myelodysplastic syndrome, chronic Myeloid Leukemia, Chronic Lymphocytic Leukemia, Non-Hodgkin Lymphoma, multiple myeloma, Plasmacytoma, Monoclonal gammopathy of undetermined significance, Waldenstrom's macroglobulinemia (lymphoplasmacytic lymphoma), Heavy chain disease, primary amyloidosis, Post-transplant lymphoproliferative disorder, Hodgkin lymphoma, MALT lymphoma, B cell Lymphoma, mantle cell lymphoma, (germinal center-like) diffuse large cell lymphoma, Burkitt's lymphoma, Bilineage leukemia, biphenotypic leukemia, Hairy cell leukemia, Precursor B acute lymphoblastic leukemia/lymphoma, Primary cutaneous follicle center lymphoma, follicular lymphoma, Marginal Zone B-cell Non-Hodgkins Lymphoma. Additionally or alternatively, in some embodiments of the methods disclosed herein, the subject is diagnosed with, or is suspected of having an autoimmune disease such as multiple sclerosis (MS), rheumatoid arthritis (RA), systemic lupus erythematosus, paraneoplastic syndromes, Pemphigus Vulgaris, type 2 diabetes, or graft-versus-host diseases.

Additionally or alternatively, in some embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally, intratumorally, or intranasally. In certain embodiments, the complex is administered into the cerebral spinal fluid or blood of the subject.

In some embodiments of the methods disclosed herein, the radioactive levels emitted by the complex are detected between 2 to 120 hours after the complex is administered. In certain embodiments of the methods disclosed herein, the radioactive levels emitted by the complex are expressed as the percentage injected dose per gram tissue (% ID/g). The reference value may be calculated by measuring the radioactive levels present in non-tumor (normal) tissues, and computing the average radioactive levels present in non-tumor (normal) tissues±standard deviation. In some embodiments, the reference value is the standard uptake value (SUV). See Thie J A, *J Nucl Med.* 45(9):1431-4 (2004). In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with a CD19-associated cancer comprising (a) administering an effective amount of an anti-DOTA bispecific antibody of the present technology to the subject, wherein the anti-DOTA bispecific antibody is configured to localize to a tumor expressing a CD19 antigen target; and (b) administering an effective amount of a radiolabeled-DOTA hapten to the subject, wherein the radiolabeled-DOTA hapten is configured to bind to the anti-DOTA bispecific antibody. In some embodiments, the subject is human.

The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the radiolabeled-DOTA hapten is administered after a time period that may be sufficient to permit clearance of unbound anti-DOTA bispecific antibody.

The radiolabeled-DOTA hapten may be administered at any time between 1 minute to 4 or more days following administration of the anti-DOTA bispecific antibody. For example, in some embodiments, the radiolabeled-DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the radiolabeled-DOTA hapten may be administered at any time after 4 or more days following administration of the anti-DOTA bispecific antibody.

Additionally or alternatively, in some embodiments, the method further comprises administering an effective amount of a clearing agent to the subject prior to administration of the radiolabeled-DOTA hapten. A clearing agent can be any molecule (dextran or dendrimer or polymer) that can be conjugated with C825-hapten. In some embodiments, the clearing agent is no more than 2000 kD, 1500 kD, 1000 kD, 900 kD, 800 kD, 700 kD, 600 kD, 500 kD, 400 kD, 300 kD, 200 kD, 100 kD, 90 kD, 80 kD, 70 kD, 60 kD, 50 kD, 40 kD, 30 kD, 20 kD, 10 kD, or 5 kD. In some embodiments, the clearing agent is a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.).

In some embodiments, the clearing agent and the radiolabeled-DOTA hapten are administered without further administration of the anti-DOTA bispecific antibody of the present technology. For example, in some embodiments, an anti-DOTA bispecific antibody of the present technology is administered according to a regimen that includes at least one cycle of: (i) administration of the anti-DOTA bispecific antibody of the present technology (optionally so that relevant tumor cells are saturated); (ii) administration of a radiolabeled-DOTA hapten and, optionally a clearing agent; (iii) optional additional administration of the radiolabeled-DOTA hapten and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Additionally or alternatively, in some embodiments of the method, the anti-DOTA bispecific antibody and/or the radiolabeled-DOTA hapten is administered intravenously, intramuscularly, intraarterially, intrathecally, intracapsularly, intraorbitally, intradermally, intraperitoneally, transtracheally, subcutaneously, intracerebroventricularly, intratumorally, orally or intranasally.

In one aspect, the present disclosure provides a method for increasing tumor sensitivity to radiation therapy in a subject diagnosed with a CD19-associated cancer comprising administering to the subject an effective amount of a complex comprising a radiolabeled-DOTA hapten and a bispecific antibody of the present technology that recognizes and binds to the radiolabeled-DOTA hapten and a CD19 antigen target, wherein the complex is configured to localize to a tumor expressing the CD19 antigen target recognized by the bispecific antibody of the complex. The complex may be administered intravenously, intramuscularly, intraarterially, intrathecally, intracapsularly, intraorbitally, intradermally, intraperitoneally, transtracheally, subcutaneously, intracerebroventricularly, orally, intratumorally, or intranasally. In some embodiments, the subject is human.

In another aspect, the present disclosure provides a method for treating cancer in a subject in need thereof comprising (a) administering an effective amount of an anti-DOTA bispecific antibody of the present technology to the subject, wherein the anti-DOTA bispecific antibody is configured to localize to a tumor expressing a CD19 antigen target; and (b) administering an effective amount of a radiolabeled-DOTA hapten to the subject, wherein the radiolabeled-DOTA hapten is configured to bind to the anti-DOTA bispecific antibody. The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the radiolabeled-DOTA hapten is administered after a time period that may be sufficient to permit clearance of unbound anti-DOTA bispecific antibody. In some embodiments, the subject is human.

Accordingly, in some embodiments, the method further comprises administering an effective amount of a clearing agent to the subject prior to administration of the radiolabeled-DOTA hapten. The radiolabeled-DOTA hapten may be administered at any time between 1 minute to 4 or more days following administration of the anti-DOTA bispecific antibody. For example, in some embodiments, the radiolabeled-DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the radiolabeled-DOTA hapten may be administered at any time after 4 or more days following administration of the anti-DOTA bispecific antibody.

The clearing agent may be a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.). In some embodiments, the clearing agent and the radiolabeled-DOTA hapten are administered without further administration of the anti-DOTA bispecific antibody. For example, in some embodiments, an anti-DOTA bispecific antibody is administered according to a regimen that includes at least one cycle of: (i) administration of the an anti-DOTA bispecific antibody of the present technology (optionally so that relevant tumor cells are saturated); (ii) administration of a radiolabeled-DOTA hapten and, optionally a clearing agent; (iii) optional additional administration of the radiolabeled-DOTA hapten and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Also provided herein are methods for treating cancer in a subject in need thereof comprising administering to the subject an effective amount of a complex comprising a radiolabeled-DOTA hapten and a bispecific antibody of the present technology that recognizes and binds to the radio-labeled-DOTA hapten and a CD19 antigen target, wherein the complex is configured to localize to a tumor expressing the CD19 antigen target recognized by the bispecific antibody of the complex. The therapeutic effectiveness of such a complex may be determined by computing the area under the curve (AUC) tumor: AUC normal tissue ratio. In some embodiments, the complex has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Toxicity. Optimally, an effective amount (e.g., dose) of an anti-CD19 antibody described herein will provide therapeutic benefit without causing substantial toxicity to the subject. Toxicity of the anti-CD19 antibody described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the anti-CD19 antibody described herein lies within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

Formulations of Pharmaceutical Compositions. According to the methods of the present technology, the anti-CD19 antibody can be incorporated into pharmaceutical compositions suitable for administration. The pharmaceutical compositions generally comprise recombinant or substantially purified antibody and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, PA 18$^{th}$ ed 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the composition are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the anti-CD19 antibody, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. An anti-CD19 antibody named in this technology can be present in unsalified or unesterified form, or in salified and/or esterified form, and the naming of such anti-CD19 antibody is intended to include both the original (unsalified and unesterified) compound and its pharmaceutically-acceptable salts and esters. Also, certain embodiments of the present technology can be present in more than one stereoisomeric form, and the naming of such anti-CD19 antibody is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present technology.

Examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the anti-CD19 antibody, use thereof in the compositions is contemplated. Supplementary active compounds can also be incorporated into the compositions.

A pharmaceutical composition of the present technology is formulated to be compatible with its intended route of administration. The anti-CD19 antibody compositions of the present technology can be administered by parenteral, topical, intravenous, oral, subcutaneous, intraarterial, intradermal, transdermal, rectal, intracranial, intrathecal, intraperitoneal, intranasal; or intramuscular routes, or as inhalants. The anti-CD19 antibody can optionally be administered in combination with other agents that are at least partly effective in treating various CD19-associated cancers or CD19-associated autoimmune diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be desirable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating an anti-CD19 antibody of the present technology in the required amount in an appropriate solvent with one or a combination of ingredients enumerated above, as required, followed by filtered sterilization. Generally, dispersions are prepared by incorporating the anti-CD19 antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The antibodies of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the anti-CD19 antibody can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the anti-CD19 antibody is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the anti-CD19 antibody is formulated into ointments, salves, gels, or creams as generally known in the art.

The anti-CD19 antibody can also be prepared as pharmaceutical compositions in the form of suppositories (e.g., with conventional suppository bases such as cocoa butter and other glycerides) or retention enemas for rectal delivery.

In one embodiment, the anti-CD19 antibody is prepared with carriers that will protect the anti-CD19 antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

C. Kits

The present technology provides kits for the detection and/or treatment of CD19-associated cancers or CD19-associated autoimmune diseases, comprising at least one immunoglobulin-related composition of the present technology (e.g., any antibody or antigen binding fragment described herein), or a functional variant (e.g., substitutional variant) thereof. Optionally, the above described components of the kits of the present technology are packed in suitable containers and labeled for diagnosis and/or treatment of CD19-associated cancers or CD19-associated autoimmune diseases. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits are useful for detecting the presence of an immunoreactive CD19 protein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more humanized, chimeric, or bispecific anti-CD19 antibodies of the present technology (or antigen binding fragments thereof) capable of binding a CD19 protein in a biological sample; means for determining the amount of the CD19 protein in the sample; and means for comparing the amount of the immunoreactive CD19 protein in the sample with a standard. One or more of the anti-CD19 antibodies may be labeled. The kit components, (e.g., reagents) can be packaged in a suitable container. The kit can further comprise instructions for using the kit to detect the immunoreactive CD19 protein.

For antibody-based kits, the kit can comprise, e.g., 1) a first antibody, e.g. a humanized, chimeric or bispecific CD19 antibody of the present technology (or an antigen binding fragment thereof), attached to a solid support, which binds to a CD19 protein; and, optionally; 2) a second, different antibody which binds to either the CD19 protein or to the first antibody, and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a CD19 protein in vitro or in vivo, or for treatment of CD19-associated cancers or CD19-associated autoimmune diseases in a subject in need thereof. In certain embodiments, the use of the reagents can be according to the methods of the present technology.

EXAMPLES

The present technology is further illustrated by the following Examples, which should not be construed as limiting in any way. The following Examples demonstrate the preparation, characterization, and use of illustrative anti-CD19 antibodies of the present technology. The following Examples demonstrate the production of chimeric, humanized, and bispecific antibodies of the present technology, and characterization of their binding specificities and in vitro and in vivo biological activities.

Example 1: Sequences and Construction of CD19-CD3 Bispecific Antibodies

CD19-CD3 BsAbs were designed using the IgG-scFv modular platform shown in FIG. 1. An anti-CD3 humanized OKT3 (huOKT3) single chain Fv fragment (scFv) was genetically fused to the carboxyl end of the light chain of FMC63 IgG1. Humanized versions of the murine FMC63 antibody were generated. Sequence elements were joined using various linkers, spacers, and the like. The sequences disclosed herein show some examples of modular sequence elements, linkers, spacers, and the like. For example, CD19-BsAbs were constructed by fusing the humanized OKT3 scFv onto the C-terminus of the light chain of the chimeric or humanized anti-CD19 antibody via a $(G_4S)_3$ linker (SEQ ID NO: 86) as previously described in Xu H et al., *Cancer Immunology Research* 3:266-277 (2015) and Lopez-Albaitero A et al., *OncoImmunology* 6:e1267891 (2017). N297A and K322A mutations were introduced in the Fc region of the antibody to eliminate FcR and complement binding activities, respectively (Shields R L et al., *Journal of Biological Chemistry* 276:6591-6604 (2001); Idusogie E E et al., *Journal of Immunology* 164:4178-4184 (2000)). When selecting the antibody, the scFv fragment and exact mechanics of joining them together, the following factors were given consideration, among various other factors:

(1) an optimal size (100-200 kd) to maximize tumor uptake. See e.g., Wittrup K D, Thurber G M, Schmidt M M, et al., *Methods Enzymol* 503:255-68 (2012);

(2) bivalency towards the tumor target to maintain avidity; (3) a scaffold that is naturally assembled like any IgG (heavy chain and light chain) in CHO cells, purifiable by standard protein A affinity chromatography;

(4) structural arrangement to render the anti-CD3 component functionally monovalent, hence reducing nonspecific activation of T cells; and (5) a platform with proven tumor targeting efficiency in animal models.

Humanization of murine FMC63. The CDRs of the heavy and light chains of FMC63 were grafted onto human IgG1 frameworks based on their homology with human frameworks IGHV4-4*08-IGHJ4*01 for $V_H$, and IGKV1-33*01-IGKJ2*01 for $V_L$, respectively. From eight heavy chain and three light chain designs, twenty-four versions of huFMC63 genes were synthesized and expressed in DG44 cells. The amino acid sequences of the murine, chimeric, and humanized FMC63 variable heavy chains are shown in FIG. 12 and FIGS. 14C-14D. The amino acid sequences of the murine, chimeric, and humanized FMC63 variable light chains are shown in FIG. 13 and FIGS. 14A-14B.

Example 2: Design of CD19-Specific BsAbs

Generation of CD19-BsAbs. CD19-BsAbs were designed as follows: The light chain polypeptide of the BsAb comprises, sequentially from the N-terminus to C-terminus: (1) a signal peptide; (2) $V_L$ domain of murine anti-CD19 antibody (FMC63) (or a humanized version thereof); (3) human $C_L$ domain; (4) $(G4S)_3$ linker (SEQ ID NO: 86) (5) $V_H$ domain of the humanized anti-CD3 antibody OKT3; (6) $(G4S)_6$ linker (SEQ ID NO: 83); and (7) $V_L$ domain of OKT3. The the heavy chain polypeptide of the BsAb comprises, sequentially from the N-terminus to C-terminus: (1) signal peptide; (2) $V_H$ domain of murine FMC63 (or a humanized version thereof); and (3) human $CH_{1-3}$ domains. See, e.g., FIGS. 14A-D and FIGS. 15A-15B.

Additional anti-CD19 BsAbs for pretargeted radioimmunotherapy. Two additional categories of CD19 BsAbs include: (a) IgG(L)-scFv platform for 3-step pretargeted radioimmunotherapy (PRIT) (PCT/US2018/040911); and (b) the multimeric antibody platform for two-step targeting (SADA) (PCT/US2018/031235). Both platforms are versatile options even for endocytosing antigens such as HER2. See, e.g., Cheal S M, Xu H, Guo H F, et al., *Eur J Nucl Med Mol Imaging* 43:925-37 (2016), and can be used with different radionuclides such as the alpha emitter lanthanides (PCT/2018/0409011). Exemplary amino acid sequences of CD19-specific DOTA-engaging bispecific antibodies or antigen binding fragments are shown in FIGS. 16A-16B through FIGS. 31A-31B.

Example 3: Expression and Characterization of CD19-CD3-specific BsAbs

DNA constructs encoding both the heavy chain and light chain of the CD19-CD3 BsAbs were inserted into a mammalian expression vector, transfected into CHO-S cells, and stable clones showing the highest levels of antibody production were selected. Selected stable clones were expanded in shaker flasks. The bispecific antibodies were purified from supernatants collected from the shaker flasks using one-step protein A affinity chromatography.

Figure 1B:
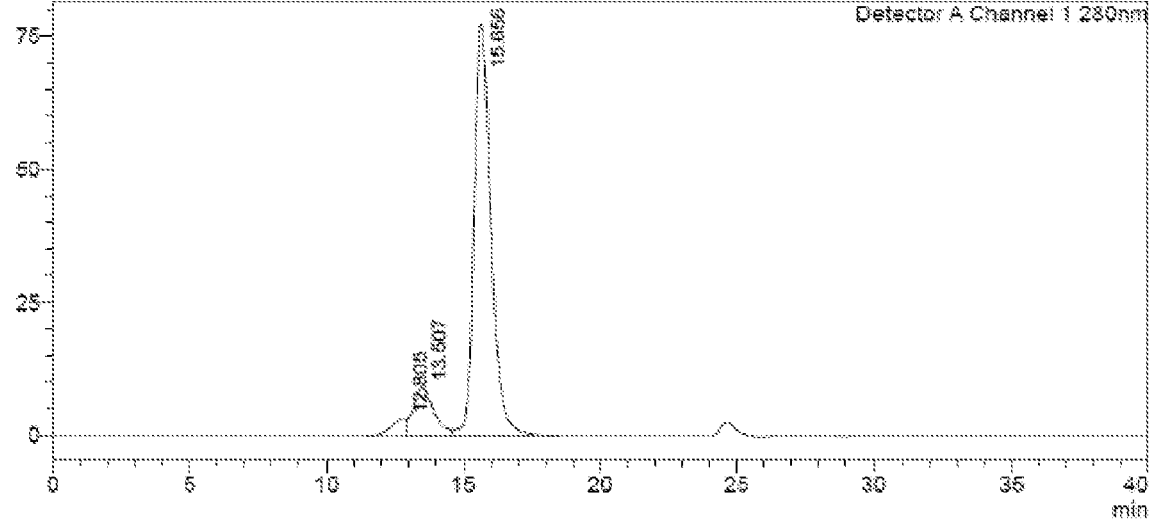
FIG. 1B is a chromatogram generated using size-exclusion chromatography-high-performance liquid chromatography (SEC-HPLC), showing purity of BC250, a CD19-BsAb of the present technology. CD19-BsAb was passed through a size-exclusion column and protein in the eluent was detected based on absorbance of ultraviolet light having wavelength 280 nm. Fractions were analyzed using sodium dodecyl sulfate—polyacrylamide gel electrophoresis (SDS-PAGE), which showed that the CD19-BsAb was eluted in peak 3 at 15.656 minutes of the chromatogram.

Purity of CD19-CD3 BsAbs. Purity of the CD19-CD3 IgG-scFv bispecific antibodies was assayed using size-exclusion chromatography-high-performance liquid chromatography (SEC-HPLC). Protein in the eluent was detected based on absorbance of ultraviolet light having a wavelength 280 nm. FIG. 1B shows SEC-HPLC profile of a purified CD19-CD3 bispecific antibody. Fractions from SEC-HPLC were analyzed using sodium dodecyl sulfate— polyacrylamide gel electrophoresis (SDS-PAGE). As shown in FIG. 1B, the CD19-BsAb was eluted in peak 3 at 15.656 minutes of the chromatogram.

Figure 2:
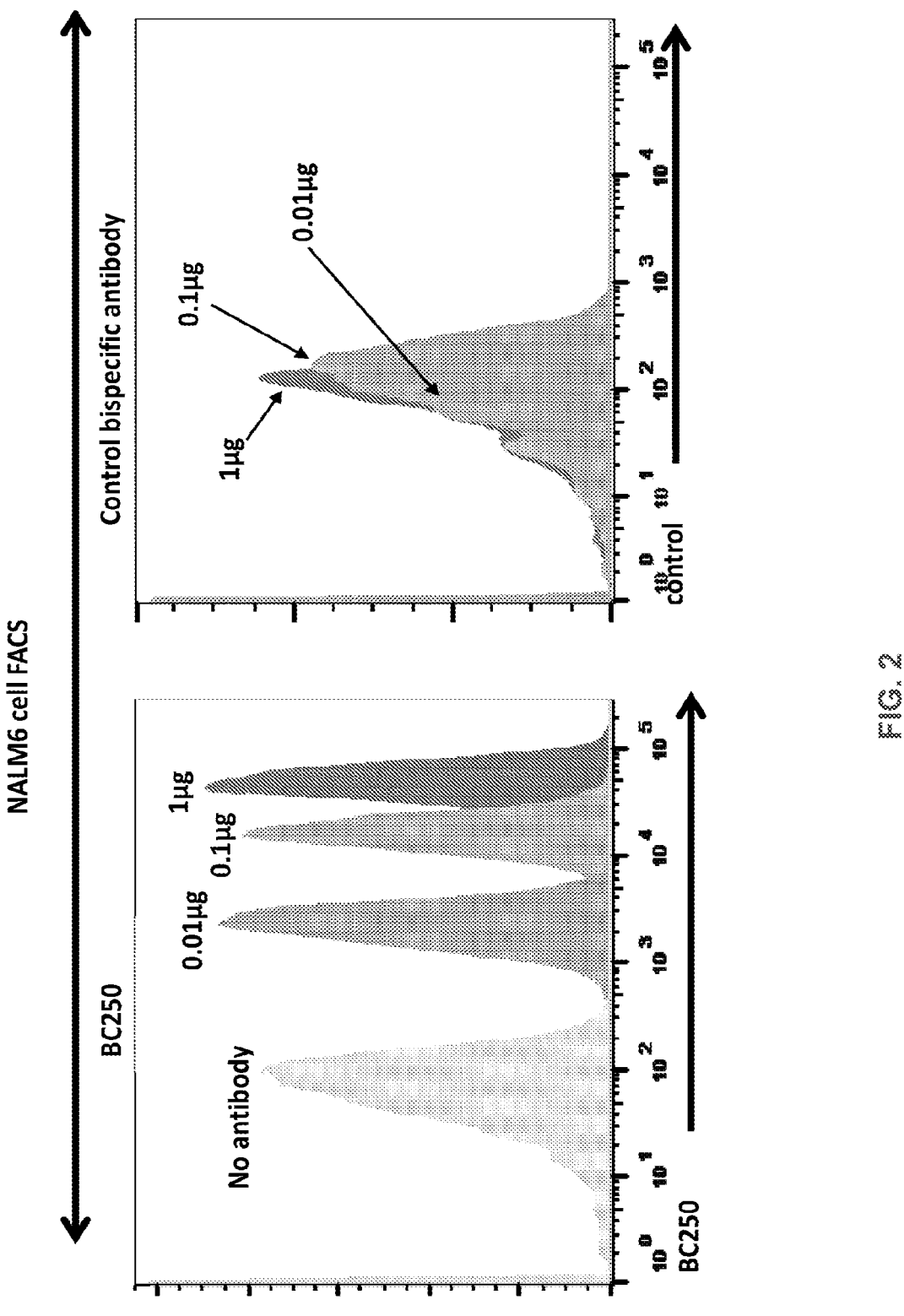
FIG. 2 shows flow cytometry profiles demonstrating binding of the CD19-BsAb BC250 to the CD19(+) acute lymphoid leukemia (ALL) cell line NALM6. Indicated amounts of the CD19-BsAb BC250 or a control BsAb were used for immunostaining. Binding of the antibodies to NALM6 cells was detected using flow cytometry. Increasing concentrations of the control BsAb did not lead to an increase in fluorescence, whereas increasing concentrations of the CD19-BsAb BC250 led to a proportional increase in fluorescence, demonstrating binding of the CD19-BsAb BC250 to the NALM6 cells.

Binding of CD19-CD3 bispecific antibody to CD19(+) cells. The binding of CD19-CD3 bispecific antibodies to the CD19(+) acute lymphoid leukemia (ALL) cell line NALM6 was assayed using flow cytometry. An unrelated bispecific antibody that binds to globo-H was used as a negative control. NALM6 cells were incubated with the indicated amounts of the CD19-BsAb BC250 or the control BsAb, followed by incubation with a fluorochrome labelled anti-human secondary antibody. Binding was detected using flow cytometry. As shown in FIG. 2, increasing concentrations of the control BsAb did not lead to an increase in fluorescence compared to the no antibody control. In contrast, increasing concentrations of the CD19-BsAb BC250 from 0.01 to 0.1 to 0.1 μg led to a proportional increase in fluorescence, demonstrating binding of the CD19-BsAb BC250 to the NALM6 cells. See FIG. 2.

Accordingly, these results demonstrate that the antibodies or antigen binding fragments of the present technology are useful in methods for detecting CD19 polypeptides in a biological sample.

Affinity of CD19 antibodies can be modulated by changing the sequence of antibody framework regions without altering the CDR sequences. Eight humanized $V_H$ and three humanized $V_L$ sequences based on the murine FMC63 antibody were developed. The humanized $V_H$ and $V_L$ sequences have CDR sequences that are identical to those of murine FMC63, but differ from each other with respect to certain amino acid residues within the $V_H$ or $V_L$ framework regions. See FIGS. 12-13.

Figure 4:
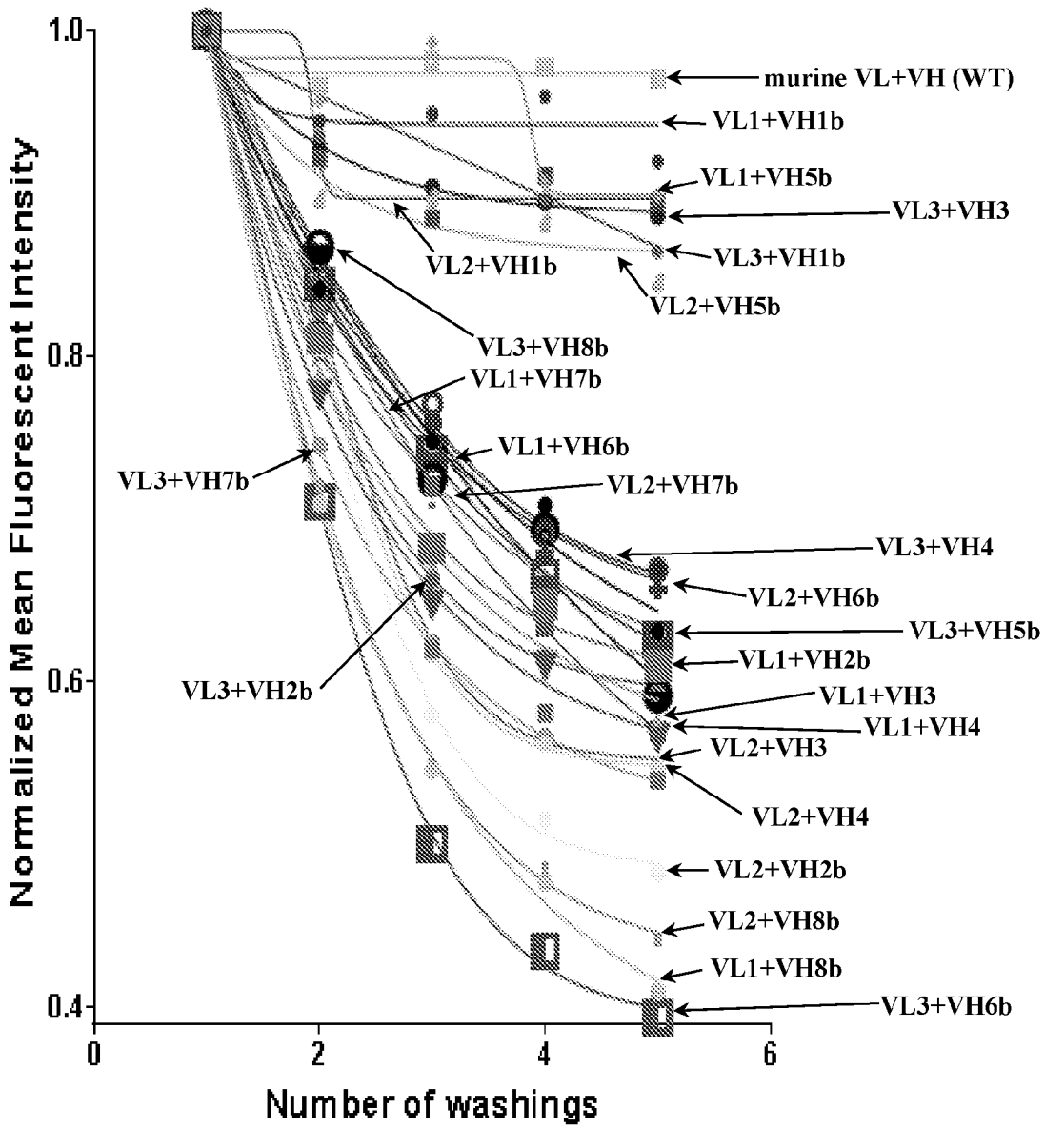
FIG. 4 shows the alteration of the binding affinity of the CD19 antibodies of the present technology by varying the amino acids of the $V_L$ and/or $V_H$ framework regions of the antibody, without manipulating the amino acid sequence of the complementarity-determining regions (CDRs). Eight humanized $V_H$ and three humanized $V_L$ sequences based on the murine FMC63 antibody were developed (See FIGS. 12-13, infra). The humanized $V_H$ and $V_L$ sequences were paired with each other to generate twenty-four distinct humanized versions of the murine FMC63 antibody. To assess their affinity to CD19, a single dose of each of the antibodies was used to stain NALM6 ALL cells (CD19 positive). The cells were washed five times after staining. An aliquot of cells was removed after each wash and incubated with a fluorochrome labelled anti-human secondary antibody. The binding of the CD19 antibody to NALM6 cells was detected using flow cytometry.
Figure 33A:
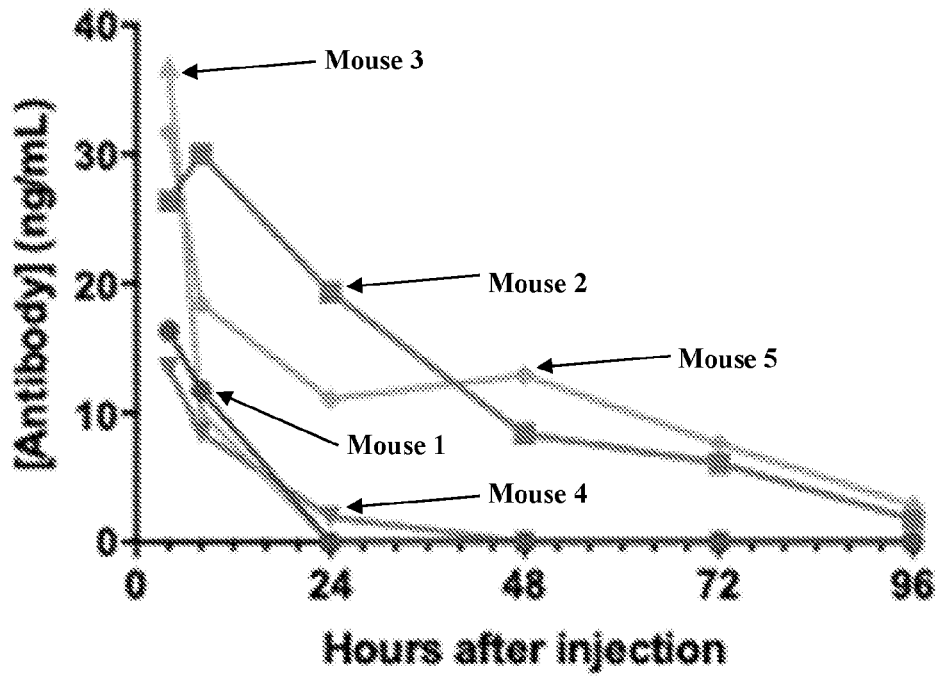
FIG. 33A shows the pharmacokinetic properties of BC250 in individual animals (n=5).
Figure 33B:
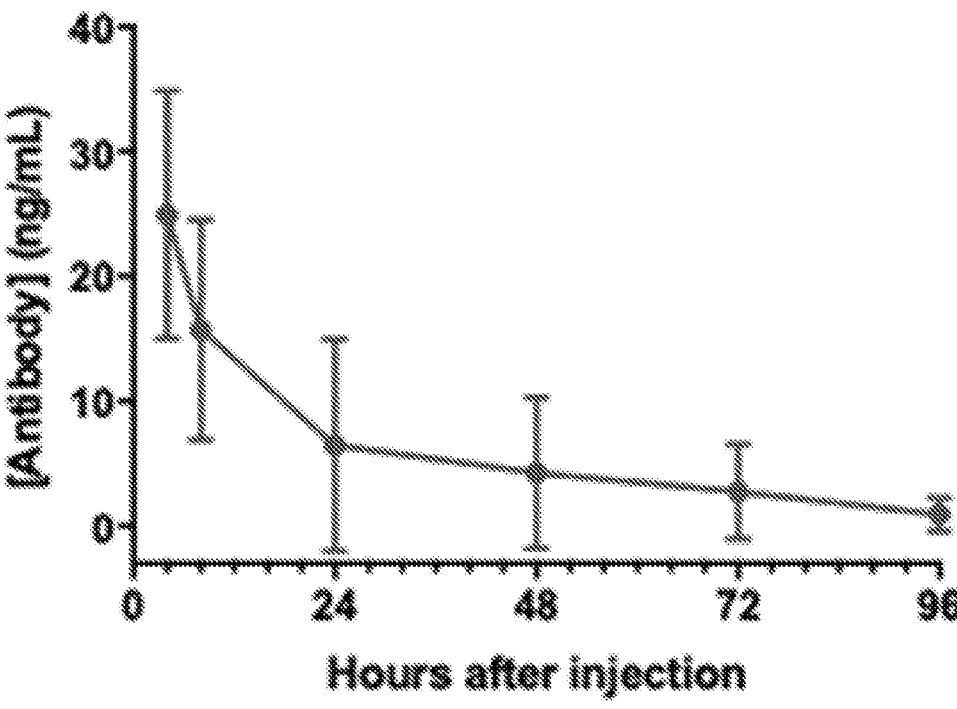
FIG. 33B shows the average pharmacokinetic activity of BC250 for the animals displayed in FIG. 33A. The pharmacokinetics of BC250 was determined by injection of the antibody to mice and bleeding the mice starting from 4 hours after injection up to 96 hours. An ELISA assay was used to determine the level of BC250 in blood.

The humanized $V_H$ and $V_L$ sequences were paired with each other to generate twenty-four humanized versions of CD19-CD3 IgG-scFv bispecific antibody. The affinity of the twenty-four humanized CD19-CD3 BsAbs towards CD19 was assayed using flow cytometry. CD19-CD3 IgG-scFv bispecific antibody comprising the $V_H$ and $V_L$ domains of murine FMC63 antibody was used as a positive antibody control. The CD19-CD3 IgG-scFv bispecific antibodies were incubated with NALM6 cells (CD19 positive). The cells were washed five times upon binding. Aliquots of cells were removed after each wash and stained with a fluorochrome labelled anti-human secondary antibody. The binding of the CD19 antibody to NALM6 cells was detected using flow cytometry and normalized fluorescent intensity was calculated. As shown in FIG. 4, there was a spectrum of affinities from low to high for the various humanized CD19-CD3 IgG-scFv bispecific antibody clones. These data demonstrate that affinity of the humanized CD19 antibodies of the present technology can be modulated by changing the sequence of the antibody framework regions, without altering the CDR sequences. FIG. 32 shows the stability data, EC50 data, and MFI data against several cell lines for each of the CD19-CD3 IgG-scFv bispecific antibody clones. FIGS. 33A-33B depict the pharmacokinetic properties of the BC250 BsAb of the present technology.

These results demonstrate that the antibodies or antigen binding fragments of the present technology are useful in methods for detecting CD19 polypeptides in a biological sample.

Example 4: Cytotoxicity of CD19-CD3 IgG-scFv BsAbs to CD19 Target Cells

Cytotoxicity of the bispecific CD19-CD3 IgG-scFv antibody BC250. To evaluate whether CD19-CD3 BsAbs were cytotoxic, T cell cytotoxicity on CD19(+) ALL cells was tested using standard 4-hour $^{51}$Cr release assays. An unrelated bispecific antibody that binds to globo-H was used as a negative control.

Figure 3:
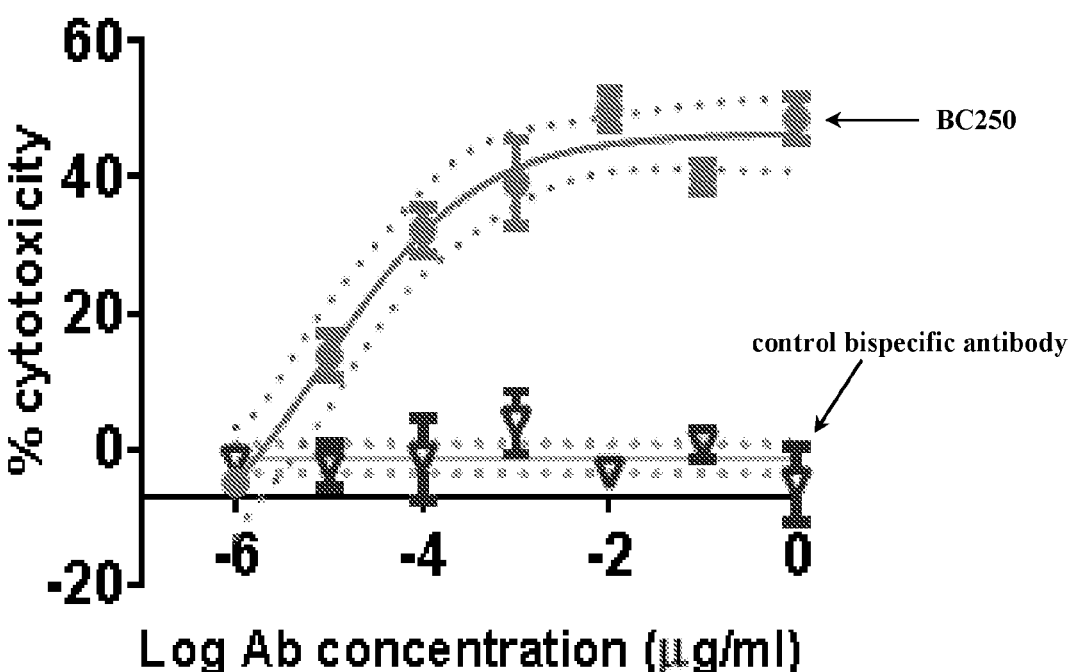
FIG. 3 shows that CD19-BsAb BC250 mediates antigen-specific T-cell cytotoxicity in acute lymphocytic leukemia (ALL). To evaluate whether a CD19-BsAb could redirect T cells to kill ALL cells, NALM6 ALL cells were loaded with $^{51}$Cr. Indicated concentrations of CD19-BsAb BC250, or a control BsAb were incubated with the $^{51}$Cr-loaded NALM6 cells, along with T cells. Standard 4-hour $^{51}$Cr release assays were performed, and the amount of released $^{51}$Cr was plotted as a function of BsAb concentration. Incubation with the control BsAb released a low baseline level of $^{51}$Cr (see inverted triangles). Incubation with the BC250 clone exhibited increased $^{51}$Cr release compared to the control BsAb, demonstrating killing of cancer cells (compare circles to inverted triangles). Based on these data, $EC_{50}$ of CD19-BsAb BC250 for cell lysis of NALM6 cells was calculated to be 42 fM.

NALM6 cells were loaded with $^{51}$Cr, and increasing concentrations of CD19-BsAb BC250, or the control BsAb were incubated with the $^{51}$Cr-loaded NALM6 cells, along with activated T cells. The amount of released $^{51}$Cr present in the recovered culture supernatants was quantitated. $^{51}$Cr release, an indicator of cell lysis, was plotted as a function of BsAb concentration. Incubation with the control BsAb released a low baseline level of $^{51}$Cr (see inverted triangles in FIG. 3). Incubation with the BC250 clone exhibited increased $^{51}$Cr release compared to the control BsAb, demonstrating killing of cancer cells (compare circles to inverted triangles). Based on these data, $EC_{50}$ of CD19-BsAb BC250 for cell lysis of NALM6 cells was calculated to be 42 fM.

Potency of the anti CD19-BsAbs correlates with their affinity to CD19. To evaluate the effect of antibody affinity on cytotoxicity potency, the humanized BsAb clones BC250, BC253, BC254 and BC255 were selected from the twenty-four humanized CD19-CD3 IgG-scFv antibodies based on their affinity towards CD19. T cell cytotoxicity on CD19(+) NALM6 ALL cells in the presence of different doses of the four BsAbs was measured using standard 4-hour $^{51}$Cr release assays. Cytotoxicity of the different BsAbs was plotted as a function of BsAb concentration. Mean Fluorescence Intensity (MFI) observed in NALM6 ALL cells with the four BsAb clones was measured by flow cytometry. The EC50 values were calculated and plotted as a function of Mean Fluorescence Intensity (MFI).

Figure 5A:
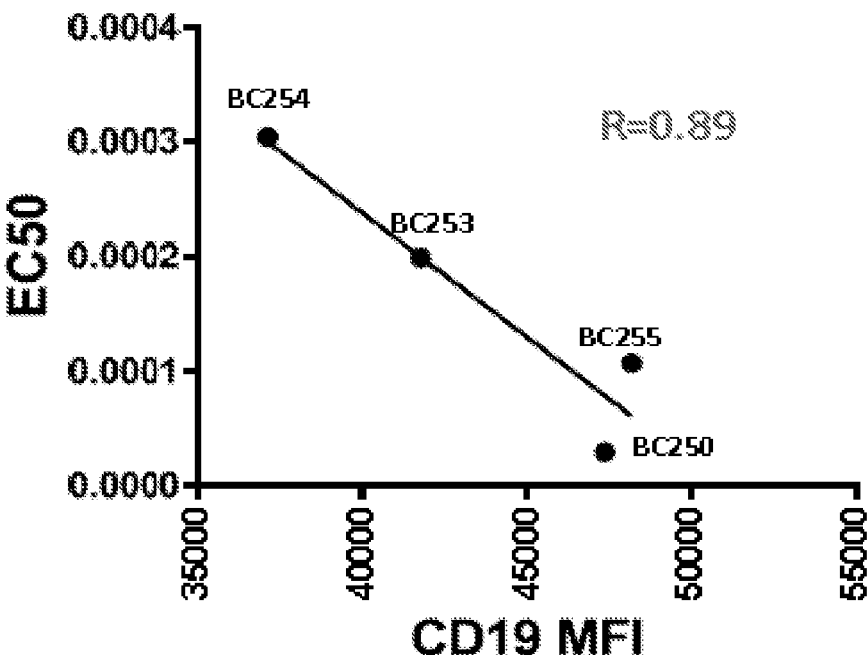
FIG. 5A shows that the potency of the anti CD19-BsAbs correlates with their binding affinity towards CD19. To evaluate the effect of antibody affinity on cytotoxic potency, the four indicated humanized BsAb clones were selected from the twenty-four humanized clones based on their affinity to CD19 (as determined by flow cytometry). T cell cytotoxicity on CD19(+) NALM6 ALL cells in the presence of different doses of the four BsAbs was measured via standard 4-hour $^{51}Cr$ release assays. The $EC_{50}$ values were calculated and were plotted as a function of Mean Fluorescence Intensity (MFI) of staining the NALM6 ALL cells, which is an indicator of the affinity of the BsAbs. Clones with higher affinity for CD19 showed greater potency in killing ALL cells (lower $EC_{50}$).
Figure 5B:
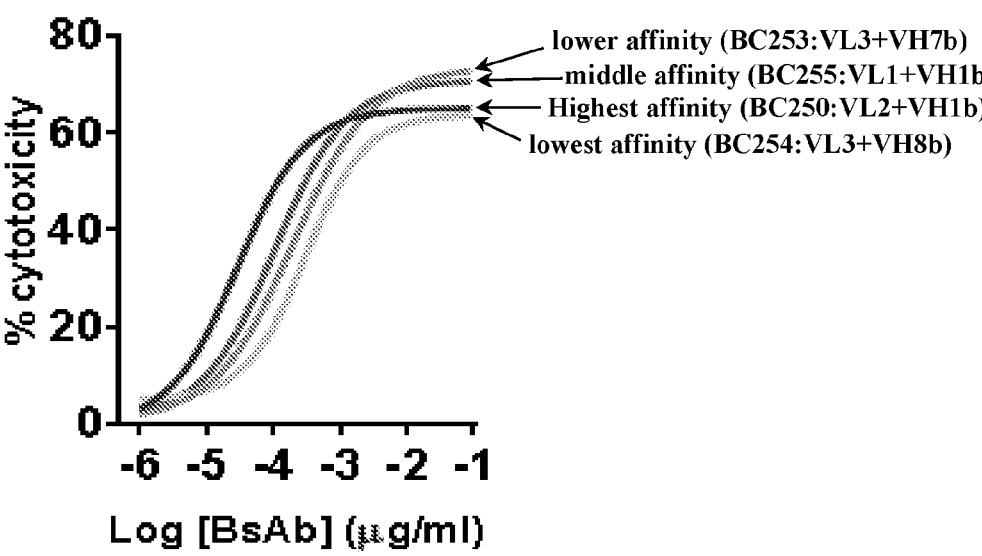
FIG. 5B shows a graph of cytotoxicity of different anti-CD19 BsAbs plotted as a function of BsAb concentration.

As shown in FIGS. 5B-5C, the potency of the anti CD19-BsAbs correlated with their affinity to CD19, with BC250 (VL-2, VH-1b) showing the highest cytotoxic potency. Clones with higher affinity for CD19 showed more potent killing of ALL cells (lower $EC_{50}$), since MFI value is an indicator of affinity of the BsAbs. See FIG. 5A. Clone BC250 (VL-2+VH-1b) was selected as the lead construct because: (1) it had high affinity to CD19; (2) it had better stability at 40° C. over time (data not shown), and (3) the humanness of the $V_L$ and $V_H$ sequences met the WHO criteria (>85%).

These results collectively demonstrate that the anti-CD19 antibodies or antigen binding fragments of the present technology can detect CD19(+) tumors and inhibit tumor growth. These results demonstrate that the antibodies or antigen binding fragments of the present technology are useful in methods for treating a CD19-associated cancer in a subject in need thereof.

Example 5: In Vivo Therapeutic Effects of the CD19-CD3 IgG-scFv BsAbs of the Present Technology Efficacy of CD19 BsAb (BC250) against human ALL NALM6 in xenograft mouse model. For in vivo studies, one million NALM6-luciferase expressing ALL cells were intravenously injected into NOD.Cg-Prkdc$^{scid}$ Il2rg$^{tm1Wjl}$/SzJ (NSG) mice on day 0. Three days later, the mice were imaged (bioluminescent imaging, BLI) and were clustered into the following 7 treatment groups: (1) activated T cells only, (2) activated T cells cell plus 100 ng BC119 (a GD2xCD3 control BsAb that does not bind NALM6 cells), (3) activated T cells cell plus BC250 (0.01 ng), (4) activated T cells cell plus BC250 (0.1 ng), (5) activated T cells cell plus BC250 (1 ng), (6) activated T cells cell plus BC250 (10 ng), and (7) activated T cells cell plus BC250 (100 ng). Treatment was initiated at day 3, once the leukemia was established. Mice received a weekly injection of 10 million activated T cells for three weeks. BsAb was administered retro-orbitally twice per week: one dose was mixed with activated T cells and the other BsAb dose was injected alone. After the last dose of activated T cells, antibody treatment was continued for 4 more doses and then stopped. To support T cell survival in vivo, 1000 IU IL2 was administered subcutaneously twice per week. Leukemia progression as monitored by BLI.

Figure 6A:
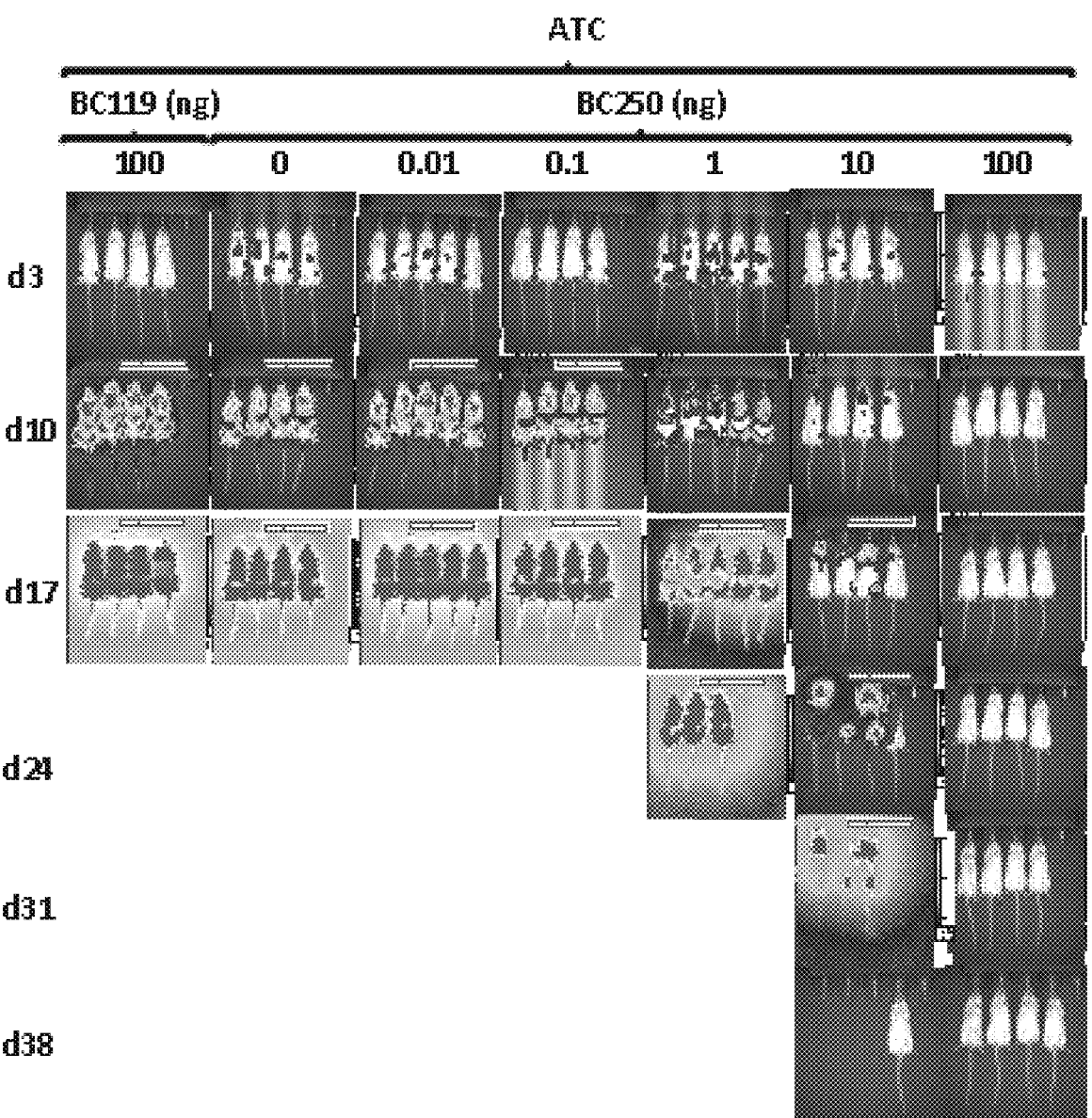
FIGS. 6A-6C show the in vivo efficacy of CD19-BsAb (BC250) against ALL NALM6 cells in a xenograft mouse model. For in vivo studies, one million NALM6-luciferase expressing ALL cells were intravenously injected into NOD.Cg-Prkdc$^{scid}$ Il2rg$^{tm1Wjl}$/SzJ (NSG) mice on day 0. Three days later, the mice were imaged (bioluminescent imaging, BLI) and were clustered into the following 7 treatment groups: (1) activated T cells only, (2) activated T cells cell plus 100 ng BC119 (a GD2×CD3 control BsAb that does not bind NALM6 cells), (3) activated T cells cell plus BC250 (0.01 ng), (4) activated T cells cell plus BC250 (0.1 ng), (5) activated T cells cell plus BC250 (1 ng), (6) activated T cells cell plus BC250 (10 ng), and (7) activated T cells cell plus BC250 (100 ng). Treatment was initiated at day 3, once the leukemia was established. Mice received a weekly injection of 10 million activated T cells for three weeks. BsAb was administered retro-orbitally twice per week: one dose was mixed with activated T cells and the other BsAb dose was injected alone. After the last dose of activated T cells, antibody treatment was continued for 4 more doses and then stopped. To support T cell survival in vivo, 1000 IU IL2 was administered subcutaneously twice per week.
Figure 6B:
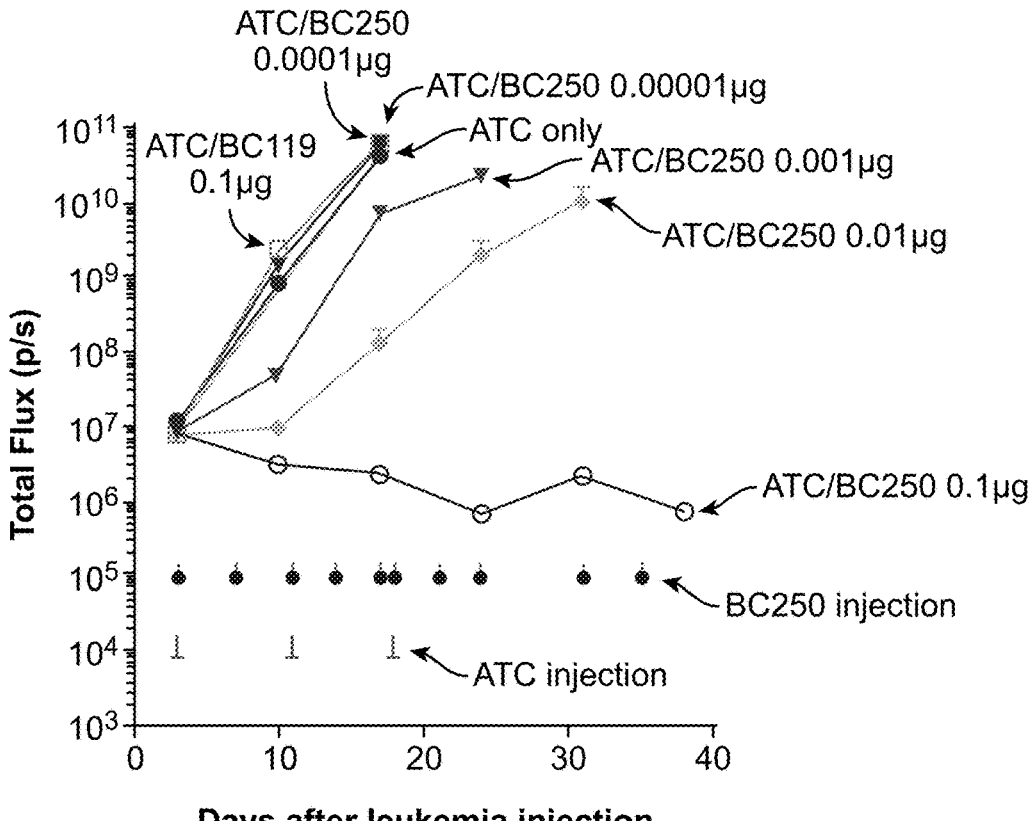
Figure 6C:
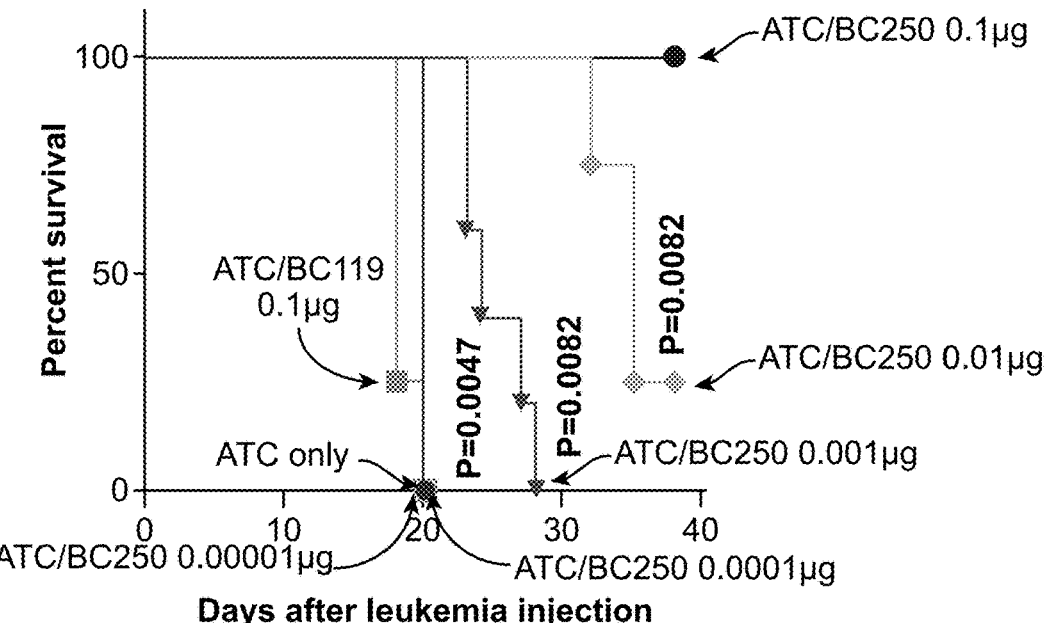

As shown in FIGS. 6A-6B, animals receiving doses≤1 ng of BC250 BsAb showed a decrease in BLI signal and total luminous flux compared to the group receiving the negative control BC119 BsAb. Thus, the BC250 BsAb can redirect activated T cells to reduce leukemia burden. As shown in FIG. 6C, treatment with 0.001 μg (1 ng), 0.01 μg (10 ng) and 0.1 μg (100 ng) BC250 BsAb showed statistically significant improvement in survival compared to treatment with the activated T cells only (no BsAb control) (p=0.0047 for activated T cells-only vs activated T cells/BC250 1 ng dose). A 100 ng/dose of BC250 was found to be curative for NALM6 cells in this in vivo model (p=0.0082 for activated T cells-only vs activated T cells/BC250 10 ng and 100 ng).

Figure 7A:
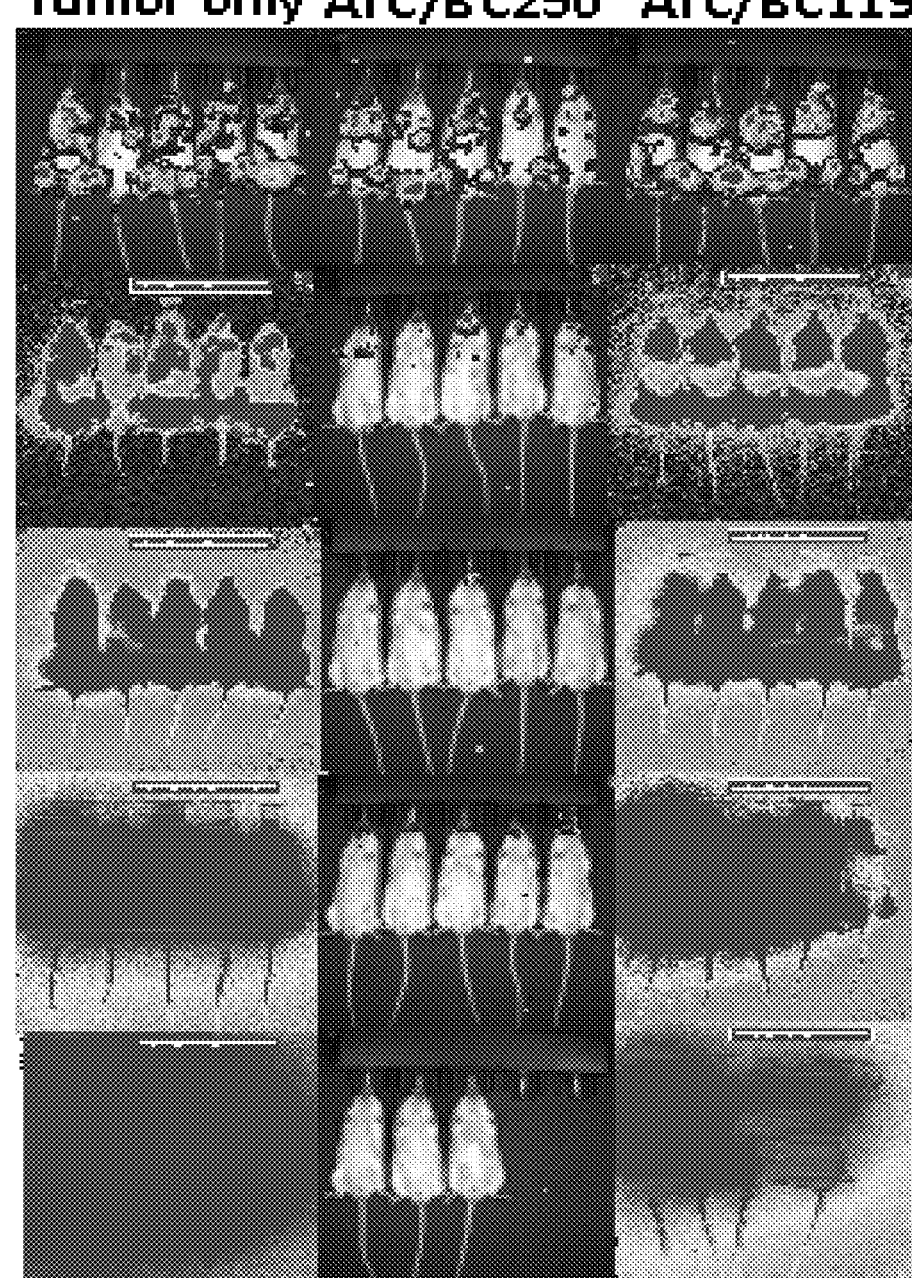
FIGS. 7A-7C show the in vivo efficacy of CD19-BsAb (BC250) against human Burkitt's lymphoma cells in a xenograft mouse model. One million Daudi cells were intravenously injected in NOD.Cg-Prkdc$^{scid}$ Il2rg$^{tm1Wjl}$/SzJ (NSG) mice on day 0. Three days later, the mice were imaged (bioluminescent imaging, BLI) and were clustered into the following 3 treatment groups: (1) no treatment (Tumor only), (2) activated T Cells (T cells) plus 100 ng BC119 (a GD2×CD3 control BsAb that does not bind Daudi cells), and (3) activated T cells plus BC250 (100 ng). Treatment was initiated at day 14, once the lymphoma was established. Mice received a weekly injection of 20 million activated T cells for three weeks. BsAb was administered retro-orbitally twice per week: one dose was mixed with activated T cells and the other BsAb dose was injected alone. After the last dose of activated T cells, antibody treatment was continued for 2 more doses and then stopped. To support T cell survival in vivo, 1000 IU IL2 was administered subcutaneously twice per week.
Figure 7B:
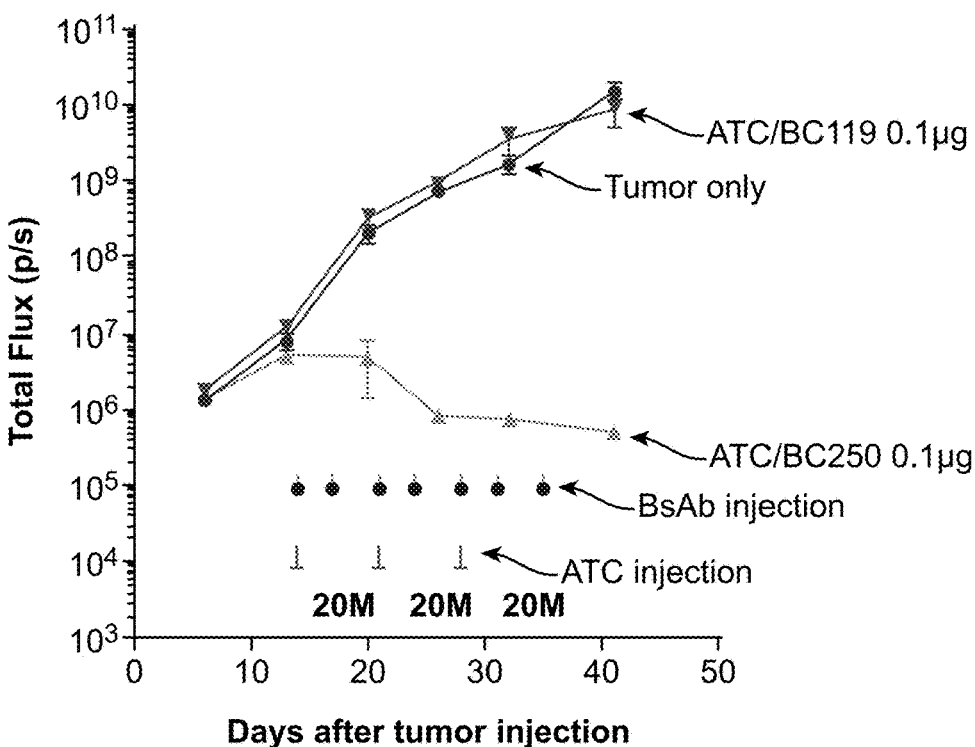
Figure 7C:
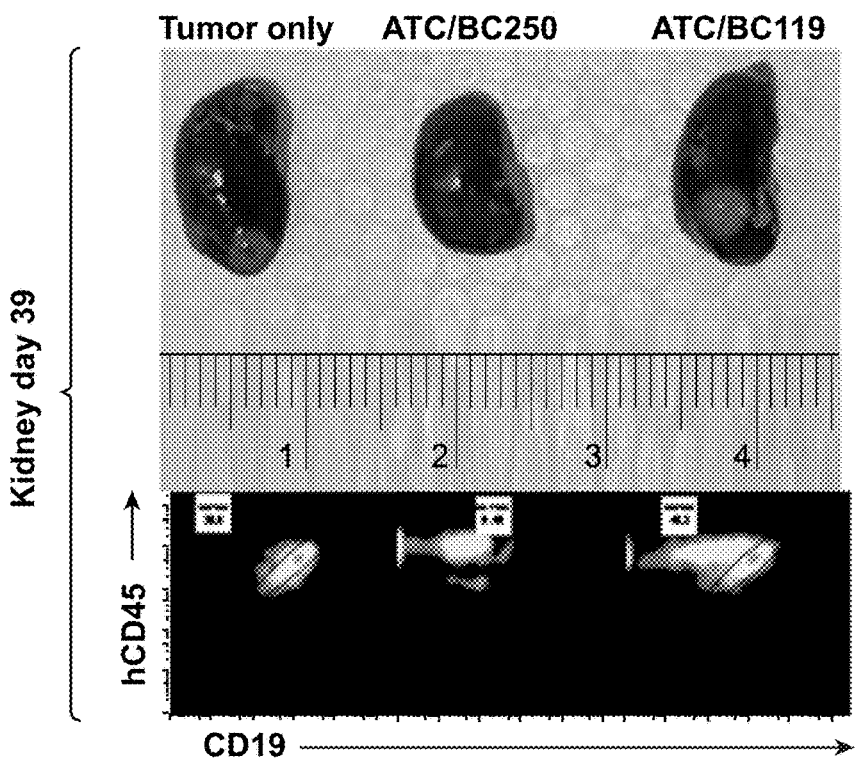

Efficacy of CD19-BsAb (BC250) against human Burkitt's lymphoma (Daudi) in xenograft mouse model. One million Daudi cells were intravenously injected in NOD.Cg-Prkd$^{scid}$ Il2rg$^{tm1Wjl}$/SzJ (NSG) mice on day 0. Three days later, the mice were imaged (bioluminescent imaging, BLI) and were clustered into the following 3 treatment groups: (1) no treatment (Tumor only), (2) activated T Cells (T cells) plus 100 ng BC119 (a GD2xCD3 control BsAb that does not bind Daudi cells), and (3) activated T cells plus BC250 (100 ng). Treatment was initiated at day 14, once the lymphoma was established. Mice received a weekly injection of 20 million activated T cells for three weeks. BsAb was administered retro-orbitally twice per week: one dose was mixed with activated T cells and the other BsAb dose was injected alone. After the last dose of activated T cells, antibody treatment was continued for 2 more doses and then stopped. To support T cell survival in vivo, 1000 IU IL2 was administered subcutaneously twice per week. Lymphoma progression was monitored by BLI. Total luminous flux from the mice as a function of the number of days post-injection of Daudi cells was plotted. As shown in FIG. 7A, 100 ng/dose of BC250 antibody was curative against Daudi xenografts. Mice treated with 100 ng/dose of BC250 antibody showed substantially reduced tumor burden compared to the control mice treated with the negative control antibody (BC119). See FIG. 7B. Moreover, mice within the groups that did not receive BC250 exhibited multiple visible metastases in the kidneys, whereas mice that were treated with T cells/BC250 showed no kidney metastasis. See FIG. 7C. Flow cytometry of the kidney homogenates revealed massive lymphoma growth within the kidneys of the control groups, while kidneys from the T cell/BC250 treatment group had no lymphoma cells, thus confirming a complete cure in BC250 treated mice.

Efficacy of CD19-BsAb (BC250) against human chronic myeloid leukemia blast crisis (CML) cell line BV173 in xenograft mouse model. One million BV173-luciferase-expressing cells were intravenously injected in NOD.Cg-Prkdc$^{scid}$ Il2rg$^{tm1Wjl}$/SzJ (NSG) mice on day 0. Three days later, the mice were imaged (bioluminescent imaging, BLI) and were clustered into the following 3 treatment groups: (1) no treatment (Tumor only), (2) activated T cells (T cells) plus 100 ng BC119 (a GD2xCD3 control BsAb that does not bind BV173 cells), and (3) activated T cells plus BC250 (100 ng). Treatment was initiated at day 14, once the leukemia was established. Mice received a single injection of 8.8 million activated T cells. BsAb was administered retro-orbitally twice per week: one dose was mixed with activated T cells and the other BsAb dose was injected alone. After the single T cell dose, antibody treatment was continued for 5 more doses and then stopped. To support T cell survival in vivo, 1000 IU IL2 was administered subcutaneously twice per week. Leukemia progression was monitored by BLI.

Figure 8A:
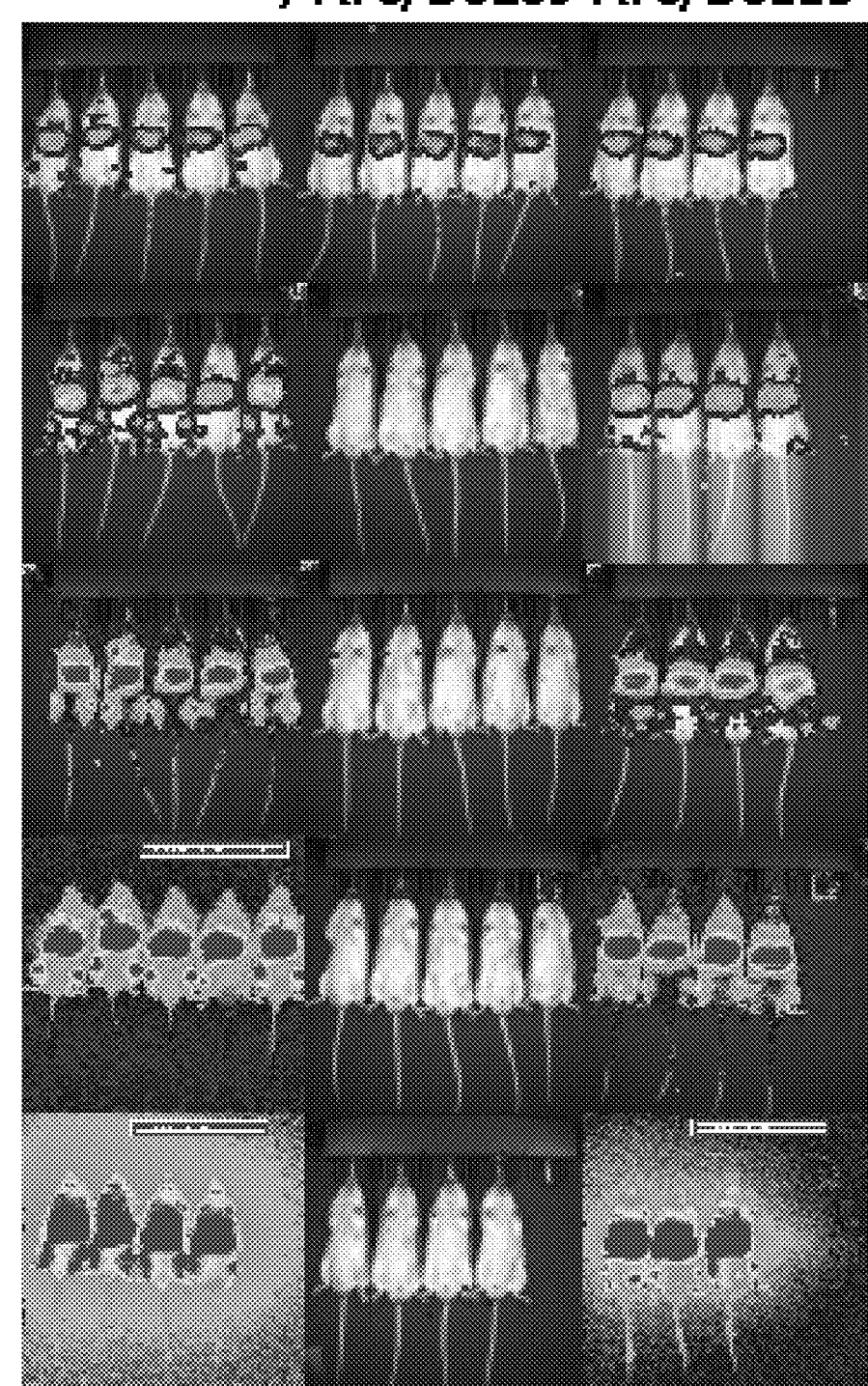
FIGS. 8A-8D show the in vivo efficacy of CD19-BsAb (BC250) against human chronic myeloid leukemia blast crisis (CML) BV173 cells in a xenograft mouse model. One million BV173-luciferase-expressing cells were intravenously injected in NOD.Cg-Prkdc$^{scid}$Il2rg$^{tm1Wjl}$/SzJ (NSG) mice on day 0. Three days later, the mice were imaged (bioluminescent imaging, BLI) and were clustered into the following 3 treatment groups: (1) no treatment (Tumor only), (2) activated T cells (T cells) plus 100 ng BC119 (a GD2×CD3 control BsAb that does not bind BV173 cells), and (3) activated T cells plus BC250 (100 ng). Treatment was initiated at day 14, once the leukemia was established. Mice received a single injection of 8.8 million activated T cells. BsAb was administered retro-orbitally twice per week: one dose was mixed with activated T cells and the other BsAb dose was injected alone. After the single T cell dose, antibody treatment was continued for 5 more doses and then stopped. To support T cell survival in vivo, 1000 IU IL2 was administered subcutaneously twice per week. Leukemia progression was monitored by BLI.
Figure 8B:
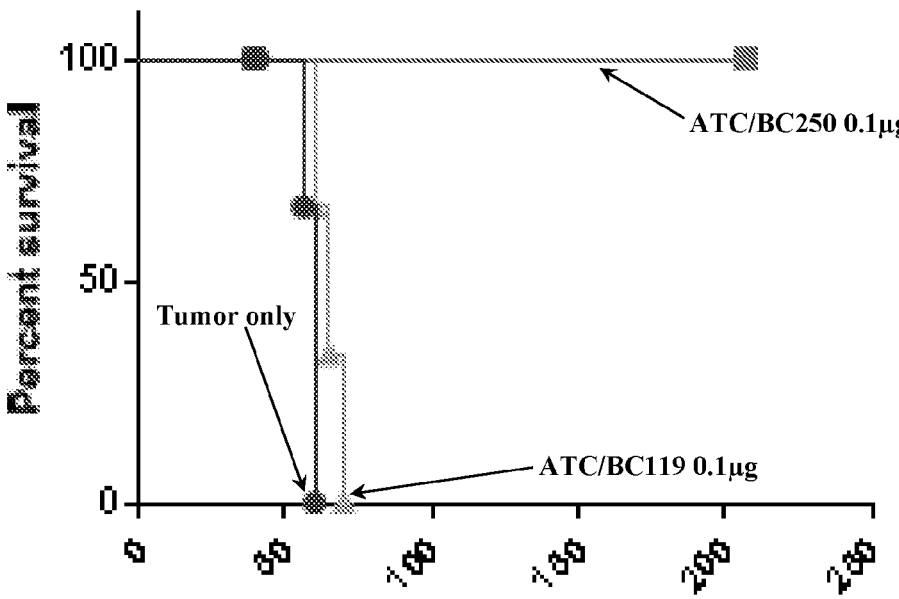
Figure 8C:
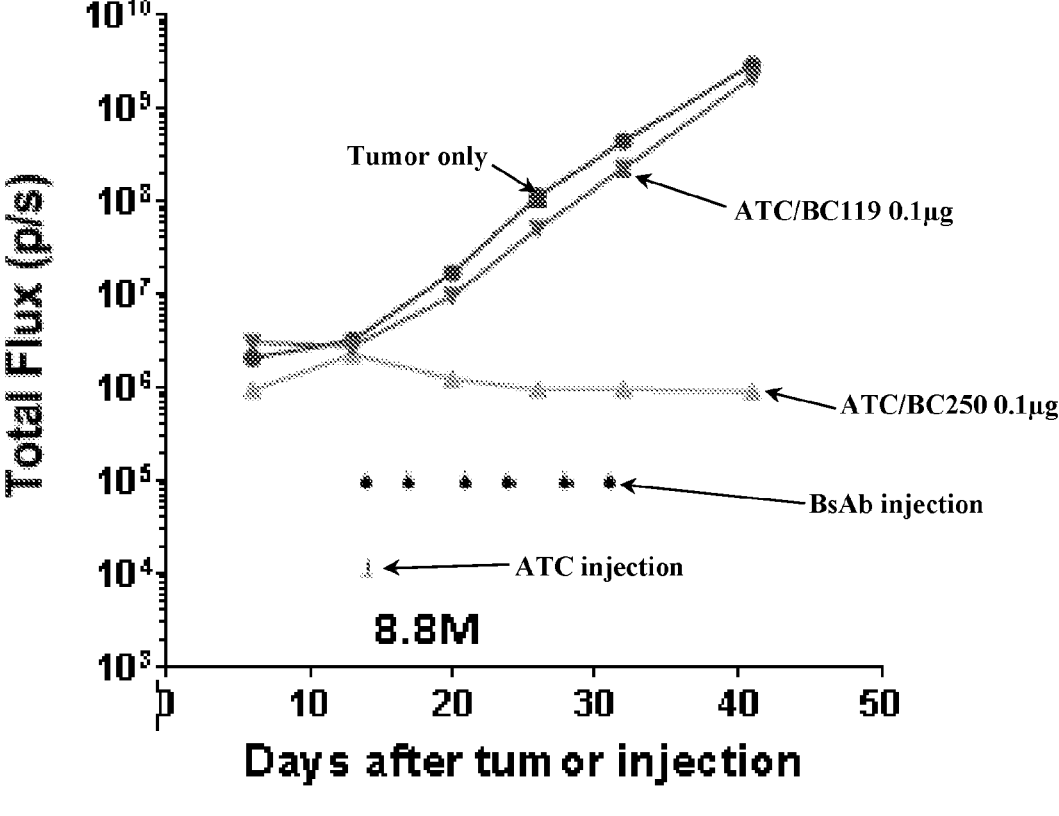
Figure 8D:
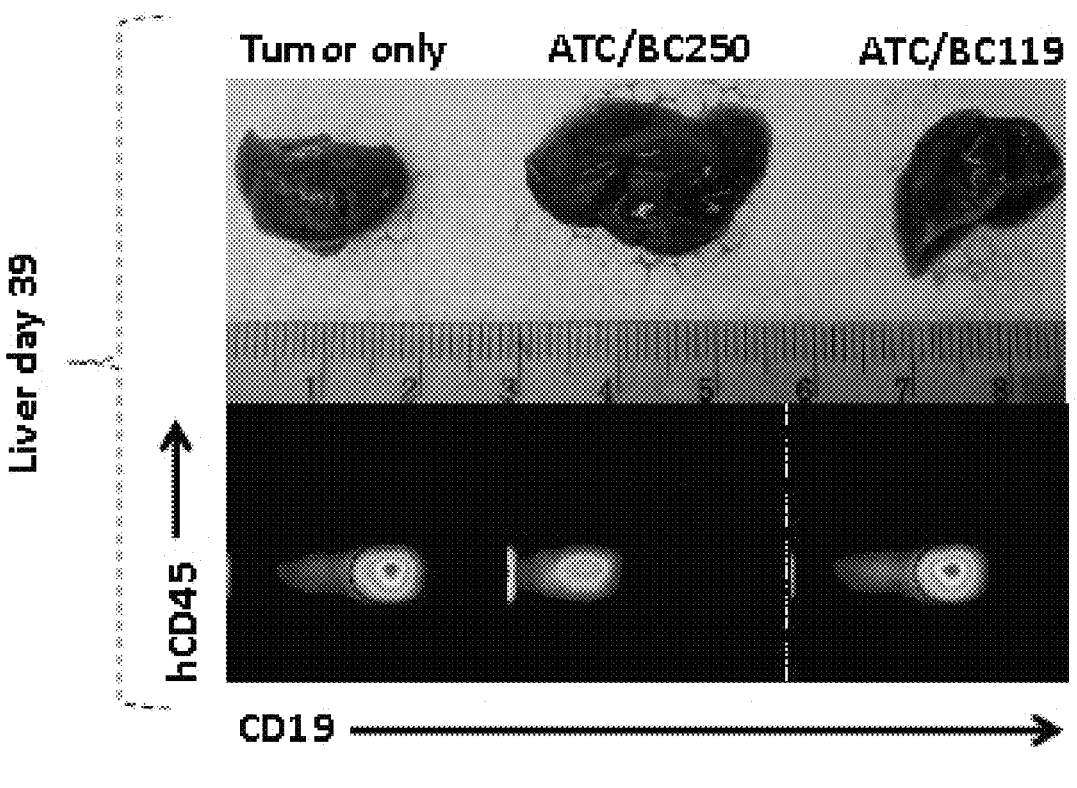

As shown in FIG. 8A, 100 ng/dose of BC250 antibody was curative against BV173 xenografts. Mice treated with 100 ng/dose of BC250 antibody showed increased survival and substantially reduced tumor burden compared to the control mice treated with the negative control antibody (BC119). See FIGS. 8B-8C. As shown in FIG. 8D, mice within the groups that did not receive BC250 exhibited multiple visible metastases in the livers, whereas mice that were treated with T cells/BC250 showed no liver metastasis. Flow cytometry of the liver homogenates revealed massive leukemia growth within the livers of the control groups, while livers from the T cell/BC250 treatment group had no leukemia cells, thus confirming a complete cure in BC250 treated mice.

Efficacy of CD19-BsAb (BC250) against human Burkitt's lymphoma (Raji) in xenograft mouse model. One million Raji-luciferase Burkitt's lymphoma cells were intravenously injected in NOD.Cg-Prkdc$^{scid}$ Il2rg$^{tm1Wjl}$/SzJ (NSG) mice on day 0. Three days later, the mice were imaged (bioluminescent imaging, BLI) and were clustered into the following 3 treatment groups: (1) no treatment (Tumor only), (2) activated T cells (T cells) plus 100 ng BC119 (a GD2×CD3 control BsAb), and (3) activated T cells plus BC250 (100 ng). Treatment was initiated at day 3, once the lymphoma was established. For three weeks, mice received 3 injections of an average of 23 million activated T cells on days 3, 7, and 10. BsAb was mixed with activated T cells and administered retro-orbitally. Two more doses of BC250 were administered on days 14 and 20. To support T cell survival in vivo, 1000 IU IL2 was administered subcutaneously twice per week. Lymphoma progression was monitored by BLI.

Figure 9A:
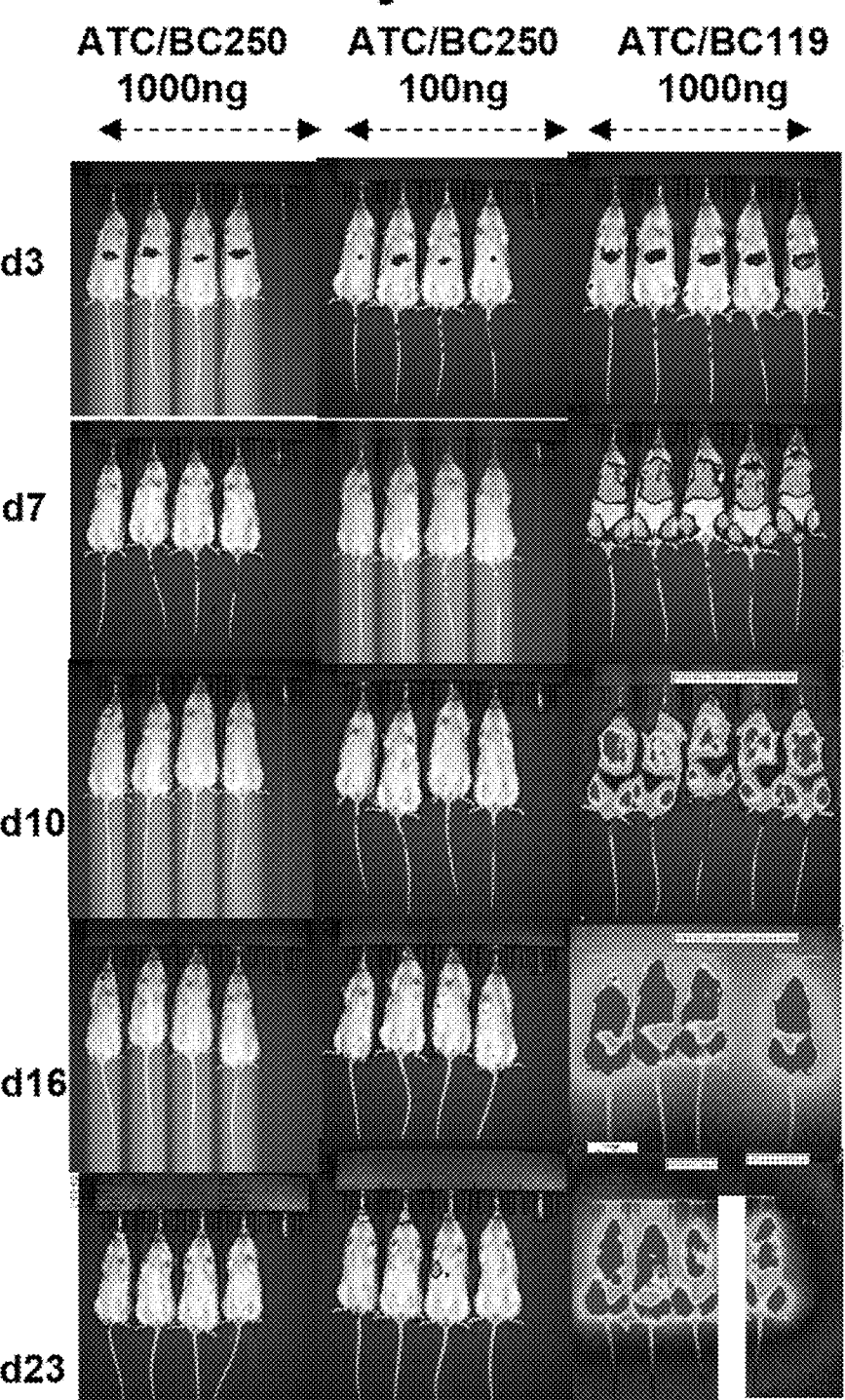
FIGS. 9A-9B show the efficacy of CD19-BsAb (BC250) against human Burkitt's lymphoma cells in a xenograft mouse model. One million Raji-luciferase Burkitt's lymphoma cells were intravenously injected in NOD.Cg-Prkdc^{scid}Il2rg^{tm1 WjIWl}/SzJ (NSG) mice on day 0. Three days later, the mice were imaged (bioluminescent imaging, BLI) and were clustered into the following 3 treatment groups: (1) no treatment (Tumor only), (2) activated T cells (T cells) plus 100 ng BC119 (a GD2×CD3 control BsAb), and (3) activated T cells plus BC250 (100 ng). Treatment was initiated at day 3, once the lymphoma was established. For three weeks, mice received 3 injections of an average of 23 million activated T cells on days 3, 7, and 10. BsAb was mixed with activated T cells and administered retro-orbitally. Two more doses of BC250 were administered on days 14 and 20. To support T cell survival in vivo, 1000 IU IL2 was administered subcutaneously twice per week.
Figure 9B:
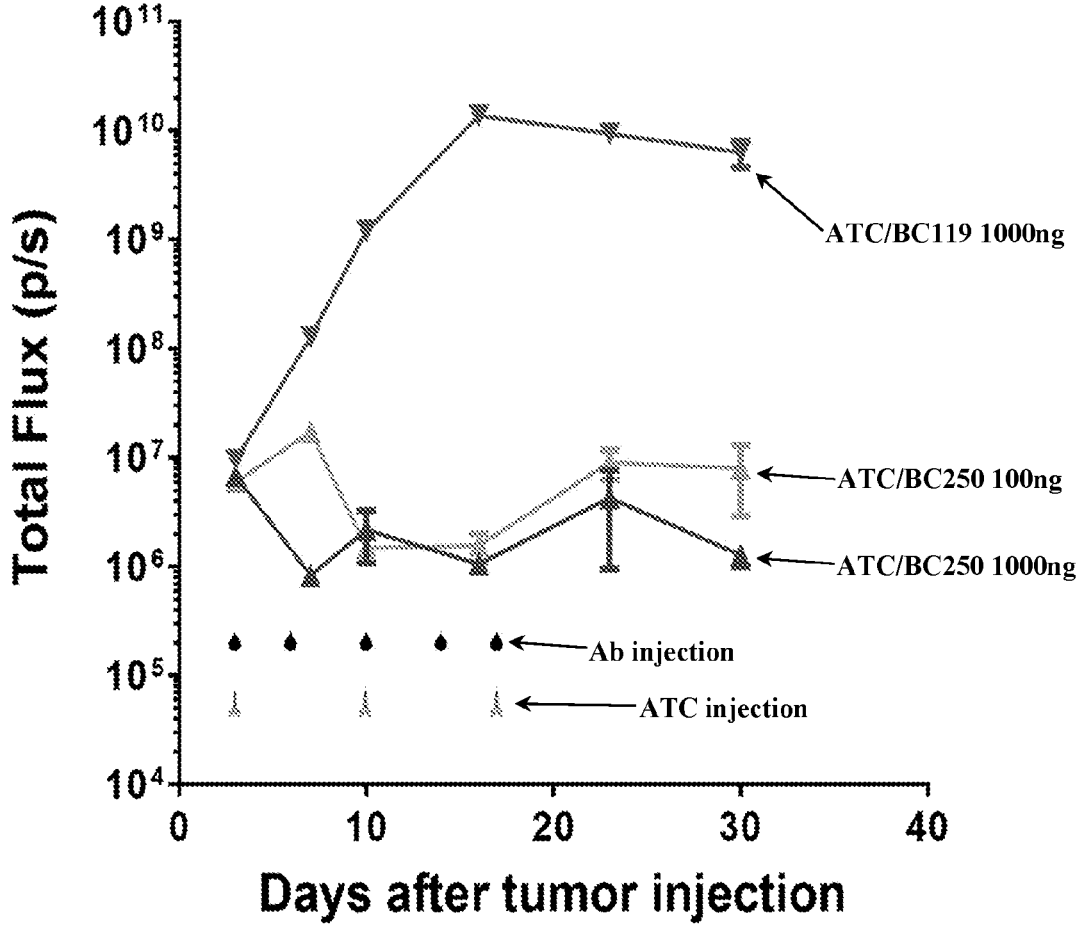

As shown in FIGS. 9A-9B, 100 ng/dose of BC250 antibody reduced the burden of Raji cell leukemia in this in vivo xenograft model compared to the no treatment (Tumor only) group or the group treated with the negative control BC119 BsAb.

Accordingly, these results demonstrate that the antibodies or antigen binding fragments of the present technology are useful in methods for treating a CD19-associated cancer in a subject in need thereof.

Figure 10A:
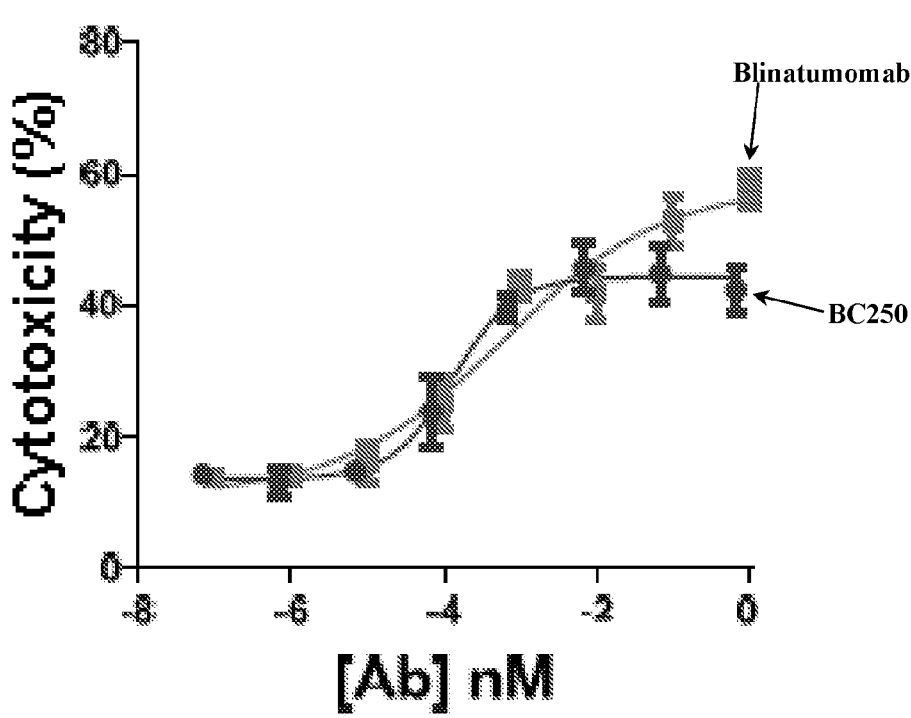
FIGS. 10A-10B show a comparison of the cytotoxic properties between the CD19-BsAb (BC250) of the present technology and the bispecific T cell engager (BiTE) Blinatumomab (the only FDA-approved BsAb against leukemia).

Example 6: Superior In Vivo Therapeutic Effects of CD19-BsAbs of the Present Technology Against ALL Xenografts Compared to the Bispecific T-cell Engager (BITE) Blinatumomab Comparison of anti-leukemic effects of BC250 BsAb with Blinatumomab in vitro. Blinatumomab is the only FDA-approved BsAb against leukemia. To compare the potency of the bispecific CD19-CD3 IgG-scFv antibody BC250 with Blinatumomab, in vitro cytotoxicity in the presence of activated T was assayed using CD19(+) NALM6 cells as target cells. Increasing concentrations of CD19-BsAb BC250, or Blinatumomab were incubated with $^{51}$Cr-loaded NALM6 cells in the presence of activated T cells. Standard 4-hour $^{51}$Cr release assays were performed and the levels of $^{51}$Cr release were plotted as a function of BsAb concentration. As shown in FIG. 10A, CD19-BsAb (BC250) BsAb, and Blinatumomab exhibited similar killing of CD19 leukemic cells in vitro.

Comparison of anti-leukemic effects of BC250 BsAb with Blinatumomab in vivo. To compare the in vivo efficacy of CD19-BsAb (BC250) and Blinatumomab against ALL xenografts, NSG mice were intravenously injected with 1 million NALM6-luciferase-expressing ALL cells on day 0. After 3 days, the mice were imaged (bioluminescent imaging, BLI) and were separated into 7 treatment groups: (1) T cells only, (2) T cells plus 5 femtomoles BC250, (3) T cells plus 50 femtomoles BC250, (4) T cells plus 500 femtomoles BC250, (5) T cells plus 10 femtomoles Blinatumomab, (6)

T cells plus 100 femtomoles Blinatumomab, and (7) T cells plus 1000 femtomoles Blinatumomab. Blinatumomab was used at 2× dose compared to BC250 to ensure that any observed differences were not attributable to the lack of identical number of available antigen binding sites. Treatment was initiated at day 4, once the leukemia was established. For three weeks, mice received 3 injections of 10 million activated T cells on days 4, 11, and 18. BsAb was administered 5 days/week. After the last dose of activated T cells, antibody was administered for 8 more doses and then stopped. To support T cell survival in vivo, 1000 IU IL2 was administered subcutaneously twice per week. Leukemia progression was monitored by BLI.

Figure 10B:
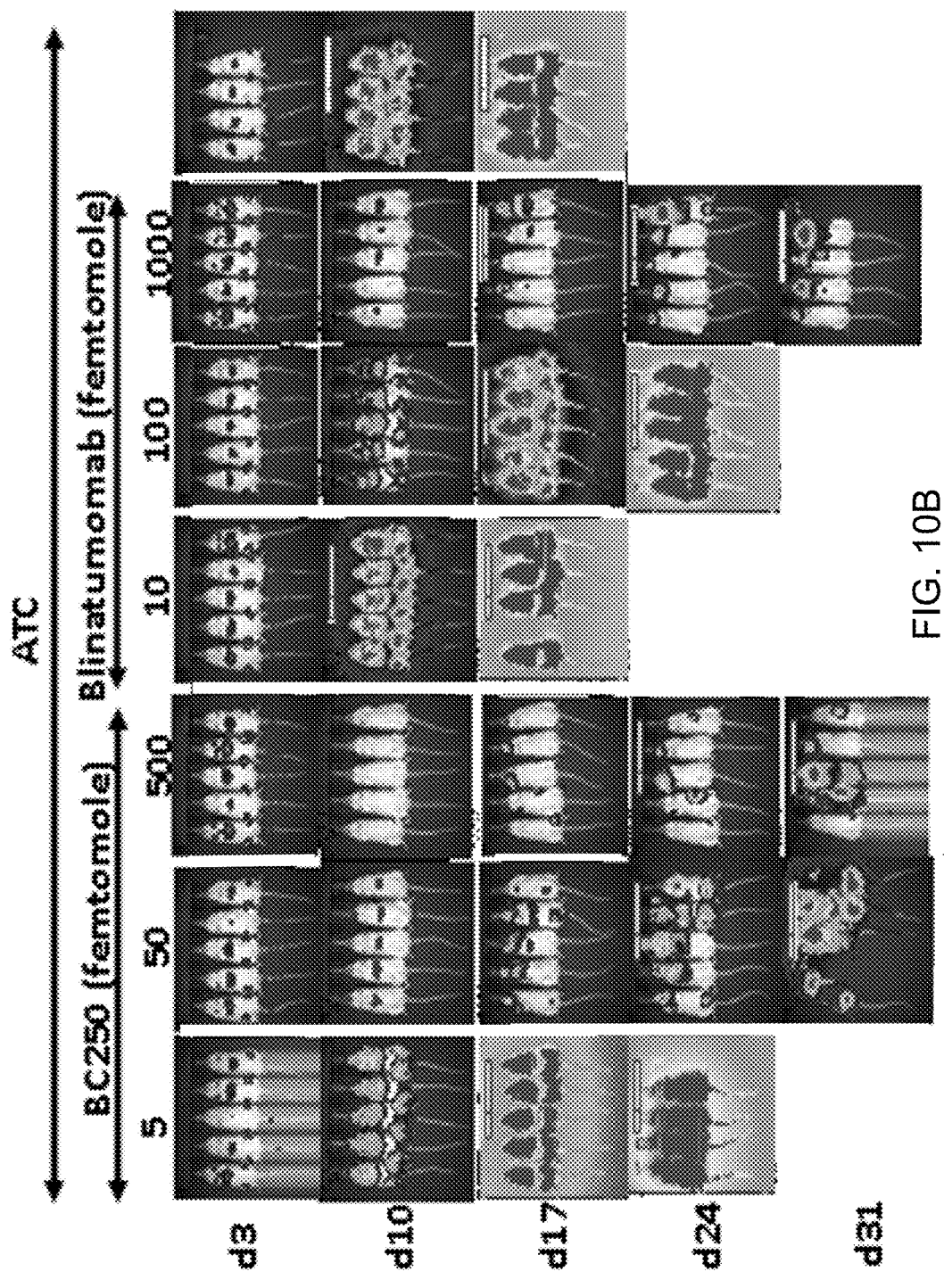
Figures 11A, 11B:
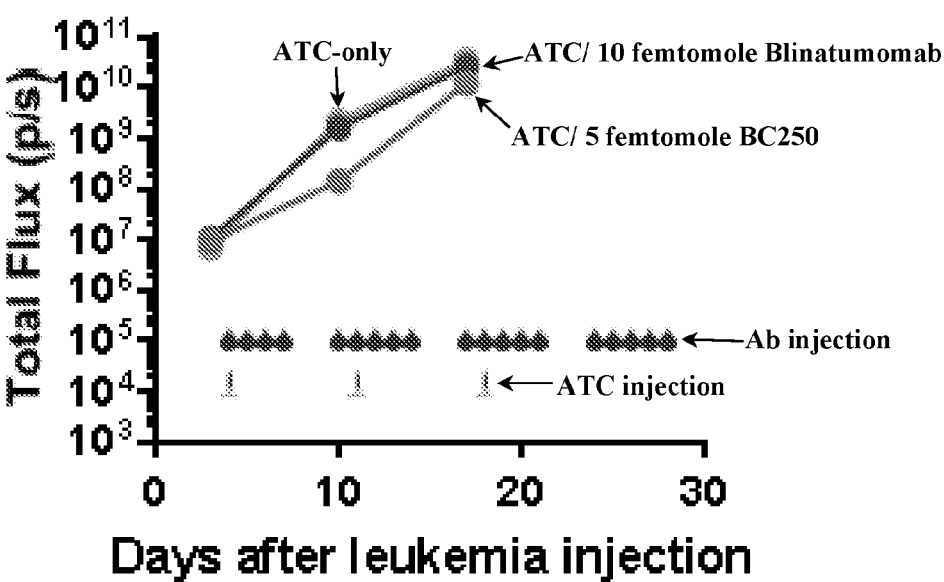
FIGS. 11A-11F show a comparison of tumor burden and survival in NALM6 xenograft mice treated with CD19-BsAb (BC250) vs. Blinatumomab.
Figure 11C:
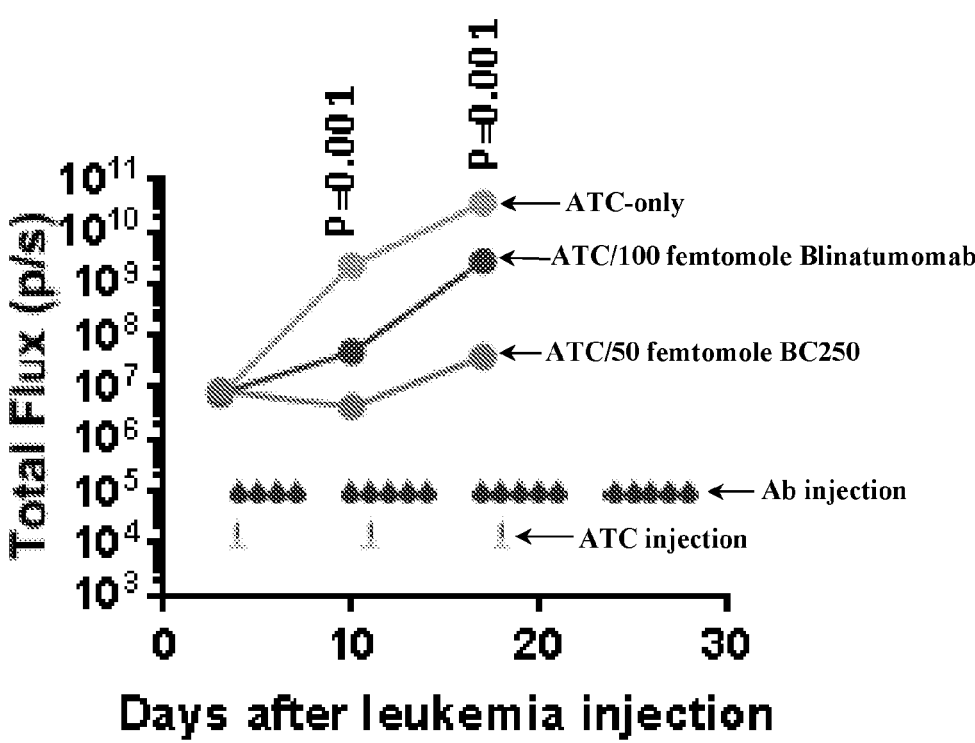
Figure 11D:
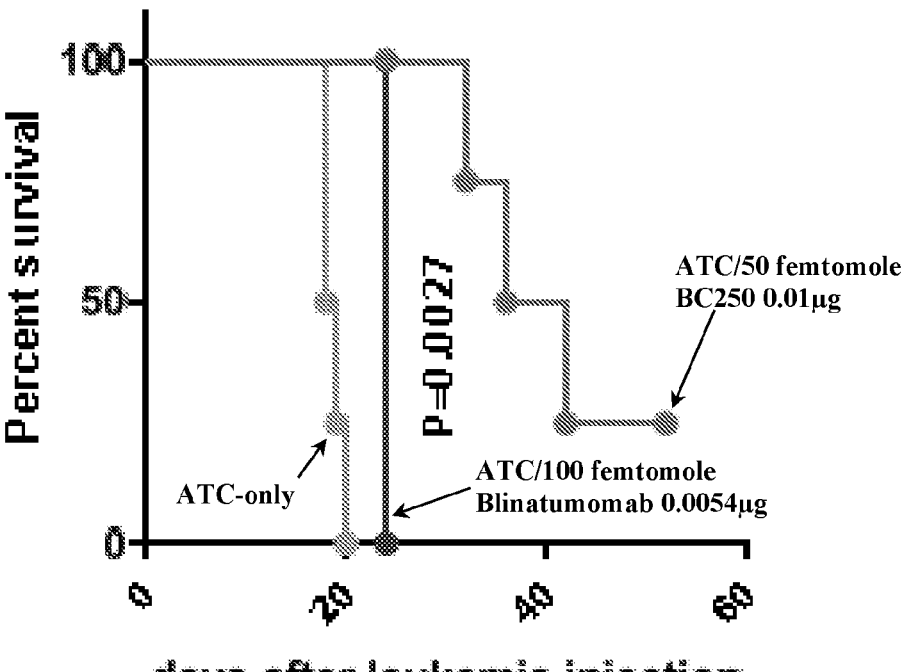
Figure 11E:
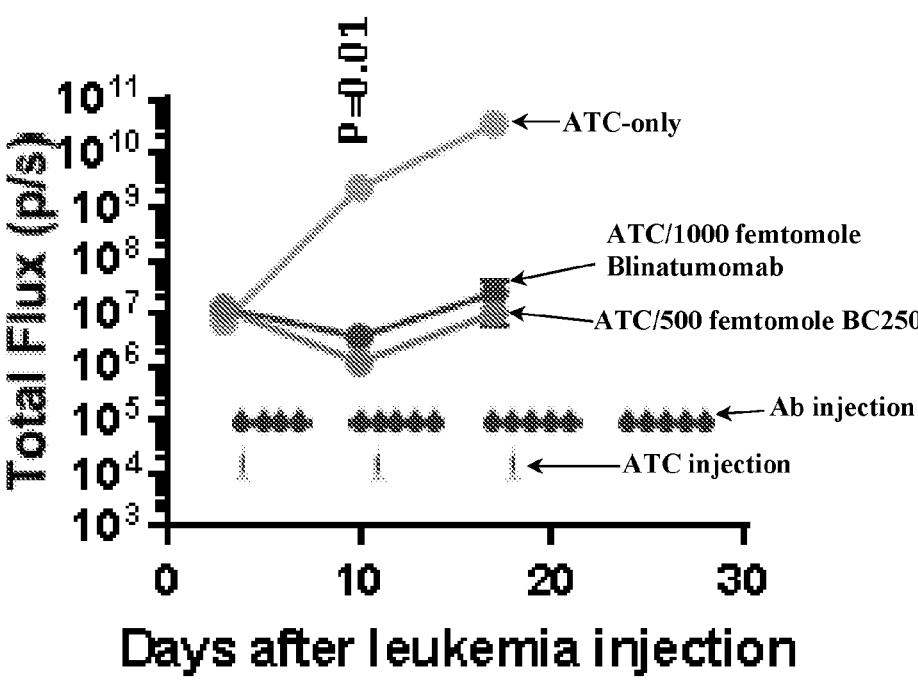
Figure 11F:
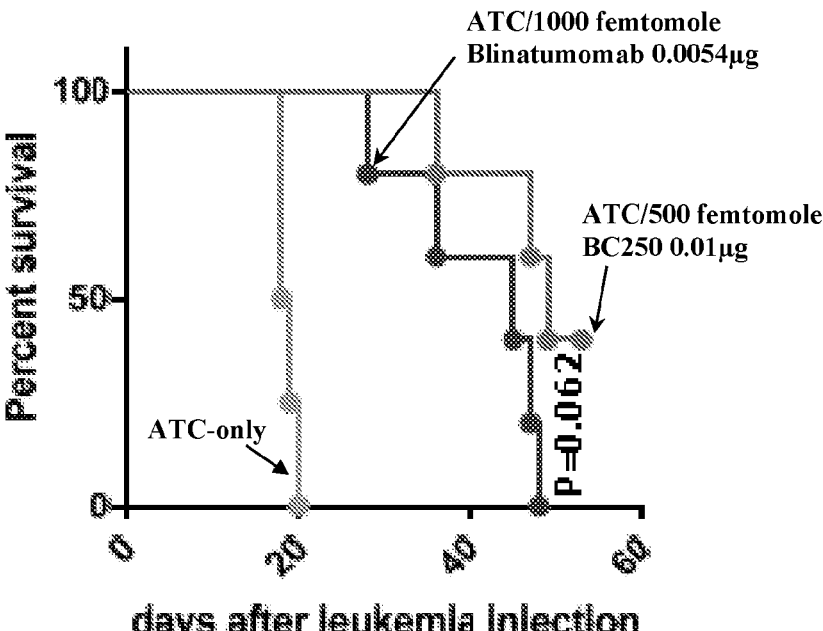
Figure 11G:
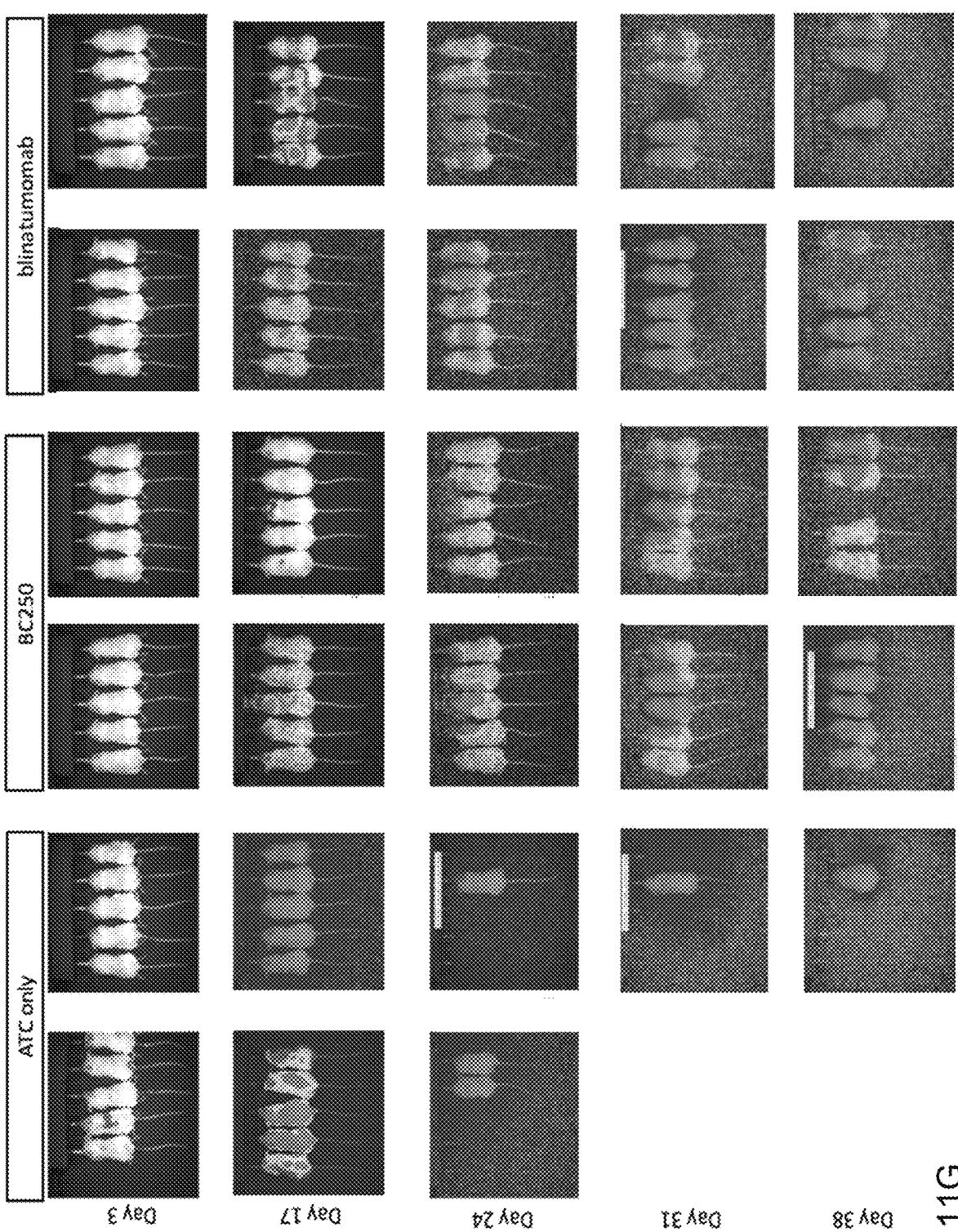
FIGS. 11G-11I show a comparison between BC250 and Blinatumomab potency in vivo. The experiment as described in FIG. 10B was repeated with 10 mice per group. Activated T cells were injected together with the bispecific antibodies to leukemic mice (NALM6 xenografted mice). To support T cell engraftment, human interleukin-2 (IL2) was injected subcutaneously. The treatment protocol is shown in FIG. 11I1. These results demonstrate the superior potency of BC250 versus Blinatumumab.
Figure 11H:
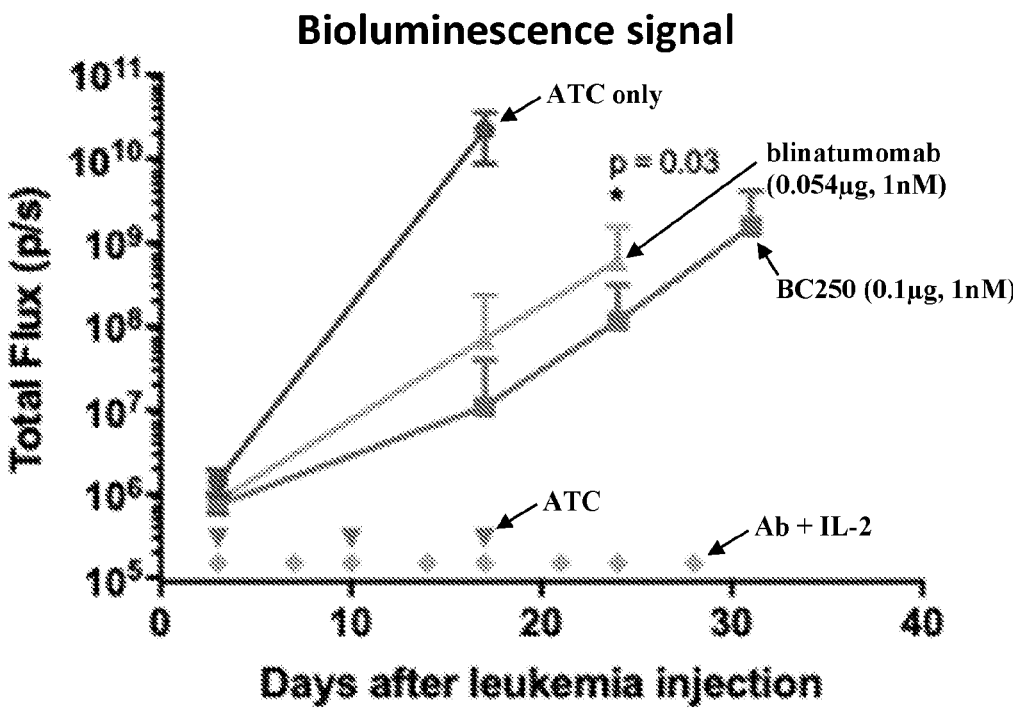
Figure 11I:
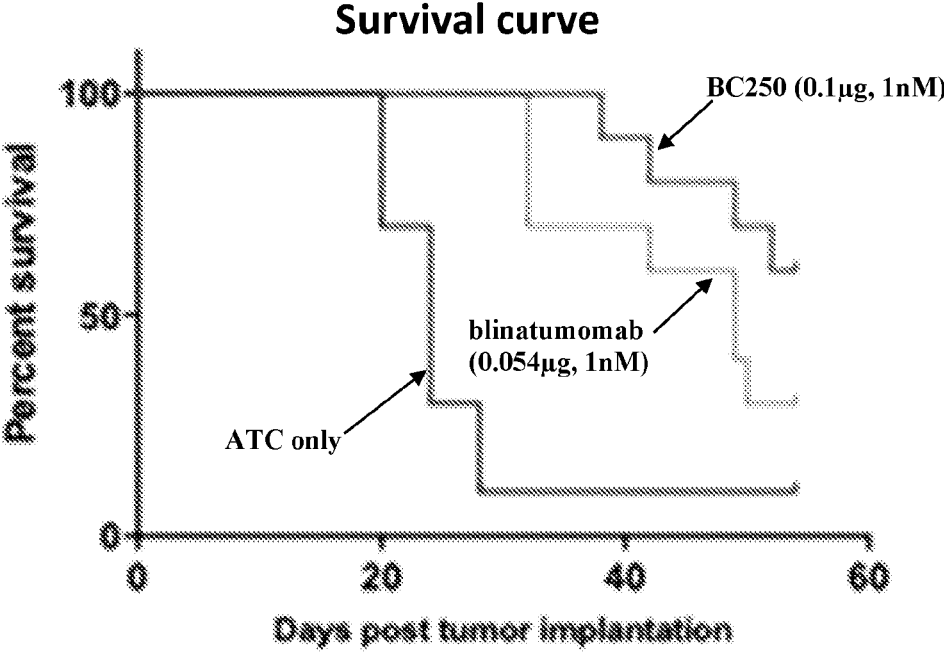
Figure 11J:
FIGS. 11J-11K show that BC250 was superior to Blinatumomab in terms of treating ALL xenografts in vivo. To compare the potency of BC250 and Blincyto in a T-cell arming experiment in vivo, NSG mice xenografted with NALM6 human ALL cells were treated with activated T-cells. The activated T cells were obtained by incubating the T cells for 20 minutes with BsAbs and subsequently washing them to remove the unbound antibodies. These results show that BC250-armed T cells reduced leukemia growth and increased the survival of mice more potently than Blinatumumab.
Figure 11K:
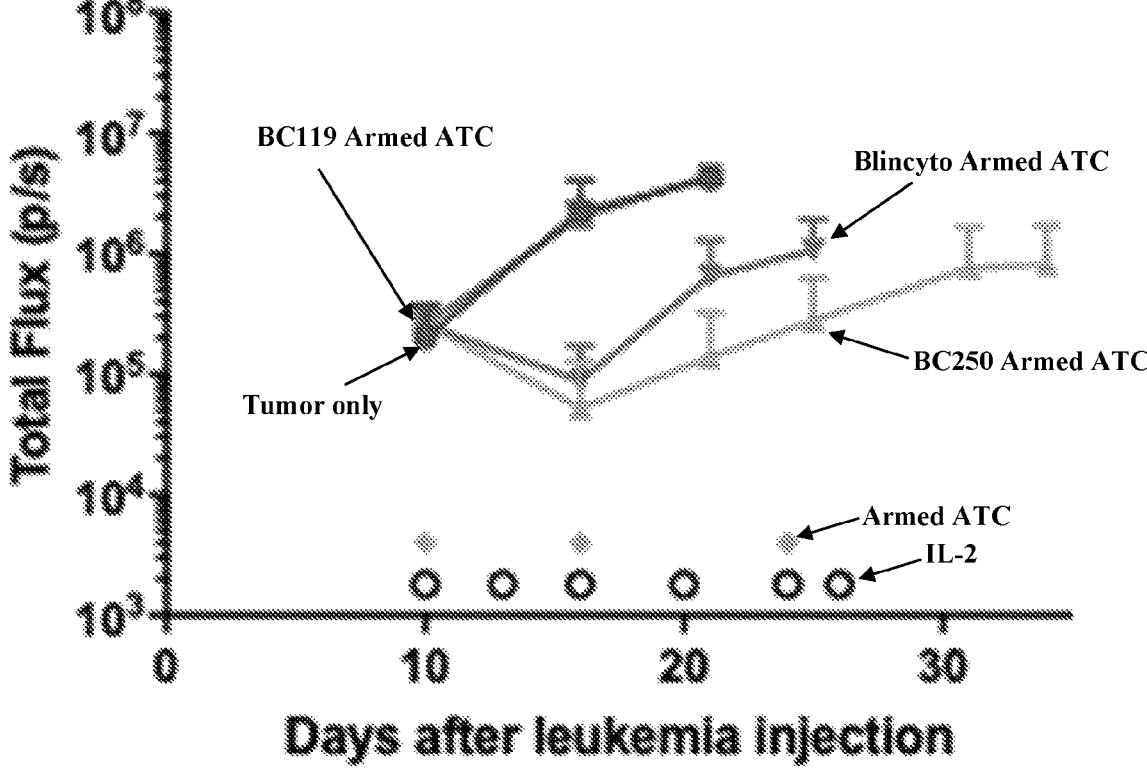

As shown in FIG. 10B, BC250- or Blinatumomab-treated mice showed a reduction in tumor burden compared to the untreated animals in the 'Tumor only' group. Moreover, the leukemia burden of mice treated with 5 femtomoles BC250 was reduced relative to that of mice treated with 10 femtomoles Blinatumomab. Likewise, the leukemia burden of mice treated with 50 and 500 femtomoles BC250 was reduced to a greater extent than that of mice treated with 100 and 1000 femtomoles Blinatumomab, respectively. See FIG. 10B.

As shown in FIGS. 11A-11F, BC250 reduces leukemia burden and increases survival more potently than Blinatumomab at all tested doses. Specifically, 50 femtomole/dose of BC250 can reduce leukemia burden 11- and 68-fold more effectively at days 11 and 17, respectively compared to 100 femtomole/dose of Blinatumomab. FIGS. 11G-11K further demonstrate that BC250 was superior to Blinatumomab in terms of treating ALL xenografts in vivo.

Figure 34A:
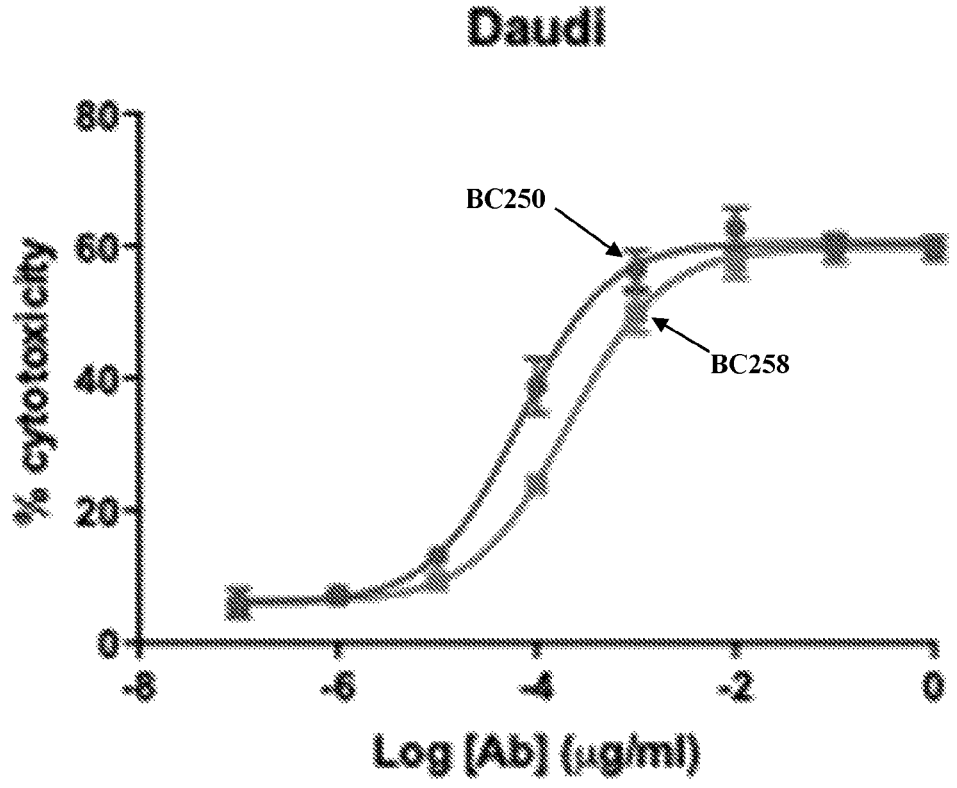
FIGS. 34A-34C show a comparison of two bispecific antibodies having N297A/K322A (BC250) and L234A/L235A (BC258) substitutions in T-cell mediated cytotoxicity assays against the CD19(+) leukemia cell lines Daudi, NALM6, and Raji, respectively. BC258 and BC250 have identical VL and VH sequences (i.e., VL-2, VH-1b), but different Fc domain sequences. BC258 has L234A/L235A (LALA) mutation in its Fc domain whereas BC250 has N297A/K322A mutations in its Fc domain. Without wishing to be bound by theory, it is believed that silencing the Fc of bispecific antibodies could prevent unwanted killing of T-cells by Fc-receptor bearing immune cells or complement activation. BC250 is more potent than BC258 in lysing leukemic cells in at least two of the three tested CD19(+) leukemia cell lines.
Figure 34B:
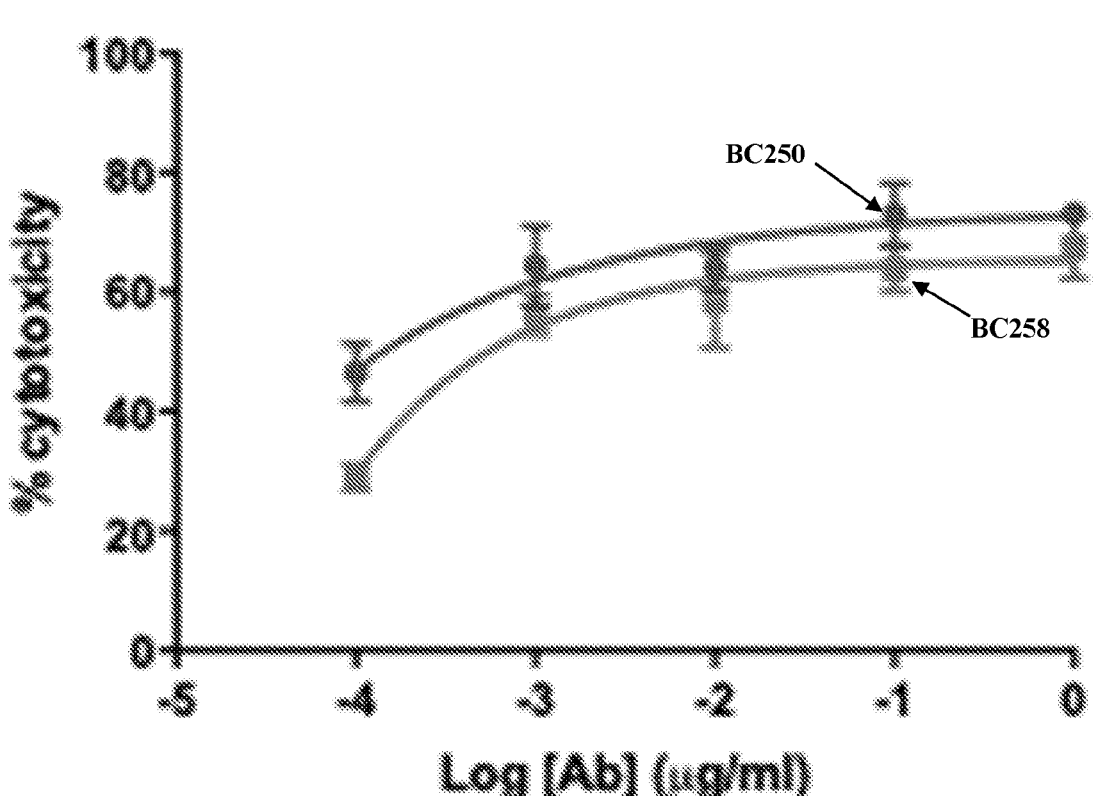
Figure 34C:
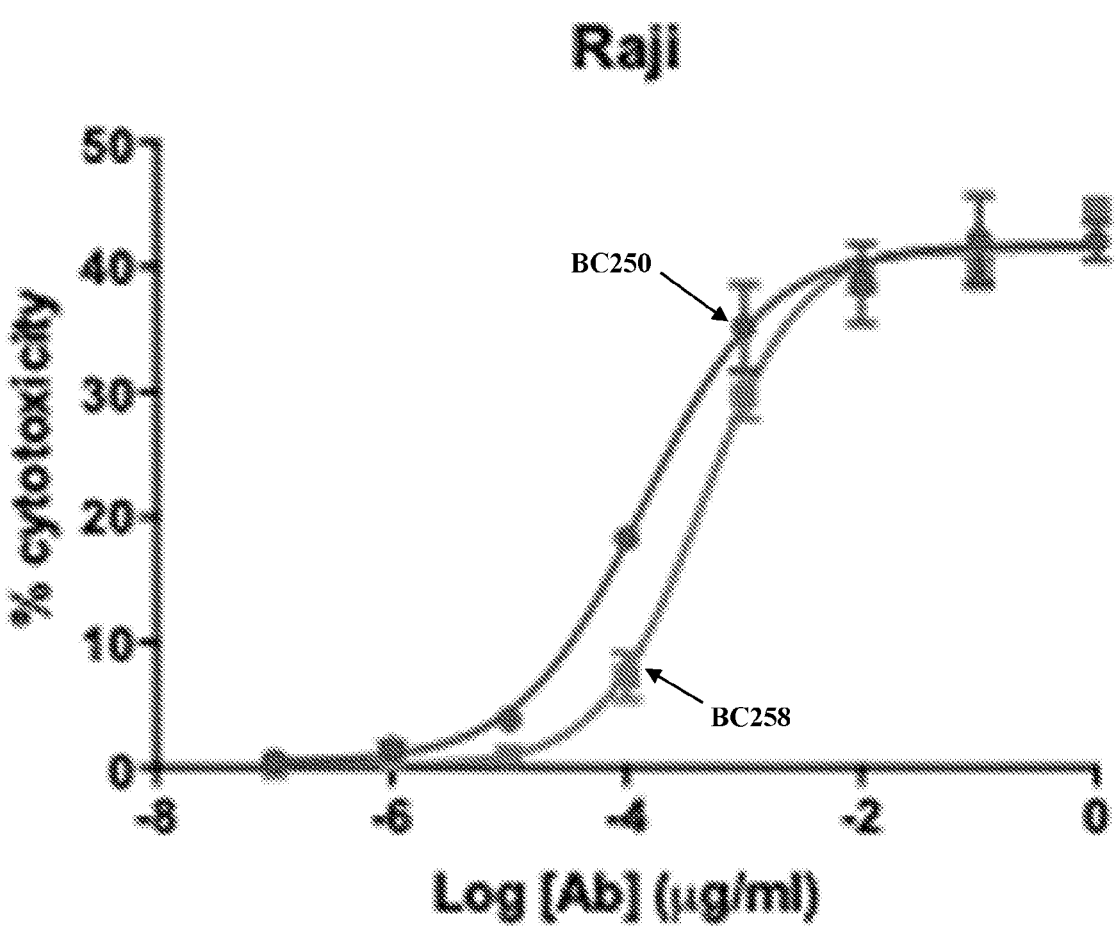
Figure 35A:
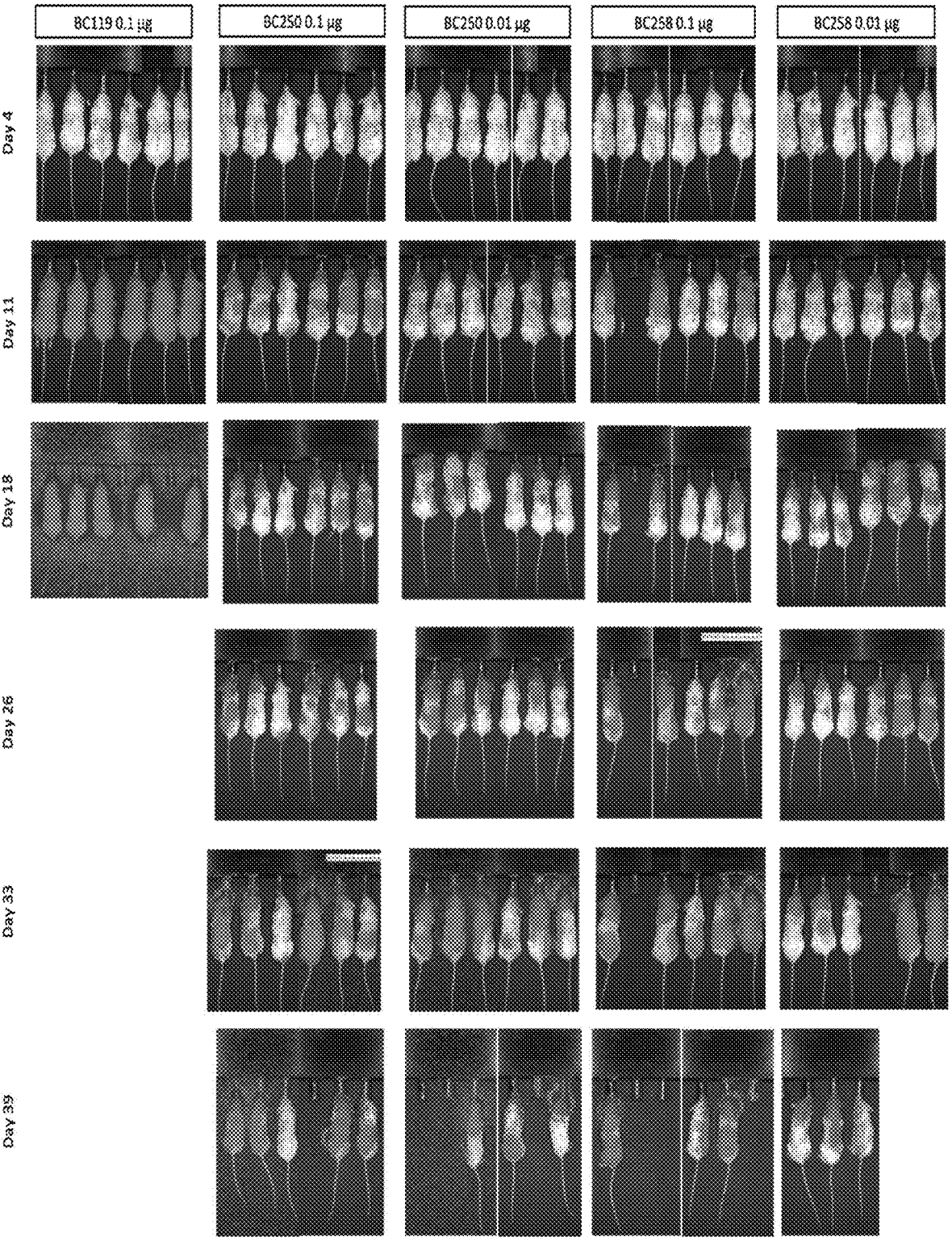
FIGS. 35A-35C show a comparison of two bispecific antibodies having N297A/K322A (BC250) and L234A/L235A (BC258) substitutions in a leukemic NALM6 xenograft mouse model. Leukemic mice were treated with activated T-cells (ATC) mixed with different doses of BC250 or BC258 and tumor growth was measured by bioluminescence imaging. Both bispecific antibodies exhibited comparable potency in vivo.
Figure 35B:
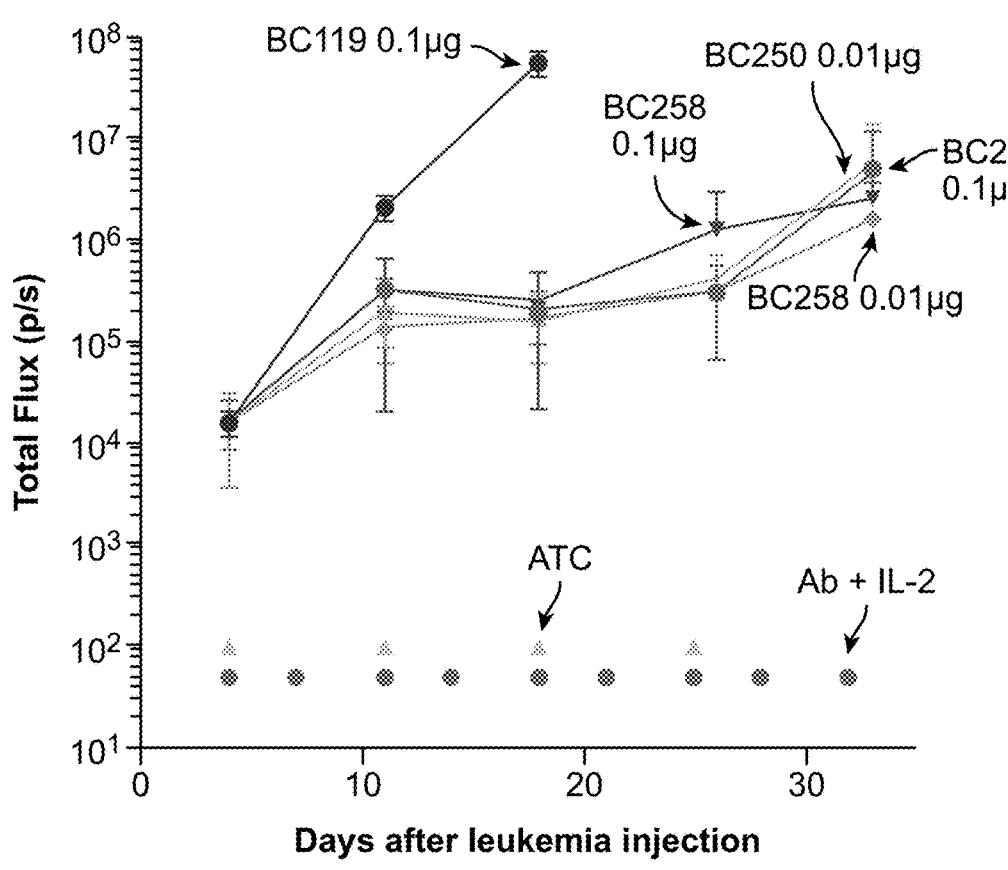
Figure 35C:
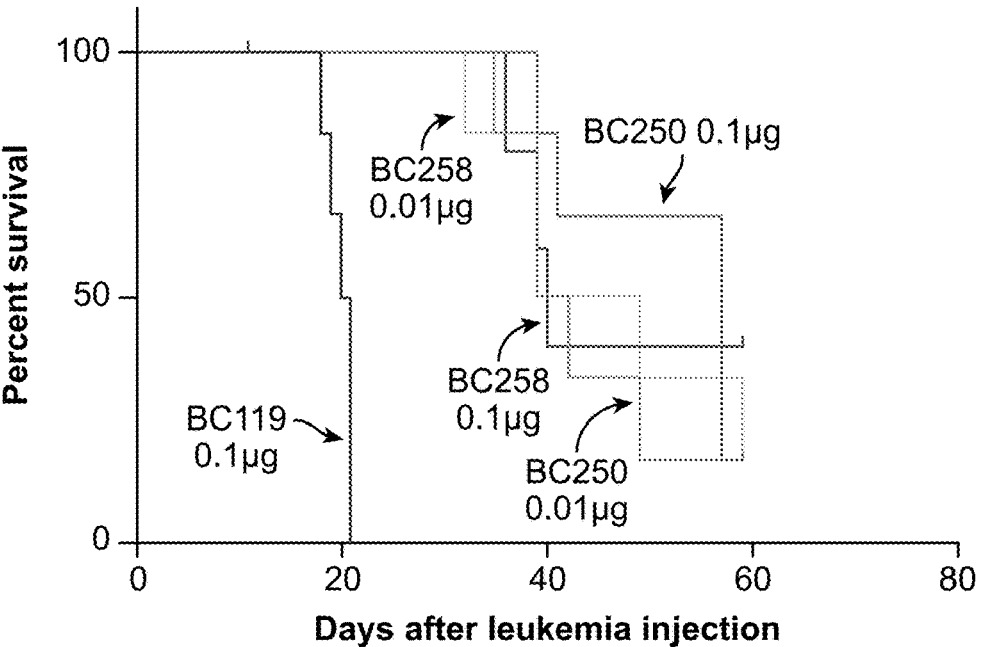

FIGS. 34A-34C show a comparison of two bispecific antibodies having N297A/K322A (BC250) and L234A/L235A (BC258) substitutions in T-cell mediated cytotoxicity assays against the CD19(+) leukemia cell lines Daudi, NALM6, and Raji, respectively. Without wishing to be bound by theory, it is believed that silencing the Fc of bispecific antibodies could prevent unwanted killing of T-cells by Fc-receptor bearing immune cells or complement activation. As shown in FIGS. 34A-34C, BC250 is more potent than BC258 in lysing leukemic cells in at least two of the three tested CD19(+) leukemia cell lines. FIGS. 35A-35C further demonstrate that both BC250 and BC258 bispecific antibodies exhibited comparable potency in vivo in a leukemic mouse model.

Accordingly, these results demonstrate that the antibodies or antigen binding fragments of the present technology are useful in methods for treating a CD19-associated cancer in a subject in need thereof.

Example 7: Use of Anti-CD19 BsAb in PRIT

IgG-based CD19-C825 BsAbs. CD19(+) leukemic cells will be injected subcutaneously, intraperitoneally, intravenously, or via other routes into animals. After tumor establishment (depending on the type of tumor and the route of injection), treatment will be initiated. Treatment is composed of one or more cycles. Each cycle comprises administration of the test BsAb (250 µg intravenously), followed by injection of a clearing agent (DOTA dextran or DOTA dendrimer; dose is 5-15% of the BsAb dose, see Cheal S M et al., *Mol Cancer Ther* 13:1803-12, 2014) after 24 to 48 hours. After 4 hours, DOTA-$^{177}$Lu (up to 1.5mCi) or DOTA-$^{225}$Ac (1 µCi) will be injected intravenously. Generally, DOTA-$^{225}$Ac is more potent than DOTA-$^{177}$Lu and may require fewer cycles for tumor eradication.

Tetramerized BsAbs. CD19(+) leukemic cells will be injected subcutaneously, intraperitoneally, intravenously, or via other routes into animals and after tumor establishment (depending on the type of tumor and the route of injection), treatment will be initiated. Treatment is composed of one or more cycles. Each cycle consists of administration of the BsAb (250 μg intravenously) followed by intravenous injection of DOTA-$^{177}$Lu (up to 1.5 mCi) or DOTA-$^{225}$Ac (1 μCi) after 24-48 hours. Generally, DOTA-$^{225}$Ac is more potent than DOTA-$^{177}$Lu and may require fewer cycles for tumor eradication.

These results demonstrate that the anti-CD19 antibodies or antigen binding fragments of the present technology can detect tumors and inhibit the progression of tumor growth and/or metastasis. Accordingly, the immunoglobulin-related compositions disclosed herein are useful for detecting and treating a CD19-associated cancer in a subject in need thereof.

Example 8: Use of Anti-CD19 Antibodies of the Present Technology to Treat Autoimmune Disease Transgenic mice that express human CD3 on mouse T cells will be crossed with transgenic mice that express human CD19 on mouse B cells. The resulting offspring will be crossed to New Zealand black (NZB) mice that spontaneously develop anemia due to autoantibodies against red blood cells (RBCs). The offspring with induced anemia will express human CD3 on mouse T cells and human CD19 on mouse B cells. Animals showing anemia will be treated with anti-CD19 BsAb or a control BsAb. Development of anemia will be detected in those mice as a readout of the experiment. It is anticipated that animals receiving the anti-CD19 BsAbs will show reduced anemia compared to those receiving a placebo because the CD19 BsAb depletes B cells that produce anti-RBC antibodies.

Accordingly, the immunoglobulin-related compositions disclosed herein are useful in methods for treating a CD19-associated autoimmune disease in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all FIG. s and tables, to the extent they are not inconsistent with the explicit teachings of this specification.

---

The invention claimed is:

1. An antibody or antigen binding fragment thereof comprising a heavy chain immunoglobulin variable domain ($V_H$) and a light chain immunoglobulin variable domain ($V_L$), wherein:
   (a) the $V_H$ comprises an amino acid sequence selected from the group consisting of: SEQ ID NOs: 5, 6, 7, 8, 9, 10, 11, and 12; and
   (b) the $V_L$ comprises an amino acid sequence selected from the group consisting of: SEQ ID NO: 17, SEQ ID NO: 18, and SEQ ID NO: 19, optionally wherein
   the antibody or antigen binding fragment binds to a CD19 polypeptide comprising the amino acid residues corresponding to positions 29-118 of SEQ ID NO: 60 or SEQ ID NO: 61, or
   the antibody is a monoclonal antibody, a chimeric antibody, a humanized antibody, or a bispecific antibody, or
   the antigen binding fragment is selected from the group consisting of Fab, F(ab')$_2$, Fab', scF$_v$, and F$_v$, or
   wherein the bispecific antibody or antigen binding fragment binds to T cells, B-cells, myeloid cells, plasma cells, mast-cells, CD3, CD4, CD8, CD20, CD19, CD21, CD23, CD46, CD80, HLA-DR, CD74, CD19, CD14, CD15, CD16, CD123, TCR gamma/delta, NKp46, KIR, or a small molecule DOTA hapten, or
   wherein the bispecific antibody or antigen binding fragment comprises an amino acid sequence selected from any one of SEQ ID NOs: 32-43, or 48-59.

2. The antibody or antigen binding fragment of claim 1, further comprising a Fc domain of an isotype selected from the group consisting of IgG1, IgG2, IgG3, IgG4, IgA1, IgA2, IgM, IgD, and IgE, optionally wherein
   IgG1 constant region comprising one or more amino acid substitutions selected from the group consisting of N297A and K322A, or IgG4 constant region comprising a S228P mutation, or the antibody lacks α-1,6-fucose modifications.

3. The antibody of claim 1 comprising a heavy chain (HC) amino acid sequence comprising SEQ ID NO: 26, SEQ ID NO: 45, SEQ ID NO: 47, and a light chain (LC) amino acid sequence comprising SEQ ID NO: 24, SEQ ID NO: 44, SEQ ID NO: 46, optionally wherein
   the antibody binds to a CD19 polypeptide comprising the amino acid residues corresponding to positions 29-118 of SEQ ID NO: 60 or SEQ ID NO: 61, or
   the antibody is a chimeric antibody, a humanized antibody, or a bispecific antibody, and optionally wherein
   the bispecific antibody binds to T cells, B-cells, myeloid cells, plasma cells, mast-cells, CD3, CD4, CD8, CD20, CD19, CD21, CD23, CD46, CD80, HLA-DR, CD74, CD19, CD14, CD15, CD16, CD123, TCR gamma/delta, NKp46, KIR, or a small molecule DOTA hapten.

4. The antibody of claim 3, comprising a HC amino acid sequence and a LC amino acid sequence selected from the group consisting of:
   SEQ ID NO: 26 and SEQ ID NO: 24 (BC250-hFMC63 VL-2/VH-1b×CD3 BsAb);
   SEQ ID NO: 45 and SEQ ID NO: 44 (hFMC63 VL-2VH-1b×mC825); and
   SEQ ID NO: 47 and SEQ ID NO: 46 (hFMC63 VL-2VH-1b×hC825), respectively.

5. A recombinant nucleic acid sequence encoding the antibody or antigen binding fragment of claim 3, optionally wherein the recombinant nucleic acid sequence is selected from the group consisting of: SEQ ID NOs: 25, and 27.

6. A host cell or vector comprising the recombinant nucleic acid sequence of claim 5.

7. A composition comprising the antibody or antigen binding fragment of claim 1 and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

8. A composition comprising the antibody of claim 3 and a pharmaceutically-acceptable carrier, wherein the antibody is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

9. A method for treating a CD19-associated cancer or a CD19-associated autoimmune disease in a subject in need thereof, comprising administering to the subject an effective amount of the antibody of claim 4 or the bispecific antibody or antigen binding fragment comprises an amino acid sequence selected from any one of SEQ ID NOs: 32-43, or 48-59, optionally wherein the CD19-associated cancer is acute myeloid leukemia, myelodysplastic syndrome, chronic myeloid leukemia, chronic lymphocytic leukemia, Non-Hodgkin Lymphoma, multiple myeloma, Plasmacytoma, Monoclonal gammopathy of undetermined significance, Waldenström's macroglobulinemia (lymphoplasmacytic lymphoma), Heavy chain disease, primary amyloidosis, Post-transplant lymphoproliferative disorder, Hodgkin lymphoma, MALT lymphoma, B cell Lymphoma, mantle cell lymphoma, (germinal center-like) diffuse large cell lymphoma, Burkitt's lymphoma, Bilineage leukemia, biphenotypic leukemia, Hairy cell leukemia, Precursor B acute lymphoblastic leukemia/lymphoma, Primary cutaneous follicle center lymphoma, follicular lymphoma, or Marginal Zone B-cell Non-Hodgkin's Lymphoma; or the CD19-associated autoimmune disease is multiple sclerosis (MS), rheumatoid arthritis (RA), systemic lupus erythematosus, paraneoplastic syndromes, Pemphigus Vulgaris, type 2 diabetes, or graft-versus-host disease.

10. The method of claim 9, wherein the antibody or antigen binding fragment is administered to the subject separately, sequentially or simultaneously with an additional therapeutic agent.

11. A method for detecting a tumor in a subject in vivo comprising (a) administering to the subject an effective amount of the antibody or antigen binding fragment of claim 3, wherein the antibody is configured to localize to a tumor expressing CD19 and is labeled with a radioisotope; and (b) detecting the presence of a tumor in the subject by detecting radioactive levels emitted by the antibody or antigen binding fragment that are higher than a reference value, optionally wherein the subject is diagnosed with or is suspected of having a CD19-associated cancer, or the radioactive levels emitted by the antibody or antigen binding fragment are detected using positron emission tomography or single photon emission computed tomography.

12. The method of claim 11, further comprising administering to the subject an effective amount of an immunoconjugate comprising a radionuclide conjugated to an antibody or antigen binding fragment thereof that comprises a VH amino acid sequence selected from the group consisting of SEQ ID NOs: 5, 6, 7, 8, 9, 10, 11, and 12; and a VL amino acid sequence selected from the group consisting of: SEQ ID NO: 17, SEQ ID NO: 18, and SEQ ID NO: 19.

13. The method of claim 12, wherein the radionuclide is an alpha particle-emitting isotope, a beta particle-emitting isotope, an Auger-emitter, or any combination thereof, optionally wherein the beta particle-emitting isotope is selected from the group consisting of $^{86}$Y, $^{90}$Y, $^{89}$Sr, $^{165}$Dy, $^{186}$Re, $^{188}$Re, $^{177}$Lu, and $^{67}$Cu.

14. The bispecific antibody or antigen binding fragment of claim 4 or the bispecific antibody or antigen binding fragment comprising an amino acid sequence selected from any one of SEQ ID NOs: 32-43, or 48-59, wherein the bispecific antibody binds to a radiolabeled DOTA hapten and a CD19 antigen.

15. A method for selecting a subject for pretargeted radioimmunotherapy comprising (a) administering to the subject an effective amount of a complex comprising a radiolabeled DOTA hapten and the bispecific antibody or antigen binding fragment of claim 14, wherein the complex is configured to localize to CD19 expressing tumor;

(b) detecting radioactive levels emitted by the complex; and (c) selecting the subject for pretargeted radioimmunotherapy when the radioactive levels emitted by the complex are higher than a reference value.

16. A method for treating cancer or increasing tumor sensitivity to radiation therapy in a subject in need thereof comprising administering to the subject an effective amount of a complex comprising a radiolabeled DOTA hapten and the bispecific antibody or antigen binding fragment of claim 14, wherein the complex is configured to localize to a CD19 expressing tumor.

17. A method for treating cancer or increasing tumor sensitivity to radiation therapy in a subject in need thereof comprising (a) administering an effective amount of the bispecific antibody or antigen binding fragment of claim 14, wherein the bispecific antibody or antigen binding fragment is configured to localize to a CD19 expressing tumor; and (b) administering an effective amount of a radiolabeled-DOTA hapten to the subject, wherein the radiolabeled-DOTA hapten is configured to bind to the bispecific antibody or antigen binding fragment.

18. The method of claim 17, further comprising administering an effective amount of a clearing agent to the subject prior to administration of the radiolabeled-DOTA hapten.

* * * * *